US011814432B2

(12) United States Patent
Zhou et al.

(10) Patent No.: US 11,814,432 B2
(45) Date of Patent: Nov. 14, 2023

(54) ANTI-HLA-A2 ANTIBODIES, RELATED CHIMERIC ANTIGEN RECEPTORS, AND USES THEREOF

(71) Applicants: THE UNIVERSITY OF BRITISH COLUMBIA, Vancouver (CA); SANGAMO THERAPEUTICS FRANCE, Valbonne Sophia Antipolis (FR)

(72) Inventors: Li Zhou, West Roxbury, MA (US); Tobias Abel, Antibes (FR); François Meyer, Porrentruy (CH); Megan Levings, Vancouver (CA); Nicolas Dawson, Vancouver (CA); Caroline Lamarche, Vancouver (CA)

(73) Assignees: The University of British Columbia, Vancouver (CA); Sangamo Therapeutics France, Valbonne Sophia Antipolis (FR)

( * ) Notice: Subject to any disclaimer, the term of this patent is extended or adjusted under 35 U.S.C. 154(b) by 487 days.

(21) Appl. No.: 16/649,426

(22) PCT Filed: Sep. 20, 2018

(86) PCT No.: PCT/CA2018/051174
§ 371 (c)(1),
(2) Date: Mar. 20, 2020

(87) PCT Pub. No.: WO2019/056106
PCT Pub. Date: Mar. 28, 2019

(65) Prior Publication Data
US 2020/0283530 A1 Sep. 10, 2020

Related U.S. Application Data

(60) Provisional application No. 62/691,027, filed on Jun. 28, 2018, provisional application No. 62/560,841, filed on Sep. 20, 2017.

(51) Int. Cl.
*C07K 16/28* (2006.01)
*A61K 35/17* (2015.01)
*C07K 14/725* (2006.01)
*C07K 14/705* (2006.01)
*A61K 35/12* (2015.01)

(52) U.S. Cl.
CPC .......... *C07K 16/2833* (2013.01); *A61K 35/17* (2013.01); *C07K 14/7051* (2013.01); *C07K 14/70517* (2013.01); *C07K 14/70575* (2013.01); *A61K 2035/122* (2013.01); *C07K 2317/24* (2013.01); *C07K 2317/33* (2013.01); *C07K 2317/622* (2013.01); *C07K 2319/02* (2013.01); *C07K 2319/03* (2013.01)

(58) Field of Classification Search
CPC ............ C07K 16/2833; C07K 14/7051; C07K 14/70517; C07K 14/70575; C07K 2317/24; C07K 2317/33; C07K 2317/622; C07K 2319/02; C07K 2319/03; A61K 35/17; A61K 2035/122
See application file for complete search history.

(56) References Cited

U.S. PATENT DOCUMENTS

| | | |
|---|---|---|
| 4,816,567 A | 3/1989 | Cabilly et al. |
| 5,229,275 A | 7/1993 | Goroff |
| 5,350,674 A | 9/1994 | Boenisch et al. |
| 5,399,346 A | 3/1995 | Anderson et al. |
| 5,530,101 A | 6/1996 | Queen et al. |
| 5,567,610 A | 10/1996 | Borrebaeck et al. |
| 5,580,859 A | 12/1996 | French |
| 5,585,362 A | 12/1996 | Wilson |
| 5,589,466 A | 12/1996 | Felgner et al. |
| 5,641,870 A | 6/1997 | Rinderknecht et al. |
| 5,677,425 A | 10/1997 | Bodmer et al. |
| 5,858,358 A | 1/1999 | June et al. |
| 5,883,223 A | 3/1999 | Gray |
| 6,326,193 B1 | 12/2001 | Liu et al. |
| 6,352,694 B1 | 3/2002 | June et al. |
| 6,534,055 B1 | 3/2003 | June et al. |
| 6,692,964 B1 | 2/2004 | June et al. |
| 6,703,199 B1 | 3/2004 | Koide |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |

(Continued)

FOREIGN PATENT DOCUMENTS

| | | |
|---|---|---|
| EP | 0404097 B1 | 9/1996 |
| WO | 1993/011161 A1 | 6/1993 |

(Continued)

OTHER PUBLICATIONS

Mariuzza, "The structural basis of antigen-antibody recognition," Ann Rev Biophys Biophys Chem (1987) 16:139-59.
Putnam et al., "Clinical grade manufacturing of human alloantigen-reactive regulatory T cells for use in transplantation," American Journal of Transplantation (2013) 13(11):3010-20.
Brinkmann and Kontermann, "The making of bispecific antibodies," MABS (2017) 9(2):182-212.
Walker et al., "New insights into the role of mast cells in autoimmunity: Evidence for a common mechanism of action?," Biochim Biophys Acta (2012) 1822(1):57-65.

(Continued)

*Primary Examiner* — Robert S Landsman
(74) *Attorney, Agent, or Firm* — Steptoe & Johnson LLP; Z. Ying Li; Wyan-Ching M. Lee

(57) ABSTRACT

The present invention relates to a novel anti-HLA-A2 antibody, and to a chimeric antigen receptor comprising said HLA-A2 antibody. The present invention further relates to an immune cell expressing said chimeric receptor antigen, and to therapeutic uses thereof, in particular for treating or preventing graft rejection or GVHD.

14 Claims, 2 Drawing Sheets

Specification includes a Sequence Listing.

(56) References Cited

U.S. PATENT DOCUMENTS

| | | | |
|---|---|---|---|
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Zhang et al. |
| 9,102,760 | B2 | 8/2015 | June et al. |
| 2004/0101519 | A1 | 5/2004 | June et al. |
| 2006/0034810 | A1 | 2/2006 | Riley et al. |
| 2006/0121005 | A1 | 6/2006 | Berenson et al. |
| 2006/0200869 | A1 | 9/2006 | Naldini et al. |
| 2007/0036773 | A1 | 2/2007 | Cooper et al. |
| 2007/0071675 | A1 | 3/2007 | Wu et al. |
| 2011/0158957 | A1 | 6/2011 | Bonini et al. |
| 2012/0060230 | A1 | 3/2012 | Collingwood et al. |
| 2012/0321667 | A1 | 12/2012 | Sentman |
| 2014/0068797 | A1 | 3/2014 | Doudna et al. |
| 2016/0024470 | A1 | 1/2016 | Aarvak et al. |
| 2020/0283529 | A1 | 9/2020 | Levings et al. |

FOREIGN PATENT DOCUMENTS

| | | |
|---|---|---|
| WO | 2001/029058 A1 | 4/2001 |
| WO | WO2001/077342 | 10/2001 |
| WO | 2001/096584 A2 | 12/2001 |
| WO | WO 2007/065957 | 6/2007 |
| WO | 2007/110785 A2 | 10/2007 |
| WO | WO 2010/137295 | 12/2010 |
| WO | 2011/058321 A1 | 5/2011 |
| WO | WO 2012/138475 | 10/2012 |
| WO | WO2014/020922 | 2/2014 |
| WO | 2018/001874 A1 | 1/2018 |
| WO | 2018/183293 A1 | 10/2018 |
| WO | 2019/056099 A1 | 3/2019 |

OTHER PUBLICATIONS

Dijke et al., "B cells in transplantation," J Heart Lung Transplant (2016) 35(6):704-10.

Zhang et al., "Engineering CAR-T cells," Biomark Res (2017) 5(22):1-6.

Nakauchi Yusuke et al., "Effective treatment against severe graft-versus-host disease with allele-specific anti-HLA monoclonal antibody in a humanized mouse model", Experimental Hematology, Feb. 2015, vol. 43, No. 2, pp. 79-88.e1-4 (14 pp.) doi: 10.1016/j.exphem.2014.10.008.

Yamazaki Satoshi et al., "A rapid and efficient strategy to generate allele-specific anti-HLA monoclonal antibodies", Journal of Immunological Methods, Mar. 31, 2009, vol. 343, No. 1, pp. 56-60 (5 pp.), doi: 10.1016/j.jim.2009.01.007.

Larson Rebecca C. and Maus Marcela V., "Recent advances and discoveries in the mechanisms and functions of CAR T cells", Nature Reviews Cancer, Mar. 2021, vol. 21, No. 3, pp. 145-161 (17 pp.), doi: 10.1038/s41568-020-00323-z.

Dawson Nicholas Aj et al., "Systematic testing and specificity mapping of alloantigen-specific chimeric antigen receptors in regulatory T cells", Journal of Clinical Investigation Insight, Mar. 21, 2019, vol. 4, No. 6, Article e123672, doi: 10.1172/jci.insight.123672.

Dawson Nicholas Aj et al., "Systematic testing and specificity mapping of alloantigen-specific chimeric antigen receptors in regulatory T cells", Journal of Clinical Investigation Insight, Mar. 21, 2019, vol. 4, No. 6, Article e123672, doi: 10.1172/jci.insight.123672—Supplementary Figures.

Dawson A. J. Nicholas and Levings Megan K., "Antigen-specific regulatory T cells: are police CARs the answer?", Translational Research, Sep. 2017, vol. 187, pp. 53-58 (6 pp.), doi: 10.1016/j.trsl.2017.06.009.

Fan Chia-Yu et al., "De novo protein sequencing, humanization and in vitro effects of an antihuman CD34 mouse monoclonal antibody", Biochemistry Biophysics Reports (2017) vol. 9, pp. 51-60 (10 pp.), doi: 10.1016/j.bbrep.2016.11.006.

Zhang Yi-Fan and Ho Mitchell, "Humanization of high-affinity antibodies targeting glypican-3 in hepatocellular carcinoma", Sep. 26, 2016, vol. 6, Article 33878, doi: 10.1038/srep33878.

U.S. Appl. No. 62/560,574, filed Sep. 19, 2017, Title: ANTI-HLA-A2 Antibodies and Methods of Using the Same.

S F Altschul et al., "Basic local alignment search tool", Journal of Molecular Biology, Oct. 5, 1990, vol. 215, No. 3, pp. 403-410 (8 pp.), doi: 10.1016/S0022-2836(05)80360-2.

Rodolphe Barrangou et al., "CRISPR provides acquired resistance against viruses in prokaryotes", Science, Mar. 23, 2007, vol. 315, No. 5819, pp. 1709-1712 (4 pp.), doi: 10.1126/science.1138140.

I J ten Berge et al., "Selective expansion of a peripheral blood CD8+ memory T cell subset expressing both granzyme B and L-selectin during primary viral infection in renal allograft recipients", Transplantation Proceedings, Dec. 1998, vol. 30, No. 8, pp. 3975-3977 (3 pp.), doi: 10.1016/s0041-1345(98)01309-8.

J Bitinaite et al., "FokI dimerization is required for DNA cleavage", Proceedings of the National Academy of Sciences of the United States of America, Sep. 1, 1998, vol. 95, No. 18, pp. 10570-10575 (6 pp.), doi: 10.1073/pnas.95.18.10570.

D A Boardman et al., "Expression of a Chimeric Antigen Receptor Specific for Donor HLA Class I Enhances the Potency of Human Regulatory T Cells in Preventing Human Skin Transplant Rejection", American Journal of Transplantation, Apr. 2017, vol. 17, No. 4, pp. 931-943 (13 pp.), doi: 10.1111/ajt.

Jens Boch et al., "Breaking the code of DNA binding specificity of TAL-type III effectors", Science, Dec. 11, 2009, vol. 326, No. 5959, pp. 1509-1512 (4 pp.), doi: 10.1126/science.1178811.

Jens Boch, "TALEs of genome targeting", Nature Biotechnology, Feb. 2011, vol. 29, No. 2, pp. 135-136 (2 pp.), doi: 10.1038/nbt.1767.

Sandrine Boissel et al., "MegaTALs: a rare-cleaving nuclease architecture for therapeutic genome engineering", Nucleic Acids Research, Feb. 2014, vol. 42, No. 4, pp. 2591-2601 (11 pp.), doi: 10.1093/nar/gkt1224.

Dana Carroll, "Genome engineering with zinc-finger nucleases", Genetics Society of America, Aug. 2011, vol. 188, No. 4, pp. 773-782 (10 pp.), doi: 10.1534/genetics.111.131433.

Toni Cathomen, "Zinc-finger nucleases: the next generation emerges", Molecular Therapy, Jul. 2008, vol. 16, No. 7, pp. 1200-1207 (8 pp.), doi: 10.1038/mt.2008.

Tomas Cermak et al., "Efficient design and assembly of custom TALEN and other TAL effector-based constructs for DNA targeting", Nucleic Acids Research, Jul. 2011, vol. 39, No. 12, Article e82 (11 pp.), doi: 10.1093/nar/gkr218.

T Clackson et al., "Making antibody fragments using phage display libraries", Nature, Aug. 15, 1991, vol. 352, No. 6336, pp. 624-628 (5 pp.), doi: 10.1038/352624a0.

Le Cong et al., "Multiplex genome engineering using CRISPR/Cas systems", HHS Public Access Author Manuscript, Science, Feb. 15, 2013, vol. 339, No. 6121, pp. 819-823 (5 pp.), doi: 10.1126/science.

C Delgado et al., "Enhanced tumour specificity of an anti-carcinoembrionic antigen Fab' fragment by poly(ethylene glycol) (PEG) modification", British Journal of Cancer, Jan. 1996, vol. 73, No. 2, pp. 175-182 (8 pp.), doi: 10.1038/bjc.1996.32.

Yannick Doyon et al., "Enhancing zinc-finger-nuclease activity with improved obligate heterodimeric architectures", Nature Methods, Jan. 2011, vol. 8, No. 1, pp. 74-79 (6 pp.), doi: 10.1038/nmeth.1539.

Narayanasamy Elango et al., "Optimized transfection of mRNA transcribed from a d(A/T)100 tail-containing vector", Biochemical and Biophysical Research Communications, May 13, 2005, vol. 330, No. 3, pp. 958-966 (9 pp.), doi: 10.1016/j.bbrc.2005.03.067.

R J Garland et al., "The use of Teflon cell culture bags to expand functionally active CD8+ cytotoxic T lymphocytes", Journal of

(56) References Cited

OTHER PUBLICATIONS

Immunological Methods, Jul. 30, 1999, vol. 227, No. 1-2, pp. 53-63 (11 pp.), doi: 10.1016/s0022-1759(99)00068-x.
René Geissler et al., "Transcriptional Activators of Human Genes with Programmable DNA-Specificity", Plos ONE, 2011, vol. 6, No. 5, Article e19509 (7 pp.), doi: 10.1371/journal.pone.0019509.
L L Green et al., "Antigen-specific human monoclonal antibodies from mice engineered with human Ig heavy and ight chain YACs", Nature Genetics, May 1994, vol. 7, No. 1, pp. 13-21 (9 pp.), doi: 10.1038/ng0594-13.
Ibtissem Grissa et al., "The CRISPRdb database and tools to display CRISPRs and to generate dictionaries of spacers and repeats", BMC Bioinformatics, May 23, 2007, vol. 8, Article 172 (10 pp.), doi: 10.1186/1471-2105-8-172.
Jing Guo et al., "Directed evolution of an enhanced and highly efficient FokI cleavage domain for zinc finger nucleases", HHS Public Access Author Manuscript, Journal of Molecular Biology, Jul. 2, 2010, vol. 400, No. 1, pp. 96-107 (12 pp.), doi: 10.1016/j.jmb.2010.04.060.
J B Haanen et al., "Selective expansion of cross-reactive CD8(+) memory T cells by viral variants", Journal of Experimental Medicine, Nov. 1, 1999, vol. 190, No. 9, pp. 1319-1328 (10 pp.), doi: 10.1084/jem.190.9.1319.
H G Hilton, "Direct binding to antigen-coated beads refines the specificity and cross-reactivity of four monoclonal antibodies that recognize polymorphic epitopes of HLA class I molecules", HHS Public Access Author Manuscript, Tissue Antigens, Apr. 2013, vol. 81, No. 4, pp. 212-220 (9 pp.), doi: 10.1111/tan.12095.
Dirk Hockemeyer et al., "Genetic engineering of human pluripotent cells using TALE nucleases", HHS Public Access Author Manuscript, Nature Biotechnology, Jul. 7, 2011, vol. 29, No. 8, pp. 731-734 (4 pp.), doi: 10.1038/nbt.1927.
Philipp Holliger and Peter J Hudson, "Engineered antibody fragments and the rise of single domains", Nature Biotechnology, Sep. 2005, vol. 23, No. 9, pp. 1126-1136 (11 pp.), doi: 10.1038/nbt1142.
P. Holliger et al., "'Diabodies': small bivalent and bispecific antibody fragments", Proceedings of the National Academy of Sciences of the United States of America, Jul. 15, 1993, vol. 90, No. 14, pp. 6444-6448 (5 pp.), doi: 10.1073/pnas.90.14.6444.
A Honegger and A Pluckthun, "Yet another No.ing scheme for immunoglobulin variable domains: an automatic modeling and analysis tool", Journal of Molecular Biology, Jun. 8, 2001, vol. 309, No. 3, pp. 657-670 (14 pp.), doi: 10.1006/jmbi.2001.4662.
Philippe Horvath and Rodolphe Barrangou, "CRISPR/Cas, the immune system of bacteria and archaea", Science, Jan. 8, 2010, vol. 327, No. 5962, pp. 167-170 (4 pp.), doi: 10.1126/science.1179555.
P T Jones et al., "Replacing the complementarity-determining regions in a human antibody with those from a mouse", Nature, May 29-Jun. 4, 1986, vol. 321, No. 6069, pp. 522-525 (4 pp.), doi: 10.1038/321522a0.
Benjamin S Jones et al., "Improving the safety of cell therapy products by suicide gene transfer", Frontiers in Pharmacology, Nov. 27, 2014, vol. 5, Article 254 (8 pp.), doi: 10.3389/fphar.2014.00254.
Carl H June, "Adoptive T cell therapy for cancer in the clinic", Journal of Clinical Investigation, Jun. 2007, vol. 117, No. 6, pp. 1466-1476 (11 pp.), doi: 10.1172/JCI32446.
Y G Kim et al., "Hybrid restriction enzymes: zinc finger fusions to Fok I cleavage domain", Proceedings of the National Academy of Sciences of the United States of America, Feb. 6, 1996, vol. 93, No. 3, pp. 1156-1160 (5 pp.), doi: 10.1073/pnas.93.3.1156.
G Kohler and C Milstein, "Continuous cultures of fused cells secreting antibody of predefined specificity", Nature, Aug. 7, 1975, vol. 256, No. 5517, pp. 495-497 (3 pp.), doi: 10.1038/256495a0.
M P Lefranc et al., "IMGT, the international ImMunoGeneTics database", Nucleic Acids Research, Jan. 1, 1999, vol. 27, No. 1, pp. 209-212 (4 pp.), doi: 10.1093/nar/27.1.209.
N Lonberg et al., "Antigen-specific human antibodies from mice comprising four distinct genetic modifications", Nature, Apr. 28, 1994, vol. 368, No. 6474, pp. 856-859 (4 pp.), doi: 10.1038/368856a0.
Katherine G MacDonald et al., "Alloantigen-specific regulatory T cells generated with a chimeric antigen receptor", Journal of Clinical Investigation, Mar. 21, 2016, vol. 126, No. 4, pp. 1413-1424 (12 pp.), doi: 10.1172/JCI82771.
Kira S Makarova et al., "A putative RNA-interference-based immune system in prokaryotes: computational analysis of the predicted enzymatic machinery, functional analogies with eukaryotic RNAi, and hypothetical mechanisms of action", Biology Direct, Mar. 16, 2006, vol. 1, Article 7 (26 pp.), doi: 10.1186/1745-6150-1-7.
J D Marks et al., "By-passing immunization. Human antibodies from V-gene libraries displayed on phage", Journal of Molecular Biology, Dec. 5, 1991, vol. 222, No. 3, pp. 581-597 (17 pp.), doi: 10.1016/0022-2836(91)90498-u.
Luciano A Marraffini and Erik J Sontheimer, "CRISPR interference limits horizontal gene transfer in staphylococci by targeting DNA", HHS Public Access Author Manuscript, Science, Dec. 19, 2008, vol. 322, No. 5909, pp. 1843-1845 (3 pp.), doi: 10.1126/science.1165771.
Jeffery C Miller et al., "A TALE nuclease architecture for efficient genome editing", Nature Biotechnology, Feb. 2011, vol. 29, No. 2, pp. 143-148 (6 pp.), doi: 10.1038/nbt.1755.
Michael C Milone et al., "Chimeric receptors containing CD137 signal transduction domains mediate enhanced survival of T cells and increased antileukemic efficacy in vivo", Molecular Therapy, Aug. 2009, vol. 17, No. 8, pp. 1453-1464 (12 pp.), doi: 10.1038/mt.2009.83.
S L Morrison et al., "Chimeric human antibody molecules: mouse antigen-binding domains with human constant region domains", Proceedings of the National Academy of Sciences of the United States of America, Nov. 1984, vol. 81, No. 21, pp. 6851-6855 (5 pp.), doi: 10.1073/pnas.81.21.6851.
Matthew J Moscou and Adam J Bogdanove, "A simple cipher governs DNA recognition by TAL effectors", Science, Dec. 11, 2009, vol. 326, No. 5959, p. 1501, doi: 10.1126/science.1178817.
Genoveva A Nacheva and Alfredo Berzal-Herranz, "Preventing nondesired RNA-primed RNA extension catalyzed by T7 RNA polymerase", European Journal of Biochemistry, Apr. 2003, vol. 270, No. 7, pp. 1458-1465 (8 pp.), doi: 10.1046/j.1432-1033.2003.03510.x.
E Ohtsuka et al., "An alternative approach to deoxyoligonucleotides as hybridization probes by insertion of deoxyinosine at ambiguous codon positions", Journal of Biological Chemistry, Mar. 10, 1985, vol. 260, No. 5, pp. 2605-2608 (4 pp.).
Mark Osborn et al., "Evaluation of TCR Gene Editing Achieved by TALENs, CRISPR/Cas9, and megaTAL Nucleases", Molecular Therapy, Mar. 2016, vol. 24, No. 3, pp. 570-581 (12 pp.), doi: 10.1038/mt.2015.197.
P Parham and F M Brodsky, "Partial purification and some properties of BB7.2. A cytotoxic monoclonal antibody with specificity for HLA-A2 and a variant of HLA-A28", Human Immunology, Dec. 1981, vol. 3, No. 4, pp. 277-299 (23 pp.), doi: 10.1016/0198-8859(81)90065-3.
Elizabeth Pennisi, "The CRISPR craze", Science, Aug. 23, 2013, vol. 341, No. 6148, pp. 833-836 (4 pp.), doi: 10.1126/science.341.6148.833.
L G Presta, "Antibody engineering", Current Opinion in Structural Biology, Aug. 1992, vol. 3, No. 4, pp. 394-398 (5 pp.), doi: 10.1016/0958-1669(92)90168-i.
Elena Provasi et al., "Editing T cell specificity towards leukemia by zinc finger nucleases and lentiviral gene transfer", HHS Public Access Author Manuscript, Nature Medicine, May 2012, vol. 18, No. 5, pp. 807-815 (9 pp.), doi: 10.1038/nm.2700.
G M Rossolini et al., "Use of deoxyinosine-containing primers vs degenerate primers for polymerase chain reaction based on ambiguous sequence information", Molecular and Cellular Probes, Apr. 1994, vol. 8, No. 2, pp. 91-98 (8 pp.), doi: 10.1006/mcpr.1994.1013.
M Ruiz et al., "IMGT, the international ImMunoGeneTics database", Nucleic Acids Research, Jan. 1, 2000, vol. 28, No. 1, pp. 219-221 (3 pp.), doi: 10.1093/nar/28.1.219.
George Scatchard, "The attractions of proteins for small molecules and ions", Annals of the New York Academy of Sciences, May 1949, vol. 51, pp. 660-672 (13 pp.) (1949) doi:10.1111/j.1749-6632.1949.tb27297.x.

(56) References Cited

OTHER PUBLICATIONS

E T Schenborn and R C Mierendorf Jr, "A novel transcription property of SP6 and T7 RNA polymerases: dependence on template structure" Nucleic Acids Research, Sep. 11, 1985, vol. 13, No. 17, pp. 6223-6236 (14 pp.), doi: 10.1093/nar/13.17.6223.

J Stepinski et al., "Synthesis and properties of mRNAs containing the novel 'anti-reverse' cap analogs 7-methyl(3'-O-methyl)GpppG and 7-methyl (3'-deoxy)GpppG", RNA, Oct. 2001, vol. 7, No. 10, pp. 1486-1495 (10 pp.).

Barry L Stoddard, "Homing endonucleases: from microbial genetic invaders to reagents for targeted DNA modification", HHS Public Access Author Manuscript, Structure, Jan. 12, 2011, vol. 19, No. 1, pp. 7-15 (9 pp.), doi: 10.1016/j.str.2010.12.003.

Michel Szczepek et al., "Structure-based redesign of the dimerization interface reduces the toxicity of zinc-finger nucleases", Nature Biotechnology, Jul. 2007, vol. 25, No. 7, pp. 786-793 (8 pp.), doi: 10.1038/nbt1317.

Ryo Takeuchi et al., "Engineering of customized meganucleases via in vitro compartmentalization and in cellulo optimization", HHS Public Access Author Manuscript, Methods in Molecular Biology, 2015, vol. 1239, pp. 105-132, doi: 10.1007/978-1-4939-1862-1_6.

D Taylor et al., "Human immunoglobulin transgenes undergo rearrangement, somatic mutation and class switching in mice that lack endogenous IgM", International Immunology, Apr. 1994, vol. 6, No. 4, pp. 579-591 (13 pp.), doi: 10.1093/intimm/6.4.579.

Hiroki Torikai et al., "Toward eliminating HLA class I expression to generate universal cells from allogeneic donors", Blood, Aug. 22, 2013, vol. 122, No. 8, pp. 1341-1349 (9 pp.), doi: 10.1182/blood-2013-03-478255.

Shengdar Q Tsai et al., "Dimeric CRISPR RNA-guided FokI nucleases for highly specific genome editing", HHS Public Access Author Manuscript, Nature Biotechnology, Jun. 2014, vol. 32, No. 6, pp. 569-576 (8 pp.), doi: 10.1038/nbt.2908.

K Ui-Tei et al., "Sensitive assay of RNA interference in *Drosophila* and Chinese hamster cultured cells using firefly luciferase gene as target", FEBS Letters, Aug. 18, 2000, vol. 479, No. 3, pp. 79-82 (4 pp.), doi: 10.1016/s0014-5793(00)01883-4.

N A Watkins et al., "The isolation and characterisation of human monoclonal HLA-A2 antibodies from an immune V gene phage display library", Tissue Antigens, Mar. 2000, vol. 55, No. 3, pp. 219-228 (10 pp.), doi: 10.1034/j.1399-0039.2000.550305.x.

Blake Wiedenheft et al., "RNA-guided genetic silencing systems in bacteria and archaea", Nature, Feb. 15, 2012, vol. 482, No. 7385, pp. 331-338 (8 pp.), doi: 10.1038/nature10886.

Andrew J Wood et al., "Targeted genome editing across species using ZFNs and TALENs", NIH Public Access Author Manuscript, Science, Jul. 15, 2011, vol. 333, No. 6040, pp. 307, doi: 10.1126/science.1207773.

Feng Zhang et al., "Efficient construction of sequence-specific TAL effectors for modulating mammalian transcription", HHS Public Access Author Manuscript, Nature Biotechnology, Feb. 2011, vol. 29, No. 2, pp. 149-153 (5 pp.), doi: 10.1038/nbt.1775.

International search report issued for WO 2019/056106.

Sofia Mumtaz et al., "Design of liposomes for circumventing the reticuloendothelial cells", Glycobiology, Nov. 1991, vol. 1, No. 5, pp. 505-510 (6 pp.), doi: 10.1093/glycob/1.5.505.

Nicolas Cougot et al., "'Cap-tabolism'", Trends in Biochemical Sciences, Aug. 2004, vol. 29, No. 8, pp. 436-444 (9 pp.), doi: 10.1016/j.tibs.2004.06.008.

Steven R Leong et al., "Adapting pharmacokinetic properties of a humanized anti-interleukin-8 antibody for therapeutic applications using site-specific pegylation", Cytokine, Nov. 7, 2001, vol. 16, No. 3, pp. 106-119 (14 pp.), doi: 10.1006/cyto.2001.0936.

J McCafferty et al., "Phage antibodies: filamentous phage displaying antibody variable domains", Nature, Dec. 6, 1990, vol. 348, No. 6301, pp. 552-553 (2 pp.), doi: 10.1038/348552a0.

Makiya Nishikawa and Leaf Huang, "Nonviral vectors in the new millennium: delivery barriers in gene transfer", Human Gene Therapy, May 20, 2001; vol. 12, No. 8, pp. 861-870 (10 pp.), doi: 10.1089/104303401750195836.

Lutz Riechmann et al., "Reshaping human antibodies for therapy", Nature, Mar. 24, 1988, vol. 332, No. 6162, pp. 323-327 (5 pp.), doi: 10.1038/332323a0.

Mark A Batzer et al., "Enhanced evolutionary PCR using oligonucleotides with inosine at the 3'-terminus", Nucleic Acid Research, Sep. 25, 1991, vol. 19, No. 18, pp. 5081 (1 pp.), doi: 10.1093/nar/19.18.5081.

Cyrus Chothia and Arthur M Lesk, "Canonical structures for the hypervariable regions of immunoglobulins", Journal of Molecular Biology, Aug. 20, 1987, vol. 196, No. 4, pp. 901-917 (17 pp.), doi: 10.1016/0022-2836(87)90412-8.

Michelle Scalley-Kim et al., "Coevolution of a homing endonuclease and its host target sequence", HHS Public Access Author Manuscript, Journal of Molecular Biology, Oct. 5, 2007, vol. 372, No. 5, pp. 1305-1319 (15 pp.), doi: 10.1016/j.jmb.2007.07.052.

Melissa S Jurica et al., "DNA recognition and cleavage by the LAGLIDADG homing endonuclease I-CreI", Molecular Cell, Oct. 1998, vol. 2, No. 4, pp. 469-476 (8 pp.), doi: 10.1016/s1097-2765(00)80146-x.

J Sethuraman et al., "Genes within genes: multiple LAGLIDADG homing endonucleases target the ribosomal protein S3 gene encoded within an rnl group I intron of Ophiostoma and related taxa", Molecular Biology and Evolution, Oct. 2009, vol. 26, No. 10, pp. 2299-2315 (17 pp.), doi: 10.1093/molbev/msp145.

Jacob Z Dalgaard et al., "Statistical modeling and analysis of the LAGLIDADG family of site-specific endonucleases and identification of an intein that encodes a site-specific endonuclease of the HNH family", Nucleic Acids Research, Nov. 15, 1997, vol. 25, No. 22, pp. 4626-4638 (13 pp.), doi: 10.1093/nar/25.22.4626.

Karen E Flick et al., "DNA binding and cleavage by the nuclear intron-encoded homing endonuclease I-PpoI", Nature, Jul. 2, 1998, vol. 394, No. 6688, pp. 96-101 (6 pp.), doi: 10.1038/27952.

Brett Chevalier et al., "Flexible DNA target site recognition by divergent homing endonuclease isoschizomers I-CreI and I-MsoI", Journal of Molecular Biology, May 30, 2003, vol. 329, No. 2, pp. 253-269 (17 pp.), doi: 10.1016/s0022-2836(03)00447-9.

Brett Chevalier et al., "The LAGLIDADG Homing Endonuclease Family", 2005, In: Belfort M., Wood D.W., Stoddard B.L., Derbyshire V. (eds) Homing Endonucleases and Inteins. Nucleic Acids and Molecular Biology, vol. 16. Springer, Berlin, Heidelberg., pp. 33-47 (15 pp.), https://doi.org/10.1007/3-540-29474-0_3.

Allan et al., "Generation of potent and stable human CD4+ T regulatory cells by activation-independent expression of FOXP3", Molecular Therapy: The Journal of the American Society of Gene Therapy, Jan. 2008, vol. 16, No. 1, pp. 194-202 (9 pp.), doi: 10.1038/sj.mt.6300341.

Barrett et al., "Relation of clinical culture method to T-cell memory status and efficacy in xenograft models of adoptive immunotherapy", NIH Public Access Author Manuscript, Cytotherapy, May 2014, vol. 16, No. 5, pp. 619-630 (12 pp.), doi: 10.1016/j.jcyt.2013.10.013.

Bierer et al., "Cyclosporin A and FK506: molecular mechanisms of immunosuppression and probes for transplantation biology", Current Opinion in Immunology, Oct. 1993, vol. 5, No. 5, pp. 763-773 (11 pp.), doi: 10.1016/0952-7915(93)90135-f.

Blat et al., "Suppression of murine colitis and its associated cancer by carcinoembryonic antigen-specific regulatory T cells", Molecular Therapy: The Journal of the American Society of Gene Therapy, May 2014, vol. 22, No. 5, pp. 1018-1028 (11 pp.), doi: 10.1038/mt.2014.41.

Bluestone et al., "Type 1 diabetes immunotherapy using polyclonal regulatory T cells", HHS Public Access Author Manuscript, Science Translational Medicine, Nov. 25, 2015, vol. 7, No. 315, Article 315ra189 (15 pp.), doi: 10.1126/scitranslmed.aad4134.

Brunstein et al., "Infusion of ex vivo expanded T regulatory cells in adults transplanted with umbilical cord blood: safety profile and detection kinetics", Blood, Jan. 20, 2011, vol. 117, No. 3, pp. 1061-1070 (10 pp.), doi: 10.1182/blood-2010-07-293795.

Brunstein et al., "Adoptive transfer of umbilical cord blood-derived regulatory T cells and early viral reactivation", HHS Public Access Author Manuscript, Biology of Blood Marrow Transplantation, Aug. 2013, vol. 19, No. 8, pp. 1271-1273 (3 pp.), doi: 10.1016/j.bbmt.2013.06.004.

(56) References Cited

OTHER PUBLICATIONS

Burton, "Immunoglobulin G: functional sites", Molecular Immunology, Mar. 1985, vol. 22, No. 3, pp. 161-206 (46 pp.), doi: 10.1016/0161-5890(85)90151-8.
Casucci et al., "Suicide gene therapy to increase the safety of chimeric antigen receptor-redirected T lymphocytes", Journal of Cancer, 2011, vol. 2, pp. 378-382 (5 pp.), doi: 10.7150/jca.2.378.
Chong et al., "Transplantation tolerance: don't forget about the B cells", Clinical and Experimental Immunology, Aug. 2017, vol. 189, No. 2, pp. 171-180 (10 pp.), doi: 10.1111/cei.12927.
Cooke et al., "An experimental model of idiopathic pneumonia syndrome after bone marrow transplantation: I. The roles of minor H antigens and endotoxin", Blood, Oct. 15, 1996, vol. 88, No. 8, pp. 3230-3239 (10 pp.).
Crome et al., "Natural killer cells regulate diverse T cell responses", Trends in Immunology, Jul. 2013, vol. 34, No. 7, pp. 342-349 (8 pp.), doi: 10.1016/j.it.2013.03.002.
Crome et al., "A distinct innate lymphoid cell population regulates tumor-associated T cells", HHS Public Access Author Manuscript, Nature Medicine, Mar. 2017, vol. 23, No. 3, pp. 368-375 (8 pp.), doi: 10.1038/nm.4278.
Delhove and Waseem Qasim, "Genome-Edited T Cell Therapies", Current Stem Cell Reports, 2017, vol. 3, No. 2, pp. 124-136 (13 pp.), doi: 10.1007/s40778-017-0077-5.
Di Ianni et al., "Tregs prevent GVHD and promote immune reconstitution in HLA-haploidentical transplantation", Blood, Apr. 7, 2011, vol. 117, No. 14, pp. 3921-3928 (8 pp.), doi: 10.1182/blood-2010-10-311894.
Dijke et al., "Discarded Human Thymus is a Novel Source of Stable and Long-Lived Therapeutic Regulatory T Cells", American Journal of Transplantation, Jan. 2016, vol. 16, No. 1, pp. 58-71 (14 pp.), doi: 10.1111/ajt.13456.
Eliceiri et al., "Biological imaging software tools", NIH Publi Access Author Manuscript, Nature Methods, Jun. 28, 2012, vol. 9, No. 7, pp. 697-710 (14 pp.), doi: 10.1038/nmeth.2084.
Elinav et al., "Redirection of regulatory T cells with predetermined specificity for the treatment of experimental colitis in mice", Gastroenterology, Jun. 2008, Volum 134, No. 7, pp. 2014-2024 (11 pp.), doi: 10.1053/j.gastro.2008.02.060.
Elinav et al., "Amelioration of colitis by genetically engineered murine regulatory T cells redirected by antigen-specific chimeric receptor", Gastroenterology, May 2009, Volum 136, No. 5, pp. 1721-1731 (11 pp.), doi: 10.1053/j.gastro.2009.01.049.
Ellis et al., "Frequencies of HLA-A2 alleles in five U.S. population groups. Predominance of A*02011 and identification of HLA-A*0231", Human Immunology, Mar. 2000, vol. 61, No. 3, pp. 334-340 (7 pp.), doi: 10.1016/s0198-8859(99)00155-x.
Eyquem et al., "Targeting a CAR to the TRAC locus with CRISPR/Cas9 enhances tumour rejection", HHS Public Access Author Manuscript, Nature, Mar. 2, 2017, vol. 543, No. 7643, pp. 113-117 (5 pp.), doi: 10.1038/nature21405.
Fischer et al., "Histopathologic features of cutaneous acute graft-versus-host disease in T-cell-depleted peripheral blood stem cell transplant recipients", HHS Public Access Author Manuscript, The American Journal of Dermatopathology, Jul. 2015, vol. 37, No. 7, pp. 523-529 (7 pp.), doi: 10.1097/DAD.0000000000000357.
Fransson et al., "CAR/FoxP3-engineered T regulatory cells target the CNS and suppress EAE upon intranasal delivery", Journal of Nueoinflammation, May 30, 2012, vol. 9, Article 112 (12 pp.), doi: 10.1186/1742-2094-9-112.
Fu et al., "Subsets of human natural killer cells and their regulatory effects", Immunology, Apr. 2014, vol. 141, No. 4, pp. 483-489 (7 pp.), doi: 10.1111/imm.12224.
Gargett et al., "The inducible caspase-9 suicide gene system as a 'safety switch' to limit on-target, off-tumor toxicities of chimeric antigen receptor T cells", Frontiers in Immunology, Oct. 28, 2014, vol. 5, Article 235 (7 pp.), doi: 10.3389/fphar.2014.00235.
Gill et al. "Going viral: chimeric antigen receptor T-cell therapy for hematological malignancies", Immunological Reviews, Jan. 2015, vol. 263, No. 1, pp. 68-89 (22 pp.), doi: 10.1111/imr.12243.
Golshayan et al., "In vitro-expanded donor alloantigen-specific CD4+CD25+ regulatory T cells promote experimental transplantation tolerance", Blood, Jan. 15, 2007, vol. 109, No. 2, pp. 827-835 (9 pp.), doi: 10.1182/blood-2006-05-025460.
Green et al., "Pancreatic lymph node-derived CD4(+)CD25(+) Treg cells: highly potent regulators of diabetes that require TRANCE-RANK signals", Immunity, Feb. 2002, vol. 16, No. 2, pp. 183-191 (9 pp.), doi: 10.1016/s1074-7613(02)00279-0.
Guillonneau et al., "CD8+ regulatory T cells in solid organ transplantation", Current Opinion in Organ Transplantation, Dec. 2012, vol. 15, No. 6, pp. 751-756 (6 pp.), doi: 10.1097/MOT.0b013e32834016d1.
Henderson et al., "Comparison of the effects of FK-506, cyclosporin A and rapamycin on IL-2 production", Immunology, Jul. 1991, vol. 73, No. 3, pp. 316-321 (6 pp.).
Hill et al., "Total body irradiation and acute graft-versus-host disease: the role of gastrointestinal damage and inflammatory cytokines", Blood, Oct. 15, 1997, vol. 90, No. 8, pp. 3204-3213 (10 pp.).
Himmel et al., "Helios+ and Helios-cells coexist within the natural FOXP3+ T regulatory cell subset in humans", Journal of Immunology, Mar. 1, 2013, vol. 190, No. 5, pp. 2001-2008 (8 pp.), doi: 10.4049/jimmunol.
Hombach et al., "Redirecting human CD4+CD25+ regulatory T cells from the peripheral blood with pre-defined target specificity", Gene Therapy, Sep. 2009, vol. 16, No. 9, pp. 1088-1096 (9 pp.), doi: 10.1038/gt.2009.75.
Hutchinson et al., "MITAP-compliant characterization of human regulatory macrophages", Transplant International, Aug. 2017, vol. 30, No. 8, pp. 765-775 (11 pp.), doi: 10.1111/tri.12988.
Jamnani et al., "T cells expressing VHH-directed oligoclonal chimeric HER2 antigen receptors: towards tumor-directed oligoclonal T cell therapy", Biochimica et Biophysica Acta, Jan. 2014, vol. 1840, No. 1, pp. 378-386 (9 pp.), doi: 10.1016/j.bbagen.2013.09.029.
Joffre et al., "Prevention of acute and chronic allograft rejection with CD4+CD25+Foxp3+ regulatory T lymphocytes", Nature Medicine, Jan. 2008, vol. 14, No. 1, pp. 88-92 (5 pp.), doi: 10.1038/nm1688.
June et al., "Adoptive cellular therapy: a race to the finish line", Science Translational Medicine, Mar. 25, 2015, vol. 7, No. 280, Article 280ps7 (8 pp.), doi: 10.1126/scitranslmed.aaa3643.
Juvet et al., "Double negative regulatory T cells in transplantation and autoimmunity: recent progress and future directions", Journal of Molecular and Cellular Biology, Feb. 2012, vol. 4, No. 1, pp. 48-58 (11 pp.), doi: 10.1093/jmcb/mjr043.
Kanitakis, "The challenge of dermatopathological diagnosis of composite tissue allograft rejection: a review", Journal of Cutaneous Pathology, Aug. 2008, vol. 35, No. 8, pp. 738-744 (7 pp.), doi: 10.1111/j.1600-0560.2007.00889.x.
Khaleghi et al., "A caspase 8-based suicide switch induces apoptosis in nanobody-directed chimeric receptor expressing T cells", International Journal of Hematology, Apr. 2012, vol. 95, No. 4, pp. 434-444 (11 pp.), doi: 10.1007/s12185-012-1037-6.
Konvalinka et al., "Utility of HLA Antibody Testing in Kidney Transplantation", Journal of the American Society of Nephrology, Jul. 2015, vol. 26, No. 7, pp. 1489-1502 (14 pp.), doi: 10.1681/ASN.2014080837.
Levings et al., "Human CD25(+)CD4(+) T regulatory cells suppress naive and memory T cell proliferation and can be expanded in vitro without loss of function", The Journal of Experimental Medicine, Jun. 4, 2001, vol. 193, No. 11, pp. 1295-1302 (7 pp.), doi: 10.1084/jem.193.11.1295.
Li et al., "Therapeutically targeting glypican-2 via single-domain antibody-based chimeric antigen receptors and immunotoxins in neuroblastoma", Proceedings of the National Academy of Sciences, Aug. 8, 2017, vol. 114, No. 32, E6623-E6631 (9 pp.), doi: 10.1073/pnas.1706055114.
Liu et al., "Calcineurin is a common target of cyclophilin-cyclosporin A and FKBP-FK506 complexes", Cell, Aug. 23, 1991, vol. 66, No. 4, pp. 807-815 (9 pp.), doi: 10.1016/0092-8674(91)90124-h.

(56) References Cited

OTHER PUBLICATIONS

Marek-Trzonkowska et al., "Administration of CD4+CD25highCD127- regulatory T cells preserves β-cell function in type 1 diabetes in children", Diabetes Care, Sep. 2012, vol. 35, No. 9, pp. 1817-1820, doi: 10.2337/dc12-0038.

Massi et al., "A reappraisal of the histopathologic criteria for the diagnosis of cutaneous allogeneic acute graft-vs-host disease", American Journal of Clinical Pathology, Dec. 1999, vol. 112, No. 6, pp. 791-800 (10 pp.).

Masteller et al., "Expansion of functional endogenous antigen-specific CD4+CD25+ regulatory T cells from nonobese diabetic mice", Journal of Immunology, Sep. 1, 2005, vol. 175, No. 5, pp. 3053-3059 (7 pp.), doi: 10.4049/jimmunol.175.5.3053.

McMurchy, et al., "Suppression assays with human T regulatory cells: a technical guide", European Journal of Immunology, Jan. 2012, vol. 42, No. 1, pp. 27-34 (8 pp.), doi: 10.1002/eji.201141651.

Nervi et al., "Factors affecting human T cell engraftment, trafficking, and associated xenogeneic graft-vs-host disease in NOD/SCID beta2mnull mice", NIH Public Access Author Manuscript, Experimental Hematology, Dec. 2007, vol. 35, No. 12, pp. 1823-1838 (16 pp.), doi: 10.1016/j.exphem.2007.06.007.

Nishimura et al., "Induction of antigen-specific immunologic tolerance by in vivo and in vitro antigen-specific expansion of naturally arising Foxp3+CD25+CD4+ regulatory T cells", International Immunology, Aug. 2004, vol. 16, No. 8, pp. 1189-1201 (13 pp.), doi: 10.1093/intimm/dxh122.

Noyan et al., "Prevention of Allograft Rejection by Use of Regulatory T Cells With an MHC-Specific Chimeric Antigen Receptor", American Journal of Transplantation, Apr. 2017, vol. 17, No. 4, pp. 917-930 (14 pp.), doi: 10.1111/ajt.14175.

Papp et al., "Regulatory immune cells and functions in autoimmunity and transplantation immunology", Autoimmune Reviews, May 2017, vol. 16, No. 5, pp. 435-444 (10 pp.), doi: 10.1016/j.autrev. 2017.03.011.

Philip et al., "A highly compact epitope-based marker/suicide gene for easier and safer T-cell therapy", Blood, Aug. 21, 2014, vol. 124, No. 8, pp. 1277-1287 (11 pp.), doi: 10.1182/blood-2014-01-545020.

Queen, et al., "A humanized antibody that binds to the interleukin 2 receptor," Proc. Natl. Acad. Sci. (1989) 86(24):10029-33.

Robinson et al., "The IPD and IMGT/HLA database: allele variant databases", Nucleic Acids Research, Jan. 2015, vol. 43, pp. D423-D431 (9 pp.), doi: 10.1093/nar/gku1161.

Rosenberg et al., "Use of tumor-infiltrating lymphocytes and interleukin-2 in the immunotherapy of patients with metastatic melanoma. A preliminary report", New England Journal of Medicine, Dec. 22, 1988, vol. 319, No. 25, pp. 1676-1680 (5 pp.), doi: 10.1056/NEJM198812223192527.

Sadelain et al., "The basic principles of chimeric antigen receptor design", Cancer Discovery, Apr. 2013, vol. 3, No. 4, pp. 388-398 (11 pp.), doi: 10.1158/2159-8290.CD-12-0548.

Sagoo et al., "Human regulatory T cells with alloantigen specificity are more potent inhibitors of alloimmune skin graft damage than polyclonal regulatory T cells", Science Translational Medicine, May 18, 2011, vol. 3, No. 83, Article 83ra42, doi: 10.1126/scitranslmed.3002076.

Sanchez-Fueyo et al., "Specificity of CD4+CD25+ regulatory T cell function in alloimmunity", HHS Public Access Author Manuscript, Journal of Immunology, Jan. 1, 2006, vol. 176, No. 1, pp. 329-334 (6 pp.), doi: 10.4049/jimmunol.176.1.329.

Schmittgen et al., "Analyzing real-time PCR data by the comparative C(T) method", Nature Protocols, vol. 3, No. 6, pp. 1101-1108 (8 pp.), doi: 10.1038/nprot.2008.73, (2008).

Schneider et al., "NIH Image to ImageJ: 25 years of image analysis", HHS Public Access Author Manuscript, Nature Methods, Jul. 2012, vol. 9, No. 7, pp. 671-675 (5 pp.), doi: 10.1038/nmeth.2089.

Stephens et al., "Curing CNS autoimmune disease with myelin-reactive Foxp3+ Treg", European Journal of Immunology, Apr. 2009, vol. 39, No. 4, pp. 1108-1117 (10 pp.), doi: 10.1002/eji. 200839073.

Tang et al., "In vitro-expanded antigen-specific regulatory T cells suppress autoimmune diabetes", The Journal of Experimental Medicine, Jun. 7, 2004, vol. 199, No. 11, pp. 1455-1465 (11 pp.), doi: 10.1084/jem.20040139.

Tarbell et al., "CD25+ CD4+ T cells, expanded with dendritic cells presenting a single autoantigenic peptide, suppress autoimmune diabetes", The Journal of Experimental Medicine, Jun. 7, 2004, vol. 199, No. 11, pp. 1467-1477 (11 pp.), doi: 10.1084/jem.20040180.

Tarbell et al., "Dendritic cell-expanded, islet-specific CD4+ CD25+ CD62L+ regulatory T cells restore normoglycemia in diabetic NOD mice", The Journal of Experimental Medicine, Jan. 22, 2007, vol. 204, No. 1, pp. 191-201 (11 pp.), doi: 10.1084/jem.20061631.

Trenado et al., "Ex vivo-expanded CD4+CD25+ immunoregulatory T cells prevent graft-versus-host-disease by inhibiting activation/differentiation of pathogenic T cells", Journal of Immunology, Jan. 15, 2006, vol. 176, No. 2, pp. 1266-1273 (8 pp.), doi: 10.4049/jimmunol.176.2.1266.

Trzonkowski et al., "First-in-man clinical results of the treatment of patients with graft versus host disease with human ex vivo expanded CD4+CD25+CD127-T regulatory cells", Clinical Immunology, Oct. 2009, vol. 133, No. 1, pp. 22-26 (5 pp.), doi: 10.1016/j.clim.2009. 06.001.

Tsang et al., "Conferring indirect allospecificity on CD4+CD25+ Tregs by TCR gene transfer favors transplantation tolerance in mice", The Journal of Clinical Investigation, Nov. 2008, vol. 118, No. 11, pp. 3619-3628 (10 pp.), doi: 10.1172/JCI33185.

Verginis et al., "Induction of antigen-specific regulatory T cells in wild-type mice: visualization and targets of suppression", Proceedings of the National Academy of Sciences of the United States of America, Mar. 4, 2008, vol. 105, No. 9, pp. 3479-3484 (6 pp.), doi: 10.1073/pnas.0800149105.

Wang et al., "New development in CAR-T cell therapy", Journal of Hematology & Oncology, Feb. 21, 2017, vol. 10, No. 1, Article 53 (11 pp.), doi: 10.1186/s13045-017-0423-1.

Watanabe et al., "Fine-tuning the CAR spacer improves T-cell potency", Oncoimmunology, Nov. 8, 2016, vol. 5, No. 12, Article e1253656 (14 pp.), doi: 10.1080/2162402X.2016.1253656.

Wesch et al., "Human gamma delta T regulatory cells in cancer: fact or fiction?", Frontiers in Immunology, Nov. 20, 2014, vol. 5, Article 598 (7 pp.), doi: 10.3389/fimmu.2014.00598.

Wood et al., "Regulatory immune cells in transplantation", Nature Review Immunology, May 25, 2012, vol. 12, No. 6, pp. 417-430 (14 pp.), doi: 10.1038/nri3227.

Zapata et al., "Engineering linear F(ab')2 fragments for efficient production in *Escherichia coli* and enhanced antiproliferative activity", Protein Engineering, Design and Selection, Oct. 1995, vol. 8, No. 10, pp. 1057-1062 (6 pp.), doi: 10.1093/protein/8.10.1057.

Zhang et al., "Regulatory T cells sequentially migrate from inflamed tissues to draining lymph nodes to suppress the alloimmune response", Immunity, Mar. 20, 2009, vol. 30, No. 3, pp. 458-469 (12 pp.), doi: 10.1016/j.immuni.2008.12.022.

Zhang et al., "A new insight in chimeric antigen receptor-engineered T cells for cancer immunotherapy", Journal of Hematology and Oncology, Jan. 3, 2017, vol. 10, No. 1, pp. 1 (11 pp.), doi: 10.1186/s13045-016-0379-6.

Maus et al., "T Cells Expressing Chimeric Antigen Receptors can Cause Anaphylaxis in Humans," Cancer Immunol Res. (2013) 1:26-31.

Pan, et al. "Blocking Neuropilin-1 Function Has an Additive Effect with Anti-VEGF to Inhibit Tumor Growth", Cancer Cell (2007) 11:53-67.

Brunner, et al. Cytotoxic T cells: Double-barreled shot guns, Nature Medicine (1999) 5(1):Abstract.

Rosano, et al., "Recombinant Protein Expression in *Escherichia coli*: Advances and Challenges", Frontiers in Microbiology (2014) 5(172):1-17, doi: 10.3389/fmicb.2014.00172.

MacDonald, K. G. et al., Alloantigen-specific regulatory T cells generated with a chimeric antigen receptor. J Clin Invest, vol. 126, Issue No. 4, pp. 1413-1424 (Apr. 2016).†

Parham, P. et al., Partial purification and some properties of BB7.2. A cytotoxic monoclonal antibody with specificity for HLA-A2 and a variant of HLA-A28. Hum Immunol, vol. 3, Issue No. 4, pp. 277-299 (Dec. 1981).†

(56) References Cited

OTHER PUBLICATIONS

Dawson, N. A. et al., Systematic testing and specificity mapping of alloantigen-specific chimeric antigen receptors in regulatory T cells. JCI Insight, vol. 4, Issue No. 6, p. e123672 (Mar. 2019).†
Riechmann, L. et al. Reshaping human antibodies for therapy. Nature, vol. 332, Issue No. 6162, pp. 323-327 (Mar. 1988).†
Queen, C. et al., A humanized antibody that binds to the interleukin 2 receptor. Proc. Natl. Acad. Sci. USA, vol. 86, Issue No. 24, pp. 10029-10033 (Dec. 1989).†

† cited by third party

ANTI-HLA-A2 ANTIBODIES, RELATED CHIMERIC ANTIGEN RECEPTORS, AND USES THEREOF

CROSS-REFERENCE TO RELATED APPLICATION

This application is a national stage application under 35 U.S.C § 371 of International Patent Application No. PCT/CA2018/051174, filed Sep. 20, 2018, which claims the benefit of U.S. Provisional Patent Application No. 62/560,841, filed Sep. 20, 2017, and U.S. Provisional Patent Application No. 62/691,027, filed Jun. 28, 2018. The disclosures of those applications are incorporated by reference herein in their entirety.

SEQUENCE LISTING

The instant application contains a Sequence Listing which has been submitted electronically in ASCII format and is hereby incorporated by reference herein in its entirety. The electronic copy of the Sequence Listing, created in September 2018, is named SL.TXT and is 103,560 bytes in size.

FIELD OF INVENTION

The present invention relates to HLA-A2 binding molecules, in particular to humanized anti-HLA-A2 antibodies. The present invention further relates to recombinant molecules comprising said HLA-A2 binding molecules, such as, for example, chimeric antigen receptors (CAR). Another object of the present invention is an engineered immune cell, e.g., a regulatory T cell comprising said CAR, and uses thereof in therapeutic methods.

BACKGROUND OF INVENTION

Class I HLA antigens are polymorphic proteins expressed on all nucleated cells and are critical targets for immune recognition in the context of transplantation. Indeed, the development of HLA class I specific T cells and/or antibodies are major risk factors for acute and chronic rejection of allograft, and the presence of pre-formed anti-donor HLA Class I antibodies can result in hyper-acute rejection. Thus, finding ways to control the immune response to HLA Class I proteins would be a major breakthrough in transplantation.

Classical HLA Class I molecules are polymorphic and encoded by many different alleles which have evolved in response to evolutionary pressure from infections. There are three loci that encode the classical HLA Class I proteins, which are named the A, B and C loci. Within the HLA-A locus, the HLA-A2 family of alleles is the largest and most diverse family, with at least 31 different HLA-A2 alleles known to exist in humans. Interestingly, contrary to many other HLA allele families, HLA-A2 is frequent in all ethnic groups, and is found in 50% of Caucasians and 35% of African-Americans. Many HLA-A2 alleles differ by only 1 to 9 amino acids, with the majority of the polymorphism centered around the peptide binding grove. HLA-A2 alleles are sub-grouped into two main branches: those derived via interallelic gene conversion events from A*0201 or A*0205.

Adoptive immunotherapy with T regulatory (Treg) cells as a way to control unwanted immunity to HLA proteins, and other antigens that drive transplant rejection is a promising treatment for allograft rejection and graft-versus-host disease (GVHD). The use of polyclonal Treg cell transfer in the prevention of graft-versus-host disease (GVHD) after allogeneic hematopoietic stem cell transplantation (HSCT) has been reported. The use of Treg cell transfer in the maintenance of c-peptide levels in type 1 diabetes has also been reported. Notably, however, it has been reported that there may be a transient risk of generalized immunosuppression associated with the use of polyclonal Treg cells for such cell therapy.

Data from animal studies indicate that the potency and specificity of cell therapy with Treg cells can be significantly enhanced by the use of antigen-specific cells. For example, in models of autoimmunity, antigen-specific Treg cells are superior to polyclonal Treg cells in reducing disease: Treg cells isolated from pancreatic lymph nodes or pulsed with islet antigen are significantly better at preventing or curing type 1 diabetes than are polyclonal Treg cells, and Treg cells expressing an autoantigen-specific transgenic T cell receptor (TCR) are superior to polyclonal Treg cells at suppressing central nervous system inflammation in a model of experimental autoimmune encephalomyelitis (EAE).

Similarly, alloantigen-specific Treg cells, enriched by alloantigen-stimulated expansion in vitro, or engineered to express a TCR transgene, are more effective than polyclonal Treg cells at preventing rejection of organ and tissue grafts. There is some evidence that Treg cells expanded with alloantigens effectively prevent GVHD and that in vivo induction of antigen-specific Treg cells promotes acceptance of hematopoietic allografts without GVHD. Humanized mouse models have shown similar results: alloantigen-expanded human Treg cells are more potent suppressors of skin graft rejection than are polyclonal Treg cells.

An alternate approach to over-expressing transgenic TCRs or antigen-stimulated expansion to enrich for antigen-specific T cells is the use of chimeric antigen receptors (CARs). In cell-based adoptive immunotherapy, immune cells isolated from a patient can be modified to express synthetic proteins that enable the cells to perform new therapeutic functions after they are subsequently transferred back into the patient. An example of such a synthetic protein is a CAR. An example of a currently used CAR is a fusion of an extracellular recognition domain (e.g., an antigen-binding domain), a transmembrane domain, and one or more intracellular signaling domains. Upon antigen engagement, the intracellular signaling portion of the CAR can initiate an activation-related response in an immune cell.

The present invention relates to immune cells, in particular immune regulatory cells, expressing a CAR that specifically binds HLA-A2, and to therapeutic uses thereof.

SUMMARY

The present invention relates to a humanized anti-HLA-A2 antibody having less reactivity to an HLA-A subtype selected from the group comprising A03, A11, A23, A25, A26, A29, A30, A31, A33, A34 and any combination thereof, preferably from the group comprising A25, A29, A30 and any combination thereof, as compared to the antibody BB7.2 or to an antibody comprising the VH and VL of the BB7.2 antibody, wherein the variable region of the heavy chain comprises at least one of the following CDRs:

```
VH-CDR1:
                                      (SEQ ID NO: 1)
SYHIQ
or
                                      (SEQ ID NO: 4)
GYTFTSY
```

-continued

VH-CDR2:
(SEQ ID NO: 2)
WIYPGDGSTQYNEKFKG
or (SEQ ID NO: 5)
YPGDGS

VH-CDR3:
(SEQ ID NO: 3)
EGTYYAMDY or any CDR having an amino acid sequence that shares at least 60% identity with SEQ ID NO: 1-5, and/or
the variable region of the light chain comprises at least one of the following CDRs:

VL-CDR1:
(SEQ ID NO: 6)
RSSQSIVHSNGNTYLE

VL-CDR2:
(SEQ ID NO: 7)
KVSNRFS

VL-CDR3:
(SEQ ID NO: 8)
FQGSHVPRT or any CDR having an amino acid sequence that shares at least 60% identity with SEQ ID NO: 6-8.

In one embodiment, the variable region of the heavy chain comprises at least one of the CDRs defined in claim 1, and the variable region of the light chain comprises at least one of the CDRs defined in claim 1.

In one embodiment,
the variable region of the heavy chain comprises the following CDRs: SYHIQ (SEQ ID NO: 1), WIYPGDGSTQYNEKFKG (SEQ ID NO: 2) and EGTYYAMDY (SEQ ID NO: 3); or GYTFTSY (SEQ ID NO: 4), YPGDGS (SEQ ID NO: 5) and EGTYYAMDY (SEQ ID NO: 3) or any CDRs having an amino acid sequence that shares at least 60% identity with said SEQ ID NO: 1-5, and
the variable region of the light chain comprises the following CDRs: RSSQSIVHSNGNTYLE (SEQ ID NO: 6), KVSNRFS (SEQ ID NO: 7) and FQGSHVPRT (SEQ ID NO: 8) or any CDRs having an amino acid sequence that shares at least 60% identity with said SEQ ID NO: 6-8.

In one embodiment, the amino acid sequence of the heavy chain variable region is SEQ ID NO: 9, or any amino acid sequence that shares at least 60% identity with said SEQ ID NO: 9.

In one embodiment, the amino acid sequence of the light chain variable region is SEQ ID NO: 10, or any amino acid sequence that shares at least 60% identity with said SEQ ID NO: 10, wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{11}$ is V or L, $X_{17}$ is A or P, $X_{18}$ is L or F and $X_{19}$ is G or A.

In one embodiment, the amino acid sequence of the light chain variable region is selected from the group comprising SEQ ID NO: 11, SEQ ID NO: 12 and SEQ ID NO: 13 or any amino acid sequence that shares at least 60% identity with said SEQ ID NO: 11-13.

In one embodiment, the amino acid sequence of the heavy chain variable region is SEQ ID NO: 9 or any amino acid sequence that shares at least 60% identity with said SEQ ID NO: 9, and the amino acid sequence of the light chain variable region is SEQ ID NO: 10 wherein $X_1$ is V or I, $X_2$ is T or S, $X_3$ is L or S or A, $X_4$ is S or T, $X_5$ is P or S, $X_6$ is T or S, $X_7$ is L or P, Xx is E or D, $X_9$ is P or R, $X_{10}$ is A or V, $X_{11}$ is S or T, $X_{12}$ is L or Q, $X_3$ is S or A, $X_{14}$ is V or I, $X_{15}$ is K or T, $X_{16}$ is V or L, $X_{17}$ is A or P, $X_{18}$ is L or F and $X_{19}$ is G or A, preferably the amino acid sequence of the light chain variable region is selected from the group comprising SEQ ID NO: 11, SEQ ID NO: 12 and SEQ ID NO: 13 or any amino acid sequence that shares at least 60% identity with said SEQ ID NO: 10-13.

In one embodiment, said antibody is a whole antibody, a single chain antibody, a dimeric single chain antibody, a Fv, a scFv, a Fab, a F(ab)'$_2$, a defucosylated antibody, a bi-specific antibody, a diabody, a triabody, a tetrabody, an antibody fragment selected from the group consisting of a unibody, a domain antibody, and a nanobody or an antibody mimetic selected from the group consisting of an affibody, an affilin, an affitin, an adnectin, an atrimer, an evasin, a DARPin, an anticalin, an avimer, a fynomer, a versabody or a duocalin.

In another embodiment, said antibody is a whole antibody, a single chain antibody, a dimeric single chain antibody, a Fv, a scFv, a Fab, a F(ab)'$_2$, a defucosylated antibody, a bi-specific antibody, a diabody, a triabody, a tetrabody, an antibody fragment selected from the group consisting of a unibody, a domain antibody, and a nanobody or an antibody mimetic selected from the group consisting of an affibody, an alphabody, an armadillo repeat protein based scaffold, a knottin, a kunitz domain peptide, an affilin, an affitin, an adnectin, an atrimer, an evasin, a DARPin, an anticalin, an avimer, a fynomer, a versabody or a duocalin.

In one embodiment, said antibody is a scFv, preferably a scFv having the sequence SEQ ID NO: 70-72 or 74-76.

The present invention further relates to a chimeric antigen receptor (CAR) comprising:
an extracellular domain comprising the humanized anti-HLA-A2 antibody as described hereinabove,
a transmembrane domain, and
a cytoplasmic domain comprising an intracellular signaling domain.

Another object of the present invention is a nucleic acid sequence encoding the CAR as described hereinabove.

Another object of the invention is an immune cell comprising the CAR as described hereinabove or the nucleic acid sequence as described hereinabove, wherein said immune cell is preferably a regulatory T cell.

The present invention further relates to a composition comprising immune cells as described hereinabove, wherein preferably said composition is a pharmaceutical composition and further comprises a pharmaceutically acceptable excipient.

The present invention further relates to an immune cell as described hereinabove, for use in inducing immune tolerance in a subject in need thereof, wherein preferably said tolerance is tolerance to a transplanted organ or tissue.

The present invention further relates to an immune cell as described hereinabove, for use in treating organ or tissue transplant rejection or graft versus host disease (GVHD).

In one embodiment, the subject is further receiving an immunosuppressive agent.

The present invention further relates to a combination of an immune cell as described in the present invention with at least one immunosuppressive agent for inducing immune tolerance in a subject in need thereof, or for treating organ or tissue transplant rejection or graft versus host disease (GVHD) in a subject in need thereof.

The present invention further relates to a kit of part comprising, in a first part, an immune cell as described in the present invention and/or reagents (e.g., a nucleic acid or vector encoding an anti-HLA-A antibody or CAR of the present disclosure) for making such immune cells and in a second part at least one immunosuppressive agent.

The present invention further relates to a method for inducing immune tolerance in a subject in need thereof, wherein said method comprises administering an immune cell according to the present invention to the subject, wherein preferably said tolerance is tolerance to a transplanted organ or tissue.

The present invention further relates to a method for treating organ or tissue transplant rejection or graft versus host disease (GVHD) in a subject in need thereof, wherein said method comprises administering an immune cell as described in the present invention to the subject.

In one embodiment, the method of the invention further comprises administering at least one immunosuppressive agent to the subject.

DEFINITIONS

Figure 1A:
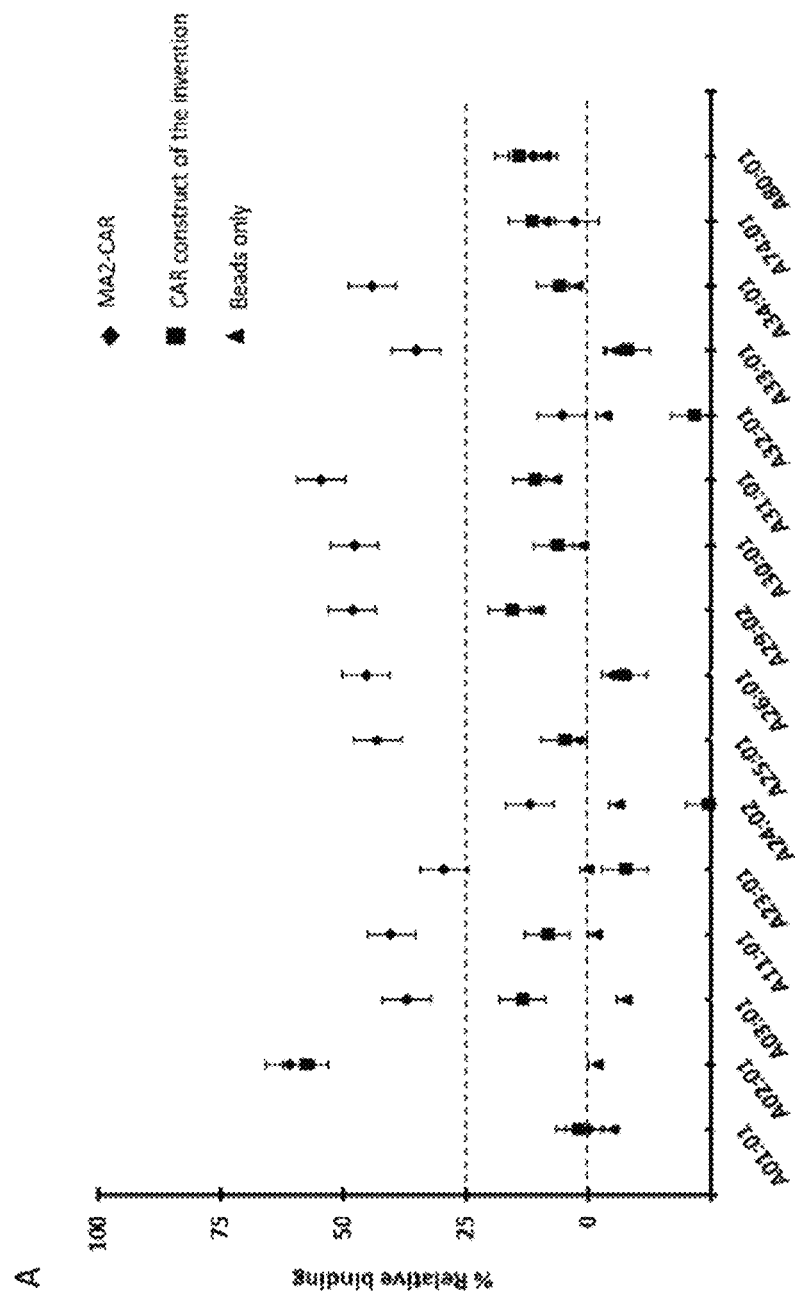
FIGS. 1A and 1B are graphs showing the cross-reactivity of the anti-HLA-A2 CAR construct of the invention with common HLA-A and HLA-B allelic variants. GFP$^+$ Treg cells expressing the CAR construct of the invention (or a murine anti-HLA-A2 CAR construct) were incubated with Flow Panel Reactive Single Antigen beads and a fixable viability dye for 30 minutes at room temperature. Samples were then washed, fixed and analyzed via flow cytometry. Data were analyzed as described in the methods. Data in FIGS. 1A and 1B show percent binding relative to control Treg cells expressing only GFP, normalized for the number of HLA negative beads collected by the cytometer. Data points above the line represent values that were more than two standard deviations from the mean of the bead-only control and thus statistically significant ($p<0.05$). Data are the average of two independent experiments. Mean±SEM.

In the present invention, the following terms have the following meanings:

In the context of the present invention, the following abbreviations for the commonly occurring nucleic acid bases are used. "A" refers to adenine, "C" refers to cytosine, "G" refers to guanine, "T" refers to thymine, and "U" refers to uracil.

The terms "a" and "an" refer to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances 5%, or in some instances ±1%, or in some instances ±0.1% from the specified value, as such variations are appropriate to perform the disclosed methods.

The term "activation" as used herein, refers to the state of a T cell (e.g., a regulatory T cell) that has been sufficiently stimulated to induce a detectable cellular response. Activation can also be associated with detectable effector function (s) such as, for example, cytokine production or suppressive activity. The term "activated" regulatory T cells refers to, among other things, regulatory T cells that are capable of suppressing an immune response.

"Adnectins", also known as monobodies, are well known in the art and refer to proteins designed to bind with high affinity and specificity to antigens. They belong to the class of molecules collectively called "antibody mimetics".

As used herein, an "alphabody", that may also be referred to as Cell-Penetrating Alphabodies, refers to a type of antibody mimetics consisting of small 10 kDa proteins engineered to bind to a variety of antigens. Alphabodies are able to reach and bind to intracellular protein targets.

An "affibody" is well known in the art and refers to affinity proteins based on a 58 amino acid residue protein domain, derived from one of the IgG binding domain of staphylococcal protein A.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more.

"Affilins" are well known in the art and refer to artificial proteins designed to selectively bind antigens. They resemble antibodies in their affinity and specificity to antigens but not in structure which makes them a type of antibody mimetic.

The term "allogeneic" refers to any material derived from a different individual of the same specie as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The terms "antibody" and "immunoglobulin" (Ig) are used interchangeably, and refer to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. The term "antibody" also includes multispecific antibodies (e.g., bispecific antibodies), and antibody fragments, so long as they exhibit the desired biological activity. Antibodies can also be multimers of immunoglobulin molecules, such as tetramers of immunoglobulin molecules.

The basic four-chain antibody unit is a heterotetrameric glycoprotein composed of two identical light (L) chains and two identical heavy (H) chains. The L chain from any vertebrate species can be assigned to one of two clearly distinct types, called kappa ([kappa]) and lambda ([lambda]), based on the amino acid sequences of their constant domains (CL). Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ([alpha]), delta ([delta]), epsilon ([epsilon]), gamma ([gamma]) and mu ([mu]), respectively. The [gamma] and [alpha] classes are further divided into subclasses on the basis of relatively minor differences in CH sequence and function, e.g., humans express the following subclasses: IgG1, IgG2, IgG3, IgG4, IgA1, and IgA2. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the [alpha] and [gamma] chains and four CH domains for [mu] and [epsilon]isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. An IgM antibody consists of five of the basic heterotetramer units along with an additional polypeptide called a J chain, and therefore, contains ten antigen binding sites, while secreted IgA antibodies can polymerize to form polyvalent assemblages comprising 2-5 of the basic 4-chain units along with J chain. In the case of IgGs, the 4-chain unit is generally about 150,000 Daltons. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The term "antibody fragment" refers to at least one portion of an intact antibody, preferably the antigen binding region or variable region of the intact antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')$_2$, Fv fragments, single chain antibody molecules, in particular scFv antibody fragments, disulfide-linked Fvs (sdFv), a Fd fragment consisting of the VH and CHI domains, linear antibodies, single domain antibodies such as, for example, sdAb (either VL or VH), camelid VHH domains, multi-specific antibodies formed from antibody fragments such as, for example, a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (see U.S. Pat. No. 6,703,199, which describes fibronectin polypeptide minibodies). Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of crosslinking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

As used herein, a "functional fragment or analog of an antibody" is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc[epsilon]RI.

The term "antibody heavy chain" refers to the larger of the two types of polypeptide chains present in antibody molecules in their naturally occurring conformations, and which normally determines the class to which the antibody belongs.

The term "antibody light chain" refers to the smaller of the two types of polypeptide chains present in antibody molecules in their naturally occurring conformations. Kappa (K) and lambda (λ) light chains refer to the two major antibody light chain isotypes.

"Anticalins" are well known in the art and refer to an antibody mimetic technology, wherein the binding specificity is derived from lipocalins. Anticalins may also be formatted as dual targeting protein, called Duocalins.

The term "antigen" or "Ag" refers to a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen does not necessarily need to be encoded solely by a full-length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen does not necessarily need to be encoded by a "gene" at all. It is readily apparent that an antigen can be synthesized or can be derived from a biological sample, or might be macromolecule besides a polypeptide. Such a biological sample can include, but is not limited to a tissue sample, a cell or a fluid with other biological components.

The term "antigen presenting cell" or "APC" refers to an immune system cell such as an accessory cell (e.g., a B-cell, a dendritic cell, and the like) that displays a foreign antigen complexed with major histocompatibility complexes (MHCs) on its surface. T-cells may recognize these complexes using their T-cell receptors (TCRs). APCs process antigens and present them to T-cells.

As used herein, an "armadillo repeat protein-based scaffold" refers to a type of antibody mimetics corresponding to artificial peptide binding scaffolds based on armadillo repeat proteins. Armadillo repeat proteins are characterized by an armadillo domain, composed of tandem armadillo repeats of approximately 42 amino acids, which mediates interactions with peptides or proteins.

"Atrimers" are well known in the art and refer to binding molecules for target protein that trimerize as a perquisite for their biological activity. They are relatively large compared to other antibody mimetic scaffolds.

The term "autologous" refers to any material derived from the same individual to whom it is later to be re-introduced.

"Avimers" are well known in the art and refer to an antibody mimetic technology.

"DARPins" (Designed Ankyrin Repeat Proteins) are well known in the art and refer to an antibody mimetic DRP (designed repeat protein) technology developed to exploit the binding abilities of non-antibody polypeptides.

The term "BB7.2" as used herein, refers to a murine hybridoma identified as ATCC Deposit HB-82. The BB7.2 hybridoma cells secrete a murine monoclonal antibody of IgG2b kappa isotype (e.g., BB7.2 antibody), which has been characterized by Parham, P. et al. and Hilton et al. (Parham, P. et al, 1981; Hilton et al., 2013). The BB7.2 antibody is commercially available, such as, for example, from Abcam (Catalog reference number: ab74674), Thermo Fisher Scientific (Catalog reference number: 17-9876-42) or Santa Cruz Biotechnology (Catalog reference number: sc-32236). The amino acid sequences of the six complementarity determining regions (CDRs) of the BB7.2 antibody are as follows:

```
Heavy chain CDR1 (HCDR1):
                            (SEQ ID NO: 62)
SYHIQ;

Heavy chain CDR2 (HCDR2):
                            (SEQ ID NO: 63)
WIYPGDGSTQYNEKFKG;

Heavy chain CDR3 (HCDR3):
                            (SEQ ID NO: 64)
EGTYYAMDY;

Light chain CDR1 (LCDR1):
                            (SEQ ID NO: 65)
RSSQSIVHSNGNTYLE Light chain CDR2 (LCDR2):
                            (SEQ ID NO: 66)
KVSNRFS;

Light chain CDR3 (LCDR3):
                            (SEQ ID NO: 67)
FQGSHVPRT.
```

As used herein, a "BB7.2 antibody" is an antibody having the VH (SEQ ID NO: 9) and VL (SEQ ID NO: 10) of the monoclonal antibody secreted by BB7.2. A BB7.2 antibody may be a whole antibody or a fragment thereof having the VH and VL of the monoclonal antibody secreted by BB7.2, such as an scFv having the VII and VL of the monoclonal antibody secreted by BB7.2.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than $10^{-7}$ M, e.g., binding with an affinity of $10^{-6}$ M, $10^{-5}$ M, $10^{-4}$ M, etc.

As used herein, a "5' cap" (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each one influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

A "chimeric antibody" is an antibody molecule in which (a) the constant region (i.e., the heavy and/or light chain), or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Chimeric antibodies also include primatized and in particular humanized antibodies. Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992). (see U.S. Pat. No. 4,816,567; and Morrison et al., Proc. Natl. Acad. Sci. USA, 81:6851-6855 (1984)).

The terms "chimeric receptor" or "chimeric antigen receptor" or "CAR" refer to one polypeptide or to a set of polypeptides, typically two in the simplest embodiments, which when in an immune cell, provides the cell with specificity for a target ligand and with intracellular signal generation. In some embodiments, the set of polypeptides are contiguous with each other. In some embodiments, the chimeric receptor is a chimeric fusion protein comprising the set of polypeptides. In some embodiments, the set of polypeptides include a dimerization switch that, upon the presence of a dimerization molecule, can couple the polypeptides to one another, e.g., can couple a ligand binding domain to an intracellular signaling domain. In one embodiment, the chimeric receptor comprises an optional leader sequence at the amino-terminus (N-ter) of the chimeric receptor fusion protein. In one embodiment, the chimeric receptor further comprises a leader sequence at the N-terminus of the extracellular ligand binding domain, wherein the leader sequence is optionally cleaved from the ligand binding domain during cellular processing and localization of the chimeric receptor to the cellular membrane.

The term "conservative sequence modifications" refers to amino acid modifications that do not significantly affect or alter the biologic function of the protein containing the amino acid sequence. Such conservative modifications include amino acid substitutions, additions and deletions. Modifications can be introduced into a protein by standard techniques known in the art, such as site-directed mutagenesis and PCR-mediated mutagenesis. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Other families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within an antibody or chimeric receptor of the invention can be replaced with other amino acid residues from the same side chain family and the altered antibody or chimeric receptor can be tested for binding to HLA-A2.

The term "constitutive promoter" refers to a nucleotide sequence which, when operably linked with a polynucleotide which encodes or specifies a gene product, causes the gene product to be produced in a cell under most or all physiological conditions of the cell.

The term "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that contribute to an efficient immune response. A costimulatory signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors.

A "cytotoxic cell" includes cytotoxic $CD8^+$ T cells, natural-killer (NK) cells, and neutrophils, which cells are capable of mediating cytotoxicity responses.

"Derived from" as that term is used herein, indicates a relationship between a first and a second molecule. It generally refers to structural similarity between the first molecule and the second molecule and does not connote or include a process or source limitation on a first molecule that is derived from a second molecule. For example, in the case of an intracellular signaling domain that is derived from a CD3zeta molecule, the intracellular signaling domain retains sufficient CD3zeta structure such that is has the required function, namely, the ability to generate a signal under the appropriate conditions. It does not connote or include a limitation to a particular process of producing the intracellular signaling domain, e.g., it does not mean that, to provide the intracellular signaling domain, one must start with a CD3zeta sequence and delete unwanted sequence, or impose mutations, to arrive at the intracellular signaling domain.

The term "diabodies" refers to small antibody fragments prepared by constructing scFv fragments with short linkers (about 5-10 residues) between the VH and VL domains such that inter-chain but not intra-chain pairing of the V domains is achieved, resulting in a bivalent fragment, i.e., fragment having two antigen binding sites. Bispecific diabodies are heterodimers of two "crossover" scFv fragments in which the VH and VL domains of the two antibodies are present on different polypeptide chains. Diabodies are described more fully in, for example, EP 0404097; WO 93/11161; and Holliger et al., Proc. Natl. Acad. Sci. USA, 90:6444-6448 (1993).

A "domain antibody" is well known in the art and refers to the smallest functional binding units of antibodies, corresponding to the variable regions of either the heavy or light chains of antibodies.

The term "encoding" refers to the inherent property of specific sequences of nucleotides in a polynucleotide, such as, for example, a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. The phrase "nucleotide sequence that encodes a protein or an RNA" may also include introns to the extent that the nucleotide sequence encoding the protein may in some version contain an intron(s).

The term "endogenous" refers to any material from or produced inside an organism, cell, tissue or system.

The terms "engineered" or "modified" are used interchangeably and refer to a cell that has been transfected, transformed or transduced.

"Evasins" are well known in the art and refer to a class of chemokine-binding proteins.

The term "exogenous" refers to any material introduced in or produced outside an organism, cell, tissue or system.

The term "expression" refers to the transcription and/or translation of a particular nucleotide sequence driven by a promoter.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including, without limitation, cosmids, plasmids (e.g., naked or contained in liposomes) and viruses (e.g., lentiviruses, retroviruses, adenoviruses, and adeno-associated viruses) that incorporate the recombinant polynucleotide.

The "Fc" fragment of an antibody comprises the carboxy-terminal portions of both H chains held together by disulfides. The effector functions of antibodies are determined by sequences in the Fc region, which region is also the part recognized by Fe receptors (FcR) found on certain types of cells.

"Framework" or "FR" residues are those variable domain residues other than the hypervariable region residues herein defined.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Fynomers" are well known in the art and refer to proteins that belong to the class of antibody mimetic. They are attractive binding molecules due to their high thermal stability and reduced immunogenicity.

The term "graft-versus-host disease" or "GVHD" as used herein refers to a medical complication following the receipt of transplanted tissue from a genetically different person. Immune cells in the donated tissue (the graft) recognize the recipient (the host) as foreign. The transplanted immune cells then attack the host's body cells. GVHD is commonly associated with stem cell transplant; however, the term includes GVHD arising from other forms of tissue graft. GVHD may also occur after a blood transfusion.

An "HLA-A subtype" as used herein refers to a protein encoded by an allele of the HLA-A gene. The term "HLA-A*25:01" as used herein refers to an HLA protein with the designation "HLA-A*25:01" according to the HLA naming system developed in 2010 by the WHO Committee for Factors of the HLA System. The terms "HLA-A*29:02" and "HLA-A*30:01" refer to HLA proteins with designations "HLA-A*29:02" and "HLA-A*30:01", respectively.

The term "HLA-A2" as used herein refers to human leukocyte antigen (HLA) proteins including cell surface proteins, encoded by the HLA-A*02 allele family at the HLA-A locus of the HLA gene complex. HLA proteins encompassed by the term "HLA-A2" include HLA proteins identified as belonging to the HLA-A*02 antigen type by serological testing or genotyping. Additional names for the HLA-A*02 antigen type include "HLA-A2", HLA-A02" and "HLA-A*2". Different naming systems have been developed which identify HLA proteins encoded by this family of alleles including the HLA naming system developed in 2010 by the WHO Committee for Factors of the HLA System. The term "HLA-A2" refer to HLA proteins encoded by alleles having designations according to this naming system which begin with "HLA-A*02", including but not limited to designations which begin with "HLA-A*02:01", "HLA-A*02:02", "HLA-A*02:03", "HLA-A*02:04", "HLA-A*02:05", "HLA-A*02:06", "HLA-A*02:07", "HLA-A*02:08", "HLA-A*02:09", "HLA-A*02:10", and "HLA-A*02:11". The allele designations may be italicized. The allele designations which begin with "HLA-A*02:" followed by 2, 3 or 4 additional digits may constitute the complete designation or a beginning portion of the designation. The term "HLA-A2" also refer to HLA proteins identified with designations which begin with "HLA-A*02" according to this naming system, including but not limited to the designations "HLA-A*02:01", "HLA-A*02:02", "HLA-A*02:03", "HLA-A*02:04", "HLA-A*02:05", "HLA-A*02:06", "HLA-A*02:07", "HLA-A*02:08", "HLA-A*02:09", "HLA-A*02:10", and "HLA-A*02:11".

The term "anti-HLA-A2 antibody" as used herein refers to an antibody that preferentially or specifically binds to HLA-A2.

The term "HLA-A*03" as used herein refers to HLA proteins including cell surface proteins, encoded by the HLA-A*03 allele family at the HLA-A locus of the HLA gene complex. HLA proteins encompassed by the term "HLA-A*03" include HLA proteins identified as belonging to the HLA-A*03 antigen type by serological testing or genotyping. Additional names for the HLA-A*03 antigen type include "HLA-A03" and "HLA-A3". The term "HLA-A*03" refers to HLA proteins encoded by alleles having designations according to the HLA naming system developed in 2010 by the WHO Committee for Factors of the HLA System which begin with "HLA-A*03:".

The terms "HLA-A*11", "HLA-A11" and "A11" as used herein each refer to HLA proteins including cell surface proteins, encoded by the HLA-A*11 allele family at the HLA-A locus of the HLA gene complex. HLA proteins encompassed by the terms "HLA-A*11", "HLA-A11" and "A11" include HLA proteins identified as belonging to the HLA-A*11 antigen type by serological testing or genotyping. Additional names for the HLA-A*11 antigen type include "HLA-A11". The terms "HLA-A*11", "HLA-A11" and "A11" refer to HLA proteins encoded by alleles having designations according to the HLA naming system developed in 2010 by the WHO Committee for Factors of the HLA System which begin with "HLA-A*11:".

The terms "HLA-A*23", "HLA-A23" and "A23" as used herein each refer to HLA proteins including cell surface proteins, encoded by the HLA-A*23 allele family at the HLA-A locus of the HLA gene complex. HLA proteins encompassed by the terms "HLA-A*23", "HLA-A23" and "A23" include HLA proteins identified as belonging to the HLA-A*23 antigen type by serological testing or genotyping. Additional names for the HLA-A*23 antigen type include "HLA-A23". The terms "HLA-A*23", "HLA-A23" and "A23" refer to HLA proteins encoded by alleles having designations according to the HLA naming system developed in 2010 by the WHO Committee for Factors of the HLA System which begin with "HLA-A*23:".

The terms "HLA-A*25", "HLA-A25" and "A25" as used herein each refer to HLA proteins including cell surface proteins, encoded by the HLA-A*25 allele family at the HLA-A locus of the HLA gene complex. HLA proteins encompassed by the terms "HLA-A*25", "HLA-A25" and "A25" include HLA proteins identified as belonging to the HLA-A*25 antigen type by serological testing or genotyping. Additional names for the HLA-A*25 antigen type include "HLA-A25". The terms "HLA-A*25", "HLA-A25" and "A25" refer to HLA proteins encoded by alleles having designations according to the HLA naming system developed in 2010 by the WHO Committee for Factors of the HLA System which begin with "HLA-A*25:".

The terms "HLA-A*26", "HLA-A26" and "A26" as used herein each refer to HLA proteins including cell surface proteins, encoded by the HLA-A*26 allele family at the HLA-A locus of the HLA gene complex. HLA proteins encompassed by the terms "HLA-A*26", "HLA-A26" and "A26" include HLA proteins identified as belonging to the HLA-A*26 antigen type by serological testing or genotyping. Additional names for the HLA-A*26 antigen type include "HLA-A26". The terms "HLA-A*26", "HLA-A26" and "A26" refer to HLA proteins encoded by alleles having designations according to the HLA naming system developed in 2010 by the WHO Committee for Factors of the HLA System which begin with "HLA-A*26:".

The terms "HLA-A*29", "HLA-A29" and "A29" as used herein each refer to HLA proteins including cell surface proteins, encoded by the HLA-A*29 allele family at the HLA-A locus of the HLA gene complex. HLA proteins encompassed by the terms "HLA-A*29", "HLA-A29" and "A29" include HLA proteins identified as belonging to the HLA-A*29 antigen type by serological testing or genotyping. Additional names for the HLA-A*29 antigen type include "HLA-A29". The terms "HLA-A*29", "HLA-A29" and "A29" refer to HLA proteins encoded by alleles having designations according to the HLA naming system developed in 2010 by the WHO Committee for Factors of the HLA System which begin with "HLA-A*29:".

The terms "HLA-A*30", "HLA-A30" and "A30" as used herein each refer to HLA proteins including cell surface proteins, encoded by the HLA-A*30 allele family at the HLA-A locus of the HLA gene complex. HLA proteins encompassed by the terms "HLA-A*30", "HLA-A30" and "A30" include HLA proteins identified as belonging to the HLA-A*30 antigen type by serological testing or genotyping. Additional names for the HLA-A*30 antigen type include "HLA-A30". The terms "HLA-A*30", "HLA-A30" and "A30" refer to HLA proteins encoded by alleles having designations according to the HLA naming system developed in 2010 by the WHO Committee for Factors of the HLA System which begin with "HLA-A*30:".

The terms "HLA-A*31", "HLA-A31" and "A31" as used herein each refer to HLA proteins including cell surface proteins, encoded by the HLA-A*31 allele family at the HLA-A locus of the HLA gene complex. HLA proteins encompassed by the terms "HLA-A*31", "HLA-A31" and "A31" include HLA proteins identified as belonging to the HLA-A*31 antigen type by serological testing or genotyping. Additional names for the HLA-A*31 antigen type include "HLA-A31". The terms "HLA-A*31", "HLA-A31" and "A31" refer to HLA proteins encoded by alleles having designations according to the HLA naming system developed in 2010 by the WHO Committee for Factors of the HLA System which begin with "HLA-A*31:".

The terms "HLA-A*33", "HLA-A33" and "A33" as used herein each refer to HLA proteins including cell surface proteins, encoded by the HLA-A*33 allele family at the HLA-A locus of the HLA gene complex. HLA proteins encompassed by the terms "HLA-A*33", "HLA-A33" and "A33" include HLA proteins identified as belonging to the HLA-A*33 antigen type by serological testing or genotyping. Additional names for the HLA-A*33 antigen type include "HLA-A33". The terms "HLA-A*33", "HLA-A33" and "A33" refer to HLA proteins encoded by alleles having designations according to the HLA naming system developed in 2010 by the WHO Committee for Factors of the HLA System which begin with "HLA-A*33:".

The terms "HLA-A*34", "HLA-A34" and "A34" as used herein each refer to HLA proteins including cell surface proteins, encoded by the HLA-A*34 allele family at the HLA-A locus of the HLA gene complex. HLA proteins encompassed by the terms "HLA-A*34", "HLA-A34" and "A34" include HLA proteins identified as belonging to the HLA-A*34 antigen type by serological testing or genotyping. Additional names for the HLA-A*34 antigen type include "HLA-A34". The terms "HLA-A*34", "HLA-A34" and "A34" refer to HLA proteins encoded by alleles having designations according to the HLA naming system developed in 2010 by the WHO Committee for Factors of the HLA System which begin with "HLA-A*34:".

"Humanized" forms of non-human (e.g., murine) antibodies are chimeric immunoglobulins, immunoglobulin chains or fragments thereof (such as, for example, Fv, scFv, Fab, Fab', F(ab')$_2$ or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. Such antibodies are designed to maintain the binding specificity of the non-human antibody from which the binding regions are derived, but to avoid an immune reaction against the non-human antibody. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as, for example, an antibody or antibody fragment, where the whole molecule is of human origin or consists of an amino acid sequence identical to a human form of the antibody or immunoglobulin. Such antibodies can be obtained from transgenic mice or other animals that have been engineered to produce specific human antibodies in response to antigenic challenge (see, e.g., Green et al., (1994) Nature Genet 7:13; Lonberg et 5 al., (1994) Nature 368:856; Taylor et al., (1994) Int Immun 6:579, the entire teachings of which are herein incorporated by reference). A fully human antibody can be constructed by genetic or chromosomal transfection methods, as well as phage display technology, all of which are known in the art (see, e.g., McCafferty et al., (1990) Nature 348:552-553). Human antibodies may also be generated by in vitro activated B cells (see, e.g., U.S. Pat. Nos. 5,567,610 and 5,229,275, which are incorporated in their entirety by reference).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the VL, and 26-32 (H1), 52-56 (H2) and 95-15 101 (H3) in the VII when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the VL, and 27-38 (H1), 56-65 (H2) and 105-120 (H3) in the VH when numbered in accordance with the IMGT numbering system; Lefranc, M. P. et al., Nucl. Acids Res. 27:209-212 (1999), Ruiz, M. et al., Nucl. Acids Res. 28:219-221 (2000)). Optionally the antibody has symmetrical insertions at one or more of the following points 28, 36 (L1), 63, 74-75 (L2) and 123 (L3) in the VL, and 28, 36 (H1), 63, 74-75 (H2) and 123 (H3) in the VH when numbered in accordance with AHo (Honneger, A. and Plunkthun, A. J. Mol. Biol. 309:657-670 (2001)).

The term "identity" or "homology", when used in a relationship between the sequences of two or more polypeptides or nucleic acid sequences, refers to the degree of sequence relatedness between polypeptides or nucleic acid sequences, as determined by the number of matches between strings of two or more amino acid residues or nucleotide residues. "Identity" measures the percent of identical matches between the smaller of two or more sequences with gap alignments (if any) addressed by a particular mathematical model or computer program (i.e., "algorithms"). When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer of ten subunits in length) of the positions in two sequences are homologous, the two sequences are 50% homologous; if 90% of the positions (e.g., 9 of 10), are matched or homologous, the two sequences are 90% homologous. Identity of related polypeptides or nucleic acid sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New 10 Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. MoI. Biol. 215, 403-410 (1990)). The BLASTX program is publicly available from the National Center for Biotechnology Information (NCBI) and other sources (BLAST Manual, Altschul et al., NCB/NLM/NIH Bethesda, Md. 20894; Altschul et al., supra). The well-known Smith Waterman algorithm may also be used to determine identity.

As used herein, the term "immune cells" generally includes white blood cells (leukocytes) which are derived from hematopoietic stem cells (HSC) produced in the bone marrow. Examples of immune cells include, but are not limited to, lymphocytes (T cells, B cells, and natural killer (NK) cells) and myeloid-derived cells (neutrophil, eosinophil, basophil, monocyte, macrophage, dendritic cells).

As used herein, the term "immune effector cell" refers to a cell of the immune system which is in a form that is capable of mounting a specific immune response.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages. Immune cells involved in the immune response include lymphocytes, such as B cells and T cells ($CD4^+$, $CD8^+$, Th1 and Th2 cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes.

As used herein, the term "immune accommodation" refers to a condition of a transplant recipient in which an organ or tissue transplant functions normally despite the presence of antibodies in the recipient which are specific for the organ or tissue transplant.

As used herein, the term "immunological tolerance" or "immune tolerance" refers to methods performed on a proportion of treated subjects in comparison with untreated subjects where: a) a decreased level of a specific immunological response (thought to be mediated at least in part by antigen-specific effector T lymphocytes, B lymphocytes, antibody, or their equivalents); b) a delay in the onset or progression of a specific immunological response; or c) a reduced risk of the onset or progression of a specific immunological response. "Specific" immunological or immune tolerance occurs when immunological or immune tolerance is preferentially invoked against certain antigens in comparison with others.

The term "inducible promoter" refers to a nucleotide sequence which, when operably linked with a polynucleotide which encodes or specifies a gene product, causes the gene product to be produced in a cell substantially only when an inducer which corresponds to the promoter is present in the cell.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the antibody, cell, and/or composition of the invention or be shipped together with a container which contains the antibody, cell and/or composition of the invention. Alternatively, the instructional material may be shipped separately from the container with the intention that the instructional material and the antibody, cell and/or composition be used cooperatively by the recipient.

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variants thereof.

An "intracellular signaling domain", as the term is used herein, refers to an intracellular portion of a molecule. The intracellular signaling domain generates a signal that promotes an immune function of the chimeric receptor containing cell. Examples of immune function in a chimeric receptor-T cell may include cytolytic activity, suppressive activity and helper activity, including the secretion of cytokines.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

The term "isolated" means altered or removed from the natural state. For example, a nucleic acid or a peptide naturally present in a living animal is not isolated, but the same nucleic acid or peptide partially or completely separated from the coexisting materials of its natural state is isolated. An isolated nucleic acid or peptide can exist in substantially purified form, or can exist in a non-native environment such as, for example, a host cell.

Typically, a preparation of isolated nucleic acid or peptide contains the nucleic acid or peptide at least about 80% pure, at least about 85% pure, at least about 90% pure, at least about 95% pure, greater than 95% pure, greater than 96% pure, greater than 97% pure, greater than 98% pure, or greater than 99% pure.

An "isolated antibody" is one that has been separated and/or recovered from a component of its natural environment. Contaminant components of its natural environment are materials that may interfere with diagnostic or therapeutic uses of the antibody, and may include enzymes, hormones, and other proteinaceous or non-proteinaceous components. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity as shown by SDS-PAGE under reducing or non-reducing conditions and using Coomassie blue or, preferably, silver staining. Isolated antibody includes the antibody in situ within recombinant cells since at least one component of the antibody's natural environment will not be present. Ordinarily, however, isolated antibody will be prepared by at least one purification step.

An "isolated nucleic acid" or "isolated nucleic sequence" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver staining.

Isolated polypeptide includes the polypeptide in situ within recombinant cells since at least one component of the polypeptide's natural environment will not be present. Ordinarily, however, isolated polypeptide will be prepared by at least one purification step.

As used herein, an "knottin" (that may also be referred to as inhibitor cystine not) refers to an antibody mimetic comprising a protein structural motif containing three disulfide bridges.

As used herein, an "kunitz domain peptide" refers to a type of antibody mimetics, and is based on the active domains of proteins inhibiting the function of proteases.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Examples of lentiviruses include, but are not limited to, HIV, SIV, and FIV.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, the LENTIVECTOR® gene delivery technology from Oxford BioMedica, the LENTIMAX™ vector system from Lentigen and the like. Non-clinical types of lentiviral vectors are also available and would be known to one skilled in the art.

The term "ligand" refers to a member of a pair ligand/receptor, and binds to the other member of the pair.

The term "monoclonal antibody" as used herein refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, a monoclonal antibody may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). A "monoclonal antibody" may also be isolated from phage antibody libraries using the techniques described in Clackson et al., Nature, 352:624-628 (1991) and Marks et al., J. Mol. Biol., 222:581-597 (1991), for example. The monoclonal antibodies herein include "chimeric" antibodies.

The term "nucleic acid" or "polynucleotide" refers to a polymer of nucleotides covalently linked by phosphodiester bonds, such as deoxyribonucleic acids (DNA) or ribonucleic acids (RNA), in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

A "nanobody" is well known in the art and refers to an antibody-derived therapeutic protein that contains the unique structural and functional properties of naturally-occurring heavy chain antibodies. These heavy chain antibodies contain a single variable domain (VHH) and two constant domains (CH2 and CH3).

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

The terms "operably linked" or "transcriptional control" refer to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

As used herein, the term "operational tolerance" refers to a clinical situation where there is a stable graft function lacking histological signs of rejection, including acute or chronic rejection, in the absence of any immunosuppressive drug therapies for at least 1 year, in an immunocompetent host capable of responding to other challenges including infections. The terms "peptide", "polypeptide" and "protein" are used interchangeably, and refer to a compound comprised of amino acid residues covalently linked by peptide bonds. A polypeptide is not limited to a specific length: it must contain at least two amino acids, and no limitation is placed on the maximum number of amino acids that can comprise a polypeptide's sequence. Peptides, oligopeptides, and proteins are included within the definition of polypeptide, and such terms may be used interchangeably herein unless specifically indicated otherwise. As used herein, the term refers to both short chains, which also commonly are referred to in the art as peptides, oligopeptides and oligomers, for example, and to longer chains, which generally are referred to in the art as proteins, of which there are many types. In one embodiment, as used herein, the term "peptides" refers to a linear polymer of amino acids linked together by peptide bonds, preferably having a chain length of less than about 50 amino acids residues; a "polypeptide" refers to a linear polymer of at least 50 amino acids linked together by peptide bonds; and a protein specifically refers to a functional entity formed of one or more peptides or polypeptides, optionally glycosylated, and optionally of non-polypeptides cofactors. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof. Particular polypeptides of interest in the context of this invention are amino acid subsequences comprising CDRs and being capable of binding an antigen.

The term "pharmaceutically acceptable excipient" or "pharmaceutically acceptable carrier" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

As used herein, a "poly(A)" is a series of adenosines monophosphate attached to the mRNA. In a preferred embodiment of a construct for transient expression, the polyA is between 50 and 5000 adenosines monophosphate, preferably greater than or equal to 64, more preferably greater than or equal to 100, most preferably greater than or equal to 300 or 400 adenosines monophosphate. Poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly (A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

The term "promoter/regulatory sequence" refers to a nucleic acid sequence (such as, for example, a DNA sequence) recognized by the synthetic machinery of the cell, or introduced synthetic machinery, required to initiate the specific transcription of a polynucleotide sequence, thereby allowing the expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "reactivity" as used herein refers to the ability of an antibody to react with (that is, bind to) a molecule (e.g., specifically bind to the molecule). A first antibody has "less reactivity" to a molecule (e.g., an HLA molecule) than a second antibody when the first antibody exhibits reduced binding to the molecule as compared to the second antibody. Approaches for readily comparing the reactivities of first and second antibodies to one or more particular HLA molecules are known. One example approach is provided in the Examples section herein, where FlowPRA® Single Antigen beads (One Lambda™) were employed to interrogate antibodies for the ability to react with (or bind to) particular HLA molecules. Such flow cytometric approaches are amenable to high-throughput antibody reactivity analyses.

The term "recombinant protein or peptide" refers to a protein or peptide (e.g., an antibody or a CAR) which is generated using recombinant DNA technology, such as, for example, a protein or peptide (e.g., an antibody or a CAR) expressed by a bacteriophage or yeast expression system. The term should also be construed to mean a protein or peptide (e.g., an antibody or a CAR) which has been generated by the synthesis of a DNA molecule encoding the protein or peptide (e.g., the antibody or CAR) and which DNA molecule expresses a protein or peptide (e.g., an antibody or a CAR), or an amino acid sequence specifying the protein or peptide (e.g., the antibody or CAR), wherein the DNA or amino acid sequence has been obtained using recombinant DNA or amino acid sequence technology which is available and well known in the art.

As used herein, the term "regulatory immune cell" refers to an immune cell that acts in a "regulatory" way to suppress activation of the immune system and thereby maintains immune system homeostasis and tolerance to self-antigens. "Regulatory immune cells" may also have effects on non-immune cells that result in an improved clinical state such as promoting tissue repair or regeneration. Regulatory immune cells may include, without limitation, regulatory T cells, $CD4^+$ regulatory T cells, $CD8^+$ regulatory T cells, regulatory γδ T cells, regulatory DN T cells, regulatory B cells, regulatory NK cells, regulatory macrophages, and regulatory dendritic cells.

"Regulatory T lymphocyte", "regulatory T cell,", "T regulatory cell", "Treg cell" or "Treg" as used in the present invention are synonymous and are intended to have its standard definition as used in the art. Treg cells are a specialized subpopulation of T cells that act in a "regulatory" way to suppress activation of the immune system and thereby maintain immune system homeostasis and tolerance to self-antigens. Tregs have sometimes been referred to as suppressor T-cells. Treg cells are often, but not always, characterized by expression of the forkhead family transcription factor Foxp3 (forkhead box p3). They may also express CD4 or CD8 surface proteins. They may also express CD25. As used in the present invention, and unless otherwise specified, Tregs include "natural" Tregs which develop in the thymus, induced/adaptive/peripheral Tregs that arise via a differentiation process which takes place outside the thymus (e.g., in tissues or secondary lymphoid organs, or in the laboratory setting under defined culture conditions), and Tregs that have been created using recombinant DNA technology. Naturally-occurring Treg cells ($CD4^+$ $CD25^+Foxp3^+$) arise like all other T cells in the thymus. In contrast, induced/adaptive/peripheral Treg cells (which include $CD4^+$ $CD25^+Foxp3^+$ Tregs, Tr1 cells, Th3 cells and others) arise outside the thymus. One way to induce Tregs is by exposure of T effector cells to IL-10 or TGF-β. T-cells may also be converted to Treg cells by transfection or transduction of the Foxp3 gene into a mixed population of T-cells. A T-cell that is caused to express Foxp3 adopts the Treg phenotype and such recombinant Tregs are also defined herein as "Tregs".

The term "rejection" refers to a state in which a transplanted organ or tissue is not accepted by the body of the recipient. Rejection results from the recipient's immune system attacking the transplanted organ or tissue. Rejection can occur days to weeks after transplantation (acute) or months to years after transplantation (chronic).

The term "single-chain Fv" or "scFv" refers to a fusion protein comprising at least one antibody fragment comprising a variable region of a light chain (VL) and at least one antibody fragment comprising a variable region of a heavy chain (VH), wherein the light and heavy chain variable regions are contiguously linked into a single polypeptide chain. In one embodiment, the scFv polypeptide further comprises a polypeptide linker between the VH and VL domains that enables the scFv to form the desired structure for antigen binding, e.g., a synthetic linker, e.g., a short flexible polypeptide linker. A scFv is thus capable of being expressed as a single chain polypeptide, and retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

As used herein, an antibody or a CAR is said to be "immunospecific", "specific for" or to "specifically bind" an antigen if it reacts at a detectable level with the antigen, preferably with an affinity constant, Ka, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$, or greater than or equal to $10^9$ $M^{-1}$, or greater than or equal to $10^{10}$ $M^{-1}$. Affinity of an antibody for its cognate antigen is also commonly expressed as a dissociation constant Kd, and in certain embodiments, an antibody specifically binds to antigen if it binds with a Kd of less than or equal to $10^{-4}$ M, less than or equal to about $10^{-5}$ M, less than or equal to about $10^{-6}$ M, less than or equal to $10^{-7}$ M, or less than or equal to $10^{-8}$ M, or less than or equal to $5.10^{-9}$ M, or less than or equal to $10^{-9}$ M, or less than or equal to $5.10^{-10}$ M, or less than or equal to $10^{-0}$ M. Affinities of antibodies or CAR can be readily determined using conventional techniques, for example, those described by Scatchard et al., (Ann. N.Y. Acad. Sci. USA 51:660 (1949)). Binding properties of an antibody to antigens, cells or tissues thereof may generally be determined and assessed using immunodetection methods including, for example, immunofluorescence-based assays, such as immunohistochemistry (IHC) and/or fluorescence-activated cell sorting (FACS). In one embodiment, the term "specifically binds" refers to an antibody, a CAR or a ligand, which recognizes and binds with a binding partner present in a sample, but which antibody or CAR or ligand does not substantially recognize or bind other molecules in the sample.

The term "signal transduction pathway" refers to the biochemical relationship between a variety of signal transduction molecules that play a role in the transmission of a signal from one portion of a cell to another portion of a cell.

The term "signaling domain" refers to the functional portion of a protein which acts by transmitting information within the cell to regulate cellular activity via defined signaling pathways by generating second messengers or functioning as effectors by responding to such messengers.

As used herein, the term "stem cell" generally includes pluripotent or multipotent stem cells. "Stem cells" include, without limitation, embryonic stem cells (ES); mesenchymal stem cells (MSC); induced-pluripotent stem cells (iPS); and committed progenitor cells (hematopoeitic stem cells (HSC); bone marrow derived cells, etc.).

The term "stimulation" refers to a primary response induced by binding of a stimulatory molecule (e.g., a TCR/CD3 complex or chimeric receptor) with its cognate ligand thereby mediating a signal transduction event, such as, but not limited to, signal transduction via the TCR/CD3 complex or signal transduction via signaling domains of the chimeric receptor. Stimulation can mediate altered expression of certain molecules.

The term "stimulatory molecule" refers to a molecule expressed by an immune cell (e.g., T cell, NK cell, or B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM.

The term "subject" is intended to include living organisms in which an immune response can be elicited. In one embodiment, the subject is a warm-blooded animal, preferably a mammal (including humans, domestic and farm animals, and zoo, sports, or pet animals, such as dogs, cats, cattle, horses, sheep, pigs, goats, rabbits, etc. . . . ), and more preferably a human. In one embodiment, a subject may be a "patient", i.e., a warm-blooded animal, more preferably a human, who/which is awaiting the receipt of, or is receiving medical care or was/is/will be the object of a medical procedure, or is monitored for the development of the targeted disease or condition. In one embodiment, the subject is an adult (for example a subject above the age of 18). In another embodiment, the subject is a child (for example a subject below the age of 18). In one embodiment, the subject is a male. In another embodiment, the subject is a female.

The term "substantially purified cell" refers to a cell that is essentially free of other cell types. A substantially purified cell also refers to a cell which has been separated from other cell types with which it is normally associated in its naturally occurring state. In one embodiment, a substantially purified cell refers to a cell which is at least about 75% free, 80% free, or 85% free, and preferably about 90%, 95%, 96%, 97%, 98%, or 99% free, from other cell types with which it is normally associated in its naturally occurring state. In some instances, a population of substantially purified cells refers to a homogenous population of cells. In one embodiment, a population of substantially purified cells refers to a population of cells at least about 75% homogenous, 80% homogenous, or 85% homogenous, and preferably about 90%, 95%, 96%, 97%, 98%, or 99% homogenous. In other instances, this term refers simply to cells that have been separated from the cells with which they are naturally associated in their natural state. In some aspects, the cells are cultured in vitro. In other aspects, the cells are not cultured in vitro.

The term "T cell" includes all types of immune cells expressing CD3 including T-helper cells ($CD4^+$ cells), $CD8^+$ T-cells (e.g., cytotoxic $CD8^+$ T cell, regulatory $CD8^+$ T cell), T-regulatory cells (Treg), gamma-delta T cells, and double negative T cells.

The terms "therapeutically effective amount" refer to an amount of immune cells or composition as described herein effective to achieve a particular biological result. Thus, the terms "effective amount" or "therapeutically effective amount" mean a level or amount of cells or compositions that is aimed at, without causing significant negative or adverse side effects to the target, (1) delaying or preventing the onset of the targeted disease or condition; (2) slowing down or stopping the progression, aggravation, or deterioration of one or more symptoms of the targeted disease or condition; (3) bringing about ameliorations of the symptoms of the targeted disease or condition; (4) reducing the severity or incidence of the targeted disease or condition; or (5) curing the targeted disease or condition. A therapeutically effective amount may be administered prior to the onset of the targeted disease or condition, for a prophylactic or preventive action. Alternatively, or additionally, the therapeutically effective amount may be administered after initiation of the targeted disease or condition, for a therapeutic action.

The term "transfected" or "transformed" or "transduced" refers to a process by which exogenous nucleic acid is transferred or introduced into a host cell. A "transfected" or "transformed" or "transduced" cell is one which has been transfected, transformed or transduced with exogenous nucleic acid. The cell includes the primary subject cell and its progeny.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a poly lysine compound, liposome, and the like. Examples of viral transfer vectors include, but are not limited to, adenoviral vectors, adeno-associated virus vectors, retroviral vectors, lentiviral vectors, and the like.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

A "transplant" as used herein, refers to cells, tissue, or organ that is introduced into an individual. The source of the transplanted material can be cultured cells, cells from another individual, or cells from the same individual (e.g., after the cells are cultured in vitro). Exemplary organ transplants are kidney, liver, heart, lung, and pancreas. An exemplary tissue transplant is islets. An exemplary cell transplant is allogeneic hematopoietic stem cell transplantation.

"Treating" or "treatment" refers to both therapeutic treatment and prophylactic or preventative measures; wherein the object is to prevent or slow down (lessen) the targeted pathologic condition or disorder. Thus, in one embodiment, these terms refer to the reduction or amelioration of the progression, severity and/or duration of a targeted disease or condition, or the amelioration of one or more symptoms (preferably, one or more discernible symptoms) of a targeted disease or condition, resulting from the administration of one or more therapies (e.g., one or more therapeutic agents such as a Treg cell of the invention). In specific embodiments, the terms "treating" and "treatment" refer to the amelioration of at least one measurable physical parameter of a targeted disease or condition. In other embodiments, the terms "treating" and "treatment" refer to the inhibition of the progression of a targeted disease or condition, either physically by, e.g., stabilization of a discernible symptom, or physiologically by, e.g., stabilization of a physical parameter, or both. Those in need of treatment include those already with the disorder as well as those prone to have the disorder or those in whom the disorder is to be prevented. A subject is successfully "treated" if, after receiving a therapeutic amount of cells or compositions according to the present invention, the subject shows observable and/or measurable reduction in the number of pathogenic cells; reduction in the percent of total cells that are pathogenic; relief to some extent of one or more of the symptoms associated with the specific disease or condition; reduced morbidity and mortality, and/or improvement in quality of life issues. The above parameters for assessing successful treatment and improvement in the disease are readily measurable by routine procedures familiar to a physician.

A "unibody" is well known in the art and refers to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

The term "variable" refers to the fact that certain segments of the V domains differ extensively in sequence among antibodies. The V domain mediates antigen binding and defines specificity of a particular antibody for its particular antigen. However, the variability is not evenly distributed across the 110 to 130-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a [beta]-sheet configuration, connected by three hypervariable regions, which form loops connecting, and in some cases forming part of, the [beta]-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The "variable region" or "variable domain" of an antibody refers to the amino-terminal domains of the heavy or light chain of the antibody. The variable domain of the heavy chain may be referred to as "VH" or "VH". The variable domain of the light chain may be referred to as "VL" or "VL". These domains are generally the most variable parts of an antibody and contain the antigen-binding sites.

A polynucleotide "variant", as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art. A polypeptide "variant", as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences and evaluating one or more biological activities of the polypeptide as described herein and/or using any of a number of techniques well known in the art. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence. For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with similar properties. It is thus contemplated that various changes may be made in the peptide sequences of the present invention, or corresponding DNA sequences that encode said peptides without appreciable loss of their biological utility or activity. In many instances, a polypeptide variant will contain one or more conservative substitutions. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

"Versabodies" are well known in the art and refer to another antibody mimetic technology. They are small proteins of 3-5 kDa with >15% cysteines, which form a high disulfide density scaffold, replacing the hydrophobic core the typical proteins have.

The term "xenogeneic" refers to any material derived from an individual of a different species. The term "xenograft" refers to a graft derived from an individual of a different species.

The term "zeta" or alternatively "zeta chain", "CD3-zeta" or "TCR-zeta" is defined as the protein provided as GenBank Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one embodiment, the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof.

DETAILED DESCRIPTION

A first object of the present invention is an antibody directed to HLA-A2, preferably a humanized antibody directed to HLA-A2.

In one embodiment, the antibody of the invention competes for binding to HLA-A2 with an antibody comprising: a heavy chain complementarity determining region 1 (HCDR1) having the amino acid sequence of SEQ ID NO: 62; a heavy chain complementarity determining region 2 (HCDR2) having the amino acid sequence of SEQ ID NO: 63; a heavy chain complementarity determining region 3 (HCDR3) having the amino acid sequence of SEQ ID NO: 64; a light chain complementarity determining region 1 (LCDR1) having the amino acid sequence of SEQ ID NO: 65; a light chain complementarity determining region 2 (LCDR2) having the amino acid sequence of SEQ ID NO: 66; and a light chain complementarity determining region 3 (LCDR3) having the amino acid sequence of SEQ ID NO: 67.

In one embodiment, the antibody of the invention binds to the same HLA-A2 epitope as an antibody comprising: a heavy chain complementarity determining region 1 (HCDR1) having the amino acid sequence of SEQ ID NO: 62; a heavy chain complementarity determining region 2 (HCDR2) having the amino acid sequence of SEQ ID NO: 63; a heavy chain complementarity determining region 3 (HCDR3) having the amino acid sequence of SEQ ID NO: 64; a light chain complementarity determining region 1 (LCDR1) having the amino acid sequence of SEQ ID NO: 65; a light chain complementarity determining region 2 (LCDR2) having the amino acid sequence of SEQ ID NO: 66; and a light chain complementarity determining region 3 (LCDR3) having the amino acid sequence of SEQ ID NO: 67.

In one embodiment, the anti-HLA-A2 antibody of the invention competes for binding to HLA-A2 with and/or binds to the same HLA-A2 epitope as the BB7.2 antibody.

In one embodiment, the anti-HLA-A2 antibody of the invention has less reactivity to an HLA-A subtype selected from the group comprising A03, A11, A23, A25, A26, A29, A30, A31, A33, A34 and any combination thereof as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to an HLA-A subtype selected from the group comprising A03:01, A11:01, A23:01, A25:01, A26:01, A29:02, A30:01, A31:01, A33:01, A34:01 and any combination thereof as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from one or more of A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from one or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from two or more of A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from two or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from three or more of A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from three or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the 13B7.2 scFv.

In one embodiment, the anti-HLA-A2 antibody of the invention has less reactivity to at least one HLA-A subtype selected from four or more of A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from four or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from five or more of A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from five or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from six or more of A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from six or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from seven or more of A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from seven or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from eight or more of A03, A11, A23, A25, A26, A29, A30, A31, A33 and A34 thereof as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from eight or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from nine or more of A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from nine or more of A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity from each of HLA-A subtype selected from the group comprising A03, A11, A23, A25, A26, A29, A30, A31, A33 and A34 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity from each of HLA-A subtype selected from the group comprising A03:01, A11:01, A23:01, A25:01, A26:01, A29:02, A30:01, A31:01, A33:01 and A34:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to an HLA-A subtype selected from the group comprising A25, A29, A30 and any combination thereof as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to an HLA-A subtype selected from the group comprising A25:01, A29:02, A30:01 and any combination thereof as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to at least one HLA-A subtype selected from one or more of A25, A29 and A30 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from one or more A25:01, A29:02 and A30:01 as compared to the antibody BB7.2 or as compared to an antibody comprising the VH and VL of the BB7.2 antibody, preferably as compared to the B137.2 scFv.

In one embodiment, the anti-HLA-A2 antibody of the invention has less reactivity to at least one HLA-A subtype selected from two or more of A25, A29 and A30 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to at least one HLA-A subtype selected from two or more of A25:01, A29:02 and A30:01 as compared to the antibody BB7.2 or as compared to an antibody comprising the VH and VL of the BB7.2 antibody, preferably as compared to the 13B7.2 scFv.

In one embodiment, the anti-HLA-A2 antibody of the invention has less reactivity from each of HLA-A subtype selected from the group comprising A25, A29 and A30 as compared to the antibody 13B7.2 or as compared to an antibody comprising the VH and VL of the BB7.2 antibody, preferably as compared to the BB7.2 scFv. In one embodiment, the anti-HLA-A2 antibody of the invention has less reactivity from each of HLA-A subtype selected from the group comprising A25:01, A29:02 and A30:01 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to HLA-A25 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A29 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A30 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A3 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A11 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A26 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A31 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A32 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A33 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A34 as compared to the antibody BB7.2 or as compared to an antibody comprising the VH and VL of the BB7.2 antibody, preferably as compared to the BB7.2 scFv.

In one embodiment, the anti-HLA-A2 antibody of the invention has less reactivity to HLA-A25:01 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A29:02 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A30:01 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A03:01 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A11:01 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A26:01 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A31:01 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A33:01 as compared to the antibody BB7.2 or as compared to an antibody comprising the VH and VL of the BB7.2 antibody, preferably as compared to the BB7.2 scFv. In one embodiment, the anti-HLA-A2 antibody of the invention has less reactivity to HLA-A34:01 as compared to the antibody BB7.2 or as compared to an antibody comprising the VH and VL of the BB7.2 antibody, preferably as compared to the BB7.2 scFv.

Methods for measuring the reactivity of an HLA-A2 antibody to HLA-A subtypes are well known to the skilled artisan, and include, without limitation, single antigen assays, such as, for example, the FlowPRA™ Single Antigen Antibody provided by ONE LAMBDA™.

In one embodiment, the anti-HLA-A2 antibody of the invention has less reactivity to an HLA-A subtype selected from the group comprising A03, A11, A23, A25, A26, A29, A30, A31, A33, A34 and any combination thereof as compared to the antibody BB7.2 or to an antibody comprising the VH and VL of the BB7.2 antibody when measured in the conditions of Test A.

In one embodiment, the anti-HLA-A2 antibody of the invention has less reactivity to an HLA-A subtype selected from the group comprising A25, A29, A30 and any combination thereof as compared to the antibody BB7.2 or to an antibody comprising the VH and VL of the BB7.2 antibody when measured in the conditions of Test A.

Test A:

$0.25 \cdot 10^6$ T cells expressing a CAR comprising the anti-HLA-A2 antibody or the BB7.2 antibody, or the VH and VL of the BB7.2 antibody (mA2 CAR)) are incubated with FlowPRA™ single antigen antibody beads panel (FL1HD01, FL1HD02, FL1HD03, FL1HD04, FL1HD06 and FL1HD08, One Lambda™) and fixable viability dye (FVD, ThermoFisher, 65-0865-14, eBioscience™) for 30 minutes at room temperature. Samples are washed, fixed with 0.5% formaldehyde and analyzed via flow cytometry. Two hundred negative control beads are acquired per sample. Beads alone were used as a negative control. For analysis, dead cells are first eliminated using the fixable viability dye. Single antigen beads are then gated after exclusion of dead cells and doublets. Then, the number of beads per HLA is determined by their respective PE intensity peak. Data are normalized by multiplying the number of beads of interest in each HLA-peak by 200, divided by the number of negative beads in the sample. For each HLA-peak the percent relative binding of CAR Tregs compared to control (non-CAR-expressing cells) is determined by subtracting the number of beads in the CAR-Treg from the number of beads in the control sample then dividing the average number of beads in the non-CAR-expressing control, times 100.

In one embodiment, the anti-HLA-A2 antibody of the invention has less reactivity to an HLA-A subtype selected from the group comprising A03, A11, A23, A25, A26, A29, A30, A31, A33, A34 and any combination thereof as compared to the antibody BB7.2 or as compared to an antibody comprising the VH and VL of BB7.2 when measured in the conditions of Test B.

In one embodiment, the anti-HLA-A2 antibody of the invention has less reactivity to an HLA-A subtype selected from the group comprising A25, A29, A30 and any combination thereof as compared to the antibody BB7.2 or as compared to an antibody comprising the VH and VL of BB7.2 when measured in the conditions of Test B.

Test B:

$0.25 \cdot 10^6$ T cells expressing an anti-HLA-A2 antibody or the BB7.2 antibody or the VH and VL of the BB7.2 antibody or a truncated NGFR transduction marker (NGFR) on the cell surface (such as, for example, as part of a chimeric antigen receptor as described herein) are incubated with FlowPRA™ single antigen antibody beads (FL1HD, One Lambda™) and fixable viability dye (FVD, 65-0865-14, eBioscience™), then fixed with 0.5% formaldehyde and analyzed via flow cytometry. For analysis, dead cells are first eliminated using the fixable viability dye. Single beads are then gated after exclusion of dead cells and doublets. Then, the number of beads per HLA is determined by their respective PE intensity. Data are normalized by dividing the number of negative beads in the sample by the number of negative beads in the Treg-NGFR sample, multiplied by the number of negative beads in the Treg-NGFR specimen. Percent relative binding is the number of beads in the NGFR specimen for one specific HLA minus the normalized number of beads in the specimen for that HLA, divided by the number of beads in the NGFR specimen time 100.

In one embodiment, the anti-HLA-A2 antibody of the invention has a reactivity to at least one HLA-A subtype selected from the group comprising A03, A11, A23, A25, A26, A29, A30, A31, A33, A34 statistically inferior to the one of the antibody 13B7.2 or statistically inferior to an antibody comprising the VH and VL of the BB7.2 antibody, preferably when measured in the conditions of Test A or Test B.

In one embodiment, the anti-HLA-A2 antibody of the invention has a reactivity to at least one HLA-A subtype selected from the group comprising A25, A29, A30 statistically inferior to the one of the antibody BB7.2 or statistically inferior to an antibody comprising the VH and VL of the BB7.2 antibody, preferably when measured in the conditions of Test A or Test B.

In one embodiment, the term "statistically inferior" means that the reactivity (i.e., for example, the relative binding in the conditions of Test A or of Test B) measured for the anti-HLA-A2 antibody of the invention is inferior to the reactivity measured for the BB7.2 antibody or for an antibody comprising the VH and VL of the BB7.2 antibody, with a p value of at most about 0.05, preferably of at most about 0.01, more preferably of at most about 0.005, and even more preferably of at most about 0.001, in particular when analyzed by 2-way ANOVA, Dunnett post-test.

In one embodiment, the anti-HLA-A2 antibody of the invention has a reactivity to at least one HLA-A subtype selected from the group comprising A03, A11, A23, A25, A26, A29, A30, A31, A33, A34 inferior to the one of the BB7.2 antibody or to the one of an antibody comprising the VH and VL of the BB7.2 antibody, preferably the anti-HLA-A2 antibody of the invention has a relative binding for at least one HLA-A subtype selected from the group comprising A03, A11, A23, A25, A26, A29, A30, A31, A33, A34 inferior to the one of the BB7.2 antibody or to the one of an antibody comprising the VH and VL of the BB7.2 antibody when measured in the conditions of Test A or Test B, more preferably the relative binding measured for the anti-HLA-A2 antibody of the invention is at most about 90%, 80%, 70%, 60%, 50%, 40%, 30%, 20%, 10% or less of the relative binding measured for the BB7.2 antibody or for an antibody comprising the VH and VL of the BB7.2 antibody.

In one embodiment, the anti-HLA-A2 antibody of the invention has a reactivity to at least one HLA-A subtype selected from the group comprising A25, A29, A30 inferior to the one of the BB7.2 antibody or to the one of an antibody comprising the VH and VL of the BB7.2 antibody, preferably the anti-HLA-A2 antibody of the invention has a relative binding for at least one HLA-A subtype selected from the group comprising A25, A29, A30 inferior to the one of the BB7.2 antibody or to the one of an antibody comprising the VH and VL of the BB7.2 antibody when measured in the conditions of Test A or Test B, more preferably the relative binding measured for the anti-HLA-A2 antibody of the invention is at most about 90%, 80%, 70%, 60%, 50%, 40%, 30%, 20%, 10% or less of the relative binding measured for the BB7.2 antibody or for an antibody comprising the VH and VL of the BB7.2 antibody.

In an embodiment, said antibody is a monoclonal antibody.

In another embodiment, said antibody is a polyclonal antibody.

In one embodiment, the variable region of the heavy chain comprises at least one of the following CDRs:

```
VH-CDR1:
                                        (SEQ ID NO: 1)
SYHIQ

VH-CDR2:
                                        (SEQ ID NO: 2)
WIYPGDGSTQYNEKFKG

VH-CDR3:
                                        (SEQ ID NO: 3)
EGTYYAMDY
```

CDR numbering and definition are according to the Kabat definition.

In one embodiment, the variable region of the heavy chain comprises at least one of the following CDRs:

```
VH-CDR1:
                                        (SEQ ID NO: 4)
GYTFTSY

VH-CDR2:
                                        (SEQ ID NO: 5)
YPGDGS

VH-CDR3:
                                        (SEQ ID NO: 3)
EGTYYAMDY
```

CDR numbering and definition are according to the Chothia definition.

In one embodiment, the variable region of the light chain comprises at least one of the following CDRs:

```
VL-CDR1:
                                        (SEQ ID NO: 6)
RSSQSIVHSNGNTYLE

VL-CDR2:
                                        (SEQ ID NO: 7)
KVSNRFS

VL-CDR3:
                                        (SEQ ID NO: 8)
FQGSHVPRT
```

CDR numbering and definition are according to the Kabat or Chothia definition.

In one embodiment of the invention, the anti-HLA-A2 antibody comprises in its heavy chain one VH-CDR1 (SYHIQ (SEQ ID NO: 1)), one VH-CDR2 (WIYPGDGSTQYNEKFKG (SEQ ID NO: 2)) and/or one VH-CDR3 (EGTYYAMDY (SEQ ID NO: 3)).

In one embodiment of the invention, the anti-HLA-A2 antibody comprises in its heavy chain the 3 CDRs: VH-CDR1 (SYHIQ (SEQ ID NO: 1)), VH-CDR2 (WIYPGDGSTQYNEKFKG (SEQ ID NO: 2)) and VH-CDR3 (EGTYYAMDY (SEQ ID NO: 3)).

In one embodiment of the invention, the anti-HLA-A2 antibody comprises in its heavy chain one VH-CDR1

(GYTFTSY (SEQ ID NO: 4)), one VH-CDR2 (YPGDGS (SEQ ID NO: 5)) and/or one VH-CDR3 (EGTYYAMDY (SEQ ID NO: 3)).

In one embodiment of the invention, the anti-HLA-A2 antibody comprises in its heavy chain the 3 CDRs: VH-CDR1 (GYTFTSY (SEQ ID NO: 4)), VH-CDR2 (YPGDGS (SEQ ID NO: 5)) and VH-CDR3 (EGTYYAMDY (SEQ ID NO: 3)).

In one embodiment of the invention, the anti-HLA-A2 antibody comprises in its light chain one VL-CDR1 (RSSQ-SIVHSNGNTYLE (SEQ ID NO: 6)), one VL-CDR2 (KVSNRFS (SEQ ID NO: 7)) and/or one VL-CDR3 (FQGSHVPRT (SEQ ID NO: 8)).

In one embodiment of the invention, the anti-HLA-A2 antibody comprises in its light chain the 3 CDRs: VL-CDR1 (RSSQSIVHSNGNTYLE (SEQ ID NO: 6)), VL-CDR2 (KVSNRFS (SEQ ID NO: 7)) and VL-CDR3 (FQGSHVPRT (SEQ ID NO: 8)).

In one embodiment of the invention, the anti-HLA-A2 antibody comprises:
  in its heavy chain the 3 CDRs SEQ ID NO: 1, SEQ ID NO: 2 and SEQ ID NO: 3; and
  in its light chain the 3 CDRs SEQ ID NO: 6, SEQ ID NO: 7 and SEQ ID NO: 8.

In one embodiment of the invention, the anti-HLA-A2 antibody comprises:
  in its heavy chain the 3 CDRs SEQ ID NO: 4, SEQ ID NO: 5 and SEQ ID NO: 3; and
  in its light chain the 3 CDRs SEQ ID NO: 6, SEQ ID NO: 7 and SEQ ID NO: 8.

According to the invention, any of the CDRs 1, 2 and 3 of the heavy and light chains may be characterized as having an amino acid sequence that shares at least about 60%, 70%, 75%, 80%, 90%, 95%, 96%, 97%, 98%, 99% of identity with the particular CDR or sets of CDRs listed in the corresponding SEQ ID NO: 1-8.

In one embodiment of the invention, the antibody anti-HLA-A2 comprises the heavy chain variable region of sequence SEQ ID NO: 9.

(SEQ ID NO: 9)
QVQLVQSGPEVKKPGASVKVSCKASGYTFTSYHIQWVRQAPGQGLEWIGW

IYPGDGSTQYNEKFKGRVTITADKSTSTAYMELSSLTSEDTAVYYCAREG

TYYAMDYWGQGTSVTVSS

In one embodiment of the invention, the heavy chain variable region of the antibody anti-HLA-A2 has a sequence that has at least about 60%, 70%, 75%, 80%, 90%, 95%, 96%, 97%, 98%, 99% of identity with SEQ ID NO: 9.

In one embodiment of the invention, the antibody anti-HLA-A2 comprises the light chain variable region of sequence SEQ ID NO: 10.

(SEQ ID NO: 10)
DX$_1$VMTQX$_2$PX$_3$X$_4$LX$_5$VX$_6$X$_7$GX$_8$X$_9$X$_{10}$X$_{11}$ISCRSSQSIVHSNGNTY

LEWYX$_{12}$QKPGQX$_{13}$PRLLIYKVSNRFSGX$_{14}$PDRFSGSGSGTDFTLX$_{15}$

ISRX$_{16}$EX$_{17}$EDX$_{18}$X$_{19}$VYYCFQGSHVPRTFGGGTKLEIKR wherein $X_1$ is V or I, $X_2$ is T or S, $X_3$ is L or S or A, $X_4$ is S or T, $X_5$ is P or S, $X_6$ is T or S, $X_7$ is L or P, Xx is E or D, $X_9$ is P or R, $X_{10}$ is A or V, $X_{11}$ is S or T, $X_{12}$ is L or Q, $X_{13}$ is S or A, $X_{14}$ is V or I, $X_5$ is K or T, $X_{11}$ is V or L, $X_{17}$ is A or P, $X_{18}$ is L or F and $X_{19}$ is G or A.

In one embodiment of the invention, the light chain variable region of the antibody anti-HLA-A2 has a sequence that has at least about 60%, 70%, 75%, 80%, 90%, 95%, 96%, 97%, 98%, 99% of identity with SEQ ID NO: 10.

In one embodiment, the light chain region has a sequence SEQ ID NO: 11, or any sequence that has at least about 60%, 70%, 75%, 80%, 90%, 95%, 96%, 97%, 98%, 99% of identity with SEQ ID NO: 11.

(SEQ ID NO: 11)
DVVMTQTPLSLPVTLGEPASISCRSSQSIVHSNGNTYLEWYLQKPGQSPR

LLIYKVSNRFSGVPDRFSGSGSGTDFTLKISRVEAEDLGVYYCFQGSHVP

RTFGGGTKLEIKR

In one embodiment, the light chain region has a sequence SEQ ID NO: 12, or any sequence that has at least about 60%, 70%, 75%, 80%, 90%, 95%, 96%, 97%, 98%, 99% of identity with SEQ ID NO: 12.

(SEQ ID NO: 12)
DVVMTQSPSSLSVTLGDRVSISCRSSQSIVHSNGNTYLEWYQQKPGQSPR

LLIYKVSNRFSGVPDRFSGSGSGTDFTLTISRVEPEDLGVYYCFQGSHVP

RTFGGGTKLEIKR

In one embodiment, the light chain region has a sequence SEQ ID NO: 13, or any sequence that has at least about 60%, 70%, 75%, 80%, 90%, 95%, 96%, 97%, 98%, 99% of identity with SEQ ID NO: 13.

(SEQ ID NO: 13)
DIVMTQSPATLSVSPGERATISCRSSQSIVHSNGNTYLEWYQQKPGQAPR

LLIYKVSNRFSGIPDRFSGSGSGTDFTLTISRLEPEDFAVYYCFQGSHVP

RTFGGGTKLEIKR

In one embodiment, the HLA-A2 antibody of the invention comprises a heavy chain variable region having a sequence SEQ ID NO: 9 and a light chain variable region having a sequence SEQ ID NO: 10 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{19}$ is L or F and $X_{19}$ is G or A, or any sequence that shares at least about 60%, 70%, 75%, 80%, 90%, 95%, 96%, 97%, 98%, 99% of identity with SEQ ID NO: 9-10.

In one embodiment, the HLA-A2 antibody of the invention comprises a heavy chain variable region having a sequence SEQ ID NO: 9 and a light chain variable region having a sequence SEQ ID NO: 11, or any sequence that shares at least about 60%, 70%, 75%, 80%, 90%, 95%, 96%, 97%, 98%, 99% of identity with SEQ ID NO: 9 and 11.

In one embodiment, the HLA-A2 antibody of the invention comprises a heavy chain variable region having a sequence SEQ ID NO: 9 and a light chain variable region having a sequence SEQ ID NO: 12, or any sequence that shares at least about 60%, 70%, 75%, 80%, 90%, 95%, 96%, 97%, 98%, 99% of identity with SEQ ID NO: 9 and 12.

In one embodiment, the HLA-A2 antibody of the invention comprises a heavy chain variable region having a sequence SEQ ID NO: 9 and a light chain variable region having a sequence that shares at least about 60%, 70%, 75%, 80%, 90%, 95%, 96%, 97%, 98%, 99% of identity with SEQ ID NO: 9 and 13.

According to the invention, one, two, three, four or more of the amino acids of the heavy chain or light chain variable regions may be substituted by a different amino acid.

In one embodiment, in the antibody of the invention, the specified variable region and CDR sequences may comprise conservative sequence modifications. Conservative sequence modifications refer to amino acid modifications that do not significantly affect or alter the binding characteristics of the antibody containing the amino acid sequence.

Such conservative modifications include amino acid substitutions, additions and deletions. Modifications can be introduced into an antibody of the invention by standard techniques known in the art, such as site-directed mutagenesis and PCR-mediated mutagenesis.

Another object of the invention is an isolated nucleic sequence encoding the heavy chain variable region of sequence SEQ ID NO: 9. In one embodiment, said nucleic acid sequence is SEQ ID NO: 86.

(SEQ ID NO: 86)
CAGGTCCAGCTAGTACAAAGCGGCCCTGAAGTAAAGAAACCTGGTGCCTC

TGTGAAGGTGAGCTGCAAGGCCAGCGGCTACACCTTCACCAGCTACCACA

TCCAGTGGGTTCGACAGGCCCCTGGACAGGGACTAGAGTGGATCGGCTGG

ATCTATCCTGGCGACGGCAGCACCCAGTACAACGAGAAGTTCAAGGGCAG

AGTTACCATCACCGCCGACAAGAGCACCAGCACAGCCTATATGGAGCTGA

GCAGCCTGACCAGCGAGGACACAGCTGTTTACTATTGTGCCAGAGAGGGC

ACCTACTACGCAATGGATTATTGGGGCCAGGGGACCAGCGTGACCGTTTC

TTCT

Another object of the invention is an isolated nucleic sequence encoding the light chain variable region of sequence SEQ ID NO: 11. In one embodiment, said nucleic acid sequence is SEQ ID NO: 87.

(SEQ ID NO: 87)
GATGTTGTAATGACCCAGACACCTCTGAGCCTGCCTGTGACCCTGGGAGA

ACCAGCATCCATCAGCTGTCGGAGCAGCCAGAGCATCGTTCACAGCAACG

GCAACACCTACCTGGAATGGTATCTACAGAAGCCCGGACAGAGCCCCAGG

CTGCTGATCTACAAGGTGTCCAACCGCTTCAGTGGTGTGCCCGATAGATT

TTCTGGCAGCGGCTCTGGCACCGACTTCACCCTGAAGATCTCCAGAGTGG

AAGCCGAGGACCTGGGCGTGTACTACTGCTTCCAAGGCAGCCATGTGCCA

AGAACCTTTGGTGGAGGCACAAAGCTGGAAATCAAGCGG

Another object of the invention is an isolated nucleic sequence encoding the light chain variable region of sequence SEQ ID NO: 12. In one embodiment, said nucleic acid sequence is SEQ ID NO: 88.

(SEQ ID NO: 88)
GATGTTGTAATGACCCAGAGCCCTAGTAGCCTGTCTGTGACCCTGGGAGA

TCGAGTATCCATCAGCTGTCGGAGCAGCCAGAGCATCGTTCACAGCAACG

GCAACACCTACCTGGAATGGTATCAACAGAAGCCCGGACAGAGCCCCAGG

CTGCTGATCTACAAGGTGTCCAACCGCTTCAGTGGTGTGCCCGATAGATT

TTCTGGCAGCGGCTCTGGCACCGACTTCACCCTGACGATCTCCAGAGTGG

AACCAGAGGACCTGGGCGTGTACTACTGCTTCCAAGGCAGCCATGTGCCA

AGAACCTTTGGTGGAGGCACAAAGCTGGAAATCAAGCGG

Another object of the invention is an isolated nucleic sequence encoding the light chain variable region of sequence SEQ ID NO: 13. In one embodiment, said nucleic acid sequence is SEQ ID NO: 89

(SEQ ID NO: 89)
GATATTGTAATGACCCAGAGCCCTGCAACACTGTCTGTGTCCCCTGGAGA

ACGAGCAACAATCAGCTGTCGGAGCAGCCAGAGCATCGTTCACAGCAACG

GCAACACCTACCTGGAATGGTATCAACAGAAGCCCGGACAGGCCCCCAGG

CTGCTGATCTACAAGGTGTCCAACCGCTTCAGTGGAATACCCGATAGATT

TTCTGGCAGCGGCTCTGGCACCGACTTCACCCTGACGATCTCCAGATTAG

AACCAGAGGACTTTGCAGTGTACTACTGCTTCCAAGGCAGCCATGTGCCA

AGAACCTTTGGTGGAGGCACAAAGCTGGAAATCAAGCGG

Another object of the invention is an expression vector comprising the nucleic sequences encoding the anti-HLA-A2 antibody of the invention.

Another object of the invention is an isolated host cell comprising said vector. Said host cell may be used for the recombinant production of the antibodies of the invention.

In one embodiment, said antibody is an antibody molecule selected from the group consisting of a whole antibody, a humanized antibody, a single chain antibody, a dimeric single chain antibody, a Fv, a scFv, a Fab, a F(ab)'$_2$, a defucosylated antibody, a bi-specific antibody, a diabody, a triabody, a tetrabody.

In another embodiment, said antibody is an antibody fragment selected from the group consisting of a unibody, a domain antibody, and a nanobody.

In another embodiment, said antibody is an antibody mimetic selected from the group consisting of an affibody, an alphabody, an armadillo repeat protein-based scaffold, a knottin, a kunitz domain peptide, an affilin, an affitin, an adnectin, an atrimer, an evasin, a DARPin, an anticalin, an avimer, a fynomer, a versabody and a duocalin.

Fragments and derivatives of antibodies of this invention (which are encompassed by the term "antibody" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific antibodies formed from antibody fragments. Fragments of the present antibodies can be obtained using standard methods.

For instance, Fab or F(ab')$_2$ fragments may be produced by protease digestion of the isolated antibodies, according to conventional techniques. It will be appreciated that immunoreactive fragments can be modified using known methods, for example to slow clearance in vivo and obtain a more desirable pharmacokinetic profile the fragment may be modified with polyethylene glycol (PEG). Methods for coupling and site-specifically conjugating PEG to a Fab' fragment are described in, for example, Leong et al., Cytokines 16 (3): 106-119 (2001) and Delgado et al., Br. J. Cancer 5 73 (2): 175-182 (1996), the disclosures of which are incorporated herein by reference.

In one embodiment, the antibody of the invention is a scFv or a scFab, preferably a scFv.

In one embodiment, the antibody of the invention is a scFv, comprising a sequence SEQ ID NO: 9 and a sequence SEQ ID NO: 10 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_1$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A, in either order to the N-terminal and C-terminal ends of the scFv. Preferably, the antibody of the invention is a scFv, comprising a sequence SEQ ID NO: 9 and a sequence SEQ ID NO: 11, 12 or 13 in either order to the N-terminal and C-terminal ends of the scFv.

In one embodiment, the sequence SEQ ID NO: 9 is N-terminal, and the sequence SEQ ID NO: 10, 11, 12 or 13 is C-terminal.

In one embodiment, the scFv of the invention comprises, from N-terminal to C-terminal: SEQ ID NO: 9, an optional linker, SEQ ID NO: 10 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_1$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A (preferably one of SEQ ID NO: 11-13).

In one embodiment, the scFv of the invention comprises, from N-terminal to C-terminal: SEQ ID NO: 10 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A (preferably one of SEQ ID NO: 11-13), an optional linker, SEQ ID NO: 9.

In one embodiment, the scFv comprises a linker. Examples of linkers include, but are not limited to, GS linkers as described herein. In one embodiment, the linker comprises or consists in a sequence GGGGSGGGGSGGGGS (SEQ ID NO: 18).

In one embodiment, the scFv of the invention comprises or consists in a sequence SEQ ID NO: 69, or any amino acid sequence with at least about 95-99% identity with SEQ ID NO: 69

(SEQ ID NO: 69)
QVQLVQSGPEVKKPGASVKVSCKASGYTFTSYHIQWVRQAPGQGLEWIGW

IYPGDGSTQYNEKFKGRVTITADKSTSTAYMELSSLTSEDTAVYYCAREG

TYYAMDYWGQGTSVTVSSGGGGSGGGGSGGGGSDX$_1$VMTQX$_2$PX$_3$X$_4$LX$_5$V

X$_6$X$_7$GX$_8$X$_9$X$_{10}$X$_{11}$ISCRSSQSIVHSNGNTYLEWYX$_{12}$QKPGQX$_{13}$PRLLIYK

VSNRFSGX$_{14}$PDRFSGSGSGTDFTLX$_{15}$ISRX$_{16}$EX$_{17}$EDX$_{18}$X$_{19}$VYYCFQGS

HVPRTFGGGTKLEIKR wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A. SEQ ID NO: 69 consists in, from N-terminal to C-terminal, SEQ ID NO: 9, SEQ ID NO: 18 and SEQ ID NO: 10.

In one embodiment, the scFv of the invention comprises or consists in a sequence SEQ ID NO: 70, 71 or 72, or any amino acid sequence with at least about 95-99% identity with SEQ ID NO: 70, 71 or 72. SEQ ID NO: 70-72 consist in, from N-terminal to C-terminal, SEQ ID NO: 9, SEQ ID NO: 18 and SEQ ID NO: 11-13 respectively.

(SEQ ID NO: 70)
QVQLVQSGPEVKKPGASVKVSCKASGYTFTSYHIQWVRQAPGQGLEWIG

WIYPGDGSTQYNEKFKGRVTITADKSTSTAYMELSSLTSEDTAVYYCAR

EGTYYAMDYWGQGTSVTVSSGGGGSGGGGSGGGGSDVVMTQTPLSLPVT

LGEPASISCRSSQSIVHSNGNTYLEWYLQKPGQSPRLLIYKVSNRFSGV

PDRFSGSGSGTDFTLKISRVEAEDLGVYYCFQGSHVPRTFGGGTKLEIK

R (SEQ ID NO: 71)
QVQLVQSGPEVKKPGASVKVSCKASGYTFTSYHIQWVRQAPGQGLEWIG

WIYPGDGSTQYNEKFKGRVTITADKSTSTAYMELSSLTSEDTAVYYCAR

EGTYYAMDYWGQGTSVTVSSGGGGSGGGGSGGGGSDVVMTQSPSSLSVT

LGDRVSISCRSSQSIVHSNGNTYLEWYQQKPGQSPRLLIYKVSNRFSGV

PDRFSGSGSGTDFTLTISRVEPEDLGVYYCFQGSHVPRTFGGGTKLEIK

R (SEQ ID NO: 72)
QVQLVQSGPEVKKPGASVKVSCKASGYTFTSYHIQWVRQAPGQGLEWIG

WIYPGDGSTQYNEKFKGRVTITADKSTSTAYMELSSLTSEDTAVYYCAR

EGTYYAMDYWGQGTSVTVSSGGGGSGGGGSGGGGSDIVMTQSPATLSVS

PGERATISCRSSQSIVHSNGNTYLEWYQQKPGQAPRLLIYKVSNRFSGI

PDRFSGSGSGTDFTLTISRLEPEDFAVYYCFQGSHVPRTFGGGTKLEIK

R

In one embodiment, the scFv of the invention further comprises a S residue in N-terminal, in order to facilitate the cleavage of an optional leader sequence.

Therefore, in one embodiment, the scFv of the invention has a sequence 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_8$ is L or F and $X_{19}$ is G or A.

In one embodiment, the scFv of the invention comprises or consists in a sequence SEQ ID NO: 74, 75 or 76.

(SEQ ID NO: 74)
SQVQLVQSGPEVKKPGASVKVSCKASGYTFTSYHIQWVRQAPGQGLEWIG

WIYPGDGSTQYNEKFKGRVTITADKSTSTAYMELSSLTSEDTAVYYCARE

-continued

GTYYAMDYWGQGTSVTVSSGGGGSGGGGSGGGGSDVVMTQSPSSLSVTLG

DRVSISCRSSQSIVHSNGNTYLEWYQQKPGQSPRLLIYKVSNRFSGVPDR

FSGSGSGTDFTLTISRVEPEDLGVYYCFQGSHVPRTFGGGTKLEIKR (SEQ ID NO: 75)
SQVQLVQSGPEVKKPGASVKVSCKASGYTFTSYHIQWVRQAPGQGLEWIG

WIYPGDGSTQYNEKFKGRVTITADKSTSTAYMELSSLTSEDTAVYYCARE

GTYYAMDYWGQGTSVTVSSGGGGSGGGGSGGGGSDVVMTQSPSSLSVTLG

DRVSISCRSSQSIVHSNGNTYLEWYQQKPGQSPRLLIYKVSNRFSGVPDR

FSGSGSGTDFTLTISRVEPEDLGVYYCFQGSHVPRTFGGGTKLEIKR (SEQ ID NO: 76)
SQVQLVQSGPEVKKPGASVKVSCKASGYTFTSYHIQWVRQAPGQGLEWIG

WIYPGDGSTQYNEKFKGRVTITADKSTSTAYMELSSLTSEDTAVYYCARE

GTYYAMDYWGQGTSVTVSSGGGGSGGGGSGGGGSDIVMTQSPATLSVSPG

ERATISCRSSQSIVHSNGNTYLEWYQQKPGQAPRLLIYKVSNRFSGIPDR

FSGSGSGTDFTLTISRLEPEDFAVYYCFQGSHVPRTFGGGTKLEIKR

Another object of the invention is a composition comprising, consisting essentially of or consisting of at least one anti-HLA-A2 antibody of the invention.

As used herein, "consisting essentially of", with reference to a composition, means that at least one anti-HLA-A2 antibody of the invention as described here above is the only one therapeutic agent or agent with a biologic activity within said composition.

Another object of the invention is a pharmaceutical composition comprising at least one anti-HLA-A2 antibody of the invention, and a pharmaceutically acceptable carrier.

Examples of pharmaceutically acceptable carriers include, but are not limited to, media, solvents, coatings, isotonic and absorption delaying agents, additives, stabilizers, preservatives, surfactants, substances which inhibit enzymatic degradation, alcohols, pH controlling agents, antioxidants; chelating agents such as EDTA or glutathione; adjuvants (e.g., aluminum hydroxide); preservatives and propellants.

Examples of pharmaceutically acceptable media include, but are not limited to, water, neutral buffered saline, phosphate buffered saline, normal saline or other physiologically buffered saline, or other solvent such as glycol, glycerol, and oil such as olive oil or an injectable organic ester. A pharmaceutically acceptable medium can also contain liposomes or micelles.

Examples of coating materials include, but are not limited to, lecithin.

Examples of isotonic agents include, but are not limited to, sugars, sodium chloride, and the like.

Examples of agents that delay absorption include, but are not limited to, aluminum monostearate and gelatin.

Examples of additives include, but are not limited to, mannitol, dextran, carbohydrates (such as, for example, glucose, mannose, sucrose or dextrans); glycine, lactose or polyvinylpyrrolidone or other additives such as antioxidants or inert gas, stabilizers or recombinant proteins (e.g. human serum albumin) suitable for in vivo administration.

Examples of suitable stabilizers include, but are not limited to, sucrose, gelatin, peptone, digested protein extracts such as NZ-Amine or NZ-Amine AS.

Pharmaceutically acceptable carriers that may be used in these compositions further include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylenepolyoxypropylene-block polymers, polyethylene glycol and wool fat.

Another object of the invention is a medicament comprising, consisting or consisting essentially of at least one anti-HLA-A2 antibody of the invention, as described hereinabove.

Another object of the invention is the use of at least one anti-HLA-A2 antibody of the invention for detecting HLA-A2 in a sample, preferably in a biological sample, in vitro or in vivo.

Examples of assays in which the anti-HLA-A2 antibody of the invention may be used, include, but are not limited to, ELISA, sandwich ELISA, RIA, FACS, tissue immunohistochemistry, Western-blot, and immunoprecipitation.

Another object of the invention is a method for detecting HLA-A2 in a sample, comprising contacting the sample with an anti-HLA-A2 antibody of the invention and detecting the anti-HLA-A2 antibody bound to HLA-A2, thereby indicating the presence of HLA-A2 in the sample.

In one embodiment of the invention, the sample is a biological sample. Examples of biological samples include, but are not limited to, bodily fluids, preferably blood, more preferably blood serum, plasma, synovial fluid, bronchoalveolar lavage fluid, sputum, lymph, ascitic fluids, urine, amniotic fluid, peritoneal fluid, cerebrospinal fluid, pleural fluid, pericardial fluid, and alveolar macrophages, tissue lysates and extracts prepared from diseased tissues or from a transplant.

In one embodiment of the invention, the term "sample" is intended to mean a sample taken from an individual prior to any analysis.

In one embodiment of the invention, the anti-HLA-A2 antibody of the invention is directly labeled with a detectable label and may be detected directly. In another embodiment, the protein of the invention is unlabeled (and is referred as the first/primary antibody) and a secondary antibody or other molecule that can bind the anti-HLA-A2 antibody is labeled. As it is well known in the art, a secondary antibody is chosen to be able to specifically bind the specific species and class of the primary antibody.

The presence of anti-HLA-A2 antibody/HLA-A2 complex in the sample can be detected and measured by detecting the presence of the labeled secondary antibody. For example, after washing away unbound secondary antibody from a well comprising the primary antibody/antigen complex or from a membrane (such as a nitrocellulose or nylon membrane) comprising the complex, the bound secondary antibody can be developed and detected based on chemiluminescence of the label for example.

Labels for the anti-HLA-A2 antibody or the secondary antibody include, but are not limited to, various enzymes, prosthetic groups, fluorescent materials, luminescent materials, magnetic agents and radioactive materials. Examples of such enzymes include but are not limited to, horseradish peroxidase, alkaline phosphatase, beta-galactosidase or acetylcholinesterase; examples of prosthetic group complexes include but are not limited to, streptavidin/biotin and avidin/biotin; examples of fluorescent materials include but are not limited to, umbelliferone, fluorescein, fluorescein isothiocyanate, rhodamine, dichlorotriazinylamine fluorescein, dansyne chloride or phycoerythrin; examples of luminescent material include but are not limited to, luminal; examples of magnetic agents include gadolinium; and examples of suitable radioactive material include $^{125}I$, $^{131}I$, $^{35}S$ or $^{3}H$.

Another object of the invention is a kit comprising at least one anti-HLA-A2 antibody of the invention, preferably a monoclonal anti-HLA-A2 antibody.

By "kit" is intended any manufacture (e.g., a package or a container) comprising at least one reagent, preferably an antibody, for specifically detecting the expression of HLA-A2.

The kit may be promoted, distributed, or sold as a unit for performing the methods of the present invention. Furthermore, any or all of the kit reagents may be provided within containers that protect them from the external environment, such as in sealed containers.

The kits may also contain a package insert describing the kit and methods for its use.

Kits for performing a sandwich ELISA generally comprise a capture antibody, optionally immobilized on a solid support (e.g., a microtiter plate), and a revelation antibody coupled with a detectable substance, such as, for example HRP, a fluorescent label, a radioisotope, beta-galactosidase, and alkaline phosphatase.

In another embodiment, the detectable substance is immobilized on a solid support (e.g., a microtiter plate).

The present invention further relates to a chimeric antigen receptor (CAR) specific for HLA-A2. CARs are chimeric protein molecules that combine antibody-based specificity for a target antigen with an immune cell receptor-activating intracellular domain.

According to the present invention, the CAR comprises, in one or more polypeptides (i) an extracellular HLA-A2 binding domain, wherein said extracellular domain comprises or consists in the anti-HLA-A2 antibody (preferably the anti-HLA-A2 scFv) of the present invention, (ii) optionally an extracellular hinge domain, (iii) optionally a transmembrane domain, and (iv) an intracellular signaling domain. In one embodiment, the chimeric receptor further comprises a Tag and/or a leader sequence.

In one embodiment, the CAR of the present invention competes for binding to HLA-A2 with an antibody comprising: a heavy chain complementarity determining region 1 (HCDR1) having the amino acid sequence of SEQ ID NO: 62; a heavy chain complementarity determining region 2 (HCDR2) having the amino acid sequence of SEQ ID NO: 63; a heavy chain complementarity determining region 3 (HCDR3) having the amino acid sequence of SEQ ID NO: 64; a light chain complementarity determining region 1 (LCDR1) having the amino acid sequence of SEQ ID NO: 65; a light chain complementarity determining region 2 (LCDR2) having the amino acid sequence of SEQ ID NO: 66; and a light chain complementarity determining region 3 (LCDR3) having the amino acid sequence of SEQ ID NO: 67.

In one embodiment, the CAR of the present invention binds to the same HLA-A2 epitope as an antibody comprising: a heavy chain complementarity determining region 1 (HCDR1) having the amino acid sequence of SEQ ID NO: 62; a heavy chain complementarity determining region 2 (HCDR2) having the amino acid sequence of SEQ ID NO: 63; a heavy chain complementarity determining region 3 (HCDR3) having the amino acid sequence of SEQ ID NO: 64; a light chain complementarity determining region 1 (LCDR1) having the amino acid sequence of SEQ ID NO: 65; a light chain complementarity determining region 2 (LCDR2) having the amino acid sequence of SEQ ID NO: 66; and a light chain complementarity determining region 3 (LCDR3) having the amino acid sequence of SEQ ID NO: 67.

In one embodiment, the CAR of the invention competes for binding to HLA-A2 with and/or binds to the same HLA-A2 epitope as the BB7.2 antibody.

In one embodiment, the CAR of the invention has less reactivity to an HLA-A subtype selected from the group comprising A03, A11, A23, A25, A26, A29, A30, A31, A33, A34 and any combination thereof as compared to a CAR comprising BB7.2 or to a CAR comprising the VH and VL of the BB7.2 antibody. In one embodiment, the CAR of the invention has less reactivity to an HLA-A subtype selected from the group comprising A03:01, A11:01, A23:01, A25:01, A26:01, A29:02, A30:01, A31:01, A33:01, A34:01 and any combination thereof as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from one or more of A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from one or more of A03:01, A11:01, A23:01, A25:01, A26:01, A29:02, A30:01, A31:01, A33:01 and A34:01 as compared to a CAR comprising BB7.2 or to a CAR comprising the VI and VL of the BB7.2 antibody.

In one embodiment, the anti-HLA-A2 antibody of the invention has less reactivity to at least one HLA-A subtype selected from two or more of A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from two or more of A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from three or more of A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from three or more of A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from four or more of A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from four or more of A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from five or more of A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from five or more of A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from six or more of A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from six or more of A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from seven or more of A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from seven or more of A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from eight or more of A03, A11, A23, A25, A26, A29, A30, A31, A33 and A34 thereof as compared to a CAR comprising BB7.2 or to a CAR comprising the VII and VL of the BB7.2 antibody. In one embodiment, the anti-HLA-A2 antibody of the invention has less reactivity to at least one HLA-A subtype selected from eight or more of A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from nine or more of A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from nine or more of A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the anti-HLA-A2 antibody of the invention has less reactivity from each of HLA-A subtype selected from the group comprising A03, A11, A23, A25, A26, A29, A30, A31, A33 and A34 as compared to a CAR comprising BB7.2 or to a CAR comprising the VH and VL of the BB7.2 antibody. In one embodiment, the anti-HLA-A2 antibody of the invention has less reactivity from each of HLA-A subtype selected from the group comprising A03:01, A11:01, A23:01, A25:01, A26:01, A29:02, A30:01, A31:01, A33:01 and A34:01 as compared to a CAR comprising BB7.2 or to a CAR comprising the VH and VL of the BB7.2 antibody.

In one embodiment, the CAR of the invention has less reactivity to an HLA-A subtype selected from the group comprising A25, A29, A30 and any combination thereof as compared to the antibody BB7.2, preferably as compared to the BB7.2 scFv or as compared to an antibody comprising the VH and VL of the BB7.2 antibody. In one embodiment, the CAR of the invention has less reactivity to an HLA-A subtype selected from the group comprising A25:01, A29:02, A30:01 and any combination thereof as compared to the antibody BB7.2, preferably as compared to the BB7.2 scFv or as compared to an antibody comprising the VH and VL of the BB7.2 antibody.

In one embodiment, the anti-HLA-A2 antibody of the invention has less reactivity to at least one HLA-A subtype selected from one or more of A25, A29 and A30 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from one or more A25:01, A29:02 and A30:01 as compared to a CAR comprising BB7.2 or to a CAR comprising the VH and VL of the BB7.2 antibody.

In one embodiment, the anti-HLA-A2 antibody of the invention has less reactivity to at least one HLA-A subtype selected from two or more of A25, A29 and A30 as compared to a CAR comprising BB7.2 or to a CAR comprising the VH and VL of the BB7.2 antibody. In one embodiment, the anti-HLA-A2 antibody of the invention has less reactivity to at least one HLA-A subtype selected from two or more of A25:01, A29:02 and A30:01 as compared to a CAR comprising BB7.2 or to a CAR comprising the VH and VL of the BB7.2 antibody.

In one embodiment, the anti-HLA-A2 antibody of the invention has less reactivity from each of HLA-A subtype selected from the group comprising A25, A29 and A30 as compared to a CAR comprising BB7.2 or to a CAR comprising the VH and VL of the BB7.2 antibody. In one embodiment, the anti-HLA-A2 antibody of the invention has less reactivity from each of HLA-A subtype selected from the group comprising A25:01, A29:02 and A30:01 as compared to a CAR comprising BB7.2 or to a CAR comprising the VII and VL of the BB7.2 antibody.

In one embodiment, the anti-HLA-A2 antibody of the invention has less reactivity to HLA-A25 as compared to a CAR comprising BB7.2 or to a CAR comprising the VH and VL of the BB7.2 antibody. In one embodiment, the anti-HLA-A2 antibody of the invention has less reactivity to HLA-A29 as compared to a CAR comprising BB7.2 or to a CAR comprising the VII and VL of the BB7.2 antibody. In one embodiment, the anti-HLA-A2 antibody of the invention has less reactivity to HLA-A30 as compared to a CAR comprising BB7.2 or to a CAR comprising the VH and VL of the BB7.2 antibody. In one embodiment, the anti-HLA-A2 antibody of the invention has less reactivity to HLA-A3 as compared to a CAR comprising BB7.2 or to a CAR comprising the VH and VL of the BB7.2 antibody. In one embodiment, the anti-HLA-A2 antibody of the invention has less reactivity to HLA-A11 as compared to a CAR comprising BB7.2 or to a CAR comprising the VH and VL of the BB7.2 antibody. In one embodiment, the anti-HLA-A2 antibody of the invention has less reactivity to HLA-A26 as compared to a CAR comprising BB7.2 or to a CAR comprising the VH and VL of the BB7.2 antibody. In one embodiment, the anti-HLA-A2 antibody of the invention has less reactivity to HLA-A31 as compared to a CAR comprising BB7.2 or to a CAR comprising the VH and VL of the BB7.2 antibody. In one embodiment, the anti-HLA-A2 antibody of the invention has less reactivity to HLA-A32 as compared to a CAR comprising BB7.2 or to a CAR comprising the VH and VL of the BB7.2 antibody. In one embodiment, the anti-HLA-A2 antibody of the invention has less reactivity to HLA-A33 as compared to a CAR comprising BB7.2 or to a CAR comprising the VH and VL of the BB7.2 antibody. In one embodiment, the anti-HLA-A2 antibody of the invention has less reactivity to HLA-A34 as compared to a CAR comprising BB7.2 or to a CAR comprising the VH and VL of the BB7.2 antibody.

In one embodiment, the anti-HLA-A2 antibody of the invention has less reactivity to HLA-A25:01 as compared to a CAR comprising BB7.2 or to a CAR comprising the VH and VL of the BB7.2 antibody. In one embodiment, the anti-HLA-A2 antibody of the invention has less reactivity to HLA-A29:02 as compared to a CAR comprising BB7.2 or to a CAR comprising the VH and VL of the BB7.2 antibody. In one embodiment, the anti-HLA-A2 antibody of the invention has less reactivity to HLA-A30: as compared to a CAR comprising BB7.2 or to a CAR comprising the VH and VL of the BB7.2 antibody. In one embodiment, the anti-HLA-A2 antibody of the invention has less reactivity to HLA-A03:01 as compared to a CAR comprising BB7.2 or to a CAR comprising the VH and VL of the BB7.2 antibody. In one embodiment, the anti-HLA-A2 antibody of the invention has less reactivity to HLA-A11:01 as compared to a CAR comprising BB7.2 or to a CAR comprising the VH and VL of the BB7.2 antibody. In one embodiment, the anti-HLA-A2 antibody of the invention has less reactivity to HLA-A26:01 as compared to a CAR comprising BB7.2 or to a CAR comprising the VH and VL of the BB7.2 antibody. In one embodiment, the anti-HLA-A2 antibody of the invention has less reactivity to HLA-A31:01 as compared to a CAR comprising BB7.2 or to a CAR comprising the VH and VL of the BB7.2 antibody. In one embodiment, the anti-HLA-A2 antibody of the invention has less reactivity to HLA-A33:01 as compared to a CAR comprising BB7.2 or to a CAR comprising the VH and VL of the BB7.2 antibody. In one embodiment, the anti-HLA-A2 antibody of the invention has less reactivity to HLA-A34:01 as compared to a CAR comprising BB7.2 or to a CAR comprising the VH and VL of the BB7.2 antibody.

Methods for measuring the reactivity of a CAR to HLA-A subtypes are well known to the skilled artisan, and include, without limitation, single antigen assays, such as, for example, the FlowPRA™ Single Antigen Antibody provided by ONE LAMBDA™.

In one embodiment, the CAR of the invention has less reactivity to an HLA-A subtype selected from the group comprising A03, A11, A23, A25, A26, A29, A30, A31, A33, A34 and any combination thereof as compared to a CAR comprising the antibody BB7.2 or as compared to a CAR comprising the VH and VL of the BB7.2 antibody when measured in the conditions of Test A.

In one embodiment, the CAR of the invention has less reactivity to an HLA-A subtype selected from the group comprising A25, A29, A30 and any combination thereof as compared to the antibody BB7.2 or as compared to an antibody comprising the VH and VL of the BB7.2 antibody when measured in the conditions of Test A.

Test A:
0.25·10$^6$ T cells expressing a CAR comprising the anti-HLA-A2 antibody or the BB7.2 antibody or the VH and VL of the BB7.2 antibody (mA2 CAR)) are incubated with FlowPRA™ single antigen antibody beads panel (FL1HD01, FL1HD02, FL1HD03, FL1HD04, FL1HD06 and FL1HD08, One Lambda™) and fixable viability dye (FVD, ThermoFisher, 65-0865-14, eBioscience™) for 30 minutes at room temperature. Samples are washed, fixed with 0.5% formaldehyde and analyzed via flow cytometry. Two hundred negative control beads are acquired per sample. Beads alone were used as a negative control. For analysis, dead cells are first eliminated using the fixable viability dye. Single antigen beads are then gated after exclusion of dead cells and doublets. Then, the number of beads per HLA is determined by their respective PE intensity peak. Data are normalized by multiplying the number of beads of interest in each HLA-peak by 200, divided by the number of negative beads in the sample. For each HLA-peak the percent relative binding of CAR Tregs compared to control (non-CAR-expressing cells) is determined by subtracting the number of beads in the CAR-Treg from the number of beads in the control sample then dividing the average number of beads in the non-CAR-expressing control, times 100.

In one embodiment, the CAR of the invention has less reactivity to an HLA-A subtype selected from the group comprising A03, A11, A23, A25, A26, A29, A30, A31, A33, A34 and any combination thereof as compared to a CAR comprising the antibody BB7.2 or as compared to a CAR comprising the VH and VL of the BB7.2 antibody, when measured in the conditions of Test B.

In one embodiment, the CAR of the invention has less reactivity to an HLA-A subtype selected from the group comprising A25, A29, A30 and any combination thereof as compared to the antibody BB7.2 or as compared to an antibody comprising the VH and VL of the BB7.2 antibody, when measured in the conditions of Test B.

Test B:
0.25·10$^6$ T cells expressing an anti-HLA-A2 antibody or the BB7.2 antibody or the VH and VL of the BB7.2 antibody or a truncated NGFR transduction marker (NGFR) on the cell surface (such as, for example, as part of a chimeric antigen receptor as described herein) are incubated with FlowPRA™ single antigen antibody beads (FL1HD, One Lambda™) and fixable viability dye (FVD, 65-0865-14, eBioscience™), then fixed with 0.5% formaldehyde and analyzed via flow cytometry. For analysis, dead cells are first eliminated using the fixable viability dye. Single beads are then gated after exclusion of dead cells and doublets. Then, the number of beads per HLA is determined by their respective PE intensity. Data are normalized by dividing the number of negative beads in the sample by the number of negative beads in the Treg-NGFR sample, multiplied by the number of negative beads in the Treg-NGFR specimen. Percent relative binding is the number of beads in the NGFR specimen for one specific HLA minus the normalized number of beads in the specimen for that HLA, divided by the number of beads in the NGFR specimen time 100.

In one embodiment, the CAR of the invention has a reactivity to at least one HLA-A subtype selected from the group comprising A03, A11, A23, A25, A26, A29, A30, A31, A33, A34 statistically inferior to the one of a CAR comprising the antibody BB7.2 or to the one of a CAR comprising the VH and VL of the BB7.2 antibody, preferably when measured in the conditions of Test A or Test B.

In one embodiment, the CAR of the invention has a reactivity to at least one HLA-A subtype selected from the group comprising A25, A29, A30 statistically inferior to the one of the antibody BB7.2 or to the one of an antibody comprising the VH and VL of the BB7.2 antibody, preferably when measured in the conditions of Test A or Test B.

In one embodiment, the term "statistically inferior" means that the reactivity (i.e., for example, the relative binding in the conditions of Test A or Test B) measured for the CAR of the invention is inferior to the reactivity measured for the BB7.2 antibody or for an antibody comprising the VH and VL of the BB7.2 antibody, with a p value of at most about 0.05, preferably of at most about 0.01, more preferably of at most about 0.005, and more preferably of at most about 0.001, in particular when analyzed by 2-way ANOVA, Dunnett post-test.

In one embodiment, the CAR of the invention has a reactivity to at least one HLA-A subtype selected from the group comprising A03, A11, A23, A25, A26, A29, A30, A31, A33, A34 inferior to the one of a CAR comprising the BB7.2 antibody or to the one of a CAR comprising the VH and VL of the BB7.2 antibody, preferably the CAR of the invention has a relative binding for at least one HLA-A subtype selected from the group comprising A03, A11, A23, A25, A26, A29, A30, A31, A33, A34 inferior to the one of a CAR comprising the BB7.2 antibody or to the one of a CAR comprising the VH and VL of the BB7.2 antibody when measured in the conditions of Test A or Test B, more preferably the relative binding measured for the anti-HLA-A2 antibody of the invention is at most about 90%, 80%, 70%, 60%, 50%, 40%, 30%, 20%, 10% or less of the relative binding measured for the BB7.2 antibody or for an antibody comprising the VH and VL of the BB7.2 antibody.

In one embodiment, the CAR of the invention has a reactivity to at least one HLA-A subtype selected from the group comprising A25, A29, A30 inferior to the one of a CAR comprising the BB7.2 antibody or to the one of a CAR comprising the VH and VL of the BB7.2 antibody, preferably the CAR of the invention has a relative binding for at least one HLA-A subtype selected from the group comprising A25, A29, A30 inferior to the one of a CAR comprising the BB7.2 antibody or to the one of a CAR comprising the VH and VL of the BB7.2 antibody when measured in the conditions of Test A or Test B, more preferably the relative binding measured for the anti-HLA-A2 antibody of the invention is at most about 90%, 80%, 70%, 60%, 50%, 40%, 30%, 20%, 10% or less of the relative binding measured for the BB7.2 antibody or for an antibody comprising the VH and VL of the B137.2 antibody.

The present invention further relates to a nucleic acid sequence encoding a CAR as described hereinabove, wherein said nucleic acid sequence comprises i) a nucleic acid sequence of a HLA-A2 binding domain (preferably wherein said HLA-A2 binding domain is an anti-HLA-A2 antibody, preferably an anti-HLA-A2 scFv as described hereinabove), (ii) optionally a nucleic acid sequence of an extracellular hinge domain, (iii) optionally a nucleic acid sequence of a transmembrane domain, (iv) one or more nucleic acid sequence(s) of an intracellular signaling domain. In one embodiment, the nucleic acid sequence further comprises a sequence encoding a Tag and/or a leader sequence.

In one embodiment, the HLA-A2 binding domain comprised in the CAR of the invention is a scFv, comprising a sequence SEQ ID NO: 9 and a sequence SEQ ID NO: 10 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, Xu is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A, in either order to the N-terminal and C-terminal ends of the scFv. Preferably, the HLA-A2 binding domain comprised in the CAR of the invention is a scFv, comprising a sequence SEQ ID NO: 9 and a sequence SEQ ID NO: 11, 12 or 13 in either order to the N-terminal and C-terminal ends of the scFv.

In one embodiment, the sequence SEQ ID NO: 9 is N-terminal, and the SEQ ID NO: 10, 11, 12 or 13 is C-terminal.

In one embodiment, the HLA-A2 binding domain comprised in the CAR of the invention comprises, from N-terminal to C-terminal: SEQ ID NO: 9, an optional linker, SEQ ID NO: 10 wherein $X_1$ is V or I, $X_2$ is T or S, $X_3$ is L or S or A, $X_4$ is S or T, $X_5$ is P or S, $X_6$ is T or S, $X_7$ is L or P, Xx is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A (preferably one of SEQ ID NO: 11-13).

In one embodiment, the HLA-A2 binding domain comprised in the CAR of the invention comprises, from N-terminal to C-terminal: SEQ ID NO: 10 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A (preferably one of SEQ ID NO: 11-13), an optional linker, SEQ ID NO: 9.

In one embodiment, the HLA-A2 binding domain comprised in the CAR of the invention comprises a linker. Examples of linkers include, but are not limited to, GS linkers as described herein. In one embodiment, the linker comprises or consists in a sequence GGGGSGGGGSGGGGS (SEQ ID NO: 18).

In one embodiment, the HLA-A2 binding domain comprised in the CAR of the invention comprises or consists in a sequence SEQ ID NO: 69 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A. SEQ ID NO: 69 consists in, from N-terminal to C-terminal, SEQ ID NO: 9, SEQ ID NO: 18 and SEQ ID NO: 10.

In one embodiment, the HLA-A2 binding domain comprised in the CAR of the invention comprises or consists in a sequence SEQ ID NO: 70, 71 or 72. SEQ ID NO: 70-72 consist in, from N-terminal to C-terminal, SEQ ID NO: 9, SEQ ID NO: 18 and SEQ ID NO: 11-13 respectively.

In one embodiment, the HLA-A2 binding domain comprised in the CAR of the invention further comprises a S residue in N-terminal, in order to facilitate the cleavage of an optional leader sequence.

Therefore, in one embodiment, the HLA-A2 binding domain comprised in the CAR of the invention has a sequence 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_5$ is K or T, $X_{16}$ is V or L, $X_{17}$ is A or P, $X_{18}$ is L or F and $X_{19}$ is G or A.

In one embodiment, the HLA-A2 binding domain comprised in the CAR of the invention comprises or consists in a sequence SEQ ID NO: 74, 75 or 76.

In one embodiment, the I-HLA-A2 binding domain may be connected to a transmembrane domain by a hinge domain.

In one embodiment, a short oligo- or polypeptide linker, preferably having a length ranging from 2 and 10 amino acids may form the hinge domain. In one embodiment, the term "linker" refers to a flexible polypeptide linker.

For example, a glycine-serine doublet provides a particularly suitable hinge domain (GS linker). In one embodiment, the hinge domain is a Gly/Ser linker. Examples of Gly/Ser linkers include, but are not limited to, GS linkers, $G_2S$ linkers, $G_3S$ linkers, $G_4S$ linkers.

Examples of $G_2S$ linkers include, but are not limited to, GGS.

$G_3S$ linkers comprise the amino acid sequence (Gly-Gly-Gly-Ser)$_n$, also referred to as (GGGS)$_n$ or (SEQ ID NO: 14)$_n$, where n is a positive integer equal to or greater than 1 (such as, example, n=1, n=2, n=3, n=4, n=5, n=6, n=7, n=8, n=9 or n=10). Examples of $G_3S$ linkers include, but are not limited to, GGGSGGGSGGGSGGGS (SEQ ID NO: 15).

Examples of $G_4S$ linkers include, but are not limited to, (Gly$_4$ Ser) corresponding to GGGGS (SEQ ID NO: 16); (Gly$_4$ Ser)$_2$ corresponding to GGGGSGGGGS (SEQ ID NO: 17); (Gly$_4$Ser)$_3$ corresponding to GGGGSGGGGSGGGGS (SEQ ID NO: 18); and (Gly$_4$ Ser)$_4$ corresponding to GGGGSGGGGSGGGGSGGGGS (SEQ ID NO: 19).

Also included within the scope of the invention are hinge domains described in WO2012/138475, incorporated herein by reference.

In one embodiment, the hinge domain comprises the amino acid sequence AGSSSSGGSTTGGSTT (SEQ ID NO: 20), the amino acid sequence GTTAASGSSGGSSSGA (SEQ ID NO: 21), the amino acid sequence SSATATAGTGSSTGST (SEQ ID NO: 22), and/or the amino acid sequence TSGSTGTAASSTSTST (SEQ ID NO: 23).

In one embodiment, the hinge domain is encoded by a nucleotide sequence of GGTGGCGGAGGTTCTGGAGGTGGAGGTTCC (SEQ ID NO: 24).

In another embodiment, the hinge domain is a $KIR_2DS_2$ hinge corresponding to KIRRDSS (SEQ ID NO: 25).

In one embodiment, the hinge domain comprises or consists in the amino acid sequence of a CD8 hinge (SEQ ID NO: 26) or an amino acid sequence with 95-99% identity to SEQ ID NO: 26. In one embodiment, the hinge domain is a CD8 hinge encoded by the nucleic acid sequence SEQ ID NO: 27 or a nucleic acid sequence with 95-99% identity to SEQ ID NO: 27.

(SEQ ID NO: 26)
TTTPAPRPPTPAPTIASQPLSLRPEACRPAAGGAVHTRGLDFACD (SEQ ID NO: 27)
ACCACGACGCCAGCGCCGCGACCACCAACACCGGCGCCCACCATCGCGTC
GCAGCCCCTGTCCCTGCGCCCAGAGGCGTGCCGGCCAGCGGCGGGGGCG
CAGTGCACACGAGGGGGCTGGACTTCGCCTGTGAT

In another embodiment, the hinge domain comprises or consists in the amino acid sequence of an IgG4 hinge (SEQ ID NO: 28), or an amino acid sequence with 95-99% identity to SEQ ID NO: 28. In one embodiment, the hinge domain is an IgG4 hinge encoded by the nucleic acid sequence SEQ ID NO: 29 or a nucleic acid sequence with 95-99% identity to SEQ ID NO: 29.

(SEQ ID NO: 28)
ESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKE
YKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQ
EGNVFSCSVMHEALHNHYTQKSLSLSLGKM (SEQ ID NO: 29)
GAGAGCAAGTACGGCCCTCCCTGCCCCCCTTGCCCTGCCCCCGAGTTCCT
GGGCGGACCCAGCGTGTTCCTGTTCCCCCCCAAGCCCAAGGACACCCTGA
TGATCAGCCGGACCCCCGAGGTGACCTGTGTGGTGGTGGACGTGTCCCAG
GAGGACCCCGAGGTCCAGTTCAACTGGTACGTGGACGGCGTGGAGGTGCA
CAACGCCAAGACCAAGCCCCGGGAGGAGCAGTTCAATAGCACCTACCGGG
TGGTGTCCGTGCTGACCGTGCTGCACCAGGACTGGCTGAACGGCAAGGAA
TACAAGTGTAAGGTGTCCAACAAGGGCCTGCCCAGCAGCATCGAGAAAAC
CATCAGCAAGGCCAAGGGCCAGCCTCGGGAGCCCCAGGTGTACACCCTGC
CCCCTAGCCAAGAGGAGATGACCAAGAACCAGGTGTCCCTGACCTGCCTG
GTGAAGGGCTTCTACCCCAGCGACATCGCCGTGGAGTGGGAGAGCAACGG
CCAGCCCGAGAACAACTACAAGACCACCCCCCCTGTGCTGGACAGCGACG
GCAGCTTCTTCCTGTACAGCCGGCTGACCGTGGACAAGAGCCGGTGGCAG
GAGGGCAACGTCTTTAGCTGCTCCGTGATGCACGAGGCCCTGCACAACCA
CTACACCCAGAAGAGCCTGAGCCTGTCCCTGGGCAAGATG

In another embodiment, the hinge domain comprises or consists in the amino acid sequence of an IgD hinge (SEQ ID NO: 30) or an amino acid sequence with 95-99% identity to SEQ ID NO: 30. In one embodiment, the hinge domain is an IgD hinge encoded by the nucleic acid sequence SEQ ID NO: 31 or a nucleic acid sequence with 95-99% identity to SEQ ID NO: 31.

(SEQ ID NO: 30)
RWPESPKAQASSVPTAQPQAEGSLAKATTAPATTRNTGRGGEEKKKEKEK
EEQEERETKTPECPSHTQPLGVYLLTPAVQDLWLRDKATFTCFVVGSDLK
DAHLTWEVAGKVPTGGVEEGLLERHSNGSQSQHSRLTLPRSLWNAGTSVT
CTLNHPSLPPQRLMALREPAAQAPVKLSLNLLASSDPPEAASWLLCEVSG
FSPPNILLMWLEDQREVNTSGFAPARPPPQPGSTTFWAWSVLRVPAPPSP
QPATYTCVVSHEDSRTLLNASRSLEVSYVTDH (SEQ ID NO: 31)
AGGTGGCCCGAAAGTCCCAAGGCCCAGGCATCTAGTGTTCCTACTGCACA
GCCCCAGGCAGAAGGCAGCCTAGCCAAAGCTACTACTGCACCTGCCACTA
CGCGCAATACTGGCCGTGGCGGGAGGAGAAGAAAAAGGAGAAAGAGAAA
GAAGAACAGGAAGAGAGGGAGACCAAGACCCCTGAATGTCCATCCCATAC
CCAGCCGCTGGGCGTCTATCTCTTGACTCCCGCAGTACAGGACTTGTGGC
TTAGAGATAAGGCCACCTTTACATGTTTCGTCGTGGGCTCTGACCTGAAG
GATGCCCATTTGACTTGGGAGGTTGCCGGAAAGGTACCCACAGGGGGGT
TGAGGAAGGGTTGCTGGAGCGCCATTCCAATGGCTCTCAGAGCCAGCACT

CAAGACTCACCCTTCCGAGATCCCTGTGGAACGCCGGGACCTCTGTCACA

TGTACTCTAAATCATCCTAGCCTGCCCCCACAGCGTCTGATGGCCCTTAG

AGAGCCAGCCGCCCAGGCACCAGTTAAGCTTAGCCTGAATCTGCTCGCCA

GTAGTGATCCCCCAGAGGCCGCCAGCTGGCTCTTATGCGAAGTGTCCGGC

TTTAGCCCGCCCAACATCTTGCTCATGTGGCTGGAGGACCAGCGAGAAGT

GAACACCAGCGGCTTCGCTCCAGCCCGGCCCCCACCCCAGCCGGGTTCTA

CCACATTCTGGGCCTGGAGTGTCTTAAGGGTCCCAGCACCACCTAGCCCC

CAGCCAGCCACATACACCTGTGTTGTGTCCCATGAAGATAGCAGGACCCT

GCTAAATGCTTCTAGGAGTCTGGAGGTTTCCTACGTGACTGACCATT

In another embodiment, the hinge region comprises or consists in the amino acid sequence of a CD28 hinge (SEQ ID NO: 32) or an amino acid sequence with 95-99% identity to SEQ ID NO: 32. In one embodiment, the hinge domain is a CD28 hinge encoded by the nucleic acid SEQ ID NO: 33 or a nucleic acid sequence with 95-99% identity to SEQ ID NO: 33.

(SEQ ID NO: 32)
IEVMYPPPYLDNEKSNGTIIHVKGKHLCPSPLFPGPSKP (SEQ ID NO: 33)
ATTGAAGTTATGTATCCTCCTCCTTACCTAGACAATGAGAAGAGCAATGG

AACCATTATCCATGTGAAAGGGAAACACCTTTGTCCAAGTCCCCTATTTC

CCGGACCTTCTAAGCCC

Examples of transmembrane domains that may be used in the chimeric receptor of the invention include, but are not limited to, transmembrane domains of an alpha, beta or zeta chain of a T-cell receptor, or of CD28, CD3 gamma, CD3 delta, CD3 epsilon, CD3 zeta, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD1 d, ITGAE, CD103, ITGAL, CD1a, LFA-1, ITGAM, CD11b, PD1, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), SLAMF6 (NTB-A, Lyl08), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In one embodiment, the transmembrane domain comprises or consists in the amino acid sequence of a CD8 transmembrane domain (SEQ ID NO: 34), or an amino acid sequence with 95-99% identity to SEQ ID NO: 34. In another embodiment, the transmembrane domain comprises or consists in an amino acid sequence having at least one, two or three modifications but not more than 20, 10 or 5 modifications of an amino acid sequence of SEQ ID NO: 34, or an amino acid sequence with 95-99% identity to SEQ ID NO: 34.

(SEQ ID NO: 34)
IYIWAPLAGTCGVLLLSLVITLYC

In another embodiment, the transmembrane domain is encoded by the nucleotide sequence of a CD8 transmembrane domain (SEQ ID NO: 35), or a nucleotide sequence with 95-99% identity to SEQ ID NO: 35.

(SEQ ID NO: 35)
ATCTACATCTGGGCGCCCTTGGCCGGGACTTGTGGGGTCCTTCTCCTGTC

ACTGGTTATCACCCTTTACTGC

In another embodiment, the transmembrane domain comprises or consists in the amino acid sequence of a CD28 transmembrane domain (SEQ ID NO: 36) or an amino acid sequence with 95-99% identity to SEQ ID NO: 36. In one embodiment, the transmembrane domain is a CD28 transmembrane domain encoded by the nucleic acid sequence SEQ ID NO: 37 or a nucleic acid sequence with 95-99% identity to SEQ ID NO: 37.

(SEQ ID NO: 36)
FWVLVVVGGVLACYSLLVTVAFIIFWV (SEQ ID NO: 37)
TTTTGGGTGCTGGTGGTGGTTGGTGGAGTCCTGGCTTGCTATAGCTTGCT

AGTAACAGTGGCCTTTATTATTTTCTGGGTG

In one embodiment, the transmembrane domain may be recombinant, in which case it will comprise predominantly hydrophobic amino acids such as valine or leucine.

The cytoplasmic domain which includes the intracellular signaling domain of the CAR is responsible for activation of at least one of the effector functions of the immune cell (e.g., regulatory T cell) in which the CAR has been placed in. The term "effector function" refers to a specialized function of an immune cell. For example, an effector function of a regulatory T cell may include suppressing or downregulating the induction and/or proliferation of other immune cells. In addition, the effector function of Tregs may include effects on non-immune cells that result in an improved clinical state such as promoting tissue repair or regeneration. Thus, the term "intracellular signaling domain" refers to the portion of a protein which transduces the effector function signal and directs the immune cell to perform its specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In one embodiment, the intracellular signaling domain can comprise the entire intracellular portion, or the entire native intracellular signaling domain, of the molecule from which it is derived, or a functional fragment or derivative thereof.

According to one embodiment, the intracellular signaling domain comprises at least one (such as, for example, one) T cell primary signaling domain (or a sequence derived therefrom) and optionally one or more intracellular domain(s) of a T cell costimulatory molecule (or sequence(s) derived therefrom).

In one embodiment, the intracellular signaling domain of the chimeric receptor of the invention consists in at least one (such as, for example, one) primary signaling domain.

In one embodiment, the intracellular signaling domain comprises one or more intracellular domain(s) of a T cell costimulatory molecule. In one embodiment, the intracellular signaling domain consists in one or more intracellular domain(s) of a T cell costimulatory molecule.

In another embodiment, the intracellular signaling domain of the chimeric receptor of the invention comprises at least one costimulatory domain and at least one (such as, for example, one) primary signaling domain.

In another embodiment, the intracellular signaling domain of the chimeric receptor of the invention comprises at least two costimulatory domains and at least one (such as, for example, one) primary signaling domain.

In one embodiment of the invention, the T cell primary signaling domain comprises a signaling domain of a protein selected in the group of CD3 zeta, CD3 gamma, CD3 delta, CD3 epsilon, common FcR gamma (FCER1G), FcR beta (Fc Epsilon Rib), CD79a, CD79b, Fcgamma RIIa, DAP10, and DAP 12 and sequences derived therefrom.

In one embodiment, the T cell primary signaling domain comprises or consists in a functional signaling domain of CD3 zeta.

In one embodiment, the T cell primary signaling domain comprises or consists in the amino acid sequence of the CD3-zeta domain of SEQ ID NO: 38, 39, 40 or 41, or an amino acid sequence with 95-99% identity to SEQ ID NO: 38-41.

(SEQ ID NO: 38)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR (SEQ ID NO: 39)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR (SEQ ID NO: 40)
RVKFSRSADAPAYKQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR (SEQ ID NO: 41)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

In another embodiment, the CD3 zeta primary signaling domain comprises or consists in an amino acid sequence having at least one, two or three modifications but not more than 20, 10 or 5 modifications of an amino acid sequence of SEQ ID NO: 38-41, or an amino acid sequence with 95-99% identity to SEQ ID NO: 38-41.

Thus, in one embodiment, the nucleic acid sequence encoding the T cell primary signaling domain comprises or consists in the nucleic acid sequence of the CD3-zeta domain of SEQ ID NO: 42 or SEQ ID NO: 43, or a nucleotide sequence with 95-99% identity to SEQ ID NO: 42 or SEQ ID NO: 43.

(SEQ ID NO: 42)
AGAGTGAAGTTCAGCAGGAGCGCAGACGCCCCCGCGTACAAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC (SEQ ID NO: 43)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGC

T cell primary signaling domains that act in a stimulatory manner may comprise signaling motifs known as immunoreceptor tyrosine-based activation motifs (ITAMS).

Examples of ITAM containing T cell primary intracellular signaling domains that are of particular use in the invention include, but are not limited to, those of (or derived from) CD3 zeta, common FcR gamma (FCER1G), Fc gamma RIIa, FcR beta (Fc Epsilon R1b), CD3 gamma, CD3 delta, CD3 epsilon, CD5, CD22, CD66b, CD79a, CD79b, DAP10, and DAP12.

In one embodiment, the T cell primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

In one embodiment, the intracellular signaling domain of the chimeric receptor of the invention comprises a T cell primary signaling domain (such as, for example, a CD3-zeta signaling domain), combined with one or more costimulatory signaling domains. A costimulatory signaling domain(s) refers to a portion of the chimeric receptor comprising at least one intracellular domain of a costimulatory molecule. A costimulatory molecule is a cell surface molecule other than an antigen receptor or its ligands that is required for an efficient response of lymphocytes to an antigen.

Examples of intracellular domains of a T cell costimulatory molecule include, but are not limited to, the signaling domains of proteins selected in the group of CD27, CD28, 4-1BB (CD137), an MHC class I molecule, BTLA, a Toll ligand receptor, OX40, CD30, CD40, PD-1, ICOS (CD278), lymphocyte function-associated antigen-1 (LFA-1), CD2, CD7, LIGHT, NKG2C, B7-H3, a ligand that specifically binds with CD83, CDS, ICAM-1, GITR, ARHR, BAFFR, HVEM (LIGHTR), SLAMF7, NKp80 (KLRF1), NKp44, NKp30, NKp46, CD160 (BY55), CD19, CD19a, CD4, CD8alpha, CD8beta, IL2ra, IL6Ra, IL2R beta, IL2R gamma, IL7R alpha, IL-13RA1/RA2, IL-33R(IL1RL1), IL-10RA/RB, IL-4R, IL-5R (CSF2RB), IL-21R, ITGA4, VLA1, CD49a, ITGA4, IA4, CD49D, ITGA6, VLA-6, CD49f, ITGAD, CD11d, ITGAE, CD103, ITGAL, CD1a/CD18, ITGAM, CD11b, ITGAX, CD11c, ITGB1, CD29, ITGB2, CD18, ITGB7, NKG2D, NKG2C, CTLA-4 (CD152), CD95, TNFR1 (CD120a/TNFRSF1A), TNFR2 (CD120b/TNFRSF1B), TGFbR1/2/3, TRANCE/RANKL, DNAM1 (CD226), SLAMF4 (CD244, 2B4), CD84, CD96 (Tactile), CEACAM1, CRTAM, Ly9 (CD229), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, common gamma chain, a ligand that specifically binds with CD83, NKp44, NKp30, NKp46, or NKG2D, and any combination thereof.

In one embodiment of the invention, the chimeric receptor comprises at least one intracellular domain of a T cell costimulatory molecule selected from the group comprising 4-1BB, ICOS, CD27, OX40, CD28, CTLA4 and PD-1 and any combination thereof.

In one embodiment, the T cell costimulatory signaling domain comprises or consists in the amino acid sequence of a 4-1BB intracellular domain (SEQ ID NO: 44) or an amino acid sequence with 95-99% identity to SEQ ID NO: 44. In another embodiment, the T cell costimulatory signaling domain comprises or consists in an amino acid sequence having at least one, two or three modifications but not more than 20, 10 or 5 modifications of an amino acid sequence of SEQ ID NO: 44.

```
                                         (SEQ ID NO: 44)
KRGRKKLLYIFKQPFMRPVQTTQEEDGCSCRFPEEEEGGCEL
```

In one embodiment, the T cell costimulatory signaling domain comprises or consists in the amino acid sequence of a CD27 intracellular domain (SEQ ID NO: 45) or an amino acid sequence with 95-99% identity to SEQ ID NO: 45. In another embodiment, the T cell costimulatory signaling domain comprises or consists in an amino acid sequence having at least one, two or three modifications but not more than 20, 10 or 5 modifications of an amino acid sequence of SEQ ID NO: 45.

```
                                         (SEQ ID NO: 45)
QRRKYRSNKGESPVEPAEPCRYSCPREEEGSTIPIQEDYRKPEPACSP
```

In one embodiment, the T cell costimulatory signaling domain comprises or consists in the amino acid sequence of a CD28 intracellular domain (SEQ ID NO: 46) or an amino acid sequence with 95-99% identity to SEQ ID NO: 46. In another embodiment, the T cell costimulatory signaling domain comprises or consists in an amino acid sequence having at least one, two or three modifications but not more than 20, 10 or 5 modifications of an amino acid sequence of SEQ ID NO: 46.

```
                                         (SEQ ID NO: 46)
RSKRSRLLHSDYMNMTPRRPGPTRKHYQPYAPPRDFAAYRS
```

In one embodiment of the invention, the chimeric receptor comprises a combination of at least two intracellular domains of a T cell costimulatory molecule, preferably selected from an intracellular domain of CD28, an intracellular domain of CD27 and an intracellular domain of 4-1BB.

In one embodiment, the chimeric receptor comprises the amino acid sequence of a 4-1BB intracellular domain (SEQ ID NO: 44) or an amino acid sequence with 95-99% identity to SEQ ID NO: 44 and the amino acid sequence of a CD27 intracellular domain (SEQ ID NO: 45) or an amino acid sequence with 95-99% identity to SEQ ID NO: 45.

In another embodiment, the chimeric receptor comprises the amino acid sequence of a 4-1BB intracellular domain (SEQ ID NO: 44) or an amino acid sequence with 95-99% identity to SEQ ID NO: 44 and the amino acid sequence of a CD28 intracellular domain (SEQ ID NO: 46) or an amino acid sequence with 95-99% identity to SEQ ID NO: 46.

In yet another embodiment, the chimeric receptor comprises the amino acid sequence of a CD27 intracellular domain (SEQ ID NO: 45) or an amino acid sequence with 95-99% identity to SEQ ID NO: 45 and the amino acid sequence of a CD28 intracellular domain (SEQ ID NO: 46) or an amino acid sequence with 95-99% identity to SEQ ID NO: 46.

In one embodiment, the chimeric receptor comprises the amino acid sequence of a 4-1BB intracellular domain (SEQ ID NO: 44) or an amino acid sequence with 95-99% identity to SEQ ID NO: 44 and the amino acid sequence of a CD27 intracellular domain (SEQ ID NO: 45) or an amino acid sequence with 95-99% identity to SEQ ID NO: 45 and the amino acid sequence of a CD28 intracellular domain (SEQ ID NO: 46) or an amino acid sequence with 95-99% identity to SEQ ID NO: 46.

Thus, in one embodiment, the nucleic acid sequence encoding the T cell costimulatory signaling domain comprises the nucleic acid sequence of a 4-1BB intracellular domain (SEQ ID NO: 47) or a nucleic acid sequence with 95-99% identity to SEQ ID NO: 47, and/or the nucleic acid sequence of a CD27 intracellular domain (SEQ ID NO: 48) or a nucleic acid sequence with 95-99% identity to SEQ ID NO: 48, and/or the nucleic acid sequence of a CD28 intracellular domain (SEQ ID NO: 49), or a nucleic acid sequence with 95-99% identity to SEQ ID NO: 49.

```
                                         (SEQ ID NO: 47)
AAACGGGGCAGAAAGAAACTCCTGTATATATTCAAACAACCATTTATGAG

ACCAGTACAAACTACTCAAGAGGAAGATGGCTGTAGCTGCCGATTTCCAG

AAGAAGAAGAAGGAGGATGTGAACTG (SEQ ID NO: 48)
CAACGAAGGAAATATAGATCAAACAAAGGAGAAAGTCCTGTGGAGCCTGC

AGAGCCTTGTCGTTACAGCTGCCCCAGGGAGGAGGAGGGCAGCACCATCC

CCATCCAGGAGGATTACCGAAAACCGGAGCCTGCCTGCTCCCCC (SEQ ID NO: 49)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC
```

In one embodiment, the intracellular signaling domain of the chimeric receptor of the invention comprises:
  the amino acid sequence of a 4-1BB intracellular domain of SEQ ID NO: 44 or an amino acid sequence with 95-99% identity to SEQ ID NO: 44, and/or the amino acid sequence of a CD27 intracellular domain of SEQ ID NO: 45 or an amino acid sequence with 95-99% identity to SEQ ID NO: 45, and/or the amino acid sequence of a CD28 intracellular domain of SEQ ID NO: 46 or an amino acid sequence with 95-99% identity to SEQ ID NO: 46; and the amino acid sequence of a CD3-zeta intracellular domain of SEQ ID NO: 38-41, or an amino acid sequence with 95-99% identity to SEQ ID NO: 38-41;

wherein the sequences comprised in the intracellular domain are expressed in the same frame and as a single polypeptide chain.

Thus, in one embodiment, the nucleic acid sequence encoding the intracellular signaling domain of the chimeric receptor of the invention comprises:

the nucleic acid sequence of a 4-1BB intracellular domain of SEQ ID NO: 47 or a nucleic acid sequence with 95-99% identity to SEQ ID NO: 47, and/or the nucleic acid sequence of a CD27 intracellular domain of SEQ ID NO: 48 or a nucleic acid sequence with 95-99% identity to SEQ ID NO: 48, and/or the nucleic acid sequence of a CD28 intracellular domain of SEQ ID NO: 49 or a nucleic acid sequence with 95-99% identity to SEQ ID NO: 49; and the nucleic acid sequence of a CD3-zeta intracellular domain of SEQ ID NO: 42 or SEQ ID NO: 43, or a sequence with 95-99% identity to SEQ ID NO: 42 or SEQ ID NO: 43.

In one embodiment, the intracellular signaling domain of the chimeric receptor of the invention comprises at least two different domains (e.g. a primary signaling domain and at least one intracellular domain of a T cell costimulatory molecule) that may be linked to each other in a random or in a specified order.

Optionally, a short oligo- or polypeptide linker, for example, between 2 and 10 amino acids (e.g., 2, 3, 4, 5, 6, 7, 8, 9, or 10 amino acids) in length may form the linkage between distinct signaling domains. In one embodiment, a glycine-serine doublet (GS) is used as a suitable linker. In one embodiment, a single amino acid, e.g., an alanine (A), a glycine (G), is used as a suitable linker.

In another embodiment, the intracellular signaling domain of the chimeric receptor of the invention comprise two or more, e.g., 2, 3, 4, 5, or more, costimulatory signaling domains. In another embodiment, the two or more, e.g., 2, 3, 4, 5, or more costimulatory signaling domains, are separated by a linker molecule, e.g., a linker molecule as described hereinabove.

In one embodiment, the intracellular signaling domain of the chimeric receptor of the invention comprises the primary signaling domain of CD3-zeta (preferably SEQ ID NO: 38, 39, 40 or 41) and the co-stimulatory signaling domain of CD28 (preferably SEQ ID NO: 46).

In another embodiment, the intracellular signaling domain of the chimeric receptor of the invention comprises the primary signaling domain of CD3-zeta (preferably SEQ ID NO: 38, 39, 40 or 41) and the co-stimulatory signaling domain of 4-1BB (preferably SEQ ID NO: 44).

In another embodiment, the intracellular signaling domain of the chimeric receptor of the invention comprises the signaling domain of CD3-zeta (preferably SEQ ID NO: 38, 39, 40 or 41) and the signaling domain of CD27 (preferably SEQ ID NO: 45).

In one embodiment, the chimeric receptor of the invention further comprises a leader sequence located N-terminally from the HLA-A2 binding domain. A non-limiting example of leader sequence is a leader sequence of CD8, that may comprise or consists in the sequence SEQ ID NO: 50.

(SEQ ID NO: 50)
MALPVTALLLPLALLLHAARP

In one embodiment, the chimeric receptor further comprises a tag, such as, for example, a tag for quality control, enrichment, tracking in vivo and the like. Said Tag may be localized N-terminally, C-terminally and/or internally. Examples of tags that may be used in the chimeric receptor of the invention are well known by the skilled artisan. For example, but without limitation, a tag used in the invention can be a tag selected from the group comprising or consisting of Hemagglutinin Tag, Poly Arginine Tag, Poly Histidine Tag, Myc Tag, Strep Tag, S-Tag, HAT Tag, 3x Flag Tag, Calmodulin-binding peptide Tag, SBP Tag, Chitin binding domain Tag, GST Tag, Maltose-Binding protein Tag, Fluorescent Protein Tag (e.g., eGFP, having the sequence SEQ ID NO: 68), T7 Tag, V5 Tag and Xpress Tag. Other examples of tag include, without limitation, NWSHPQFEK (SEQ ID NO: 51) or SAWSHPQFEK (SEQ ID NO: 52).

(SEQ ID NO: 51)
NWSHPQFEK (SEQ ID NO: 52)
SAWSHPQFEK (SEQ ID NO: 68)
MVSKGEELFTGVVPILVELDGDVNGHKFSVSGEGEGDATYGKLTLKFI

CTTGKLPVPWPTLVTTLTYGVQCFSRYPDHMKQHDFFKSAMPEGYVQE

RTIFFKDDGNYKTRAEVKFEGDTLVNRIELKGIDFKEDGNILGHKLEY

NYNSHNVYIMADKQKNGIKVNFKIRHNIEDGSVQLADHYQQNTPIGDG

PVLLPDNHYLSTQSALSKDPNEKRDHMVLLEFVTAAGITLGMDELYK

In one embodiment, the chimeric receptor of the invention further comprises a ribosomal cleavage site located C-terminally from the intracellular signaling domain. A non-limiting example of a ribosomal cleavage site is the P2A ribosomal cleavage site sequence ASGSGATNFSLLKQAGDVEENPGP (SEQ ID NO: 61).

According to a first embodiment, the chimeric receptor of the invention comprises a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A, more preferably one of SEQ ID NO: 70-72 or 74-76), optionally an extracellular hinge domain, a transmembrane domain, and a T cell primary signaling domain.

In one embodiment, the chimeric receptor of the invention comprises a HLA-A2 marker binding domain; a transmembrane domain of CD8 (preferably SEQ ID NO: 34); and a CD3-zeta primary signaling domain (preferably SEQ ID NO: 38, 39, 40 or 41).

In one embodiment, the chimeric receptor of the invention comprises a HLA-A2 marker binding domain; a transmembrane domain of CD28 (preferably SEQ ID NO: 36); and a CD3-zeta primary signaling domain (preferably SEQ ID NO: 38, 39, 40 or 41).

In another embodiment, the chimeric receptor of the invention comprises a HLA-A2 marker binding domain; a hinge domain of CD8 (preferably SEQ ID NO: 26); a transmembrane domain of CD8 (preferably SEQ ID NO: 34); and a CD3-zeta primary signaling domain (preferably SEQ ID NO: 38, 39, 40 or 41). In one embodiment, the chimeric receptor of the invention comprises a HLA-A2 binding domain; a hinge domain of CD8 (preferably SEQ ID NO: 26); a transmembrane domain of CD28 (preferably SEQ ID NO: 36); and a CD3-zeta primary signaling domain (preferably SEQ ID NO: 38, 39, 40 or 41).

In another embodiment, the chimeric receptor of the invention comprises a HLA-A2 binding domain; a hinge domain of IgG4 (preferably SEQ ID NO: 28); a transmembrane domain of CD8 (preferably SEQ ID NO: 34); and a CD3-zeta primary signaling domain (preferably SEQ ID NO: 38, 39, 40 or 41). In one embodiment, the chimeric receptor of the invention comprises a HLA-A2 binding domain; a hinge domain of IgG4 (preferably SEQ ID NO: 28); a transmembrane domain of CD28 (preferably SEQ ID NO: 36); and a CD3-zeta primary signaling domain (preferably SEQ ID NO: 38, 39, 40 or 41).

In another embodiment, the chimeric receptor of the invention comprises a HLA-A2 binding domain; a hinge domain of IgD (preferably SEQ ID NO: 30); a transmembrane domain of CD8 (preferably SEQ ID NO: 34); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD28 (preferably SEQ ID NO: 36); and a CD3-zeta primary signaling domain (preferably SEQ ID NO: 38, 39, 40 or 41).

In another embodiment, the chimeric receptor of the invention comprises a HLA-A2 binding domain; a hinge domain of CD28 (preferably SEQ ID NO: 32); a transmembrane domain of CD8 (preferably SEQ ID NO: 34); and a CD3-zeta primary signaling domain (preferably SEQ ID NO: 38, 39, 40 or 41). In one embodiment, the chimeric receptor of the invention comprises a HLA-A2 binding domain; a hinge domain of CD28 (preferably SEQ ID NO: 32); a transmembrane domain of CD28 (preferably SEQ ID NO: 36); and a CD3-zeta primary signaling domain (preferably SEQ ID NO: 38, 39, 40 or 41).

According to a second embodiment, the chimeric receptor of the invention comprises a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A, more preferably one of SEQ ID NO: 70-72 or 74-76), optionally an extracellular hinge domain, a transmembrane domain, a single intracellular domain of a T cell costimulatory molecule and a T cell primary signaling domain.

In one embodiment, the chimeric receptor of the invention comprises a HLA-A2 binding domain; a transmembrane domain of CD8 (preferably SEQ ID NO: 34); an intracellular domain of 4-1BB (preferably SEQ ID NO: 44); and a CD3-zeta primary signaling domain (preferably SEQ ID NO: 38, 39, 40 or 41). In one embodiment, the chimeric receptor of the invention comprises a HLA-A2 binding domain; a transmembrane domain of CD8 (preferably SEQ ID NO: 34); an intracellular domain of CD27 (preferably SED ID NO: 45); and a CD3-zeta primary signaling domain (preferably SEQ ID NO: 38, 39, 40 or 41).

In one embodiment, the chimeric receptor of the invention comprises a HLA-A2 binding domain; a transmembrane domain of CD8 (preferably SEQ ID NO: 34); an intracellular domain of CD28 (preferably SED ID NO: 46); and a CD3-zeta primary signaling domain (preferably SEQ ID NO: 38, 39, 40 or 41).

In one embodiment, the chimeric receptor of the invention comprises a HLA-A2 binding domain; a transmembrane domain of CD28 (preferably SEQ ID NO: 36); an intracellular domain of 4-1BB (preferably SED ID NO: 44); and a CD3-zeta primary signaling domain (preferably SEQ ID NO: 38, 39, 40 or 41). In one embodiment, the chimeric receptor of the invention comprises a HLA-A2 binding domain; a transmembrane domain of CD28 (preferably SEQ ID NO: 36); an intracellular domain of CD27 (preferably SED ID NO: 45); and a CD3-zeta primary signaling domain (preferably SEQ ID NO: 38, 39, 40 or 41).

In one embodiment, the chimeric receptor of the invention comprises a HLA-A2 binding domain; a transmembrane domain of CD28 (preferably SEQ ID NO: 36); an intracellular domain of CD28 (preferably SED ID NO: 46); and a CD3-zeta primary signaling domain (preferably SEQ ID NO: 38, 39, 40 or 41).

In another embodiment, the chimeric receptor of the invention comprises a HLA-A2 binding domain; a hinge domain of CD8 (preferably SEQ ID NO: 26); a transmembrane domain of CD8 (preferably SEQ ID NO: 34); an intracellular domain of 4-1BB (preferably SED ID NO: 44); and a CD3-zeta primary signaling domain (preferably SEQ ID NO: 38, 39, 40 or 41). In one embodiment, the chimeric receptor of the invention comprises a HLA-A2 binding domain; a hinge domain of CD8 (preferably SEQ ID NO: 26); a transmembrane domain of CD8 (preferably SEQ ID NO: 34); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of CD8 (preferably SEQ ID NO: 26); a transmembrane domain of CD8 (preferably SEQ ID NO: 34); an intracellular domain of CD28 (preferably SEQ ID NO: 46); and a CD3-zeta primary signaling domain (preferably SEQ ID NO: 38, 39, 40 or 41).

In one embodiment, the chimeric receptor of the invention comprises a HLA-A2 binding domain; a hinge domain of CD8 (preferably SEQ ID NO: 26); a transmembrane domain of CD28 (preferably SEQ ID NO: 36); an intracellular domain of 4-1BB (preferably SEQ ID NO: 44); and a CD3-zeta primary signaling domain (preferably SEQ ID NO: 38, 39, 40 or 41). In one embodiment, the chimeric receptor of the invention comprises a HLA-A2 binding domain; a hinge domain of CD8 (preferably SEQ ID NO: 26); a transmembrane domain of CD28 (preferably SEQ ID NO: 36); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of CD8 (preferably SEQ ID NO: 26); a transmembrane domain of CD28 (preferably SEQ ID NO: 36); an intracellular domain of CD28 (preferably SEQ ID NO: 46); and a CD3-zeta primary signaling domain (preferably SEQ ID NO: 38, 39, 40 or 41).

In another embodiment, the chimeric receptor of the invention comprises a HLA-A2 binding domain; a hinge domain of IgG4 (preferably SEQ ID NO: 28); a transmembrane domain of CD8 (preferably SEQ ID NO: 34); an intracellular domain of 4-1BB (preferably SED ID NO: 44); and a CD3-zeta primary signaling domain (preferably SEQ ID NO: 38, 39, 40 or 41). In one embodiment, the chimeric receptor of the invention comprises a HLA-A2 binding domain; a hinge domain of IgG4 (preferably SEQ ID NO: 28); a transmembrane domain of CD8 (preferably SEQ ID NO: 34); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of IgG4 (preferably SEQ ID NO: 28); a transmembrane domain of CD8 (preferably SEQ ID NO: 34); an intracellular domain of CD28 (preferably SEQ ID NO: 46); and a CD3-zeta primary signaling domain (preferably SEQ ID NO: 38, 39, 40 or 41).

In one embodiment, the chimeric receptor of the invention comprises a HLA-A2 binding domain; a hinge domain of IgG4 (preferably SEQ ID NO: 28); a transmembrane domain of CD28 (preferably SEQ ID NO: 36); an intracellular domain of 4-1BB (preferably SED ID NO: 44); and a CD3-zeta primary signaling domain (preferably SEQ ID NO: 38, 39, 40 or 41). In one embodiment, the chimeric receptor of the invention comprises a HLA-A2 binding domain; a hinge domain of IgG4 (preferably SEQ ID NO: 28); a transmembrane domain of CD28 (preferably SEQ ID NO: 36); an intracellular domain of CD27 (preferably SED ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of IgG4 (preferably SEQ ID NO: 28); a transmembrane domain of CD28 (preferably SEQ ID NO: 36); an intracellular domain of CD28 (preferably SED ID NO: 46); and a CD3-zeta primary signaling domain (preferably SEQ ID NO: 38, 39, 40 or 41).

In another embodiment, the chimeric receptor of the invention comprises a HLA-A2 binding domain; a hinge domain of IgD (preferably SEQ ID NO: 30); a transmembrane domain of CD8 (preferably SEQ ID NO: 34); an intracellular domain of 4-1BB (preferably SED ID NO: 44); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD8 (preferably SEQ ID NO: 34); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD8 (preferably SEQ ID NO: 34); an intracellular domain of CD28 (preferably SEQ ID NO: 46); and a CD3-zeta primary signaling domain (preferably SEQ ID NO: 38, 39, 40 or 41).

In one embodiment, the chimeric receptor of the invention comprises a HLA-A2 binding domain; a hinge domain of IgD (preferably SEQ ID NO: 30); a transmembrane domain of CD28 (preferably SEQ ID NO: 36); an intracellular domain of 4-1BB (preferably SED ID NO: 44); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD28 (preferably SEQ ID NO: 36); an intracellular domain of CD27 (preferably SED ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD28 (preferably SEQ ID NO: 36); an intracellular domain of CD28 (preferably SEQ ID NO: 46); and a CD3-zeta primary signaling domain (preferably SEQ ID NO: 38, 39, 40 or 41).

In another embodiment, the chimeric receptor of the invention comprises a HLA-A2 binding domain; a hinge domain of CD28 (preferably SEQ ID NO: 32); a transmembrane domain of CD8 (preferably SEQ ID NO: 34); an intracellular domain of 4-1BB (preferably SED ID NO: 44); and a CD3-zeta primary signaling domain (preferably SEQ ID NO: 38, 39, 40 or 41). In one embodiment, the chimeric receptor of the invention comprises a HLA-A2 binding domain; a hinge domain of CD28 (preferably SEQ ID NO: 32); a transmembrane domain of CD8 (preferably SEQ ID NO: 34); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of CD28 (preferably SEQ ID NO: 32); a transmembrane domain of CD8 (preferably SEQ ID NO: 34); an intracellular domain of CD28 (preferably SEQ ID NO: 46); and a CD3-zeta primary signaling domain (preferably SEQ ID NO: 38, 39, 40 or 41).

In one embodiment, the chimeric receptor of the invention comprises a HLA-A2 binding domain; a hinge domain of CD28 (preferably SEQ ID NO: 32); a transmembrane domain of CD28 (preferably SEQ ID NO: 36); an intracellular domain of 4-1BB (preferably SED ID NO: 44); and a CD3-zeta primary signaling domain (preferably SEQ ID NO: 38, 39, 40 or 41). In one embodiment, the chimeric receptor of the invention comprises a HLA-A2 binding domain; a hinge domain of CD28 (preferably SEQ ID NO: 32); a transmembrane domain of CD28 (preferably SEQ ID NO: 36); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of CD28 (preferably SEQ ID NO: 32); a transmembrane domain of CD28 (preferably SEQ ID NO: 36); an intracellular domain of CD28 (preferably SED ID NO: 46); and a CD3-zeta primary signaling domain (preferably SEQ ID NO: 38, 39, 40 or 41).

According to a third embodiment, the chimeric receptor of the invention comprises a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_{15}$ is L or F and $X_{19}$ is G or A, more preferably one of SEQ ID NO: 70-72 or 74-76), optionally an extracellular hinge domain, a transmembrane domain, two intracellular domains of a T cell costimulatory molecule and a T cell primary signaling domain.

In one embodiment, the chimeric receptor of the invention comprises a HLA-A2 binding domain; a transmembrane domain of CD8 (preferably SEQ ID NO: 34); an intracellular domain of 4-1BB (preferably SED ID NO: 44); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a transmembrane domain of CD8 (preferably SEQ ID NO: 34); an intracellular domain of 4-1BB (preferably SEQ ID NO: 44); an intracellular domain of CD28 (preferably SEQ ID NO: 46); and a CD3-zeta primary signaling domain (preferably SEQ ID NO: 38, 39, 40 or 41). In one embodiment, the chimeric receptor of the invention comprises a HLA-A2 binding domain; a transmembrane domain of CD8 (preferably SEQ ID NO: 34); an intracellular domain of CD27 (preferably SEQ ID NO: 45); an intracellular domain of CD28 (preferably SEQ ID NO: 46); and a CD3-zeta primary signaling domain (preferably SEQ ID NO: 38, 39, 40 or 41).

In one embodiment, the chimeric receptor of the invention comprises a HLA-A2 binding domain; a transmembrane domain of CD28 (preferably SEQ ID NO: 36); an intracellular domain of 4-1BB (preferably SED ID NO: 44); an intracellular domain of CD27 (preferably SED ID NO: 45); and a CD3-zeta primary signaling domain (preferably SEQ ID NO: 38, 39, 40 or 41). In one embodiment, the chimeric receptor of the invention comprises a HLA-A2 binding domain; a transmembrane domain of CD28 (preferably SEQ ID NO: 36); an intracellular domain of 4-1BB (preferably SED ID NO: 44); an intracellular domain of CD28 (preferably SEQ ID NO: 46); and a CD3-zeta primary signaling domain (preferably SEQ ID NO: 38, 39, 40 or 41). In one embodiment, the chimeric receptor of the invention comprises a HLA-A2 binding domain; a transmembrane domain of CD28 (preferably SEQ ID NO: 36); an intracellular domain of CD27 (preferably SED ID NO: 45); an intracellular domain of CD28 (preferably SED ID NO: 46); and a CD3-zeta primary signaling domain (preferably SEQ ID NO: 38, 39, 40 or 41).

In another embodiment, the chimeric receptor of the invention comprises a HLA-A2 binding domain; a hinge domain of CD8 (preferably SEQ ID NO: 26); a transmembrane domain of CD8 (preferably SEQ ID NO: 34); an intracellular domain of 4-1BB (preferably SED ID NO: 44); an intracellular domain of CD27 (preferably SED ID NO: 45); and a CD3-zeta primary signaling domain (preferably SEQ ID NO: 38, 39, 40 or 41).

In one embodiment, the chimeric receptor of the invention comprises a HLA-A2 binding domain; a hinge domain of CD8 (preferably SEQ ID NO: 26); a transmembrane domain of CD8 (preferably SEQ ID NO: 34); an intracellular domain of 4-1BB (preferably SED ID NO: 44); an intracellular domain of CD28 (preferably SED ID NO: 46); and a CD3-zeta primary signaling domain (preferably SEQ ID NO: 38, 39, 40 or 41). In one embodiment, the chimeric receptor of the invention comprises a HLA-A2 binding domain; a hinge domain of CD8 (preferably SEQ ID NO: 26); a transmembrane domain of CD8 (preferably SEQ ID NO: 34); an intracellular domain of CD27 (preferably SEQ ID NO: 45); an intracellular domain of CD28 (preferably SEQ ID NO: 46); and a CD3-zeta primary signaling domain (preferably SEQ ID NO: 38, 39, 40 or 41).

In one embodiment, the chimeric receptor of the invention comprises a HLA-A2 binding domain; a hinge domain of CD8 (preferably SEQ ID NO: 26); a transmembrane domain of CD28 (preferably SEQ ID NO: 36); an intracellular domain of 4-1BB (preferably SED ID NO: 44); an intracellular domain of CD27 (preferably SED ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of CD8 (preferably SEQ ID NO: 26); a transmembrane domain of CD28 (preferably SEQ ID NO: 36); an intracellular domain of 4-1BB (preferably SEQ ID NO: 44); an intracellular domain of CD28 (preferably SEQ ID NO: 46); and a CD3-zeta primary signaling domain (preferably SEQ ID NO: 38, 39, 40 or 41). In one embodiment, the chimeric receptor of the invention comprises a HLA-A2 binding domain; a hinge domain of CD8 (preferably SEQ ID NO: 26); a transmembrane domain of CD28 (preferably SEQ ID NO: 36); an intracellular domain of CD27 (preferably SED ID NO: 45); an intracellular domain of CD28 (preferably SEQ ID NO: 46); and a CD3-zeta primary signaling domain (preferably SEQ ID NO: 38, 39, 40 or 41).

In another embodiment, the chimeric receptor of the invention comprises a HLA-A2 binding domain; a hinge domain of IgG4 (preferably SEQ ID NO: 28); a transmembrane domain of CD8 (preferably SEQ ID NO: 34); an intracellular domain of 4-1BB (preferably SED ID NO: 44); an intracellular domain of CD27 (preferably SEQ ID NO: 45); and a CD3-zeta primary signaling domain (preferably SEQ ID NO: 38, 39, 40 or 41).

In one embodiment, the chimeric receptor of the invention comprises a HLA-A2 binding domain; a hinge domain of IgG4 (preferably SEQ ID NO: 28); a transmembrane domain of CD8 (preferably SEQ ID NO: 34); an intracellular domain of 4-1BB (preferably SED ID NO: 44); an intracellular domain of CD28 (preferably SEQ ID NO: 46); and a CD3-zeta primary signaling domain (preferably SEQ ID NO: 38, 39, 40 or 41). In one embodiment, the chimeric receptor of the invention comprises a HLA-A2 binding domain; a hinge domain of IgG4 (preferably SEQ ID NO: 28); a transmembrane domain of CD8 (preferably SEQ ID NO: 34); an intracellular domain of CD27 (preferably SEQ ID NO: 45); an intracellular domain of CD28 (preferably SED ID NO: 46); and a CD3-zeta primary signaling domain (preferably SEQ ID NO: 38, 39, 40 or 41).

In one embodiment, the chimeric receptor of the invention comprises a HLA-A2 binding domain; a hinge domain of IgG4 (preferably SEQ ID NO: 28); a transmembrane domain of CD28 (preferably SEQ ID NO: 36); an intracellular domain of 4-1BB (preferably SED ID NO: 44); an intracellular domain of CD27 (preferably SED ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of IgG4 (preferably SEQ ID NO: 28); a transmembrane domain of CD28 (preferably SEQ ID NO: 36); an intracellular domain of 4-1BB (preferably SEQ ID NO: 44); an intracellular domain of CD28 (preferably SEQ ID NO: 46); and a CD3-zeta primary signaling domain (preferably SEQ ID NO: 38, 39, 40 or 41). In one embodiment, the chimeric receptor of the invention comprises a HLA-A2 binding domain; a hinge domain of IgG4 (preferably SEQ ID NO: 28); a transmembrane domain of CD28 (preferably SEQ ID NO: 36); an intracellular domain of CD27 (preferably SED ID NO: 45); an intracellular domain of CD28 (preferably SEQ ID NO: 46); and a CD3-zeta primary signaling domain (preferably SEQ ID NO: 38, 39, 40 or 41).

In another embodiment, the chimeric receptor of the invention comprises a HLA-A2 binding domain; a hinge domain of IgD, preferably comprising the amino acid sequence SEQ ID NO: 30; a transmembrane domain of CD8 (preferably SEQ ID NO: 34); an intracellular domain of 4-1BB (preferably SEQ ID NO: 44); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD8 (preferably SEQ ID NO: 34); an intracellular domain of 4-1BB (preferably SED ID NO: 44); an intracellular domain of CD28 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD8 (preferably SEQ ID NO: 34); an intracellular domain of CD27 (preferably SEQ ID NO: 45); an intracellular domain of CD28 (preferably SEQ ID NO: 46); and a CD3-zeta primary signaling domain (preferably SEQ ID NO: 38, 39, 40 or 41).

In one embodiment, the chimeric receptor of the invention comprises a HLA-A2 binding domain; a hinge domain of IgD (preferably SEQ ID NO: 30); a transmembrane domain of CD28 (preferably SEQ ID NO: 36); an intracellular domain of 4-1BB (preferably SED ID NO: 44); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD28 (preferably SEQ ID NO: 36); an intracellular domain of 4-1BB (preferably SED ID NO: 44); an intracellular domain of CD28 (preferably SED ID NO: 46); and a CD3-zeta primary signaling domain (preferably SEQ ID NO: 38, 39, 40 or 41). In one embodiment, the chimeric receptor of the invention comprises a HLA-A2 binding domain; a hinge domain of IgD (preferably SEQ ID NO: 30); a transmembrane domain of CD28 (preferably SEQ ID NO: 36); an intracellular domain of CD27 (preferably SED ID NO: 45); an intracellular domain of CD28 (preferably SED ID NO: 46); and a CD3-zeta primary signaling domain (preferably SEQ ID NO: 38, 39, 40 or 41).

In another embodiment, the chimeric receptor of the invention comprises a HLA-A2 binding domain; a hinge domain of CD28 (preferably SEQ ID NO: 34); a transmembrane domain of CD8 (preferably SEQ ID NO: 36); an intracellular domain of 4-1BB (preferably SED ID NO: 44); an intracellular domain of CD27 (preferably SEQ ID NO: 45); and a CD3-zeta primary signaling domain (preferably SEQ ID NO: 38, 39, 40 or 41).

In one embodiment, the chimeric receptor of the invention comprises a HLA-A2 binding domain; a hinge domain of CD28 (preferably SEQ ID NO: 32); a transmembrane domain of CD8 (preferably SEQ ID NO: 34); an intracellular domain of 4-1BB (preferably SED ID NO: 44); an intracellular domain of CD28 (preferably SEQ ID NO: 46); and a CD3-zeta primary signaling domain (preferably SEQ ID NO: 38, 39, 40 or 41). In one embodiment, the chimeric receptor of the invention comprises a HLA-A2 binding domain; a hinge domain of CD28 (preferably SEQ ID NO: 32); a transmembrane domain of CD8 (preferably SEQ ID NO: 34); an intracellular domain of CD27 (preferably SEQ ID NO: 45); an intracellular domain of CD28 (preferably SEQ ID NO: 46); and a CD3-zeta primary signaling domain (preferably SEQ ID NO: 38, 39, 40 or 41).

In one embodiment, the chimeric receptor of the invention comprises a HLA-A2 binding domain; a hinge domain of CD28 (preferably SEQ ID NO: 32); a transmembrane domain of CD28 (preferably SEQ ID NO: 36); an intracellular domain of 4-1BB (preferably SEQ ID NO: 44); an intracellular domain of CD27 (preferably SEQ ID NO: 45); and a CD3-zeta primary signaling domain (preferably SEQ ID NO: 38, 39, 40 or 41). In one embodiment, the chimeric receptor of the invention comprises a HLA-A2 binding domain; a hinge domain of CD28 (preferably SEQ ID NO: 32); a transmembrane domain of CD28 (preferably SEQ ID NO: 36); an intracellular domain of 4-1BB (preferably SEQ ID NO: 44); an intracellular domain of CD28 (preferably SEQ ID NO: 46); and a CD3-zeta primary signaling domain (preferably SEQ ID NO: 38, 39, 40 or 41). In one embodiment, the chimeric receptor of the invention comprises a HLA-A2 binding domain; a hinge domain of CD28 (preferably SEQ ID NO: 32); a transmembrane domain of CD28 (preferably SEQ ID NO: 36); an intracellular domain of CD27 (preferably SED ID NO: 45); an intracellular domain of CD28 (preferably SED ID NO: 46); and a CD3-zeta primary signaling domain (preferably SEQ ID NO: 38, 39, 40 or 41).

In one embodiment, the chimeric receptor of the invention comprises (i) a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_5$ is K or T, $X_{16}$ is V or L, $X_{17}$ is A or P, $X_{18}$ is L or F and $X_{19}$ is G or A, more preferably one of SEQ ID NO: 70-72 or 74-76), (ii) a hinge region of human CD28, (iii) a transmembrane domain of human CD28, (iv) an intracellular domain of human CD28 and (v) an intracellular domain of human CD3ζ chain.

In one embodiment, the part of the chimeric receptor comprising a hinge region of human CD28, a transmembrane domain of human CD28, an intracellular domain of human CD28 and an intracellular domain of human CD3 chain corresponds to the amino acid sequence of SEQ ID NO: 53 or 54 or an amino acid sequence with 95-99% identity to SEQ ID NO: 53 or 54.

```
                                              (SEQ ID NO: 53)
AAAIEVMYPPPYLDNEKSNGTIIHVKGKHLCPSPLFPGPSKPFWVLVV

VGGVLACYSLLVTVAFIIFWVRSKRSRLLHSDYMNMTPRRPGPTRKHY

QPYAPPRDFAAYRSRVKFSRSADAPAYQQGQNQLYNELNLGRREEYDV

LDKRRGRDPEMGGKPRRKNPQEGLYNELQKDKMAEAYSEIGMKGERRR

GKGHDGLYQGLSTATKDTYDALHMQALPPR (SEQ ID NO: 54)
AAAIEVMYPPPYLDNEKSNGTIIHVKGKHLCPSPLFPGPSKPFWVLVV

VGGVLACYSLLVTVAFIIFWVRSKRSRLLHSDYMNMTPRRPGPTRKHY

QPYAPPRDFAAYRSRVKFSRSADAPAYQQGQNQLYNELNLGRREEYDV

LDKRRGRDPEMGGKPQRRKNPQEGLYNELQKDKMAEAYSEIGMKGERR

RGKGHDGLYQGLSTATKDTYDALHMQALPPR
```

In one embodiment, the chimeric receptor of the invention comprises a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or, $X_{15}$ is K or T, $X_{16}$ is V or L, $X_{17}$ is A or P, $X_{18}$ is L or F and $X_{19}$ is G or A, more preferably one of SEQ ID NO: 70-72 or 74-76), linked to an amino acid sequence of SEQ ID NO: 53 or 54 or a sequence or an amino acid sequence with 95-99% identity to SEQ ID NO: 53 or 54.

In another embodiment, the chimeric receptor of the invention comprises (i) a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_1$ is S or T, $X_{12}$ is L or Q, $X_3$ is S or A, $X_{14}$ is V or I, $X_{15}$ is K or T, $X_{16}$ is V or L, $X_{17}$ is A or P, $X_{18}$ is L or F and $X_{19}$ is G or A, more preferably one of SEQ ID NO: 70-72 or 74-76), (ii) a hinge region of human CD8, (iii) a transmembrane domain of human CD8, (iv) an intracellular domain of human 4-1BB and (v) an intracellular domain of human CD3ζ. In one embodiment, the part of the chimeric receptor comprising a hinge region of human CD8, a transmembrane domain of human CD8, an intracellular domain of human 4-1BB and an intracellular domain of human CD3ζ comprises or consists in the amino acid sequence SEQ ID NO:

55, 56, 57 or 58, or any amino acid sequence with 95-99% identity with SEQ ID NO: 55-58.

(SEQ ID NO: 55)
TTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDG
CSCRFPEEEEGGCELRVKFSRSADAPAYQQGQNQLYNELNLGRREEYD
VLDKRRGRDPEMGGKPRRKNPQEGLYNELQKDKMAEAYSEIGMKGERR
RGKGHDGLYQGLSTATKDTYDALHMQALPPR (SEQ ID NO: 56)
NWSHPQFEKMHTTTPAPRPPTPAPTIASQPLSLRPEACRPAAGGAVHT
RGLDFACDIYIWAPLAGTCGVLLLSLVITLYCKRGRKKLLYIFKQPFM
RPVQTTQEEDGCSCRFPEEEEGGCELTRRVKFSRSADAPAYQQGQNQL
YNELNLGRREEYDVLDKRRGRDPEMGGKPRRKNPQEGLYNELQKDKMA
EAYSEIGMKGERRRGKGHDGLYQGLSTATKDTYDALHMQALPPR (SEQ ID NO: 57)
TTTPAPRPPTPAPTIASQPLSLRPEACRPAAGGAVHTRGLDFACDIYI
WAPLAGTCGVLLLSLVITLYCKRGRKKLLYIFKQPFMRPVQTTQEEDG
CSCRFPEEEEGGCELRVKFSRSADAPAYQQGQNQLYNELNLGRREEYD
VLDKRRGRDPEMGGKPQRRKNPQEGLYNELQKDKMAEAYSEIGMKGER
RRGKGHDGLYQGLSTATKDTYDALHMQALPPR (SEQ ID NO: 58)
NWSHPQFEKMHTTTPAPRPPTPAPTIASQPLSLRPEACRPAAGGAVHT
RGLDFACDIYIWAPLAGTCGVLLLSLVITLYCKRGRKKLLYIFKQPFM
RPVQTTQEEDGCSCRFPEEEEGGCELTRRVKFSRSADAPAYQQGQNQL
YNELNLGRREEYDVLDKRRGRDPEMGGKPQRRKNPQEGLYNELQKDKM
AEAYSEIGMKGERRRGKGHDGLYQGLSTATKDTYDALHMQALPPR

In one embodiment, the chimeric receptor of the invention comprises a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_6$ is V or L, $X_7$ is A or P, $X_{18}$ is L or F and $X_{19}$ is G or A, more preferably one of SEQ ID NO: 70-72 or 74-76), linked to an amino acid sequence of SEQ ID NO: 55-58 or a sequence or an amino acid sequence with 95-99% identity to SEQ ID NO: 55-58.

In one embodiment, the chimeric receptor of the invention comprises or consists in a sequence as set forth in SEQ ID NO: 77, or any amino acid sequence with 95-99% identity with SEQ ID NO: 77

(SEQ ID NO: 77)
SQVQLVQSGPEVKKPGASVKVSCKASGYTFTSYHIQWVRQAPGQGLEW
IGWIYPGDGSTQYNEKFKGRVTITADKSTSTAYMELSSLTSEDTAVYY
CAREGTYYAMDYWGQGTSVTVSSGGGGSGGGGSGGGGSDX$_1$VMTQX$_2$P
X$_3$X$_4$LX$_5$VX$_6$X$_7$GX$_8$X$_9$X$_{10}$X$_{11}$ISCRSSQSIVHSNGNTYLEWYX$_{12}$Q
KPGQX$_{13}$PRLLIYKVSNRFSGX$_{14}$PDRFSGSGSGTDFTLX$_{15}$ISRX$_{16}$
EX$_{17}$EDX$_{18}$X$_{19}$VYYCFQGSHVPRTFGGGTKLEIKRRTTTPAPRPPTP

APTIASQPLSLRPEACRPAAGGAVHTRGLDFACDIYIWAPLAGTCGVL
LLSLVITLYCKRGRKKLLYIFKQPFMRPVQTTQEEDGCSCRFPEEEEG
GCELRVKFSRSADAPAYQQGQNQLYNELNLGRREEYDVLDKRRGRDPE
MGGKPRRKNPQEGLYNELQKDKMAEAYSEIGMKGERRRGKGHDGLYQG
LSTATKDTYDALHMQALPPR wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_{17}$ is A or P, $X_8$ is L or F and $X_{19}$ is G or A.

In one embodiment, the chimeric receptor of the invention further comprises a leader sequence in N-term, preferably having the sequence SEQ ID NO: 50, and comprises or consists in a sequence SEQ ID NO: 81, wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, Xu is S or T, $X_{12}$ is L or Q, $X_{13}$ is S or A, $X_{14}$ is V or I, $X_{15}$ is K or T, $X_{16}$ is V or L, $X_{17}$ is A or P, $X_{18}$ is L or F and $X_{19}$ is G or A, or any amino acid sequence with 95-99% identity with SEQ ID NO: 81.

(SEQ ID NO: 81)
MALPVTALLLPLALLLHAARPSQVQLVQSGPEVKKPGASVKVSCKASG
YTFTSYHIQWVRQAPGQLEWIGWIYPGDGSTQYNEKFKGRVTITADKS
TSTAYMELSSLTSEDTAVYYCAREGTYYAMDYWGQGTSVTVSSGGGGS
GGGGSGGGGSDX$_1$VMTQX$_2$PX$_3$XX$_4$LX$_5$VX$_6$X$_7$GX$_8$X$_9$X$_{10}$X$_{11}$ISCR
SSQSIVHSNGNTYLEWYX$_{12}$QKPGQX$_{13}$PRLLIYKVSNRFSGX14PDR
FSGSGSGTDFTLX15ISRX16EX17EDX18X$_{19}$VYYCFQGSHVPRTFG
GGTKLEIKRRTTTPAPRPPTPAPTIASQPLSLRPEACRPAAGGAVHTR
GLDFACDIYIWAPLAGTCGVLLLSLVITLYCKRGRKKLLYIFKQPFMR
PVQTTQEEDGCSCRFPEEEEGGCELRVKFSRSADAPAYQQGQNQLYNE
LNLGRREEYDVLDKRRGRDPEMGGKPRRKNPQEGLYNELQKDKMAEAY
SEIGMKGERRRGKGHDGLYQGLSTATKDTYDALHMQALPPR

In one embodiment, the chimeric receptor of the invention comprises or consists in a sequence as set forth in SEQ ID NO: 78, or any amino acid sequence with 95-99% identity with SEQ ID NO: 78

(SEQ ID NO: 78)
SQVQLVQSGPEVKKPGASVKVSCKASGYTFTSYHIQWVRQAPGQGLEW
IGWIYPGDGSTQYNEKFKGRVTITADKSTSTAYMELSSLTSEDTAVYY
CAREGTYYAMDYWGQGTSVTVSSGGGGSGGGGSGGGGSDVVMTQTPLS
LPVTLGEPASISCRSSQSIVHSNGNTYLEWYLQKPGQSPRLLIYKVSN
RFSGVPDRFSGSGSGTDFTLKISRVEAEDLGVYYCFQGSHVPRTFGGG
TKLEIKRRTTTPAPRPPTPAPTIASQPLSLRPEACRPAAGGAVHTRGL
DFACDIYIWAPLAGTCGVLLLSLVITLYCKRGRKKLLYIFKQPFMRPV
QTTQEEDGCSCRFPEEEEGGCELRVKFSRSADAPAYQQGQNQLYNELN

LGRREEYDVLDKRRGRDPEMGGKPRRKNPQEGLYNELQKDKMAEAYSE

IGMKGERRRGKGHDGLYQGLSTATKDTYDALHMQALPPR

In one embodiment, the chimeric receptor of the invention further comprises a leader sequence in N-term, preferably having the sequence SEQ ID NO: 50, and comprises or consists in a sequence SEQ ID NO: 82, or any amino acid sequence with 95-99% identity with SEQ ID NO: 82.

(SEQ ID NO: 82)
MALPVTALLLPLALLLHAARPSQVQLVQSGPEVKKPGASVKVSCKASG

YTFTSYHIQWVRQAPGQGLEWIGWIYPGDGSTQYNEKFKGRVTITADK

STSTAYMELSSLTSEDTAVYYCAREGTYYAMDYWGQGTSVTVSSGGGG

SGGGGSGGGGSDVVMTQTPLSLPVTLGEPASISCRSSQSIVHSNGNTY

LEWYLQKPGQSPRLLIYKVSNRFSGVPDRFSGSGSGTDFTLKISRVEA

EDLGVYYCFQGSHVPRTFGGGTKLEIKRRTTTPAPRPPTPAPTIASQP

LSLRPEACRPAAGGAVHTRGLDFACDIYIWAPLAGTCGVLLLSLVITL

YCKRGRKKLLYIFKQPFMRPVQTTQEEDGCSCRFPEEEEGGCELRVKF

SRSADAPAYQQGQNQLYNELNLGRREEYDVLDKRRGRDPEMGGKPRRK

NPQEGLYNELQKDKMAEAYSEIGMKGERRRGKGHDGLYQGLSTATKDT

YDALHMQALPPR

In one embodiment, the chimeric receptor of the invention comprises or consists in a sequence as set forth in SEQ ID NO: 79, or any amino acid sequence with 95-99% identity with SEQ ID NO: 79

(SEQ ID NO: 79)
SQVQLVQSGPEVKKPGASVKVSCKASGYTFTSYHIQWVRQAPGQGLEW

IGWIYPGDGSTQYNEKFKGRVTITADKSTSTAYMELSSLTSEDTAVYY

CAREGTYYAMDYWGQGTSVTVSSGGGGSGGGGSGGGGSDVVMTQSPSS

LSVTLGDRVSISCRSSQSIVHSNGNTYLEWYQQKPGQSPRLLIYKVSN

RFSGVPDRFSGSGSGTDFTLTISRVEPEDLGVYYCFQGSHVPRTFGGG

TKLEIKRRTTTPAPRPPTPAPTIASQPLSLRPEACRPAAGGAVHTRGL

DFACDIYIWAPLAGTCGVLLLSLVITLYCKRGRKKLLYIFKQPFMRPV

QTTQEEDGCSCRFPEEEEGGCELRVKFSRSADAPAYQQGQNQLYNELN

LGRREEYDVLDKRRGRDPEMGGKPRRKNPQEGLYNELQKDKMAEAYSE

IGMKGERRRGKGHDGLYQGLSTATKDTYDALHMQALPPR

In one embodiment, the chimeric receptor of the invention further comprises a leader sequence in N-term, preferably having the sequence SEQ ID NO: 50, and comprises or consists in a sequence SEQ ID NO: 83, or any amino acid sequence with 95-99% identity with SEQ ID NO: 83.

(SEQ ID NO: 83)
MALPVTALLLPLALLLHAARPSQVQLVQSGPEVKKPGASVKVSCKASG

YTFTSYHIQWVRQAPGQGLEWIGWIYPGDGSTQYNEKFKGRVTITADK

STSTAYMELSSLTSEDTAVYYCAREGTYYAMDYWGQGTSVTVSSGGGG

SGGGGSGGGGSDVVMTQSPSSLSVTLGDRVSISCRSSQSIVHSNGNTY

LEWYQQKPGQSPRLLIYKVSNRFSGVPDRFSGSGSGTDFTLTISRVEP

EDLGVYYCFQGSHVPRTFGGGTKLEIKRRTTTPAPRPPTPAPTIASQP

LSLRPEACRPAAGGAVHTRGLDFACDIYIWAPLAGTCGVLLLSLVITL

YCKRGRKKLLYIFKQPFMRPVQTTQEEDGCSCRFPEEEEGGCELRVKF

SRSADAPAYQQGQNQLYNELNLGRREEYDVLDKRRGRDPEMGGKPRRK

NPQEGLYNELQKDKMAEAYSEIGMKGERRRGKGHDGLYQGLSTATKDT

YDALHMQALPPR

In one embodiment, the chimeric receptor of the invention comprises or consists in a sequence as set forth in SEQ ID NO: 80, or any amino acid sequence with 95-99% identity with SEQ ID NO: 80

(SEQ ID NO: 80)
SQVQLVQSGPEVKKPGASVKVSCKASGYTFTSYHIQWVRQAPGQGLEW

IGWIYPGDGSTQYNEKFKGRVTITADKSTSTAYMELSSLTSEDTAVYY

CAREGTYYAMDYWGQGTSVTVSSGGGGSGGGGSGGGGSDIVMTQSPAT

LSVSPGERATISCRSSQSIVHSNGNTYLEWYQQKPGQAPRLLIYKVSN

RFSGIPDRFSGSGSGTDFTLTISRLEPEDFAVYYCFQGSHVPRTFGGG

TKLEIKRRTTTPAPRPPTPAPTIASQPLSLRPEACRPAAGGAVHTRGL

DFACDIYIWAPLAGTCGVLLLSLVITLYCKRGRKKLLYIFKQPFMRPV

QTTQEEDGCSCRFPEEEEGGCELRVKFSRSADAPAYQQGQNQLYNELN

LGRREEYDVLDKRRGRDPEMGGKPRRKNPQEGLYNELQKDKMAEAYSE

IGMKGERRRGKGHDGLYQGLSTATKDTYDALHMQALPPR

In one embodiment, the chimeric receptor of the invention further comprises a leader sequence in N-term, preferably having the sequence SEQ ID NO: 50, and comprises or consists in a sequence SEQ ID NO: 84, or any amino acid sequence with 95-99% identity with SEQ ID NO: 84.

(SEQ ID NO: 84)
MALPVTALLLPLALLLHAARPSQVQLVQSGPEVKKPGASVKVSCKASG

YTFTSYHIQWVRQAPGQGLEWIGWIYPGDGSTQYNEKFKGRVTITADK

STSTAYMELSSLTSEDTAVYYCAREGTYYAMDYWGQGTSVTVSSGGGG

SGGGGSGGGGSDIVMTQSPATLSVSPGERATISCRSSQSIVHSNGNTY

LEWYQQKPGQAPRLLIYKVSNRFSGIPDRFSGSGSGTDFTLTISRLEP

EDFAVYYCFQGSHVPRTFGGGTKLEIKRRTTTPAPRPPTPAPTIASQP

LSLRPEACRPAAGGAVHTRGLDFACDIYIWAPLAGTCGVLLLSLVITL

YCKRGRKKLLYIFKQPFMRPVQTTQEEDGCSCRFPEEEEGGCELRVKF

SRSADAPAYQQGQNQLYNELNLGRREEYDVLDKRRGRDPEMGGKPRRK

NPQEGLYNELQKDKMAEAYSEIGMKGERRRGKGHDGLYQGLSTATKDT

YDALHMQALPPR

In another embodiment, the chimeric receptor of the invention comprises (i) a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_5$ is K or T, $X_{16}$ is V or L, $X_{17}$ is A or P, $X_{18}$ is L or F and $X_{19}$ is G or A, more preferably one of SEQ ID NO: 70-72 or 74-76), (ii) a hinge region of human CD8, (iii) a transmembrane domain of human CD8, (iv) an intracellular domain of human CD28 and (v) an intracellular domain of human CD3ζ. In one embodiment, the part of the chimeric receptor comprising a hinge region of human CD8, a transmembrane domain of human CD8, an intracellular domain of human CD28 and an intracellular domain of human CD3ζ comprises or consists in the amino acid sequence SEQ ID NO: 59 or 60, or any amino acid sequence with 95-99% identity with SEQ ID NO: 59 or 60.

(SEQ ID NO: 59)
MHTTTPAPRPPTPAPTIASQPLSLRPEACRPAAGGAVHTRGLDFACDI

YIWAPLAGTCGVLLLSLVITLYCRSKRSRLLHSDYMNMTPRRPGPTRK

HYQPYAPPRDFAAYRSTRRVKFSRSADAPAYQQGQNQLYNELNLGRRE

EYDVLDKRRGRDPEMGGKPRRKNPQEGLYNELQKDKMAEAYSEIGMKG

ERRRGKGHDGLYQGLSTATKDTYDALHMQALPPR (SEQ ID NO: 60)
MHTTTPAPRPPTPAPTIASQPLSLRPEACRPAAGGAVHTRGLDFACDI

YIWAPLAGTCGVLLLSLVITLYCRSKRSRLLHSDYMNMTPRRPGPTRK

HYQPYAPPRDFAAYRSTRRVKFSRSADAPAYQQGQNQLYNELNLGRRE

EYDLDKRRGRDPEMGGKPQRRKNPQEGLYNELQKDKMAEAYSEIGMKG

ERRRGKGHDGLYQGLSTATKDTYDALHMQALPPR

In one embodiment, the chimeric receptor of the invention comprises a HLA-A2 binding domain (preferably SEQ ID NO: 69 or 73 wherein $X_1$ is V or I, $X_2$ is T or S, $X_3$ is L or S or A, $X_4$ is S or T, $X_5$ is P or S, $X_6$ is T or S, $X_7$ is L or P, $X_8$ is E or D, $X_9$ is P or R, $X_{10}$ is A or V, $X_{11}$ is S or T, $X_{12}$ is L or Q, $X_{13}$ is S or A, $X_{14}$ is V or I, $X_{15}$ is K or T, $X_{16}$ is V or L, $X_7$ is A or P, $X_{18}$ is L or F and $X_{19}$ is G or A, more preferably one of SEQ ID NO: 70-72 or 74-76), linked to an amino acid sequence of SEQ ID NO: 59-60 or a sequence or an amino acid sequence with 95-99% identity to SEQ ID NO: 59-60.

The present invention further relates to an immune cell expressing the CAR as described hereinabove, and to a population of such immune cells.

In one embodiment, the nucleic acid encoding a CAR of the present invention is introduced into an immune cell, thereby generating an engineered cell expressing the CAR of the present invention on the cell surface.

According to the invention, the immune cell of the invention is genetically modified to express a chimeric receptor recognizing HLA-A2. The immune cell of the invention may thus be defined as a redirected immune cell.

As used herein, the term "redirected" refers to an immune cell carrying a chimeric receptor as described herein, which confers to the immune cell the ability to bind to and be activated by a ligand (i.e., HLA-A2) that is different from the one the immune cell is or would have been specific or be activated by. In one embodiment, the chimeric receptor is capable of being expressed in an immune cell such that the immune cell is activated by HLA-A2.

In one embodiment, the immune cell of the invention is a mammal immune cell, preferably a human immune cell.

In one embodiment, the immune cell of the invention has been frozen and thawed.

In one embodiment, the immune cell is selected from the group comprising lymphocytes, myeloid-derived cells, and any combination thereof.

In one embodiment, the immune cell is a lymphocyte selected from the group comprising T cells, B cells, natural killer (NK) cells, and any combination thereof.

In one embodiment, the immune cell is a T cell. In one embodiment, the T cell is selected from the group consisting of $CD4^+$ T cells, $CD8^+$ T cells, γδ T cells, double negative (DN) T cells, and any combination thereof.

In one embodiment, the immune cell is a $CD4^+$ T cell, such as, for example, a T helper cell, a regulatory T cell, and any combination thereof.

In one embodiment, the immune cell is a $CD4^+$ regulatory T cell (Treg). In one embodiment, the Treg is a thymus derived Treg or an adaptive or induced Treg. In one embodiment, the Treg is a $CD4^+FOXP3^+$ regulatory T cell or a $CD4^+$ $FOXP3^-$ regulatory T cell (Tr1 cell), preferably a $CD4^+$ $FOXP3^+$ regulatory T cell.

In one embodiment, the immune cell is a $CD8^+$ T cell such as, for example, a cytotoxic $CD8^+$ T cell or a $CD8^+$ regulatory T cell.

Preferably, the immune cell is a $CD8^+$ regulatory T cell (Treg). In one embodiment, the $CD8'$ regulatory T cell is selected from the group consisting of a $CD8^+$ $CD28^-$ regulatory T cell, a $CD8^+$ $CD103^+$ regulatory T cell, a $CD8^+$ $FoxP3^+$ regulatory T cell, a $CD8^+$ $CD122^+$ regulatory T cell, and any combination thereof.

In one embodiment, the immune cell is an $INFγ^+IL10^+$ $IL34^+CD8^+$ $CD45RC^{low}$ regulatory T cell.

In one embodiment, the immune cell is a γδ T cell, preferably a regulatory γδ T cell.

In one embodiment, the immune cell is a DN T cell, preferably a regulatory DN T cell.

In one embodiment, the immune cell is a B cell, preferably a regulatory B cell. In one embodiment, the regulatory B cell is a $CD19^+CD24^{hi}CD38^{hi}$ B cell.

In one embodiment, the immune cell is a NK cell, preferably a regulatory NK cell.

In one embodiment, the immune cell is a myeloid-derived cell, preferably selected from the group comprising neutrophils, eosinophils, basophils, monocytes, macrophages, dendritic cells, or any combination thereof.

In one embodiment, the immune cell is a macrophage, preferably a regulatory macrophage.

In one embodiment, the immune cell is a dendritic cell, preferably a regulatory dendritic cell.

Preferably, the immune cell is a regulatory immune cell, such as, for example, any regulatory immune cell suitable for use in cellular therapy.

In one embodiment, the regulatory immune cell is selected from the group consisting of a regulatory T cell, a $CD4^+$ regulatory T cell, a $CD8^+$ regulatory T cell, a regulatory γδ T cell, a regulatory DN T cell, a regulatory B cell, a regulatory NK cell, a regulatory macrophage, a regulatory dendritic cell, and any combination thereof.

In one embodiment, the regulatory immune cell is a $CD8^+$ regulatory T cell. Examples of $CD8^+$ regulatory T cells include, but are not limited to, a $CD8^+$ $CD28^-$ regulatory T cell, a $CD8^+$ $CD103^+$ regulatory T cell, a $CD8^+$ $FoxP3^+$ regulatory T cell, a $CD8^+$ CD122+ regulatory T cell, and any combination thereof.

In one embodiment, the regulatory immune cell is a regulatory γδ T cell.

In one embodiment, the regulatory immune cell is a regulatory DN T cell.

In one embodiment, the regulatory immune cell is a regulatory B cell. Examples of regulatory B cells include, but re not limited to, a $CD19^+CD24^{hi}CD38^{hi}$ B cell.

In one embodiment, the regulatory immune cell is a regulatory NK cell.

In one embodiment, the regulatory immune cell is a regulatory macrophage.

In one embodiment, the regulatory immune cell is a regulatory dendritic cell.

In one embodiment, the regulatory immune cell is a regulatory T cell, in particular a thymus derived Treg or an adaptive or induced Treg. Examples of Tregs include, but are not limited to, a $CD4^+$ $FOXP3^+$ regulatory T cell or a $CD4^+FOXP3^-$ regulatory T cell (Tr1 cell).

In one embodiment, the regulatory immune cell has the following phenotype: $CD4^+$ $CD25^+$, such as, for example, $CD4^+$ $CD25^+CD127^-$, such as, for example, $CD4^+$ $CD25^+$ $CD127^-CD45RA^+$. Preferably, the regulatory immune cell has the following phenotype: $FoxP3^+CD4^+$ $CD25^+$, such as, for example, $FoxP3^+CD4^+$ $CD25^+CD127^-$, such as, for example, $FoxP3^+CD4^+$ $CD25^+CD127^-CD45RA^+$.

In one embodiment, the immune regulatory cell presents at least one of the following phenotypes: $CD4^+$ $CD25^+$, $FoxP3^+$, $CD127^{lo/-}$, $CTLA-4^+$, $CD39^+$, $Helios^+$, $CD62^{+/hi}$, $VLA4^+$, $LFA1^+$, $CD49b^{int}$, $ITGb7^{int}$, $PSGL-1^+$, $ICOS^+$, $GITR^+$, $PD-1^{int}$, $Perf^{lo/-}$, $CCR7^+$. In one embodiment, the immune regulatory cell does not express Granzyme A and/or Granzyme B.

In one embodiment, the determination of the expression level of molecules is conducted by flow cytometry, immunofluorescence or image analysis, for example high content analysis. Preferably, the determination of the expression level of molecules is conducted by flow cytometry. In one embodiment, before conducting flow cytometry analysis, cells are fixed and permeabilized, thereby allowing detecting intracellular proteins.

In one embodiment, the determination of the expression level of a molecule in a cell population comprises determining the percentage of cells of the cell population expressing the molecule (i.e. cells "+" for the molecule). Preferably, said percentage of cells expressing the molecule is measured by FACS.

The terms "expressing (or +)" and "not expressing (or −)" are well known in the art and refer to the expression level of the cell marker of interest, in that the expression level of the cell marker corresponding to "+" is high or intermediate, also referred as "+/−", and the expression level of the cell marker corresponding to "−" is null.

The term "low" or "lo" or "lo/−" is well known in the art and refers to the expression level of the cell marker of interest, in that the expression level of the cell marker is low by comparison with the expression level of that cell marker in the population of cells being analyzed as a whole. More particularly, the term "lo" refers to a distinct population of cells that express the cell marker at a lower level than one or more other distinct population of cells.

The term "high" or "hi" or "bright" is well known in the art and refers to the expression level of the cell marker of interest, in that the expression level of the cell marker is high by comparison with the expression level of that cell marker in the population of cells being analyzed as a whole.

Generally, cells in the top 2, 3, 4, or 5% of staining intensity are designated "hi", with those falling in the top half of the population categorized as being "+". Those cells falling below 50%, of fluorescence intensity are designated as "lo" cells and below 5% as "−" cells.

The expression level of the cell marker of interest is determined by comparing the Median Fluorescence Intensity (MFI) of the cells from the cell population stained with fluorescently labeled antibody specific for this marker to the fluorescence intensity (FI) of the cells from the same cell population stained with fluorescently labeled antibody with an irrelevant specificity but with the same isotype, the same fluorescent probe and originated from the same specie (referred as Isotype control). The cells from the population stained with fluorescently labeled antibody specific for this marker and that show equivalent MFI or a lower MFI than the cells stained with the isotype controls are not expressing this marker and then are designated (−) or negative. The cells from the population stained with fluorescently labeled antibody specific for this marker and that show a MFI value superior to the cells stained with the isotype controls are expressing this marker and then are designated (+) or positive.

In one embodiment, the immune cell of the invention expresses at its cell surface a CAR of the invention, and another receptor (herein referred to as "second receptor"), that binds to another ligand than HLA-A2. According to the invention, this second receptor comprises an extracellular ligand binding domain, optionally a hinge, optionally a transmembrane domain, and an intracellular signaling domain, as previously described.

In one embodiment, the second receptor is endogenous (such as, for example, the endogenous TCR). In another embodiment, the second receptor is exogenous, and its expression is induced in the immune cell of the invention by transformation or transduction of a nucleic acid encoding it. Said exogenous receptor may be an exogenous TCR or a chimeric antigen receptor. Therefore, in one embodiment, the immune cell of the invention expresses two chimeric antigen receptors, wherein the first one recognizes HLA-A2, and the second one recognizes a distinct ligand.

In another embodiment, the immune cell of the invention expresses at its cell surface a CAR of the invention, and another receptor (herein referred to as "second receptor"), that binds to another epitope in HLA-A2. According to the invention, this second receptor comprises an extracellular ligand binding domain, optionally a hinge, optionally a transmembrane domain, and an intracellular signaling domain, as previously described.

In another embodiment, the immune cell of the invention expresses two CARs, wherein the first one recognizes a first epitope of HLA-A2, and the second one recognizes a distinct epitope on HLA-A2.

In one embodiment, the CAR of the invention comprises a first intracellular signaling domain, and the second receptor comprises a distinct second intracellular signaling domain. In a first embodiment, the CAR of the invention comprises a T cell primary signaling domain (such as, for example, CD3zeta), and the second receptor comprises a costimulatory signaling domain (such as, for example, of 4-1BB, CD28 or a combination of costimulatory signaling domain of 4-1BB and CD28). In a second embodiment, the CAR of the invention comprises a costimulatory signaling domain (such as, for example, of 4-1BB, CD28 or a combination of costimulatory signaling domain of 4-1BB and CD28), and the second receptor comprises a T cell primary signaling domain (such as, for example, CD3zeta).

Consequently, according to these embodiments, the complete activation of the immune cell of the invention requires both the binding of the CAR of the invention to HLA-A2, and the binding of the second receptor to the ligand to which it is directed.

In one embodiment, the ligand recognized by the second receptor is expressed or present at a diseased tissue or organ, or at a site of an autoimmune response.

Examples of ligands that may be recognized by the second receptor include, but are not limited to, food antigens from the common human diet, autoantigens, inhaled allergens, ingested allergens or contact allergens.

The term "food antigen from common human diet" refers to an immunogenic peptide, which comes from foodstuffs common for humans, such as food antigens of the following non-limiting list: bovine antigens such as lipocalin, Ca-binding S100, alpha-lactalbumin, lactoglobulins such as beta-lactoglobulin, bovine serum albumin, caseins. Food-antigens may also be atlantic salmon antigens such as parvalbumin; chicken antigens such as, for example, ovomucoid, ovalbumin, Ag22, conalbumin, lysozyme or chicken serum albumin; peanut antigens; shrimp antigens such as tropomyosin; wheat antigens such as agglutinin or gliadin; celery antigens such as celery profilin; carrot antigens such as carrot profilin; apple antigens such as thaumatin, apple lipid transfer protein, or apple profilin; pear antigens such as pear profilin, or isoflavone reductase; avocado antigens such as endochitinase; apricot antigens such as apricot lipid transfer protein; peach antigens such as peach lipid transfer protein or peach profilin; soybean antigens such as HPS, soybean profilin or (SAM22) PR-I0 prot; fragments, variants and mixtures thereof.

In one embodiment, said autoantigen is a multiple sclerosis-associated antigen, a joint-associated antigen, an eye-associated antigen, a human HSP antigen, a skin-associated antigen or an antigen involved in graft rejection or GVHD The term "multiple sclerosis-associated antigen" refers to myelin basic protein (MBP). myelin associated glycoprotein (MAG), myelin oligodendrocyte glycoprotein (MOG), proteolipid protein (PLP), oligodendrocyte myelin oligoprotein (OMGP), myelin associated oligodendrocyte basic protein (MOBP), oligodendrocyte specific protein (OSP/Claudinl 1), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase), fragments, variants and mixtures thereof.

The term "joint-associated antigen" refers to citrulline-substituted cyclic and linear filaggrin peptides, type II collagen peptides, human cartilage glycoprotein 39 (HCgp39) peptides, HSP, heterogeneous nuclear ribonucleoprotein (hnRNP) A2 peptides, hnRNP B1, hnRNP D, Ro60/52, HSP60, HSP65, HSP70 and HSP90, BiP, keratin, vimentin, fibrinogen, type I, III, IV and V collagen peptides, annexin V, Glucose 6 phosphate isomerase (GPI), acetyl-calpastatin, pyruvate dehydrogenase (PDH), aldolase, topoisomerase I, snRNP, PARP, Scl-70, Scl-100, phospholipid antigens including anionic cardiolipin and phosphatidylserine, neutrally charged phosphatidylethanolamine and phosphatidylcholine, matrix metalloproteinase, fibrillin, aggreccan, fragments, variants and mixtures thereof.

The term "eye-associated antigen" refers to type II collagen, retinal arrestin, S-arrestin, interphotoreceptor retinoid-binding proteins (IRBP1), beta-crystallin B1, retinal proteins, choroid proteins and fragments, variants and mixtures thereof.

The term "human HSP antigen" refers to human HSP60, HSP70, HSP90, fragments, variants and mixtures thereof.

Examples of skin-associated antigens include, but are not limited to, keratinocytes antigens, an antigen present in the dermis or epidermis, a melanocyte antigen (such as, for example, melanin or tyrosinase), desmoglein (e.g., desmoglein 1 or 3, that may also be referred to as Dsg1/3), BP180, BP230, plectin, integrins (e.g., integrin α4β6), collagens (e.g., collagen type VII), laminins (e.g., laminin 332 or laminin γ1), plakins (e.g., envoplakin, periplakin, or desmoplakins), keratins (e.g., KRT5, KRT8, KRT15, KRT17 and KRT31), keratin filament-associated proteins, filaggrin, corneodesmosin, and elastin.

In one embodiment, the ligand is an antigen involved in graft rejection or GVHD.

Examples of such antigens include, but are not limited to, the MHC specific to the transplanted tissue or to the host, P2-microglobulin, antigens from ABO system, antigens from rhesus system (in particular antigens from the C, c, E et e and D system) and isohaemagglutinins. Other examples of antigens that may be involved in graft rejection or GVHD include, but are not limited to HLA-DR (in particular during the first six months following grafting), HLA-B (in particular during the first two years following grafting), minor histocompatibility antigens (miHA, e.g., HLA-E, HLA-F and HLA-G), HLAs corresponding to MHC class I (B, and C), HLAs corresponding to MHC class II (DP, DM, DOA, DOB, DQ, and DR) and HLAs corresponding to MHC class III (e.g., components of the complement system).

Other examples of autoantigens include, without limitation, aquaporin water channels (such as, for example, aquaporin-4 water channel (AQP4)), Hu, Ma2, collapsin response-mediator protein 5 (CRMP5), and amphiphysin, voltage-gated potassium channel (VGKC), N-methyl-d-aspartate receptor (NMDAR), α-amino-3-hydroxy-5-methyl-4-isoxazoleproprionic acid (AMPAR), thyroid peroxidase, thyroglobulin, anti-N-methyl-D-aspartate receptor (NR1 subunit), Rh blood group antigens, I antigen, desmoglein 1 or 3 (Dsg1/3), BP180, BP230, Acetylcholine nicotinic post-synaptic receptors, thyrotropin receptors, platelet integrin, GpIIb:IIIa, Collagen (such as, for example, Collagen alpha-3(IV) chain), rheumatoid factor, calpastatin, citrullinated proteins, Myelin basic protein (MBP), Myelin oligodendrocyte glycoprotein (MOG) peptides, alpha-beta-crystallin, DNA, histone, ribosomes, RNP, tissue transglutaminase (TG2), intrinsic factor, 65-kDa antigen, phosphatidylserine, ribosomal phosphoproteins, anti-neutrophil cytoplasmic antibody, Scl-70, U1-RNP, ANA, SSA, anti-SSB, anti-nuclear antibodies (ANA), antineutrophil cytoplasm antibodies (ANCA), Jo-1, antimitochondrial antibodies, gp210, p62, sp100, antiphospholipid antibodies, U1-70 kd snRNP, GQ1b ganglioside, GM1, asialo GM1, GD1b, anti-smooth muscle antibodies (ASMA), anti-liver-kidney microsome-1 antibodies (ALKM-1), anti-liver cytosol antibody-1 (ALC-1), IgA antiendomysial antibodies, neutrophil granule proteins, streptococcal cell wall antigen, intrinsic factor of gastric parietal cells, insulin (IAA), glutamic acid decarboxylase (GAA or GAD) and protein tyrosine phosphatase (such as, for example, IA2 or ICA512), PLA2R1 and THSD7A1.

In one embodiment, said ligand is selected from the group comprising ovalbumin, MOG, type II collagen fragments, variants and mixtures thereof.

In one embodiment, said ligand is ovalbumin, fragments, variants and mixtures thereof.

In another embodiment, said ligand is MOG, fragments, variants and mixtures thereof.

In another embodiment, said ligand is type II collagen, fragments, variants and mixtures thereof.

In another embodiment, said ligand is IL23R, fragments, variants and mixtures thereof.

In one embodiment, the CAR of the invention further comprises an extracellular ligand binding domain recognizing a ligand distinct from HLA-A2. In one embodiment, said ligand binding domain is an antibody or an antigen binding fragment thereof.

In one embodiment, the ligand binding domain of the CAR of the invention is a multifunctional antibody recognizing multiple distinct epitopes on HLA-A2. In one embodiment, the ligand binding domain of the CAR of the invention is a bifunctional antibody recognizing two distinct epitopes on HLA-A2.

In one embodiment, the CAR of the invention comprises an extracellular ligand binding domain comprising a HLA-A2 binding domain and another ligand binding domain recognizing a ligand distinct from HLA-A2. In one embodiment, said ligand binding domain is a bifunctional antibody recognizing both HLA-A2 and the distinct ligand.

Examples of ligands distinct from HLA-A2 that may be recognized by the CAR of the invention are listed hereinabove.

The invention also relates to an isolated and/or substantially purified population of immune cells as defined hereinabove.

Thus, one object of the invention is an isolated and/or substantially purified population of immune cells, wherein the cells of the population comprise a CAR, wherein said CAR recognizes HLA-A2.

As used herein, an "isolated population" refers to a cell population that is removed from its natural environment (such as the peripheral blood) and that is isolated, purified or separated, and is at least about 75% free, 80% free, 85% free and preferably about 90%, 95%, 96%, 97%, 98%, 99% free, from other cells with which it is naturally present, but which lack the cell surface markers based on which the cells were isolated.

The present invention further relates to an enriched population of immune cells as defined hereinabove.

In one embodiment, the isolated, purified and/or enriched immune cell population of the invention has been frozen and thawed.

Another object of the invention is a vector comprising the nucleic acid sequence encoding a chimeric antigen receptor (CAR) as described hereinabove.

Examples of vectors that may be used in the present invention include, but are not limited to, a DNA vector, a RNA vector, a plasmid, a phagemid, a phage derivative, an animal virus and a cosmid.

Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., as described in WO01/96584; WO01/29058; and U.S. Pat. No. 6,326,193 incorporated herein by reference).

A number of viral based systems have been developed for gene transfer into mammalian cells. For example, retroviruses provide a convenient platform for gene delivery systems.

A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional transcriptionally active elements, e.g., promoters and enhancers, may regulate the frequency of transcriptional initiation. Typically, regarding core promoter, these are located in the region 30-110 bp upstream of the start site, although a number of promoters have recently been shown to contain functional elements downstream of the start site as well, and enhancers elements are generally located 500-2000 bp upstream of the start site.

The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1a). Another example of a suitable promoter is phosphoglycerate kinase (PGK) promoter. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked to when such expression is desired, or turning off the expression when expression is not desired. Examples of inducible promoters include, but are not limited to a metallothionine promoter, a glucocorticoid promoter, a progesterone promoter, and a tetracycline promoter. In addition, bi-directional promoters allowing efficient and coordinate expression of two or more genes may also be of interest in the present invention. Examples of bi-directional promoters include but are not limited to the promoters described in US2006200869 (U.S. Pat. No. 8,501,464), incorporated herein by reference, disclosing a bi-directional promoter comprising i) a first minimal promoter sequence derived from cytomegalovirus (CMV) or mouse mammary tumor virus (MMTV) genomes and ii) a full efficient promoter sequence derived from an animal gene.

In order to assess the expression of a CAR polypeptide or portions thereof, the expression vector to be introduced into an immune cell can also contain either a selectable marker gene such as, for example, CD34 or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

In some embodiments of the invention, suicide gene technology may be used. Different suicide gene technologies are described in the art depending on their mechanism of action (Jones et al. Frontiers in Pharmacology, 2014 (5): 254). Examples of gene-directed enzyme prodrug therapy (GDEPT) converting a nontoxic drug to a toxic drug include herpes simplex virus thymidine kinase (HSV-TK) and cytosine deaminase (CD). Other examples are chimeric proteins composed of a drug binding domain linked to apoptotic components such as for example the inducible Fas (iFas) or the inducible Caspase 9 (iCasp9) systems. Other examples include systems mediated by therapeutic antibodies such as inducing overexpression of c-myc at the surface of the engineered cell to induce their deletion by administration of an anti-c-myc antibody. The use of EGFR is described as a similar system compared to the c-myc system.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, membrane disruption and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanoparticules (nanospheres, nanocapsules), microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Mumtaz et al. (1991) Glycobiology 5: 505-10). However, compositions that have different structures in solution than the normal vesicular structure are also encompassed.

For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the genetically modified immune cells of the invention are modified through the introduction of RNA. In one embodiment, an in vitro transcribed RNA CAR can be introduced in a cell as a form of transient transfection. The RNA may be produced by in vitro transcription using a polymerase chain reaction (PCR)-generated template.

DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention.

In one embodiment, the DNA to be used for PCR contains an open reading frame. The DNA can be from a naturally occurring DNA sequence from the genome of an organism. In one embodiment, the DNA is a full-length gene of interest or a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR may be used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art.

"Forward primers" are primers that contain a region of nucleotides that are substantially complementary to nucleotides on the DNA template that are upstream of the DNA sequence that is to be amplified. "Upstream" is used herein to refer to a location 5', to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA. The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatemeric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270: 1485-65 (2003).

The conventional method of integration of polyA/T stretches into a DNA template is molecular cloning. However, polyA/T sequence integrated into plasmid DNA can cause plasmid DNA instability, which is why DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning is highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA. 5' caps on RNAs also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7: 1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa® Nucleofector-II® (Amaxa Biosystems, Cologne, Germany)), (ECM® 830 (BTX®) (Harvard Instruments, Boston, Mass.) or the Gene Pulser® II (BioRad, Denver, Colo.), Multiporator® (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

In one embodiment, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In another embodiment, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA.

The method used can be for any purpose where transient expression is required or sufficient.

In another embodiment, the desired CAR can be expressed in the cells by way of transposons.

In one embodiment, the immune cell of the invention is a T cell. Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation or Sepax separation system. In one preferred embodiment, cells from the circulating blood of an individual are obtained by apheresis.

The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD4^+$ $CD25^+$, in particular, $CD4^+CD25^+$ $CD127^{lo}$, such as, for example, $CD4^+$ $CD25^+CD127^{lo}CD45RA^+$, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such as in isolating tumor infiltrating lymphocytes (TIL) from tumor tissue or from immune-compromised individuals. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention.

In another embodiment, it may be desirable to perform the selection procedure and use the "unselected" cells in the activation and expansion process. "Unselected" cells can also be subjected to further rounds of selection. Enrichment of a T cell population by negative selection can be accomplished with a combination of antibodies directed to surface markers unique to the negatively selected cells. One method is cell sorting and/or selection via negative magnetic immuno-adherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11 b, CD16, HLA-DR, and CD8. In certain embodiments, it may be desirable to enrich for or positively select for regulatory T cells having typically the following phenotype $CD4^+$, $CD25^+$, $CD62L^{hi}$, $GITR^*$, and $FoxP3^+$. Alternatively, in certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time.

Whether prior to or after genetic modification of the T cells (preferably Treg cells) to express a desirable CAR, the T cells can be activated and expanded generally using methods as described, for example, in U.S. Pat. Nos. 6,352, 694; 6,534,055; 6,905,680; 6,692,964; 5,858,358; 6,887, 466; 6,905,681; 7,144,575; 7,067,318; 7,172,869; 7,232, 566; 7,175,843; 5,883,223; 6,905,874; 6,797,514; 6,867, 041; and US20060121005 (U.S. Pat. No. 7,572,631), incorporated herein by reference.

Generally, the T cell (preferably Treg cell) population of the invention is expanded by contact with a surface having attached thereto an agent that stimulates a CD3/TCR complex associated signal and a ligand that stimulates a co-stimulatory molecule on the surface of the cells of the T (preferably Treg) cell population. In particular, the T (preferably Treg) cell population may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells, an anti-CD3 antibody and an anti-CD28 antibody may be used. Examples of an anti-CD28 antibody include, without being limited to, 9.3, B-T3, XR-CD28 (Diaclone, Besancon, France). Other expansion methods commonly known in the art can be used (Berge et al., Transplant Proc. 30(8):3975-3977, 1998; Haanen et al., J. Exp. Med. 190(9): 13191328, 1999; Garland et al., J. Immunol Meth. 227(1-2):53-63, 1999).

In certain embodiments, the primary stimulatory signal and the co-stimulatory signal for the cells of the T (preferably Treg) cell population may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, US20040101519 (U.S. Pat. No. 7,745,140) and 20060034810 (U.S. Pat. No. 7,754,482), incorporated herein by reference, for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments, the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the T cells (preferably Treg cells) are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the cells of the Treg cell population. In one embodiment, the cells (for example, 10$^4$ to 10$^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate that any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more.

Conditions appropriate for T cell culture include an appropriate media (e.g., Minimal Essential Media or RPMI Media 1640 or, X-vivo 15™, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V™, DMEM, MEM, a-MEM, F-12, X-Vivo™ 15, and X-Vivo™ 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (Th, $CD4^+$) that is greater than the cytotoxic or suppressor T cell population (Tc, $CD8^+$). Ex vivo expansion of T cells by stimulating CD3 and CD28 receptors produces a population of T cells that prior to about days 8-9 consists predominately of Th cells, while after about days 8-9, the population of T cells comprises an increasingly greater population of Tc cells. Accordingly, depending on the purpose of treatment, infusing a subject with a T cell population comprising predominately of Th cells may be advantageous. Similarly, if an antigen-specific subset of Tc cells has been isolated it may be beneficial to expand this subset to a greater degree. Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In one embodiment of the invention, the T cells may be cultured in the presence of rapamycin in order to obtain regulatory T cells, as described for example in WO2007110785 incorporated herein by reference. Another method to generate regulatory T cells is described in US2016024470 incorporated herein by reference, where T cells are cultured with a T cell receptor (TCR)/CD3 activator such as for example TCR/CD3 antibodies, a TCR co-stimulator activator such as for example CD28, CD137 (4-1 BB), GITR, B7-1/2, CD5, ICOS, OX40, CD40 or CD137 antibodies, and rapamycin.

In one embodiment of the invention, the T cells genetically modified by expression of the CAR may also have been genetically modified by expression of at least one intracellular factor such as ROR-C, Foxo1, T-bet, or Gata 3, c-Maf, AhR. In one embodiment, the genetically modified immune cell of the invention expresses Foxo1.

In one embodiment, the genetically modified cells of the present invention can be an allogeneic immune cell, such as, for example, an allogenic T or Treg cell. For example, the allogeneic immune cell can be an immune cell lacking expression of a functional human leukocyte antigen (HLA), e.g., HLA class I and/or HLA class II, or lacking expression of a functional T cell receptor (TCR).

In one embodiment, a T cell lacking a functional TCR can be engineered such that it does not express any functional TCR on its surface, engineered such that it does not express one or more subunits that comprise a functional TCR or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not elicit an adverse immune reaction in a host.

In another embodiment, the genetically modified cells described herein can be engineered such that it does not express a functional HLA on its surface. For example, an immune cell described herein, can be engineered such that cell surface expression HLA, e.g., HLA class 1 and/or HLA class II or non-classical HLA molecules is downregulated.

In another embodiment, the T cell can lack a functional TCR and a functional HLA such as HLA class I and/or HLA class II.

Modified immune cells (such as, for example, modified T or Treg cells) that lack expression of a functional TCR and/or HLA can be obtained by any suitable means, including a knock out or knock down of one or more subunit of TCR and/or HLA. For example, the immune cell can include a knock down of TCR and/or HLA using siRNA, shRNA, clustered regularly interspaced short palindromic repeats (CRISPR) transcription-activator like effector nuclease (TALEN), zinc finger endonuclease (ZFN), meganuclease (mn, also known as homing endonuclease), or megaTAL (combining a TAL effector with a mn cleavage domain) (Osborn et al, "Evaluation of TCR Gene Editing Achieved by TALENs, CRISPR/Cas9, and megaTAL Nucleases" Mol Ther. 2016 March; 24(3):570-81).

In one embodiment, TCR expression and/or HLA expression can be inhibited using siRNA or shRNA that targets a nucleic acid encoding a TCR and/or HLA in a T cell. Expression of siRNA and shRNAs in T cells can be achieved using any conventional expression system, e.g., such as a lentiviral expression system. Exemplary siRNA and shRNA that downregulate expression of HLA class I and/or HLA class II genes are described, e.g., in US2007/0036773. Exemplary shRNAs that downregulate expression of components of the TCR are described, e.g., in US2012/0321667 (U.S. Pat. No. 9,181,527).

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaea. Grissa et al. (2007) BMC Bioinformatics 8: 172. This system is a type of prokaryotic immune system that confers resistance to foreign genetic elements such as plasmids and phages and provides a form of acquired immunity. Barrangou et al. (2007) Science 315: 1709-1712; Marraffini et al. (2008) Science 322: 1843-1845. The CRISPR/Cas system has been modified for use in gene editing (silencing, enhancing or changing specific genes) in eukaryotes such as mice or primates. Wiedenheft et al. (2012) Nature 482: 331-8. This is accomplished by introducing into the eukaryotic cell a plasmid containing a specifically designed CRISPR and one or more appropriate Cas. The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence. RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) Science 327: 167-170; Makarova et al. (2006) Biology Direct 1: 7. The spacers thus serve as templates for RNA molecules, analogously to siRNAs. Pennisi (2013) Science 341: 833-836. The CRISPR/Cas system can thus be used to edit a TCR and/or HLA gene (adding or deleting a base pair), or introducing a premature stop which thus decreases expression of a TCR and/or HLA. The CRISPR/Cas system can alternatively be used like RNA interference, turning off HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in US20140068797 (U.S. Pat. No. 10,266,850), and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865,406; 8,795,965; 8,771,945; and U.S. Pat. No. 8,697,359.

"TALEN" or "TALEN to TCR and/or HLA" or "TALEN to inhibit TCR and/or HLA" refers to a transcription activator-like effector nuclease, an artificial nuclease which can be used to edit the TCR and/or HLA. TALENs are produced artificially by fusing a TAL effector DNA binding domain to a DNA cleavage domain. Transcription activator-like effectors (TALEs) can be engineered to bind any desired DNA sequence, including a portion of the TCR and/or HLA gene. By combining an engineered TALE with a DNA cleavage domain, a restriction enzyme can be produced which is specific to any desired DNA sequence, including a TCR and/or HLA sequence. These can then be introduced into a cell, wherein they can be used for genome editing. Boch (2011) Nature Biotech. 29: 135-6; and Boch et al. (2009) Science 326: 1509-12; Moscou et al. (2009) Science 326: 3501.

TALEs are proteins secreted by *Xanthomonas* bacteria. The DNA binding domain contains a repeated, highly conserved 33-34 amino acid sequence, with the exception of the $12^{th}$ and $13^{th}$ amino acids. These two positions are highly variable, showing a strong correlation with specific nucleotide recognition. They can thus be engineered to bind a desired DNA sequence. To produce a TALEN, a TALE protein is fused to a nuclease (N), which is a wild-type or mutated FokI endonuclease. Several mutations to FokI have been made for its use in TALENs; these, for example, improve cleavage specificity or activity.

Cermak et al. (2011) Nucl. Acids Res. 39: e82; Miller et al. (2011) Nature Biotech. 29: 143-8; Hockemeyer et al. (2011) Nature Biotech. 29: 731-734; Wood et al. (2011) Science 333: 307; Doyon et al. (2010) Nature Methods 8: 74-79; Szczepek et al. (2007) Nature Biotech. 25: 786-793; and Guo et al. (2010)/. Mol. Biol. 200: 96. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) Nature Biotech. 29: 143-8. A TCR and/or HLA TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the TCR and/or HLA gene or introduce such a defect into a wt TCR and/or HLA gene, thus decreasing expression of TCR and/or HLA. TALENs specific to sequences in TCR and/or HLA can be constructed using any method known in the art, including various schemes using modular components. Zhang et al. (2011) Nature Biotech. 29: 149-53; Geibler et al. (2011) PLoS ONE 6: e19509.

"ZFN" or "Zinc Finger Nuclease" or "ZFN to TCR and/or HLA" or "ZFN to inhibit TCR and/or HLA" refer to a zinc finger nuclease, an artificial nuclease which can be used to edit the TCR and/or HLA gene. Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) Genetics Society of America 188: 773-782; and Kim et al. (1996) Proc. Natl. Acad. Sci. USA 93: 1156-1160. A zinc finger is a small protein structural motif stabilized by one or more zinc ions. A zinc finger can comprise, for example, $Cys_2His_2$, and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells. Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) Proc. Natl. Acad. Sci. USA 95: 10570-5. Also like a TALEN, a ZFN can create a double-stranded break in the DNA, which can create a frame-shift mutation if improperly repaired, leading to a decrease in the expression and amount of TCR and/or HLA in a cell. ZFNs can also be used with homologous recombination to mutate in the TCR and/or HLA gene. ZFNs specific to sequences in TCR and/or HLA can be constructed using any method known in the art. See, e.g., Provasi (2011) Nature Med. 18: 807-815; Torikai (2013) Blood 122: 1341-1349; Cathomen et al. (2008) Mol. Ther. 16: 1200-7; Quo et al. (2010)/. Mol. Biol. 400: 96;

US2011/0158957 (U.S. Pat. No. 8,956,828); and US2012/0060230 (U.S. Pat. No. 8,945,868).

"Meganuclease" or "meganuclease to TCR and/or HLA" or "meganuclease to inhibit TCR and/or HLA" refers to a monomeric endonuclease with large (>14 base pairs) recognition sites, which can be used to edit the TCR and/or HLA gene. Meganucleases (mn) are monomeric proteins with innate nuclease activity that are derived from bacterial homing endonucleases and engineered for a unique target site. Homing endonucleases are DNA-cleaving enzymes that can generate double strand breaks at individual loci in their host genomes, and thereby drive site-specific gene conversion events. (Stoddard, Structure. 2011 Jan. 12; 19(1):7-15). Despite their small size, homing endonucleases recognize long DNA sequences (typically 20 to 30 base pairs). Homing endonucleases are extremely widespread and are found in microbes, as well as in phages and viruses. The LAGLIDADG and His-Cys box enzymes (which are the most sequence-specific of these enzymes) rely upon antiparallel β-sheets that dock into the major grooves of their DNA target sites (Flick et al., 1998; Jurica et al., 1998). There they establish a collection of sequence-specific and non-specific contacts that are distributed nonuniformly across multiple consecutive basepairs (Chevalier et al., 2003; Scalley-Kim et al., 2007).

The LAGLIDADG homing endonuclease (LHE) family is the primary source of the engineered enzymes used for gene targeting applications. The LHE family is primarily encoded within archaea and in the chloroplast and mitochondrial genomes of algae and fungi (Chevalier et al., 2005; Dalgaard et al., 1997; Sethuraman et al., 2009).

Meganucleases that possess a single conserved LAGLIDADG motif (SEQ ID NO: 85) per protein chain form homodimeric proteins that cleave palindromic and nearly palindromic DNA target sequences, while those that contain two such motifs per protein chain form larger, pseudo-symmetric monomers that can target completely asymmetric DNA sequences.

Meganucleases can be engineered to target TCR and/or HLA and thus create a double-stranded break in the DNA, which can create a frame-shift mutation if improperly repaired, leading to a decrease in the expression and amount of TCR and/or HLA in a cell.

"MegaTAL" or "megaTAL to TCR and/or HLA" or "megaTAL to inhibit TCR and/or HLA" refers to an artificial nuclease, which can be used to edit the TCR and/or HLA gene. MegaTALs are hybrid monomeric nucleases obtained through the fusion of minimal TAL (transcription activator-like) effector domains to the N-terminus of meganucleases derived from the LAGLIDADG homing endonuclease family (Nucleic Acids Res. 2014 February; 42(4):2591-601; Takeuchi et al, Methods Mol Biol. 2015; 1239:105-32. doi: 10.1007/978-1-4939-1862-1_6). MegaTALs thus consist of a site-specific meganuclease cleavage head with additional affinity and specificity provided by a TAL effector DNA binding domain. MegaTALs can be engineered to target TCR and/or HLA and thus create a double-stranded break in the DNA, which can create a frame-shift mutation if improperly repaired, leading to a decrease in the expression and amount of HLA in a cell. A variant of the I-Onul meganuclease (mn) was used to design a TCRα-megaTAL to knockout the T-cell receptor alpha (TCRα) gene. The TCRα mn was fused to a 10.5 repeat TALE array designed to bind a DNA sequence upstream of the TCRα mn binding site. It was found that the megaTAL targeting TCRα achieved extremely high gene disruption with no detectable off-target cleavage in human primary T-cells (Boissel et al, Nucleic Acids Res. 2014 February; 42(4):2591-601).

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117: 1466-1476 (2007). Thus, in an embodiment, the genetically modified immune cell of the invention ectopically expresses a telomerase subunit, e.g., the catalytic subunit of telomerase, e.g., TERT, e.g., hTERT. In some aspects, this disclosure provides a method of producing a CAR-expressing immune cell, comprising contacting an immune cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CAR.

Another object of the invention is a composition comprising, consisting or consisting essentially of at least one immune cell or population of the invention.

In one embodiment, said composition comprises, consist or consists essentially of at least one isolated and/or substantially purified immune cell population of the invention.

In one embodiment, said composition has been frozen and thawed.

Another object of the invention is a pharmaceutical composition comprising, consisting or consisting essentially of at least one immune cell or population as described hereinabove and at least one pharmaceutically acceptable excipient.

Another object of the invention is a medicament comprising, consisting or consisting essentially of at least one immune cell population as described hereinabove.

In one embodiment, the pharmaceutical composition or medicament comprises an isolated and/or substantially purified immune cell population of the invention.

As used herein, the term "consisting essentially of", with reference to a pharmaceutical composition or medicament, means that the at least one immune cell or population of the invention is the only one therapeutic agent or agent with a biologic activity within said pharmaceutical composition or medicament.

Such compositions and medicaments may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The administration of the compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the immune cell compositions of the present invention are administered to a patient by intradermal or subcutaneous injection.

In one embodiment, the at least one immune cell or population of the present invention are administered by i.v. injection.

The compositions of the present invention are thus, in one embodiment, formulated for intravenous administration.

In one embodiment, the engineered immune cell of the invention may be used as a means to recruit said immune cell to sites of specific immune or inflammatory response, and to activate the immune cell to suppress the immunological activity of immune effector cells at these sites. The CAR-mediated recruitment and activation of immune cells may thus provide a method of preventing or treating a number of immunological diseases or disorders for which such immune suppression activity is beneficial.

In one embodiment, the immune cell is a regulatory immune cell as described hereinabove, preferably selected from the group comprising a regulatory T cell, a $CD4^+$ regulatory T cell, a $CD8^+$ regulatory T cell, a regulatory γδ T cell, a regulatory DN T cell, a regulatory B cell, a regulatory NK cell, a regulatory macrophage, a regulatory dendritic cell, and any combination thereof.

In one embodiment, the immune cell is a regulatory T cell. Although activation of regulatory T cells is antigen-dependent, the suppressive action of these cells is antigen-, TCR-, and MHC-independent. Accordingly, expression of CARs in regulatory T cells redirects these cells and their activation to the appropriate target tissue so that they are activated in an antigen-specific manner; however, their suppressive effects take place without a need for further recognition of disease-associated-antigens. Therefore, as long as the regulatory T cells are in the correct vicinity of where immune effector cells are located and mediating their undesired effects, the redirected regulatory T cells can be triggered or activated at that location to provide their suppressive effects.

In one embodiment, the target HLA-A2 antigen may be present or expressed at a site or target tissue of an undesirable immune or inflammatory response mediated by immune effector cells.

In one embodiment, the CAR-engineered immune cells of the invention may be used in the treatment of one or more diseases, disorders, symptoms, or conditions associated with organ or tissue transplant (e.g., organ or tissue rejection/dysfunction, GVHD, and/or conditions associated therewith). Transplant rejection involves the destruction of the donor's transplanted tissue by the recipient's immune cells through an immune response. An immune response is also involved in GVHD; however, in this case, the recipient's tissues are destroyed by the donor's immune cells transferred to the recipient via the transplant. Accordingly, CAR-mediated redirection and activation of immune cells provide a method of suppressing rejection of mismatched cells and/or tissues by immune effector cells in transplant recipients or inhibiting the pathogenic action of transplanted immunocompetent cells in the case of GVHD. In one embodiment, the mismatched cells and/or tissues comprise HLA-A2 mismatched cells and/or tissues.

Another object of the present invention is thus a method for treating one or more diseases, disorders, symptoms, or conditions associated with organ or tissue transplant (e.g., organ or tissue rejection/dysfunction, GVHD, and/or conditions associated therewith) in a subject, wherein said method comprises administering to the subject a CAR-engineered immune cell or a composition as described herein.

In one embodiment, the method is a cell therapy method. In one embodiment, the cell therapy is autologous. In one embodiment, the cell therapy is heterologous. In one embodiment, the cell therapy is allogenic. In one embodiment, the method is a gene therapy method.

Another object of the present invention is thus a CAR-engineered immune cell or a composition as described herein for use in treating one or more diseases, disorders, symptoms, or conditions associated with organ or tissue transplant (e.g., organ or tissue rejection/dysfunction, GVHD, and/or conditions associated therewith) in a subject.

The CAR-modified immune cells of the invention may further be used to promote immune tolerance, operational tolerance, and/or immune accommodation in a subject, in particular following organ or tissue transplantation.

Another object of the present invention is thus a method of promoting immune tolerance, operational tolerance, and/or immune accommodation in a subject, the method comprising administering to the subject a CAR-engineered immune cell, or a pharmaceutical composition as described herein. In one embodiment, the method may be for promoting immune tolerance, operational tolerance, and/or immune accommodation to a transplanted organ or tissue in a subject.

In one embodiment, the CAR-engineered immune cell (preferably the CAR-engineered Treg cell) of the invention is administered at the same time as, before, or after the transplantation of the organ or tissue.

In one embodiment, the CAR-engineered immune cells (preferably the CAR-engineered Treg cells) of the present invention may be used to prevent or treat rejection of a transplanted organ or tissue. Examples of rejection of a transplanted organ or tissue include, but are not limited to, hyperacute rejection of a transplanted organ or tissue, and antibody-mediated rejection of a transplanted organ or tissue.

In one embodiment, the method of the invention comprises administering CAR-engineered immune cells (preferably the CAR-engineered Treg cells) of the present invention to a subject exposed to a transplanted organ or tissue.

In one embodiment, the transplanted organ or tissue may encompass a bone marrow transplant, an organ transplant, a blood transfusion or any other foreign tissue or cell that is purposefully introduced into a subject.

In one embodiment, the CAR-engineered immune cells (preferably the CAR-engineered Treg cells) of the present invention may be used as a therapy to inhibit graft rejection following transplantation, including, without limitation, allograft rejection or xenograft rejection.

Another object of the invention is a method of preventing or treating organ or tissue transplant rejection in a subject, the method comprising administering to the subject CAR-engineered immune cells (preferably the CAR-engineered Treg cells) of the invention, or a pharmaceutical composition comprising said immune cells.

Another object of the present invention is thus a CAR-engineered immune cell (preferably the CAR-engineered Treg cells) of the invention, or a pharmaceutical composition comprising said immune cells, for use in preventing or treating organ or tissue transplant rejection in a subject.

Another object of the invention is a method of increasing the time period of graft survival in a subject, the method comprising administering to the subject CAR-engineered immune cells (preferably the CAR-engineered Treg cells) of the present invention, or a pharmaceutical composition comprising the same.

In one embodiment, the method provides a time period of graft survival of 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, 50 years, 60 years, 70 years, 80 years, 90 years, 100 years, or the lifetime of the subject.

In one embodiment, the subject is not undergoing any immunosuppressant agent therapies.

In one embodiment, the administration of an immune cell or composition of the invention allows reducing the amount of an immunosuppressant agent therapy received by the subject.

In one embodiment, the graft is an allograft. In one embodiment, the transplant may be exposed to the CAR-engineered immune cells (preferably the CAR-engineered Treg cells) of the present invention at the same time as, before, or after the transplantation of the transplant into the recipient. In one embodiment, the organ or tissue transplant may be a heart, heart valve, lung, kidney, liver, pancreas, intestine, skin, blood vessels, bone marrow, stem cells, bone, or, islet cells. However, the invention is not limited to a specific type of transplantation.

In one embodiment, the donor transplant may be "preconditioned" or "pretreated" by treating the organ or tissue transplant prior to transplantation into the recipient with the CAR-engineered immune cells of the invention in order to reduce the immunogenicity of the transplant against the recipient, thereby reducing or preventing graft rejection.

In one embodiment, the transplant host or recipient is HLA-A2 negative. In one embodiment, the transplant host or recipient is HLA-A2 negative and is positive for an HLA-A subtype selected from the group consisting of HLA-A03, HLA-A11, HLA-A23, HLA-A25, HLA-A26, HLA-A29, HLA-A30, HLA-A31, HLA-A33, and HLA-A34. In one embodiment, the transplant host or recipient is HLA-A2 negative and is positive for an HLA-A subtype selected from the group consisting of HLA-A25, HLA-A29 and HLA-A30.

In one embodiment, the transplant is HLA-A2 positive.

In one embodiment, the CAR-engineered immune cells (preferably the CAR-engineered Treg cells) of the present invention may be used to prevent or treat graft versus host disease (GVHD). In one embodiment, the method comprises administering CAR-engineered immune cells (preferably the CAR-engineered Treg cells) of the present invention to a subject exposed to a transplanted organ or tissue. In one embodiment, the transplanted organ or tissue may encompass a bone marrow transplant, an organ transplant, a blood transfusion, or any other foreign tissue or cell that is purposefully introduced into a subject. For example, GVHD may occur after heart, heart valve, lung, kidney, liver, pancreas, intestine, skin, blood vessel, bone marrow, stem cell, bone or islet cell transplantation. However, the invention is not limited to a specific type of transplantation.

In one embodiment, the GVHD may occur after hematopoietic stem cell transplantation.

Another object of the invention is thus a method of preventing or treating graft versus host disease (GVHD) in a subject, the method comprising administering to the subject CAR-engineered immune cells (preferably the CAR-engineered Treg cells) or a pharmaceutical composition as described herein.

In one embodiment, the invention provides a method of contacting a donor transplant, for example, a biocompatible lattice or a donor tissue, organ or cell, with CAR-engineered immune cells (preferably the CAR-engineered Treg cells) of the present invention at the same time as, before, or after the transplantation of the transplant into a recipient.

In one embodiment, the CAR-engineered immune cells (preferably the CAR-engineered Treg cells) of the present invention may be used to ameliorate, inhibit or reduce an adverse response by the donor transplant against the recipient, thereby preventing or treating GVHD.

Another object of the present invention is thus a method of preventing or delaying onset of GVHD in a subject, the method comprising administering to the subject CAR-engineered immune cells (preferably the CAR-engineered Treg cells) or a pharmaceutical composition as described herein.

In one embodiment, the onset of GVHD is delayed for 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, 50 years, 60 years, 70 years, 80 years, 90 years, 100 years, or the lifetime of the subject.

In one embodiment, the subject is not undergoing any immunosuppressant agent therapies.

In one embodiment, the subject is undergoing an immunosuppressant therapy. In one embodiment, the immune cells of the invention are administered to the subject with the aim to decrease the therapeutically effective amount of said immunosuppressant therapy.

In one embodiment, GVHD may be acute GVHD or chronic GVHD.

In one embodiment, the donor transplant may be "preconditioned" or "pretreated" by treating the transplant prior to transplantation into the recipient with CAR-engineered immune cells (preferably the CAR-engineered Treg cells) of the invention in order to reduce the immunogenicity of the transplant against the recipient, thereby reducing or preventing GVHD. In one embodiment, the transplant may be contacted with cells or a tissue from the recipient prior to transplantation in order to activate T cells that may be associated with the transplant. Following the treatment of the transplant with cells or a tissue from the recipient, the cells or tissue may be removed from the transplant. The treated transplant may be then further contacted with CAR-engineered immune cells (preferably the CAR-engineered Treg cells) of the present invention to reduce, inhibit or eliminate the activity of the immune effector cells that were activated by the treatment of the cells or tissue from the recipient. Following this treatment of the transplant with CAR-engineered immune cells (preferably the CAR-engineered Treg cells) of the present invention, the CAR-modified immune cells may be removed from the transplant prior to transplantation into the recipient. However, some CAR-engineered immune cells (e.g., the CAR-engineered Treg cells) may adhere to the transplant, and therefore, may be introduced to the recipient with the transplant. In this situation, the CAR-engineered immune cells (e.g., the CAR-engineered Treg cells) introduced into the recipient may suppress an immune response against the recipient caused by a cell associated with the transplant.

In one embodiment, the transplant host or recipient is HLA-A2 negative. In one embodiment, the transplant host or recipient is HLA-A2 negative and is positive for an HLA-A subtype selected from the group consisting of HLA-A03, HLA-A11, HLA-A23, HLA-A25, HLA-A26, HLA-A29, HLA-A30, HLA-A31, HLA-A33, and HLA-A34. In one embodiment, the transplant host or recipient is HLA-A2 negative and is positive for an HLA-A subtype selected from the group consisting of HLA-A25, HLA-A29 and HLA-A30.

In one embodiment, the transplant is HLA-A2 positive.

Another object of the invention is a method of expanding a population of immune cells in a subject wherein the immune cells are modified to express a chimeric antigen receptor (CAR) according to the invention, the method comprising administering to the subject an engineered immune cell as described anywhere herein, wherein the administered engineered immune cell produces a population of progeny immune cells in the subject.

In one embodiment, the immune cell is a regulatory immune cell, preferably selected from the group comprising regulatory T cells, $CD4^+$ regulatory T cells, $CD8^+$ regulatory T cells, regulatory γδ T cells, regulatory DN T cells, regulatory B cells, regulatory NK cells, regulatory macrophages, regulatory dendritic cells, and any combination thereof, and more preferably regulatory T cells.

In one embodiment, the CAR-engineered Treg cells of the present invention are able to replicate in vivo, thereby resulting in long-term persistence that can lead to sustained suppression of an immune response of a targeted cell and immune tolerance.

Another object of the present invention is thus a method of generating a persisting population of regulatory T cells in a subject wherein the regulatory T cells are modified to express a chimeric antigen receptor (CAR) of the invention, the method comprising administering to the subject a regulatory T cell as described anywhere herein, wherein the persisting population of modified regulatory T cells persists in the subject for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 30 days, 40 days, 50 days, 60 days, 70 days, 80 days, 90 days, 100 days, 200 days, 300 days, 400 days, 500 days, 600 days, 700 days, 800 days, 900 days, or 1000 days after administration.

In one embodiment, the CAR-Treg cells of the invention may be capable of self-renewing and being re-activated in vivo to suppress an immune response of a targeted cell. In one embodiment, the CAR-Treg cells may be memory CAR-Treg cells that can be re-activated to suppress an immune response of a targeted cell.

The immune cells may be obtained from any source. For example, in one embodiment, immune cells may be obtained from the tissue donor, the transplant recipient or an otherwise unrelated source (a different individual or species altogether) for generation of CAR-modified immune cells of the present invention. Accordingly, CAR-modified immune cells of the present invention may be autologous, allogeneic or xenogeneic to the transplant recipient or an otherwise unrelated source. In one embodiment, the CAR-Treg cells of the present invention may be autologous, allogeneic or xenogeneic to the transplant recipient. In one embodiment, the CAR-Treg cells of the present invention may be autologous to the transplant recipient.

In one embodiment, the subject may be a mammal. In one embodiment, the subject may be a human.

In one embodiment, it may be desirable to administer activated T cells to a subject and then subsequently redraw blood (or have an apheresis performed), activate T cells therefrom according to the present invention, and reinfuse the subject with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The CAR-engineered immune cells of the present invention may be administered either alone or as a pharmaceutical composition in combination with diluents and/or with other components, including, without limitation, IL-2 or other cytokines or cell populations.

In one embodiment, the pharmaceutical compositions of the present invention may comprise a CAR-engineered immune cell or cell population as described anywhere herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The pharmaceutical compositions of the present invention may be administered to a subject in any suitable manner, including by aerosol inhalation, injection, ingestion, transfusion, implantation or transplantation. The pharmaceutical compositions described anywhere herein may be administered to a subject by parenteral administration. The pharmaceutical compositions described anywhere herein may be administered to a subject subcutaneously, intradermally, intratumorally, intranodally, intramedullary, intramuscularly, intrasternally, by intravenous (i.v.) injection, by infusion techniques or intraperitoneally. In one embodiment, the CAR-modified immune cell compositions of the present invention may be administered to a subject by intradermal or subcutaneous injection. In another embodiment, the CAR-modified immune cell compositions of the present invention may be administered by i.v. injection. In one embodiment, the compositions of CAR-modified immune cells may be injected directly into a lymph node, site of infection, site of inflammation or site of tissue or organ rejection.

Pharmaceutical compositions of the present invention may be administered in a manner appropriate to the disease to be prevented or treated. The quantity and frequency of administration will be determined by such factors as the condition of the subject, and the type and severity of the subject's disease, although appropriate dosages may be determined by clinical trials.

When an "effective amount" or "therapeutic amount" is indicated, the precise amount of the compositions of the present invention to be administered may be determined with consideration of individual differences in age, weight, antibody titer, and condition of the subject. It can generally be stated that a pharmaceutical composition comprising the CAR-engineered immune cells as described anywhere herein may be administered at a dosage of $1\times10^4$ to $1\times10^9$ cells/kg body weight or $1\times10^5$ to $100\times10^5$ cells/kg body weight, including all integer values within those ranges. CAR-engineered immune cell compositions may also be administered multiple times at these dosages. The CAR-engineered immune cells can be administered by using infusion techniques that are commonly known in immunotherapy. The optimal dosage and treatment regimen for a particular subject can readily be determined by monitoring the subject for signs of disease and adjusting the treatment accordingly.

In one embodiment, the at least one CAR-engineered immune cell of the invention is administered to the subject in need thereof in combination with another active agent.

According to one embodiment, the at least one immune cell population is administered before, at the same time or after the administration of another active agent.

In one embodiment, the CAR-engineered immune cells of the present invention may be administered to a subject in conjunction with (e.g., before, simultaneously or following) any number of relevant treatment modalities, including but not limited to treatment with agents such as antiviral therapy, chemotherapy, radiation, immunosuppressive agents, antibodies, immunoablative agents, cytokines, and irradiation.

In one embodiment, the CAR-engineered immune cells of the present invention may be administered in conjunction with an immunosuppressant agent. Any immunosuppressant agent known in the art may be used.

Examples of immunosuppressant agents include, but are not limited to, calcineurin inhibitors such as cyclosporine, tacrolimus, azathioprine, methotrexate, methoxsalen, rapamycin, mycophenolate mofetil, mycophenolic acid, mycophenolate sodium, 6-mercaptopurine, 6-thioguanine, rituximab, mTOR inhibitors such as sirolimus, everolimus, basiliximab, daclizumab, belatacept, alemtuzumab, muromonab-CD3, anti-thymocyte globulin, glucorticosteroids, or adrenocortical steroids such as prednisone and prednisolone, or any combination thereof.

The CAR-engineered immune cells of the present invention may be administered to the subject before, after, or concomitant with the immunosuppressant agent.

The CAR-engineered immune cells of the present invention and/or the immunosuppressant agent may be administered to the subject after transplantation. Alternatively, or in addition, the CAR-engineered immune cells of the present invention and/or the immunosuppressant agent may be administered to the subject before transplantation. The CAR-engineered immune cells of the present invention and/or the immunosuppressant agent may be administered to the subject during transplantation surgery.

In one embodiment, the method of the invention of administering CAR-engineered immune cells to the subject is carried out once immunosuppressive therapy has been initiated.

In some embodiments, the method is carried out more than once, e.g., to monitor the transplant recipient over time, and, if applicable, in different immunosuppressive therapy regimes.

In some embodiments, immunosuppressive therapy is reduced if the transplant recipient is predicted to be tolerant of the transplant. In some embodiments, no immunosuppressive therapy is prescribed, e.g., immunosuppressive therapy is ceased, if the transplant recipient is predicted to be tolerant of the transplant.

The present invention thus further relates to a kit of part comprising, in a first part, an immune cell or an immune cell population of the present invention, and in a second part, another active agent, including without limitations, antiviral therapy, chemotherapy, radiation, immunosuppressive agents, antibodies, immunoablative agents, cytokines, and irradiation. Preferably, the kit of part of the present invention comprises in a first part, an immune cell or an immune cell population of the present invention, and in a second part, one or more immunosuppressive agents.

In one embodiment, the kit of parts comprises one or more reagents (e.g., a nucleic acid or expression vector encoding an anti-HLA-A antibody or CAR of the present disclosure) for making the cells of the present invention.

Examples of immunosuppressive agents that may be present in the kit of the invention include, but are not limited to, calcineurin inhibitors such as cyclosporine, tacrolimus, azathioprine, methotrexate, methoxsalen, rapamycin, mycophenolate mofetil, mycophenolic acid, mycophenolate sodium, 6-mercaptopurine, 6-thioguanine, rituximab, mTOR inhibitors such as sirolimus, everolimus, basiliximab, daclizumab, belatacept, alemtuzumab, muromonab-CD3, anti-thymocyte globulin, glucorticosteroids, or adrenocortical steroids such as prednisone and prednisolone, or any combination thereof.

Another object of the invention is a method of preventing or treating organ or tissue transplant rejection in a subject, the method comprising administering to the subject (i) at least one immunosuppressive agent and (ii) CAR-engineered immune cells (preferably the CAR-engineered Treg cells) of the invention, or a pharmaceutical composition comprising said immune cells.

Another object of the present invention is thus a combination of a CAR-engineered immune cell (preferably the CAR-engineered Treg cells) of the invention, or a pharmaceutical composition comprising said immune cells, and of at least one immunosuppressive agent, for use in preventing or treating organ or tissue transplant rejection in a subject.

Another object of the invention is a method of increasing the time period of graft survival in a subject, the method comprising administering to the subject at least one immunosuppressive agent and CAR-engineered immune cells (preferably the CAR-engineered Treg cells) of the present invention, or a pharmaceutical composition comprising the same.

In one embodiment, a combination of at least one immunosuppressive agent with CAR-engineered immune cells (preferably the CAR-engineered Treg cells) of the present invention is used to prevent or treat graft versus host disease (GVHD).

In one embodiment, the GVHD may occur after hematopoietic stem cell transplantation.

Another object of the invention is thus a method of preventing or treating graft versus host disease (GVHD) in a subject, the method comprising administering to the subject at least one immunosuppressive agent and CAR-engineered immune cells (preferably the CAR-engineered Treg cells) or a pharmaceutical composition as described herein.

In one embodiment, the invention provides a method of contacting a donor transplant, for example, a biocompatible lattice or a donor tissue, organ or cell, with at least one immunosuppressive agent and CAR-engineered immune cells (preferably the CAR-engineered Treg cells) of the present invention at the same time as, before, or after the transplantation of the transplant into a recipient.

In one embodiment, the combination of at least one immunosuppressive agent with CAR-engineered immune cells (preferably the CAR-engineered Treg cells) of the present invention may be used to ameliorate, inhibit or reduce an adverse response by the donor transplant against the recipient, thereby preventing or treating GVHD.

Another object of the present invention is thus a method of preventing or delaying onset of GVHD in a subject, the method comprising administering to the subject at least one immunosuppressive agent and CAR-engineered immune cells (preferably the CAR-engineered Treg cells) or a pharmaceutical composition as described herein.

In one embodiment, the CAR-engineered immune cells of the invention and the at least one immunosuppressive agent are administered simultaneously or sequentially.

In one embodiment, the CAR-engineered immune cells of the present invention, and optionally the at least one other active agent, preferably immunosuppressive agent, is administered in conjunction with (e.g., before, simultaneously or following) the transplant.

The CAR-engineered immune cells of the present invention may be administered following a diagnosis of transplant organ or tissue rejection followed by doses of both the CAR-engineered immune cells of the invention and an immunosuppressant agent until symptoms of organ or tissue rejection subside.

In a further embodiment, the CAR-engineered immune cell compositions of the present invention may be administered to a subject in conjunction with (e.g., before, simultaneously or following) bone marrow transplantation.

In another embodiment, the CAR-engineered immune cells of the present invention may be administered following B-cell ablative therapy such as agents that react with CD20, e.g., Rituximab. For example, in one embodiment, subjects may undergo standard treatment with high dose chemotherapy followed by peripheral blood stem cell transplantation. In certain embodiments, following the transplant, subjects may receive an infusion of the expanded CAR-engineered immune cells of the present invention. In an additional embodiment, expanded CAR-engineered immune cells may be administered before or following surgery.

In one embodiment, the subject (e.g., human) receives an initial administration of the at least one immune cell or population of the invention, and one or more subsequent administrations, wherein the one or more subsequent administrations are administered less than 15 days, e.g., 14, 13, 12, 11, 10, 9, 8, 7, 6, 5, 4, 3, or 2 days after the previous administration.

In one embodiment, a therapeutically effective amount of immune cells of the invention is administered or is to be administered to the subject.

In one embodiment, the amount of immune cells of the at least one immune cell population of the invention administered to the subject is at least of $10^2$, $10^3$, $10^4$, $10^5$, $10^6$, $10^7$, $10^8$ or $10^9$ cells.

In one embodiment, the amount of immune cells of the invention administered to the subject ranges from about $10^2$ to about $10^9$, from about $10^3$ to about $10^8$, from about $10^4$ to about $10^7$, or from about $10^5$ to about $10^6$ cells.

In another embodiment, the amount of immune cells of the invention administered to the subject ranges from about $10^6$ to about $10^9$, from about $10^6$ to $10^7$, from about $10^6$ to $10^8$, from about $10^7$ to $10^9$, from about $10^7$ to $10^8$, from about $10^8$ to $10^9$. In another embodiment the amount of immune cells of the invention administered to the subject is about $10^6$, about $10^7$, about $10^8$, or is about $10^9$.

In one embodiment, the amount of immune cells of the at least one immune cell population of the invention administered to the subject is at least of $10^2$, $10^3$, $10^4$, $10^5$, $10^6$, $10^7$, $10^8$ or $10^9$ cells/kg body.

In one embodiment, the amount of immune cells of the invention administered to the subject ranges from about $10^4$ to $10^9$ cells/kg body weight or $10^5$ to $10^8$ cells/kg body weight, including all integer values within those ranges.

In one embodiment, more than one administration of the at least one immune cell or population of the invention are administered to the subject (e.g., human) per week, e.g., 2, 3, or 4 administrations of the genetically modified immune cell or population of the invention are administered per week.

Another object of the present invention is an article of manufacture containing materials useful for the prevention and/or treatment of transplant rejection or GVHD.

The article of manufacture may comprise a container and a label or package insert on or associated with the container. Suitable containers include, for example, bottles, vials, syringes, etc. The containers may be formed from a variety of materials such as glass or plastic. The container holds a composition which is effective for preventing and/or treating the immunological condition, such as transplant rejection or GVHD, and may have a sterile access port (for example the container may be an intravenous solution bag or a vial having a stopper pierceable by a hypodermic injection needle). At least one active agent in the composition is a CAR-engineered immune cell of the present invention, preferably a CAR-engineered Treg.

The label or package insert may indicate that the composition is used for preventing or treating transplant rejection or GVHD.

The article of manufacture, label or package insert may further comprise instructional material for administering the CAR-engineered immune cell composition to the patient.

Additionally, the article of manufacture may further comprise a second container comprising a pharmaceutically acceptable buffer, such as, for example, bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes (e.g., for preventing or treating transplant rejection or GVHD). Kits can be provided which contain the CAR-engineered immune cells. As with the article of manufacture, the kit may comprise a container and a label or package insert on or associated with the container. The container holds a composition comprising at least one CAR-engineered immune cell, preferably a CAR-engineered Treg of the present invention. Additional containers may be included that contain, e.g., diluents and buffers. The label or package insert may provide a description of the composition as well as instructions for the intended use.

Examples

The present invention is further illustrated by the following examples.

Example 1

Materials and Methods

Generation of humanized HLA-A2-specific scFvs. The sequence for HLA-A2 specific scFv was derived from the sequence disclosed in the patent application US2013/0078243 A1. Codon optimized gene-sequences coding for the humanized scFv were synthetized by GeneArt®, Life Technologies (Regensburg) as "Strings", using the codon optimization algorithm provided by the supplier. ScFv's were flanked N-terminally by a Kozak sequence, and a CD8-Signal sequence. The constructs were further flanked by BamHI and MfeI restriction sites which allowed in frame cloning to the CD8-hinge region of a self-inactivating, lentiviral CAR-expression plasmid. The PGK-promoter driven CAR-expression plasmid contained the human CD8 hinge and CD8 transmembrane domain, which is followed by an intracellular human 41BB costimulatory domain fused to a human CD3. Following the CAR-sequence an EGFP reporter protein was connected in frame via a self-cleavable 2A-site for detection of gene transfer in cells.

Generation of HLA-A2-CARs. Viral vectors were generated by polyethylenimine based transient transfection in HEK 293T cells using $3^{rd}$ generation packaging plasmids (Trono lab, EPFL (École polytechnique fédérale de Lausanne)).

Jurkat NFAT. Jurkat-Lucia NFAT-reporter cell lines were cultivated in RPMI (Gibco™, Life Technologies™) supplemented with 10% Fetal calf serum. Cells were transduced using incubation at different concentrations of viral vectors to achieve 30-50% of transduction to avoid multiple vector integrations. Expression and display of correctly folded CARs was demonstrated by binding to an APC-conjugated HLA-A2-multimer (Dextramer®, WB2666, Immudex; Copenhagen, Denmark). Activation via the CAR was achieved by coincubation of HLA-A2-specific CARs with HLA-A2 positive or HLA-A2 negative cell lines. NFAT-activation dependent Luciferase secretion in the Medium was analyzed on a luminometer (GloMax®, Promega) using the QUANTI-Luc™ substrate (Invivogen).

Treg sorting, transduction, and expansion. CD4$^+$ T cells were isolated from HLA-A2-donors via RosetteSep™ (Stemcell™) and enriched for CD25$^+$ cells (Miltenyi) prior to sorting live CD4$^+$ CD127$^{lo}$CD25$^{hi}$ Tregs using a FACSAria™ II (BD® Biosciences). Sorted Tregs were stimulated with L cells and αCD3 mAb (OKT3; 200 ng/mL) in 1000 U/ml of IL-2. One day later, cells were transduced with lentivirus at a multiplicity of infection of 10 virus particles:1 cell. At day 7, cells were re-stimulated with L cells as above and expanded for 5 days. To test effects of HLA-A2-mediated stimulation, Tregs were cultured overnight with limiting IL-2 (100 U/mL) and subsequently re-stimulated with irradiated anti-CD3/anti-CD28 loaded K562.64 cells or K562.64.HLA-A2 cells, at a 1:2 (K562:T cell) ratio for 24 hours.

Flow cytometry. For phenotypic analysis, cells were stained with fixable viability dye (FVD, 65-0865-14, eBioscience™; 423102, Biolegend®) and for surface markers before fix/perm with FOXP3/Transcription Factor Staining Buffer Set (eBioscience™) and staining for intracellular proteins. Samples were read on a Cytoflex (Beckman-Coulter) and results analyzed using FlowJo™ Software version 9.9.4 and 10.3 (Tree Star). Surface staining was performed for CD3 (564465, BD® Biosciences), CD4 (317410, Biolegend®), CD25 (130-091-024, Miltenyi), LAP (25-9829-42, eBioscience™), CD69 (310946, Biolegend®), and CD154 (555702, BD® Biosciences), and CD127 (48-1278-42, eBiosciences™). Tetramer staining was performed with HLA-A*02:01 monomers made into tetramers with streptavidin-allophycocyanin (PJ27S, Prozyme). Intracellular staining was performed for CTLA-4 (369606, Biolegend®).

HLA allele cross reactivity assay. 0.25×10$^6$ Tregs expressing a CAR according to the present invention, or a CAR comprising the VH and VL of the BB7.2 antibody (mA2 CAR), were incubated with FlowPRA® Single Antigen Antibody beads panel (FL1HD01, FL1HD02, FL1HD03, FL1HD04, FL1HD06 and FL1HD08, One Lambda) and fixable viability dye (FVD, ThermoFisher, 65-0865-14, eBioscience™) for 30 minutes at room temperature. Samples were washed, fixed with 0.5% formaldehyde and analyzed via flow cytometry. Two hundred negative control beads were acquired per sample. Beads alone were used as a negative control. For analysis, dead cells were first eliminated using the fixable viability dye. Single antigen beads were then gated after exclusion of dead cells and doublets. Then, the number of beads per HLA antigen was determined by their respective PE intensity peak. Data were normalized by multiplying the number of beads of interest in each HLA-peak by 200, divided by the number of negative beads in the sample. For each HLA-peak the percent relative binding of CAR Tregs compared to control (non-CAR-expressing cells) was determined by subtracting the number of beads in the CAR-Treg from the number of beads in the control sample then dividing the average number of beads in the non-CAR-expressing control, times 100.

Results:

Construction of Humanized HLA-A2-Specific CARs 1 humanized heavy chain and 3 different humanized light chains were generated, and a total of 3 different chimeric antigen receptors were generated by combining the humanized heavy and light chains.

Expression and correct folding of the CAR were verified using Jurkat NFAT-reporter cell lines.

Cross Reactivity of HLA-A2-CAR Constructs on Other Class I HLA Alleles

There are many different alleles of HLA that have evolved over time from a smaller number of ancestor alleles. Consequently, there are allele families that may differ by only a few amino acids and a single anti-HLA antibody may recognize multiple alleles within an evolutionarily-related family. The mouse monoclonal antibody (BB7.2) is known to have cross reactivity to additional HLA-A alleles (Hilton & Parham, 2013). Specifically, when tested in a solid-phase assay, BB7.2 was found to recognize five subtypes of HLA-A2 (*02:01, *02:02, *02:03, *02:05, *02:06) and to be cross reactive with HLA-A*69:01, and when tested at high concentrations, also with HLA-A*23:01, A*24:02, A*24:03, A*68:01, and A*68:02 (Hilton & Parham, 2013). To assess the cross reactivity of humanized anti-HLA-A2 antibodies of the invention and compare to an antibody comprising the VH and VL of the BB7.2 antibody, we adapted the ONE Lambda™ solid phase assay, which is designed for measuring anti-HLA-antibodies in serum, to measure HLA-coated bead binding to the humanized CARs of interest. GFP$^+$ Tregs expressing the indicated humanized CARs were incubated with Flow Panel Reactive Single Antigen beads, with binding to a single class of beads quantified as the loss of signal in the bead gate in the forward/side scatter plot. The data were normalized to the number of negative control beads in the sample, and the amount of relative binding to hCAR-expressing Tregs was calculated in relation to the amount of binding by GFP+-control Tregs by the number of negative beads in the GFP specimen multiplied by the number of negative beads in the GFP specimen.

Figure 1B:
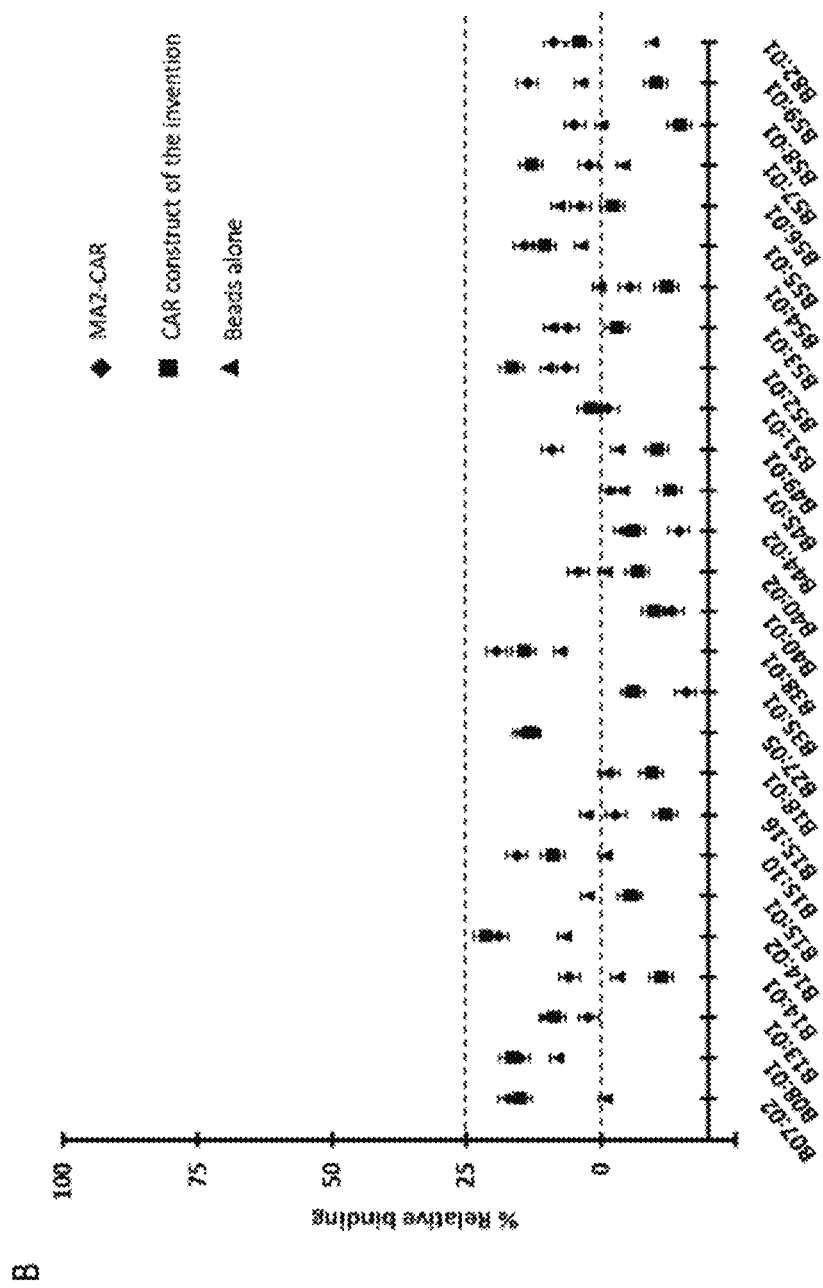

Results are shown on FIG. 1 for the construct comprising a scFv having the sequence SEQ ID NO: 72). This HLA-A2-CAR construct significantly bound HLA-A*02:01 (FIG. 1A). Surprisingly, for the CAR construct of the invention, we did not observe any statistically significant binding to any HLA-A or B alleles tested other than A*02:01. (FIG. 1A-B).

The invention claimed is:

1. A humanized anti-HLA-A2 antibody, or an antigen-binding fragment thereof, comprising a heavy chain variable domain (VH) that comprises the amino acid sequence of SEQ ID NO: 9, and a light chain variable domain (VL) that comprises the amino acid sequence of SEQ ID NO: 13.

2. The humanized antibody or antigen-binding fragment of claim 1, wherein said antibody is a whole antibody, a single-chain antibody, a dimeric single-chain antibody, a Fv, an scFv, a Fab, a F(ab)'$_2$, a defucosylated antibody, a bi-specific antibody, a diabody, a triabody, a tetrabody, or a unibody.

3. The humanized antibody of claim 1, wherein said antibody is an scFv.

4. The humanized antibody of claim 3, wherein the scFv comprises the amino acid sequence of SEQ ID NO: 72.

5. A chimeric antigen receptor (CAR) comprising:
  a) an extracellular domain comprising the humanized anti-HLA-A2 antibody or antigen-binding fragment of claim 1;
  b) a transmembrane domain; and
  c) a cytoplasmic domain comprising an intracellular signaling domain.

6. The CAR of claim 5, wherein the CAR specifically binds to HLA-A*02:01.

7. The CAR of claim 5, wherein the transmembrane domain is a CD8 transmembrane domain and the intracellular signaling domain comprises a 4-1BB costimulatory domain and a CD3 zeta primary signaling domain.

8. The CAR of claim 5, wherein the humanized anti-HLA-A2 antibody or antigen-binding fragment is an scFv comprising the amino acid sequence of SEQ ID NO: 72.

9. A nucleic acid molecule encoding the CAR of claim 5.

10. An immune cell comprising the CAR of claim 5.

11. The immune cell of claim 10, wherein the immune cell is a regulatory T cell.

12. A pharmaceutical composition comprising the immune cell of claim 10 and a pharmaceutically acceptable excipient.

13. A method for:
  a) treating organ or tissue transplant rejection in a subject;
  b) treating graft versus host disease (GVHD) in a subject;
  c) inducing immune tolerance in a subject in need thereof;
  d) inducing tolerance to a transplanted organ or tissue in a subject; or
  e) any combination of a)-d);
  wherein said method comprises administering an immune cell of claim 10 to the subject.

14. The method of claim 13, further comprising administering at least one immunosuppressive agent to the subject.

* * * * *

SEQUENCE LISTING

<160> NUMBER OF SEQ ID NOS: 89

<210> SEQ ID NO 1
<211> LENGTH: 5
<212> TYPE: PRT
<213> ORGANISM: Artificial Sequence
<220> FEATURE:
<223> OTHER INFORMATION: VH-CDR1

```
<400> SEQUENCE: 1

Ser Tyr His Ile Gln
1               5

<210> SEQ ID NO 2
<211> LENGTH: 17
<212> TYPE: PRT
<213> ORGANISM: Artificial Sequence
<220> FEATURE:
<223> OTHER INFORMATION: VH-CDR2

<400> SEQUENCE: 2

Trp Ile Tyr Pro Gly Asp Gly Ser Thr Gln Tyr Asn Glu Lys Phe Lys
1               5                   10                  15

Gly

<210> SEQ ID NO 3
<211> LENGTH: 9
<212> TYPE: PRT
<213> ORGANISM: Artificial Sequence
<220> FEATURE:
<223> OTHER INFORMATION: VH-CDR3

<400> SEQUENCE: 3

Glu Gly Thr Tyr Tyr Ala Met Asp Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: VH-CDR1

<400> SEQUENCE: 4

Gly Tyr Thr Phe Thr Ser Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: VH-CDR2

<400> SEQUENCE: 5

Tyr Pro Gly Asp Gly Ser
1               5

<210> SEQ ID NO 6
<211> LENGTH: 16
<212> TYPE: PRT
<213> ORGANISM: Artificial Sequence
<220> FEATURE:
<223> OTHER INFORMATION: VL-CDR1

<400> SEQUENCE: 6

Arg Ser Ser Gln Ser Ile Val His Ser Asn Gly Asn Thr Tyr Leu Glu
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: VL-CDR2
```

```
<400> SEQUENCE: 7

Lys Val Ser Asn Arg Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: VL-CDR3

<400> SEQUENCE: 8

Phe Gln Gly Ser His Val Pro Arg Thr
1               5

<210> SEQ ID NO 9
<211> LENGTH: 118
<212> TYPE: PRT
<213> ORGANISM: Artificial Sequence
<220> FEATURE:
<223> OTHER INFORMATION: VH

<400> SEQUENCE: 9

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Ile
            35                  40                  45

Gly Trp Ile Tyr Pro Gly Asp Gly Ser Thr Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Ser Val Thr Val Ser Ser
        115

<210> SEQ ID NO 10
<211> LENGTH: 113
<212> TYPE: PRT
<213> ORGANISM: Artificial Sequence
<220> FEATURE:
<223> OTHER INFORMATION: VL
<220> FEATURE:
<221> NAME/KEY: SITE
<222> LOCATION: 2
<223> OTHER INFORMATION: X is V or I
<220> FEATURE:
<221> NAME/KEY: SITE
<222> LOCATION: 7
<223> OTHER INFORMATION: X is T or S
<220> FEATURE:
<221> NAME/KEY: SITE
<222> LOCATION: 9
<223> OTHER INFORMATION: X is L or S or A
<220> FEATURE:
<221> NAME/KEY: SITE
<222> LOCATION: 10
<223> OTHER INFORMATION: X is S or T
<220> FEATURE:
<221> NAME/KEY: SITE
<222> LOCATION: 12
```

-continued

```
<223> OTHER INFORMATION: X is P or S
<220> FEATURE:
<221> NAME/KEY: SITE
<222> LOCATION: 14
<223> OTHER INFORMATION: X is T or S
<220> FEATURE:
<221> NAME/KEY: SITE
<222> LOCATION: 15
<223> OTHER INFORMATION: X is L or P
<220> FEATURE:
<221> NAME/KEY: SITE
<222> LOCATION: 17
<223> OTHER INFORMATION: X is E or D
<220> FEATURE:
<221> NAME/KEY: SITE
<222> LOCATION: 18
<223> OTHER INFORMATION: X is P or R
<220> FEATURE:
<221> NAME/KEY: SITE
<222> LOCATION: 19
<223> OTHER INFORMATION: X is A or V
<220> FEATURE:
<221> NAME/KEY: SITE
<222> LOCATION: 20
<223> OTHER INFORMATION: X is S or T
<220> FEATURE:
<221> NAME/KEY: SITE
<222> LOCATION: 42
<223> OTHER INFORMATION: X is L or Q
<220> FEATURE:
<221> NAME/KEY: SITE
<222> LOCATION: 48
<223> OTHER INFORMATION: X is S or A
<220> FEATURE:
<221> NAME/KEY: SITE
<222> LOCATION: 63
<223> OTHER INFORMATION: X is V or I
<220> FEATURE:
<221> NAME/KEY: SITE
<222> LOCATION: 79
<223> OTHER INFORMATION: X is K or T
<220> FEATURE:
<221> NAME/KEY: SITE
<222> LOCATION: 83
<223> OTHER INFORMATION: X is V or L
<220> FEATURE:
<221> NAME/KEY: SITE
<222> LOCATION: 85
<223> OTHER INFORMATION: X is A or P
<220> FEATURE:
<221> NAME/KEY: SITE
<222> LOCATION: 88
<223> OTHER INFORMATION: X is L or F
<220> FEATURE:
<221> NAME/KEY: SITE
<222> LOCATION: 89
<223> OTHER INFORMATION: X is G or A

<400> SEQUENCE: 10

Asp Xaa Val Met Thr Gln Xaa Pro Xaa Xaa Leu Xaa Val Xaa Xaa Gly
1               5                   10                  15

Xaa Xaa Xaa Xaa Ile Ser Cys Arg Ser Ser Gln Ser Ile Val His Ser
            20                  25                  30

Asn Gly Asn Thr Tyr Leu Glu Trp Tyr Xaa Gln Lys Pro Gly Gln Xaa
        35                  40                  45

Pro Arg Leu Leu Ile Tyr Lys Val Ser Asn Arg Phe Ser Gly Xaa Pro
    50                  55                  60

Asp Arg Phe Ser Gly Ser Gly Ser Gly Thr Asp Phe Thr Leu Xaa Ile
65                  70                  75                  80

Ser Arg Xaa Glu Xaa Glu Asp Xaa Xaa Val Tyr Tyr Cys Phe Gln Gly
                85                  90                  95

Ser His Val Pro Arg Thr Phe Gly Gly Gly Thr Lys Leu Glu Ile Lys
```

-continued

```
                100                 105                 110
Arg

<210> SEQ ID NO 11
<211> LENGTH: 113
<212> TYPE: PRT
<213> ORGANISM: Artificial Sequence
<220> FEATURE:
<223> OTHER INFORMATION: VL

<400> SEQUENCE: 11

Asp Val Val Met Thr Gln Thr Pro Leu Ser Leu Pro Val Thr Leu Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
            100                 105                 110

Arg

<210> SEQ ID NO 12
<211> LENGTH: 113
<212> TYPE: PRT
<213> ORGANISM: Artificial Sequence
<220> FEATURE:
<223> OTHER INFORMATION: VL

<400> SEQUENCE: 12

Asp Val Val Met Thr Gln Ser Pro Ser Ser Leu Ser Val Thr Leu Gly
1               5                   10                  15

Asp Arg Val Ser Ile Ser Cys Arg Ser Ser Gln Ser Ile Val His Ser
            20                  25                  30

Asn Gly Asn Thr Tyr Leu Glu Trp Tyr Gln Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Arg Val Glu Pro Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
            100                 105                 110

Arg

<210> SEQ ID NO 13
<211> LENGTH: 113
<212> TYPE: PRT
<213> ORGANISM: Artificial Sequence
<220> FEATURE:
<223> OTHER INFORMATION: VL

<400> SEQUENCE: 13
```

```
Asp Ile Val Met Thr Gln Ser Pro Ala Thr Leu Ser Val Ser Pro Gly
1               5                   10                  15

Glu Arg Ala Thr Ile Ser Cys Arg Ser Gln Ser Ile Val His Ser
            20                  25                  30

Asn Gly Asn Thr Tyr Leu Glu Trp Tyr Gln Gln Lys Pro Gly Gln Ala
        35                  40                  45

Pro Arg Leu Leu Ile Tyr Lys Val Ser Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Phe Gln Gly
                85                  90                  95

Ser His Val Pro Arg Thr Phe Gly Gly Gly Thr Lys Leu Glu Ile Lys
            100                 105                 110

Arg

<210> SEQ ID NO 14
<211> LENGTH: 4
<212> TYPE: PRT
<213> ORGANISM: Artificial Sequence
<220> FEATURE:
<223> OTHER INFORMATION: G3S linker

<400> SEQUENCE: 14

Gly Gly Gly Ser
1

<210> SEQ ID NO 15
<211> LENGTH: 16
<212> TYPE: PRT
<213> ORGANISM: Artificial Sequence
<220> FEATURE:
<223> OTHER INFORMATION: G3S linker

<400> SEQUENCE: 15

Gly Gly Gly Ser Gly Gly Gly Ser Gly Gly Gly Ser Gly Gly Gly Ser
1               5                   10                  15

<210> SEQ ID NO 16
<211> LENGTH: 6
<212> TYPE: PRT
<213> ORGANISM: Artificial Sequence
<220> FEATURE:
<223> OTHER INFORMATION: G4S linker

<400> SEQUENCE: 16

Gly Gly Gly Gly Gly Ser
1               5

<210> SEQ ID NO 17
<211> LENGTH: 10
<212> TYPE: PRT
<213> ORGANISM: Artificial Sequence
<220> FEATURE:
<223> OTHER INFORMATION: G4S linker

<400> SEQUENCE: 17

Gly Gly Gly Gly Ser Gly Gly Gly Gly Ser
1               5                   10

<210> SEQ ID NO 18
<211> LENGTH: 15
```

```
<212> TYPE: PRT
<213> ORGANISM: Artificial Sequence
<220> FEATURE:
<223> OTHER INFORMATION: G4S linker

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 20
<212> TYPE: PRT
<213> ORGANISM: Artificial Sequence
<220> FEATURE:
<223> OTHER INFORMATION: G4S linker

<400> SEQUENCE: 19

Gly Gly Gly Gly Ser Gly Gly Gly Gly Ser Gly Gly Gly Gly Ser Gly
1               5                   10                  15

Gly Gly Gly Ser
            20

<210> SEQ ID NO 20
<211> LENGTH: 16
<212> TYPE: PRT
<213> ORGANISM: Artificial Sequence
<220> FEATURE:
<223> OTHER INFORMATION: Hinge domain

<400> SEQUENCE: 20

Ala Gly Ser Ser Ser Ser Gly Gly Ser Thr Thr Gly Gly Ser Thr Thr
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Hinge domain

<400> SEQUENCE: 21

Gly Thr Thr Ala Ala Ser Gly Ser Ser Gly Gly Ser Ser Ser Gly Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Hinge domain

<400> SEQUENCE: 22

Ser Ser Ala Thr Ala Thr Ala Gly Thr Gly Ser Ser Thr Gly Ser Thr
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Hinge domain

<400> SEQUENCE: 23

Thr Ser Gly Ser Thr Gly Thr Ala Ala Ser Ser Thr Ser Thr Ser Thr
1               5                   10                  15
```

-continued

```
<210> SEQ ID NO 24
<211> LENGTH: 30
<212> TYPE: DNA
<213> ORGANISM: Artificial Sequence
<220> FEATURE:
<223> OTHER INFORMATION: Hinge domain

<400> SEQUENCE: 24
ggtggcggag gttctggagg tggaggttcc                                          30

<210> SEQ ID NO 25
<211> LENGTH: 7
<212> TYPE: PRT
<213> ORGANISM: Artificial Sequence
<220> FEATURE:
<223> OTHER INFORMATION: Hinge domain

<400> SEQUENCE: 25

Lys Ile Arg Arg Asp Ser Ser
1               5

<210> SEQ ID NO 26
<211> LENGTH: 45
<212> TYPE: PRT
<213> ORGANISM: Artificial Sequence
<220> FEATURE:
<223> OTHER INFORMATION: CD8 Hinge domain

<400> SEQUENCE: 26

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 27
<211> LENGTH: 135
<212> TYPE: DNA
<213> ORGANISM: Artificial Sequence
<220> FEATURE:
<223> OTHER INFORMATION: CD8 Hinge domain

<400> SEQUENCE: 27
accacgacgc cagcgccgcg accaccaaca ccggcgccca ccatcgcgtc gcagcccctg         60
tccctgcgcc cagaggcgtg ccggccagcg gcggggggcg cagtgcacac gagggggctg        120
gacttcgcct gtgat                                                         135

<210> SEQ ID NO 28
<211> LENGTH: 230
<212> TYPE: PRT
<213> ORGANISM: Artificial Sequence
<220> FEATURE:
<223> OTHER INFORMATION: IgG4 Hinge domain

<400> SEQUENCE: 28

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
```

```
                 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230

<210> SEQ ID NO 29
<211> LENGTH: 690
<212> TYPE: DNA
<213> ORGANISM: Artificial Sequence
<220> FEATURE:
<223> OTHER INFORMATION: IgG4 Hinge domain

<400> SEQUENCE: 29
gagagcaagt acggccctcc ctgcccccct tgccctgccc ccgagttcct gggcggaccc     60
agcgtgttcc tgttcccccc caagcccaag acaccctga tgatcagccg gacccccgag    120
gtgacctgtg tggtggtgga cgtgtcccag gaggaccccg aggtccagtt caactggtac    180
gtggacggcg tggaggtgca caacgccaag accaagcccc gggaggagca gttcaatagc    240
acctaccggg tggtgtccgt gctgaccgtg ctgcaccagg actggctgaa cggcaaggaa    300
tacaagtgta aggtgtccaa caagggcctg cccagcagca tcgagaaaac catcagcaag    360
gccaagggcc agcctcggga gccccaggtg tacaccctgc cccctagcca agaggagatg    420
accaagaacc aggtgtccct gacctgcctg gtgaagggct tctaccccag cgacatcgcc    480
gtggagtggg agagcaacgg ccagcccgag aacaactaca agaccacccc ccctgtgctg    540
gacagcgacg gcagcttctt cctgtacagc cggctgaccg tggacaagag ccggtggcag    600
gagggcaacg tctttagctg ctccgtgatg cacgaggccc tgcacaacca ctacacccag    660
aagagcctga gcctgtccct gggcaagatg                                    690

<210> SEQ ID NO 30
<211> LENGTH: 282
<212> TYPE: PRT
<213> ORGANISM: Artificial Sequence
<220> FEATURE:
<223> OTHER INFORMATION: IgD Hinge domain

<400> SEQUENCE: 30
```

```
Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
            35                  40                  45

Glu Lys Glu Glu Gln Glu Glu Arg Glu Thr Lys Thr Pro Glu Cys Pro
50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Gly Leu Leu Glu Arg His Ser Asn Gly
            115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Glu Ala Ala Ser
            180                 185                 190

Trp Leu Leu Cys Glu Val Ser Gly Phe Ser Pro Asn Ile Leu Leu
            195                 200                 205

Met Trp Leu Glu Asp Gln Arg Glu Val Asn Thr Ser Gly Phe Ala Pro
210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
            275                 280

<210> SEQ ID NO 31
<211> LENGTH: 847
<212> TYPE: DNA
<213> ORGANISM: Artificial Sequence
<220> FEATURE:
<223> OTHER INFORMATION: IgD Hinge domain

<400> SEQUENCE: 31
aggtggcccg aaagtcccaa ggcccaggca tctagtgttc ctactgcaca gccccaggca       60
gaaggcagcc tagccaaagc tactactgca cctgccacta cgcgcaatac tggccgtggc      120
ggggaggaga agaaaaagga gaaagagaaa gaagaacagg aagagaggga gaccaagacc      180
cctgaatgtc catcccatac ccagccgctg ggcgtctatc tcttgactcc cgcagtacag      240
gacttgtggc ttagagataa ggccaccttt acatgtttcg tcgtgggctc tgacctgaag      300
gatgcccatt tgacttggga ggttgccgga aaggtaccca caggggggt tgaggaaggg      360 ttgctggagc gccattccaa tggctctcag agccagcact caagactcac ccttccgaga      420
tccctgtgga acgccgggac ctctgtcaca tgtactctaa atcatcctag cctgccccca      480
```

```
cagcgtctga tggcccttag agagccagcc gcccaggcac cagttaagct tagcctgaat      540
ctgctcgcca gtagtgatcc cccagaggcc gccagctggc tcttatgcga agtgtccggc      600
tttagcccgc ccaacatctt gctcatgtgg ctggaggacc agcgagaagt gaacaccagc      660
ggcttcgctc cagcccggcc cccacccag ccggggttcta ccacattctg ggcctggagt      720
gtcttaaggg tcccagcacc acctagcccc cagccagcca catacacctg tgttgtgtcc      780
catgaagata gcaggaccct gctaaatgct tctaggagtc tggaggtttc ctacgtgact      840
gaccatt                                                                847

<210> SEQ ID NO 32
<211> LENGTH: 39
<212> TYPE: PRT
<213> ORGANISM: Artificial Sequence
<220> FEATURE:
<223> OTHER INFORMATION: CD28 Hinge domain

<400> SEQUENCE: 32

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 33
<211> LENGTH: 117
<212> TYPE: DNA
<213> ORGANISM: Artificial Sequence
<220> FEATURE:
<223> OTHER INFORMATION: CD28 Hinge domain

<400> SEQUENCE: 33
attgaagtta tgtatcctcc tccttaccta gacaatgaga agagcaatgg aaccattatc      60
catgtgaaag ggaaacacct tgtccaagt ccctatttc ccggaccttc taagccc           117

<210> SEQ ID NO 34
<211> LENGTH: 24
<212> TYPE: PRT
<213> ORGANISM: Artificial Sequence
<220> FEATURE:
<223> OTHER INFORMATION: CD8 transmembrane domain

<400> SEQUENCE: 34

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 35
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 35
atctacatct gggcgccctt ggccgggact tgtgggggtcc ttctcctgtc actggttatc     60
accctttact gc                                                          72
```

-continued

```
<210> SEQ ID NO 36
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 36

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 37
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 37
ttttgggtgc tggtggtggt tggtggagtc ctggcttgct atagcttgct agtaacagtg      60
gccttattta ttttctgggt g                                                81

<210> SEQ ID NO 38
<211> LENGTH: 112
<212> TYPE: PRT
<213> ORGANISM: Artificial Sequence
<220> FEATURE:
<223> OTHER INFORMATION: CD3zeta

<400> SEQUENCE: 38

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 39
<211> LENGTH: 112
<212> TYPE: PRT
<213> ORGANISM: Artificial Sequence
<220> FEATURE:
<223> OTHER INFORMATION: CD3zeta

<400> SEQUENCE: 39

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45
```

```
Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65              70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110
```

<210> SEQ ID NO 40
<211> LENGTH: 113
<212> TYPE: PRT
<213> ORGANISM: Artificial Sequence
<220> FEATURE:
<223> OTHER INFORMATION: CD3zeta

<400> SEQUENCE: 40

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65              70                  75                  80

Arg Arg Arg Gly Lys Gly His Asp Gly Leu Tyr Gln Gly Leu Ser Thr
            85                  90                  95

Ala Thr Lys Asp Thr Tyr Asp Ala Leu His Met Gln Ala Leu Pro Pro
            100                 105                 110

Arg
```

<210> SEQ ID NO 41
<211> LENGTH: 113
<212> TYPE: PRT
<213> ORGANISM: Artificial Sequence
<220> FEATURE:
<223> OTHER INFORMATION: CD3zeta

<400> SEQUENCE: 41

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65              70                  75                  80

Arg Arg Arg Gly Lys Gly His Asp Gly Leu Tyr Gln Gly Leu Ser Thr
            85                  90                  95

Ala Thr Lys Asp Thr Tyr Asp Ala Leu His Met Gln Ala Leu Pro Pro
            100                 105                 110

Arg
```

```
<210> SEQ ID NO 42
<211> LENGTH: 336
<212> TYPE: DNA
<213> ORGANISM: Artificial Sequence
<220> FEATURE:
<223> OTHER INFORMATION: CD3zeta

<400> SEQUENCE: 42
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336

<210> SEQ ID NO 43
<211> LENGTH: 336
<212> TYPE: DNA
<213> ORGANISM: Artificial Sequence
<220> FEATURE:
<223> OTHER INFORMATION: CD3zeta

<400> SEQUENCE: 43
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgc                             336

<210> SEQ ID NO 44
<211> LENGTH: 42
<212> TYPE: PRT
<213> ORGANISM: Artificial Sequence
<220> FEATURE:
<223> OTHER INFORMATION: 4-1BB intracellular domain

<400> SEQUENCE: 44

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 45
<211> LENGTH: 48
<212> TYPE: PRT
<213> ORGANISM: Artificial Sequence
<220> FEATURE:
<223> OTHER INFORMATION: CD27 intracellular domain

<400> SEQUENCE: 45

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
```

35                  40                  45

<210> SEQ ID NO 46
<211> LENGTH: 41
<212> TYPE: PRT
<213> ORGANISM: Artificial Sequence
<220> FEATURE:
<223> OTHER INFORMATION: CD28 intracellular domain

<400> SEQUENCE: 46

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 47
<211> LENGTH: 126
<212> TYPE: DNA
<213> ORGANISM: Artificial Sequence
<220> FEATURE:
<223> OTHER INFORMATION: 4-1BB intracellular domain

<400> SEQUENCE: 47
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 48
<211> LENGTH: 144
<212> TYPE: DNA
<213> ORGANISM: Artificial Sequence
<220> FEATURE:
<223> OTHER INFORMATION: CD27 intracellular domain

<400> SEQUENCE: 48
caacgaagga aatatagatc aaacaaagga gaaagtcctg tggagcctgc agagccttgt      60
cgttacagct gccccaggga ggaggagggc agcaccatcc ccatccagga ggattaccga     120
aaaccggagc ctgcctgctc cccc                                            144

<210> SEQ ID NO 49
<211> LENGTH: 123
<212> TYPE: DNA
<213> ORGANISM: Artificial Sequence
<220> FEATURE:
<223> OTHER INFORMATION: CD28 intracellular domain

<400> SEQUENCE: 49
aggagtaaga ggagcaggct cctgcacagt gactacatga acatgactcc ccgccgcccc      60
gggcccaccc gcaagcatta ccagccctat gccccaccac gcgacttcgc agcctatcgc     120
tcc                                                                   123

<210> SEQ ID NO 50
<211> LENGTH: 21
<212> TYPE: PRT
<213> ORGANISM: Artificial Sequence
<220> FEATURE:
<223> OTHER INFORMATION: CD8 leader sequence

<400> SEQUENCE: 50

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 51
<211> LENGTH: 9
<212> TYPE: PRT
<213> ORGANISM: Artificial Sequence
<220> FEATURE:
<223> OTHER INFORMATION: Tag

<400> SEQUENCE: 51

```
Asn Trp Ser His Pro Gln Phe Glu Lys
1               5
```

<210> SEQ ID NO 52
<211> LENGTH: 10
<212> TYPE: PRT
<213> ORGANISM: Artificial Sequence
<220> FEATURE:
<223> OTHER INFORMATION: Tag

<400> SEQUENCE: 52

```
Ser Ala Trp Ser His Pro Gln Phe Glu Lys
1               5                   10
```

<210> SEQ ID NO 53
<211> LENGTH: 222
<212> TYPE: PRT
<213> ORGANISM: Artificial Sequence
<220> FEATURE:
<223> OTHER INFORMATION: CAR

<400> SEQUENCE: 53

```
Ala Ala Ala Ile Glu Val Met Tyr Pro Pro Tyr Leu Asp Asn Glu
1               5                   10                  15

Lys Ser Asn Gly Thr Ile Ile His Val Lys Gly Lys His Leu Cys Pro
                20                  25                  30

Ser Pro Leu Phe Pro Gly Pro Ser Lys Pro Phe Trp Val Leu Val Val
            35                  40                  45

Val Gly Gly Val Leu Ala Cys Tyr Ser Leu Leu Val Thr Val Ala Phe
    50                  55                  60

Ile Ile Phe Trp Val Arg Ser Lys Arg Ser Arg Leu Leu His Ser Asp
65                  70                  75                  80

Tyr Met Asn Met Thr Pro Arg Arg Pro Gly Pro Thr Arg Lys His Tyr
                85                  90                  95

Gln Pro Tyr Ala Pro Pro Arg Asp Phe Ala Ala Tyr Arg Ser Arg Val
            100                 105                 110

Lys Phe Ser Arg Ser Ala Asp Ala Pro Ala Tyr Gln Gln Gly Gln Asn
        115                 120                 125

Gln Leu Tyr Asn Glu Leu Asn Leu Gly Arg Arg Glu Glu Tyr Asp Val
    130                 135                 140

Leu Asp Lys Arg Arg Gly Arg Asp Pro Glu Met Gly Gly Lys Pro Arg
145                 150                 155                 160

Arg Lys Asn Pro Gln Glu Gly Leu Tyr Asn Glu Leu Gln Lys Asp Lys
                165                 170                 175

Met Ala Glu Ala Tyr Ser Glu Ile Gly Met Lys Gly Glu Arg Arg Arg
            180                 185                 190

Gly Lys Gly His Asp Gly Leu Tyr Gln Gly Leu Ser Thr Ala Thr Lys
```

```
            195                 200                 205
Asp Thr Tyr Asp Ala Leu His Met Gln Ala Leu Pro Pro Arg
    210                 215                 220

<210> SEQ ID NO 54
<211> LENGTH: 223
<212> TYPE: PRT
<213> ORGANISM: Artificial Sequence
<220> FEATURE:
<223> OTHER INFORMATION: CAR

<400> SEQUENCE: 54

Ala Ala Ala Ile Glu Val Met Tyr Pro Pro Tyr Leu Asp Asn Glu
1               5                   10                  15

Lys Ser Asn Gly Thr Ile Ile His Val Lys Gly Lys His Leu Cys Pro
                20                  25                  30

Ser Pro Leu Phe Pro Gly Pro Ser Lys Pro Phe Trp Val Leu Val Val
            35                  40                  45

Val Gly Gly Val Leu Ala Cys Tyr Ser Leu Leu Val Thr Val Ala Phe
    50                  55                  60

Ile Ile Phe Trp Val Arg Ser Lys Arg Ser Arg Leu Leu His Ser Asp
65                  70                  75                  80

Tyr Met Asn Met Thr Pro Arg Arg Pro Gly Pro Thr Arg Lys His Tyr
                85                  90                  95

Gln Pro Tyr Ala Pro Pro Arg Asp Phe Ala Ala Tyr Arg Ser Arg Val
            100                 105                 110

Lys Phe Ser Arg Ser Ala Asp Ala Pro Ala Tyr Gln Gln Gly Gln Asn
        115                 120                 125

Gln Leu Tyr Asn Glu Leu Asn Leu Gly Arg Arg Glu Glu Tyr Asp Val
    130                 135                 140

Leu Asp Lys Arg Arg Gly Arg Asp Pro Glu Met Gly Gly Lys Pro Gln
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg
    210                 215                 220

<210> SEQ ID NO 55
<211> LENGTH: 223
<212> TYPE: PRT
<213> ORGANISM: Artificial Sequence
<220> FEATURE:
<223> OTHER INFORMATION: CAR

<400> SEQUENCE: 55

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
    50                  55                  60
```

```
Ile Thr Leu Tyr Cys Lys Arg Gly Arg Lys Lys Leu Leu Tyr Ile Phe
 65                  70                  75                  80

Lys Gln Pro Phe Met Arg Pro Val Gln Thr Thr Gln Glu Glu Asp Gly
                 85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Gln Gln Gly Gln
        115                 120                 125

Asn Gln Leu Tyr Asn Glu Leu Asn Leu Gly Arg Arg Glu Glu Tyr Asp
    130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg
    210                 215                 220
```

```
<210> SEQ ID NO 56
<211> LENGTH: 236
<212> TYPE: PRT
<213> ORGANISM: Artificial Sequence
<220> FEATURE:
<223> OTHER INFORMATION: CAR

<400> SEQUENCE: 56

Asn Trp Ser His Pro Gln Phe Glu Lys Met His Thr Thr Thr Pro Ala
  1               5                  10                  15

Pro Arg Pro Pro Thr Pro Ala Pro Thr Ile Ala Ser Gln Pro Leu Ser
                 20                  25                  30

Leu Arg Pro Glu Ala Cys Arg Pro Ala Ala Gly Gly Ala Val His Thr
            35                  40                  45

Arg Gly Leu Asp Phe Ala Cys Asp Ile Tyr Ile Trp Ala Pro Leu Ala
        50                  55                  60

Gly Thr Cys Gly Val Leu Leu Leu Ser Leu Val Ile Thr Leu Tyr Cys
 65                  70                  75                  80

Lys Arg Gly Arg Lys Lys Leu Leu Tyr Ile Phe Lys Gln Pro Phe Met
                 85                  90                  95

Arg Pro Val Gln Thr Thr Gln Glu Glu Asp Gly Cys Ser Cys Arg Phe
            100                 105                 110

Pro Glu Glu Glu Glu Gly Gly Cys Glu Leu Thr Arg Arg Val Lys Phe
        115                 120                 125

Ser Arg Ser Ala Asp Ala Pro Ala Tyr Gln Gln Gly Gln Asn Gln Leu
    130                 135                 140

Tyr Asn Glu Leu Asn Leu Gly Arg Arg Glu Glu Tyr Asp Val Leu Asp
145                 150                 155                 160

Lys Arg Arg Gly Arg Asp Pro Glu Met Gly Gly Lys Pro Arg Arg Lys
                165                 170                 175

Asn Pro Gln Glu Gly Leu Tyr Asn Glu Leu Gln Lys Asp Lys Met Ala
            180                 185                 190

Glu Ala Tyr Ser Glu Ile Gly Met Lys Gly Glu Arg Arg Arg Gly Lys
        195                 200                 205
```

```
Gly His Asp Gly Leu Tyr Gln Gly Leu Ser Thr Ala Thr Lys Asp Thr
        210                 215                 220

Tyr Asp Ala Leu His Met Gln Ala Leu Pro Pro Arg
225                 230                 235

<210> SEQ ID NO 57
<211> LENGTH: 224
<212> TYPE: PRT
<213> ORGANISM: Artificial Sequence
<220> FEATURE:
<223> OTHER INFORMATION: CAR

<400> SEQUENCE: 57

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Gln Gln Gly Gln
        115                 120                 125

Asn Gln Leu Tyr Asn Glu Leu Asn Leu Gly Arg Arg Glu Glu Tyr Asp
130                 135                 140

Val Leu Asp Lys Arg Arg Gly Arg Asp Pro Glu Met Gly Gly Lys Pro
145                 150                 155                 160

Gln Arg Arg Lys Asn Pro Gln Glu Gly Leu Tyr Asn Glu Leu Gln Lys
                165                 170                 175

Asp Lys Met Ala Glu Ala Tyr Ser Glu Ile Gly Met Lys Gly Glu Arg
            180                 185                 190

Arg Arg Gly Lys Gly His Asp Gly Leu Tyr Gln Gly Leu Ser Thr Ala
        195                 200                 205

Thr Lys Asp Thr Tyr Asp Ala Leu His Met Gln Ala Leu Pro Pro Arg
    210                 215                 220

<210> SEQ ID NO 58
<211> LENGTH: 237
<212> TYPE: PRT
<213> ORGANISM: Artificial Sequence
<220> FEATURE:
<223> OTHER INFORMATION: CAR

<400> SEQUENCE: 58

Asn Trp Ser His Pro Gln Phe Glu Lys Met His Thr Thr Thr Pro Ala
1               5                   10                  15

Pro Arg Pro Pro Thr Pro Ala Pro Thr Ile Ala Ser Gln Pro Leu Ser
            20                  25                  30

Leu Arg Pro Glu Ala Cys Arg Pro Ala Ala Gly Gly Ala Val His Thr
        35                  40                  45

Arg Gly Leu Asp Phe Ala Cys Asp Ile Tyr Ile Trp Ala Pro Leu Ala
    50                  55                  60
```

```
Gly Thr Cys Gly Val Leu Leu Leu Ser Leu Val Ile Thr Leu Tyr Cys
 65                  70                  75                  80

Lys Arg Gly Arg Lys Leu Leu Tyr Ile Phe Lys Gln Pro Phe Met
                 85                  90                  95

Arg Pro Val Gln Thr Thr Gln Glu Glu Asp Gly Cys Ser Cys Arg Phe
            100                 105                 110

Pro Glu Glu Glu Glu Gly Gly Cys Glu Leu Thr Arg Arg Val Lys Phe
            115                 120                 125

Ser Arg Ser Ala Asp Ala Pro Ala Tyr Gln Gln Gly Gln Asn Gln Leu
130                 135                 140

Tyr Asn Glu Leu Asn Leu Gly Arg Arg Glu Glu Tyr Asp Val Leu Asp
145                 150                 155                 160

Lys Arg Arg Gly Arg Asp Pro Glu Met Gly Gly Lys Pro Gln Arg Arg
                165                 170                 175

Lys Asn Pro Gln Glu Gly Leu Tyr Asn Glu Leu Gln Lys Asp Lys Met
            180                 185                 190

Ala Glu Ala Tyr Ser Glu Ile Gly Met Lys Gly Glu Arg Arg Arg Gly
            195                 200                 205

Lys Gly His Asp Gly Leu Tyr Gln Gly Leu Ser Thr Ala Thr Lys Asp
210                 215                 220

Thr Tyr Asp Ala Leu His Met Gln Ala Leu Pro Pro Arg
225                 230                 235

<210> SEQ ID NO 59
<211> LENGTH: 226
<212> TYPE: PRT
<213> ORGANISM: Artificial Sequence
<220> FEATURE:
<223> OTHER INFORMATION: CAR

<400> SEQUENCE: 59

Met His Thr Thr Thr Pro Ala Pro Arg Pro Pro Thr Pro Ala Pro Thr
 1               5                  10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp Ile
            35                  40                  45

Tyr Ile Trp Ala Pro Leu Ala Gly Thr Cys Gly Val Leu Leu Leu Ser
        50                  55                  60

Leu Val Ile Thr Leu Tyr Cys Arg Ser Lys Arg Ser Arg Leu Leu His
 65                  70                  75                  80

Ser Asp Tyr Met Asn Met Thr Pro Arg Arg Pro Gly Pro Thr Arg Lys
                85                  90                  95

His Tyr Gln Pro Tyr Ala Pro Pro Arg Asp Phe Ala Ala Tyr Arg Ser
            100                 105                 110

Thr Arg Arg Val Lys Phe Ser Arg Ser Ala Asp Ala Pro Ala Tyr Gln
        115                 120                 125

Gln Gly Gln Asn Gln Leu Tyr Asn Glu Leu Asn Leu Gly Arg Arg Glu
    130                 135                 140

Glu Tyr Asp Val Leu Asp Lys Arg Arg Gly Arg Asp Pro Glu Met Gly
145                 150                 155                 160

Gly Lys Pro Arg Arg Lys Asn Pro Gln Glu Gly Leu Tyr Asn Glu Leu
                165                 170                 175

Gln Lys Asp Lys Met Ala Glu Ala Tyr Ser Glu Ile Gly Met Lys Gly
            180                 185                 190
```

```
Glu Arg Arg Arg Gly Lys Gly His Asp Gly Leu Tyr Gln Gly Leu Ser
        195                 200                 205

Thr Ala Thr Lys Asp Thr Tyr Asp Ala Leu His Met Gln Ala Leu Pro
        210                 215                 220

Pro Arg
225

<210> SEQ ID NO 60
<211> LENGTH: 227
<212> TYPE: PRT
<213> ORGANISM: Artificial Sequence
<220> FEATURE:
<223> OTHER INFORMATION: CAR

<400> SEQUENCE: 60

Met His Thr Thr Thr Pro Ala Pro Arg Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Val Ile Thr Leu Tyr Cys Arg Ser Lys Arg Ser Arg Leu Leu His
65                  70                  75                  80

Ser Asp Tyr Met Asn Met Thr Pro Arg Arg Pro Gly Pro Thr Arg Lys
                85                  90                  95

His Tyr Gln Pro Tyr Ala Pro Pro Arg Asp Phe Ala Ala Tyr Arg Ser
            100                 105                 110

Thr Arg Arg Val Lys Phe Ser Arg Ser Ala Asp Ala Pro Ala Tyr Gln
        115                 120                 125

Gln Gly Gln Asn Gln Leu Tyr Asn Glu Leu Asn Leu Gly Arg Arg Glu
    130                 135                 140

Glu Tyr Asp Val Leu Asp Lys Arg Arg Gly Arg Asp Pro Glu Met Gly
145                 150                 155                 160

Gly Lys Pro Gln Arg Arg Lys Asn Pro Gln Glu Gly Leu Tyr Asn Glu
                165                 170                 175

Leu Gln Lys Asp Lys Met Ala Glu Ala Tyr Ser Glu Ile Gly Met Lys
            180                 185                 190

Gly Glu Arg Arg Arg Gly Lys Gly His Asp Gly Leu Tyr Gln Gly Leu
        195                 200                 205

Ser Thr Ala Thr Lys Asp Thr Tyr Asp Ala Leu His Met Gln Ala Leu
    210                 215                 220

Pro Pro Arg
225

<210> SEQ ID NO 61
<211> LENGTH: 24
<212> TYPE: PRT
<213> ORGANISM: Artificial Sequence
<220> FEATURE:
<223> OTHER INFORMATION: P2A ribosomal cleavage site

<400> SEQUENCE: 61

Ala Ser Gly Ser Gly Ala Thr Asn Phe Ser Leu Leu Lys Gln Ala Gly
1               5                   10                  15

Asp Val Glu Glu Asn Pro Gly Pro
```

<210> SEQ ID NO 62
<211> LENGTH: 5
<212> TYPE: PRT
<213> ORGANISM: Artificial Sequence
<220> FEATURE:
<223> OTHER INFORMATION: Heavy chain CDR1 of BB7.2

<400> SEQUENCE: 62

Ser Tyr His Ile Gln
1               5

<210> SEQ ID NO 63
<211> LENGTH: 17
<212> TYPE: PRT
<213> ORGANISM: Artificial Sequence
<220> FEATURE:
<223> OTHER INFORMATION: Heavy chain CDR2 of BB7.2

<400> SEQUENCE: 63

Trp Ile Tyr Pro Gly Asp Gly Ser Thr Gln Tyr Asn Glu Lys Phe Lys
1               5                   10                  15

Gly

<210> SEQ ID NO 64
<211> LENGTH: 9
<212> TYPE: PRT
<213> ORGANISM: Artificial Sequence
<220> FEATURE:
<223> OTHER INFORMATION: Heavy chain CDR3 of BB7.2

<400> SEQUENCE: 64

Glu Gly Thr Tyr Tyr Ala Met Asp Tyr
1               5

<210> SEQ ID NO 65
<211> LENGTH: 16
<212> TYPE: PRT
<213> ORGANISM: Artificial Sequence
<220> FEATURE:
<223> OTHER INFORMATION: Light chain CDR1 of BB7.2

<400> SEQUENCE: 65

Arg Ser Ser Gln Ser Ile Val His Ser Asn Gly Asn Thr Tyr Leu Glu
1               5                   10                  15

<210> SEQ ID NO 66
<211> LENGTH: 7
<212> TYPE: PRT
<213> ORGANISM: Artificial Sequence
<220> FEATURE:
<223> OTHER INFORMATION: Light chain CDR2 of BB7.2

<400> SEQUENCE: 66

Lys Val Ser Asn Arg Phe Ser
1               5

<210> SEQ ID NO 67
<211> LENGTH: 9
<212> TYPE: PRT
<213> ORGANISM: Artificial Sequence
<220> FEATURE:
<223> OTHER INFORMATION: Light chain CDR3 of BB7.2

<400> SEQUENCE: 67

Phe Gln Gly Ser His Val Pro Arg Thr
1               5

<210> SEQ ID NO 68
<211> LENGTH: 239
<212> TYPE: PRT
<213> ORGANISM: Artificial Sequence
<220> FEATURE:
<223> OTHER INFORMATION: eGFP

<400> SEQUENCE: 68

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 69
<211> LENGTH: 246
<212> TYPE: PRT
<213> ORGANISM: Artificial Sequence
<220> FEATURE:
<223> OTHER INFORMATION: scFv
<220> FEATURE:
<221> NAME/KEY: SITE
<222> LOCATION: 135
<223> OTHER INFORMATION: X is for V or I
<220> FEATURE:
<221> NAME/KEY: SITE
<222> LOCATION: 140
<223> OTHER INFORMATION: X is for T or S
<220> FEATURE:
<221> NAME/KEY: SITE
<222> LOCATION: 142
<223> OTHER INFORMATION: X is for L or S or A
<220> FEATURE:
<221> NAME/KEY: SITE

```
<222> LOCATION: 143
<223> OTHER INFORMATION: X is for S or T
<220> FEATURE:
<221> NAME/KEY: SITE
<222> LOCATION: 145
<223> OTHER INFORMATION: X is for P or S
<220> FEATURE:
<221> NAME/KEY: SITE
<222> LOCATION: 147
<223> OTHER INFORMATION: X is for T or S
<220> FEATURE:
<221> NAME/KEY: SITE
<222> LOCATION: 148
<223> OTHER INFORMATION: X is for L or P
<220> FEATURE:
<221> NAME/KEY: SITE
<222> LOCATION: 150
<223> OTHER INFORMATION: X is for E or D
<220> FEATURE:
<221> NAME/KEY: SITE
<222> LOCATION: 151
<223> OTHER INFORMATION: X is for P or R
<220> FEATURE:
<221> NAME/KEY: SITE
<222> LOCATION: 152
<223> OTHER INFORMATION: X is for A or V
<220> FEATURE:
<221> NAME/KEY: SITE
<222> LOCATION: 153
<223> OTHER INFORMATION: X is for S or T
<220> FEATURE:
<221> NAME/KEY: SITE
<222> LOCATION: 175
<223> OTHER INFORMATION: X is for L or Q
<220> FEATURE:
<221> NAME/KEY: SITE
<222> LOCATION: 181
<223> OTHER INFORMATION: X is for S or A
<220> FEATURE:
<221> NAME/KEY: SITE
<222> LOCATION: 196
<223> OTHER INFORMATION: X is for V or I
<220> FEATURE:
<221> NAME/KEY: SITE
<222> LOCATION: 212
<223> OTHER INFORMATION: X is for K or T
<220> FEATURE:
<221> NAME/KEY: SITE
<222> LOCATION: 216
<223> OTHER INFORMATION: X is for V or L
<220> FEATURE:
<221> NAME/KEY: SITE
<222> LOCATION: 218
<223> OTHER INFORMATION: X is for A or P
<220> FEATURE:
<221> NAME/KEY: SITE
<222> LOCATION: 221
<223> OTHER INFORMATION: X is for L or F
<220> FEATURE:
<221> NAME/KEY: SITE
<222> LOCATION: 222
<223> OTHER INFORMATION: X is for G or A

<400> SEQUENCE: 69

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Ile
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Ala Asp Lys Ser Thr Ser Thr Ala Tyr
65                  70                  75                  80
```

```
Met Glu Leu Ser Ser Leu Thr Ser Glu Asp Thr Ala Val Tyr Tyr Cys
                 85                  90                  95

Ala Arg Glu Gly Thr Tyr Tyr Ala Met Asp Tyr Trp Gly Gln Gly Thr
                100                 105                 110

Ser Val Thr Val Ser Ser Gly Gly Gly Ser Gly Gly Gly Gly Ser
            115                 120                 125

Gly Gly Gly Gly Ser Asp Xaa Val Met Thr Gln Xaa Pro Xaa Xaa Leu
            130                 135                 140

Xaa Val Xaa Xaa Gly Xaa Xaa Xaa Ile Ser Cys Arg Ser Gln
145                 150                 155                 160

Ser Ile Val His Ser Asn Gly Asn Thr Tyr Leu Glu Trp Tyr Xaa Gln
                165                 170                 175

Lys Pro Gly Gln Xaa Pro Arg Leu Leu Ile Tyr Lys Val Ser Asn Arg
                180                 185                 190

Phe Ser Gly Xaa Pro Asp Arg Phe Ser Gly Ser Gly Ser Gly Thr Asp
                195                 200                 205

Phe Thr Leu Xaa Ile Ser Arg Xaa Glu Xaa Glu Asp Xaa Xaa Val Tyr
            210                 215                 220

Tyr Cys Phe Gln Gly Ser His Val Pro Arg Thr Phe Gly Gly Gly Thr
225                 230                 235                 240

Lys Leu Glu Ile Lys Arg
                245

<210> SEQ ID NO 70
<211> LENGTH: 246
<212> TYPE: PRT
<213> ORGANISM: Artificial Sequence
<220> FEATURE:
<223> OTHER INFORMATION: scFv

<400> SEQUENCE: 70

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
                20                  25                  30

His Ile Gln Trp Val Arg Gln Ala Pro Gly Gln Gly Leu Glu Trp Ile
            35                  40                  45

Gly Trp Ile Tyr Pro Gly Asp Gly Ser Thr Gln Tyr Asn Glu Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Glu Gly Thr Tyr Tyr Ala Met Asp Tyr Trp Gly Gln Gly Thr
                100                 105                 110

Ser Val Thr Val Ser Ser Gly Gly Gly Ser Gly Gly Gly Gly Ser
            115                 120                 125

Gly Gly Gly Gly Ser Asp Val Val Met Thr Gln Thr Pro Leu Ser Leu
            130                 135                 140

Pro Val Thr Leu Gly Glu Pro Ala Ser Ile Ser Cys Arg Ser Ser Gln
145                 150                 155                 160

Ser Ile Val His Ser Asn Gly Asn Thr Tyr Leu Glu Trp Tyr Leu Gln
                165                 170                 175

Lys Pro Gly Gln Ser Pro Arg Leu Leu Ile Tyr Lys Val Ser Asn Arg
                180                 185                 190
```

```
Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Leu Gly Val Tyr
        210                 215                 220

Tyr Cys Phe Gln Gly Ser His Val Pro Arg Thr Phe Gly Gly Gly Thr
225                 230                 235                 240

Lys Leu Glu Ile Lys Arg
            245

<210> SEQ ID NO 71
<211> LENGTH: 246
<212> TYPE: PRT
<213> ORGANISM: Artificial Sequence
<220> FEATURE:
<223> OTHER INFORMATION: scFv

<400> SEQUENCE: 71

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Ile
        35                  40                  45

Gly Trp Ile Tyr Pro Gly Asp Gly Ser Thr Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Ser Val Thr Val Ser Ser Gly Gly Gly Ser Gly Gly Gly Gly Ser
        115                 120                 125

Gly Gly Gly Gly Ser Asp Val Val Met Thr Gln Ser Pro Ser Ser Leu
    130                 135                 140

Ser Val Thr Leu Gly Asp Arg Val Ser Ile Ser Cys Arg Ser Ser Gln
145                 150                 155                 160

Ser Ile Val His Ser Asn Gly Asn Thr Tyr Leu Glu Trp Tyr Gln Gln
                165                 170                 175

Lys Pro Gly Gln Ser Pro Arg Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Thr Ile Ser Arg Val Glu Pro Glu Asp Leu Gly Val Tyr
        210                 215                 220

Tyr Cys Phe Gln Gly Ser His Val Pro Arg Thr Phe Gly Gly Gly Thr
225                 230                 235                 240

Lys Leu Glu Ile Lys Arg
            245

<210> SEQ ID NO 72
<211> LENGTH: 246
<212> TYPE: PRT
<213> ORGANISM: Artificial Sequence
<220> FEATURE:
<223> OTHER INFORMATION: scFv
```

```
<400> SEQUENCE: 72

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Ile Gln Trp Val Arg Gln Ala Pro Gly Gln Gly Leu Glu Trp Ile
        35                  40                  45

Gly Trp Ile Tyr Pro Gly Asp Gly Ser Thr Gln Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Ser Val Thr Val Ser Ser Gly Gly Gly Gly Ser Gly Gly Gly Gly Ser
            115                 120                 125

Gly Gly Gly Gly Ser Asp Ile Val Met Thr Gln Ser Pro Ala Thr Leu
        130                 135                 140

Ser Val Ser Pro Gly Glu Arg Ala Thr Ile Ser Cys Arg Ser Ser Gln
145                 150                 155                 160

Ser Ile Val His Ser Asn Gly Asn Thr Tyr Leu Glu Trp Tyr Gln Gln
                165                 170                 175

Lys Pro Gly Gln Ala Pro Arg Leu Leu Ile Tyr Lys Val Ser Asn Arg
            180                 185                 190

Phe Ser Gly Ile Pro Asp Arg Phe Ser Gly Ser Gly Ser Gly Thr Asp
        195                 200                 205

Phe Thr Leu Thr Ile Ser Arg Leu Glu Pro Glu Asp Phe Ala Val Tyr
210                 215                 220

Tyr Cys Phe Gln Gly Ser His Val Pro Arg Thr Phe Gly Gly Gly Thr
225                 230                 235                 240

Lys Leu Glu Ile Lys Arg
                245

<210> SEQ ID NO 73
<211> LENGTH: 247
<212> TYPE: PRT
<213> ORGANISM: Artificial Sequence
<220> FEATURE:
<223> OTHER INFORMATION: scFv
<220> FEATURE:
<221> NAME/KEY: SITE
<222> LOCATION: 136
<223> OTHER INFORMATION: X is V or I
<220> FEATURE:
<221> NAME/KEY: SITE
<222> LOCATION: 141
<223> OTHER INFORMATION: X is for T or S
<220> FEATURE:
<221> NAME/KEY: SITE
<222> LOCATION: 143
<223> OTHER INFORMATION: X is for L or S or A
<220> FEATURE:
<221> NAME/KEY: SITE
<222> LOCATION: 144
<223> OTHER INFORMATION: X is for S or T
<220> FEATURE:
<221> NAME/KEY: SITE
<222> LOCATION: 146
<223> OTHER INFORMATION: X is for P or S
<220> FEATURE:
<221> NAME/KEY: SITE
```

```
<222> LOCATION: 148
<223> OTHER INFORMATION: X is for T or S
<220> FEATURE:
<221> NAME/KEY: SITE
<222> LOCATION: 149
<223> OTHER INFORMATION: X is for L or P
<220> FEATURE:
<221> NAME/KEY: SITE
<222> LOCATION: 151
<223> OTHER INFORMATION: X is for E or D
<220> FEATURE:
<221> NAME/KEY: SITE
<222> LOCATION: 152
<223> OTHER INFORMATION: X is for P or R
<220> FEATURE:
<221> NAME/KEY: SITE
<222> LOCATION: 153
<223> OTHER INFORMATION: X is for A or V
<220> FEATURE:
<221> NAME/KEY: SITE
<222> LOCATION: 154
<223> OTHER INFORMATION: X is for S or T
<220> FEATURE:
<221> NAME/KEY: SITE
<222> LOCATION: 176
<223> OTHER INFORMATION: X is for L or Q
<220> FEATURE:
<221> NAME/KEY: SITE
<222> LOCATION: 182
<223> OTHER INFORMATION: X is for S or A
<220> FEATURE:
<221> NAME/KEY: SITE
<222> LOCATION: 197
<223> OTHER INFORMATION: X is for V or I
<220> FEATURE:
<221> NAME/KEY: SITE
<222> LOCATION: 213
<223> OTHER INFORMATION: X is for K or T
<220> FEATURE:
<221> NAME/KEY: SITE
<222> LOCATION: 217
<223> OTHER INFORMATION: X is for V or L
<220> FEATURE:
<221> NAME/KEY: SITE
<222> LOCATION: 219
<223> OTHER INFORMATION: X is for A or P
<220> FEATURE:
<221> NAME/KEY: SITE
<222> LOCATION: 222
<223> OTHER INFORMATION: X is for L or F
<220> FEATURE:
<221> NAME/KEY: SITE
<222> LOCATION: 223
<223> OTHER INFORMATION: X is for G or A

<400> SEQUENCE: 73

Ser Gln Val Gln Leu Val Gln Ser Gly Pro Glu Val Lys Lys Pro Gly
1               5                   10                  15

Ala Ser Val Lys Val Ser Cys Lys Ala Ser Gly Tyr Thr Phe Thr Ser
            20                  25                  30

Tyr His Ile Gln Trp Val Arg Gln Ala Pro Gly Gln Gly Leu Glu Trp
        35                  40                  45

Ile Gly Trp Ile Tyr Pro Gly Asp Gly Ser Thr Gln Tyr Asn Glu Lys
    50                  55                  60

Phe Lys Gly Arg Val Thr Ile Thr Ala Asp Lys Ser Thr Ser Thr Ala
65                  70                  75                  80

Tyr Met Glu Leu Ser Ser Leu Thr Ser Glu Asp Thr Ala Val Tyr Tyr
                85                  90                  95

Cys Ala Arg Glu Gly Thr Tyr Tyr Ala Met Asp Tyr Trp Gly Gln Gly
            100                 105                 110

Thr Ser Val Thr Val Ser Ser Gly Gly Gly Gly Ser Gly Gly Gly Gly
```

```
            115                 120                 125
Ser Gly Gly Gly Gly Ser Asp Xaa Val Met Thr Gln Xaa Pro Xaa Xaa
        130                 135                 140

Leu Xaa Val Xaa Xaa Gly Xaa Xaa Xaa Ile Ser Cys Arg Ser Ser
145                 150                 155                 160

Gln Ser Ile Val His Ser Asn Gly Asn Thr Tyr Leu Glu Trp Tyr Xaa
                    165                 170                 175

Gln Lys Pro Gly Gln Xaa Pro Arg Leu Leu Ile Tyr Lys Val Ser Asn
                180                 185                 190

Arg Phe Ser Gly Xaa Pro Asp Arg Phe Ser Gly Ser Gly Ser Gly Thr
            195                 200                 205

Asp Phe Thr Leu Xaa Ile Ser Arg Xaa Glu Xaa Glu Asp Xaa Xaa Val
        210                 215                 220

Tyr Tyr Cys Phe Gln Gly Ser His Val Pro Arg Thr Phe Gly Gly Gly
225                 230                 235                 240

Thr Lys Leu Glu Ile Lys Arg
                245

<210> SEQ ID NO 74
<211> LENGTH: 247
<212> TYPE: PRT
<213> ORGANISM: Artificial Sequence
<220> FEATURE:
<223> OTHER INFORMATION: scFv

<400> SEQUENCE: 74

Ser Gln Val Gln Leu Val Gln Ser Gly Pro Glu Val Lys Lys Pro Gly
1               5                   10                  15

Ala Ser Val Lys Val Ser Cys Lys Ala Ser Gly Tyr Thr Phe Thr Ser
            20                  25                  30

Tyr His Ile Gln Trp Val Arg Gln Ala Pro Gly Gln Gly Leu Glu Trp
        35                  40                  45

Ile Gly Trp Ile Tyr Pro Gly Asp Gly Ser Thr Gln Tyr Asn Glu Lys
    50                  55                  60

Phe Lys Gly Arg Val Thr Ile Thr Ala Asp Lys Ser Thr Ser Thr Ala
65                  70                  75                  80

Tyr Met Glu Leu Ser Ser Leu Thr Ser Glu Asp Thr Ala Val Tyr Tyr
                85                  90                  95

Cys Ala Arg Glu Gly Thr Tyr Tyr Ala Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Val Val Met Thr Gln Thr Pro Leu Ser
        130                 135                 140

Leu Pro Val Thr Leu Gly Glu Pro Ala Ser Ile Ser Cys Arg Ser Ser
145                 150                 155                 160

Gln Ser Ile Val His Ser Asn Gly Asn Thr Tyr Leu Glu Trp Tyr Leu
                    165                 170                 175

Gln Lys Pro Gly Gln Ser Pro Arg Leu Leu Ile Tyr Lys Val Ser Asn
                180                 185                 190

Arg Phe Ser Gly Val Pro Asp Arg Phe Ser Gly Ser Gly Ser Gly Thr
            195                 200                 205

Asp Phe Thr Leu Lys Ile Ser Arg Val Glu Ala Glu Asp Leu Gly Val
        210                 215                 220

Tyr Tyr Cys Phe Gln Gly Ser His Val Pro Arg Thr Phe Gly Gly Gly
```

Thr Lys Leu Glu Ile Lys Arg
            245

<210> SEQ ID NO 75
<211> LENGTH: 247
<212> TYPE: PRT
<213> ORGANISM: Artificial Sequence
<220> FEATURE:
<223> OTHER INFORMATION: scFv

<400> SEQUENCE: 75

Ser Gln Val Gln Leu Val Gln Ser Gly Pro Glu Val Lys Lys Pro Gly
1               5                   10                  15

Ala Ser Val Lys Val Ser Cys Lys Ala Ser Gly Tyr Thr Phe Thr Ser
            20                  25                  30

Tyr His Ile Gln Trp Val Arg Gln Ala Pro Gly Gln Gly Leu Glu Trp
        35                  40                  45

Ile Gly Trp Ile Tyr Pro Gly Asp Gly Ser Thr Gln Tyr Asn Glu Lys
    50                  55                  60

Phe Lys Gly Arg Val Thr Ile Thr Ala Asp Lys Ser Thr Ser Thr Ala
65                  70                  75                  80

Tyr Met Glu Leu Ser Ser Leu Thr Ser Glu Asp Thr Ala Val Tyr Tyr
                85                  90                  95

Cys Ala Arg Glu Gly Thr Tyr Tyr Ala Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Val Val Met Thr Gln Ser Pro Ser Ser
    130                 135                 140

Leu Ser Val Thr Leu Gly Asp Arg Val Ser Ile Ser Cys Arg Ser Ser
145                 150                 155                 160

Gln Ser Ile Val His Ser Asn Gly Asn Thr Tyr Leu Glu Trp Tyr Gln
                165                 170                 175

Gln Lys Pro Gly Gln Ser Pro Arg Leu Leu Ile Tyr Lys Val Ser Asn
            180                 185                 190

Arg Phe Ser Gly Val Pro Asp Arg Phe Ser Gly Ser Gly Ser Gly Thr
        195                 200                 205

Asp Phe Thr Leu Thr Ile Ser Arg Val Glu Pro Glu Asp Leu Gly Val
    210                 215                 220

Tyr Tyr Cys Phe Gln Gly Ser His Val Pro Arg Thr Phe Gly Gly Gly
225                 230                 235                 240

Thr Lys Leu Glu Ile Lys Arg
            245

<210> SEQ ID NO 76
<211> LENGTH: 247
<212> TYPE: PRT
<213> ORGANISM: Artificial Sequence
<220> FEATURE:
<223> OTHER INFORMATION: scFv

<400> SEQUENCE: 76

Ser Gln Val Gln Leu Val Gln Ser Gly Pro Glu Val Lys Lys Pro Gly
1               5                   10                  15

Ala Ser Val Lys Val Ser Cys Lys Ala Ser Gly Tyr Thr Phe Thr Ser
            20                  25                  30

-continued

```
Tyr His Ile Gln Trp Val Arg Gln Ala Pro Gly Gln Gly Leu Glu Trp
             35                  40                  45
Ile Gly Trp Ile Tyr Pro Gly Asp Gly Ser Thr Gln Tyr Asn Glu Lys
 50                  55                  60
Phe Lys Gly Arg Val Thr Ile Thr Ala Asp Lys Ser Thr Ser Thr Ala
 65                  70                  75                  80
Tyr Met Glu Leu Ser Ser Leu Thr Ser Glu Asp Thr Ala Val Tyr Tyr
                 85                  90                  95
Cys Ala Arg Glu Gly Thr Tyr Tyr Ala Met Asp Tyr Trp Gly Gln Gly
                100                 105                 110
Thr Ser Val Thr Val Ser Ser Gly Gly Gly Ser Gly Gly Gly
                115                 120                 125
Ser Gly Gly Gly Gly Ser Asp Ile Val Met Thr Gln Ser Pro Ala Thr
130                 135                 140
Leu Ser Val Ser Pro Gly Glu Arg Ala Thr Ile Ser Cys Arg Ser Ser
145                 150                 155                 160
Gln Ser Ile Val His Ser Asn Gly Asn Thr Tyr Leu Glu Trp Tyr Gln
                165                 170                 175
Gln Lys Pro Gly Gln Ala Pro Arg Leu Leu Ile Tyr Lys Val Ser Asn
                180                 185                 190
Arg Phe Ser Gly Ile Pro Asp Arg Phe Ser Gly Ser Gly Ser Gly Thr
                195                 200                 205
Asp Phe Thr Leu Thr Ile Ser Arg Leu Glu Pro Glu Asp Phe Ala Val
                210                 215                 220
Tyr Tyr Cys Phe Gln Gly Ser His Val Pro Arg Thr Phe Gly Gly Gly
225                 230                 235                 240
Thr Lys Leu Glu Ile Lys Arg
                245

<210> SEQ ID NO 77
<211> LENGTH: 471
<212> TYPE: PRT
<213> ORGANISM: Artificial Sequence
<220> FEATURE:
<223> OTHER INFORMATION: CAR
<220> FEATURE:
<221> NAME/KEY: SITE
<222> LOCATION: 136
<223> OTHER INFORMATION: X is for V or I
<220> FEATURE:
<221> NAME/KEY: SITE
<222> LOCATION: 141
<223> OTHER INFORMATION: X is for T or S
<220> FEATURE:
<221> NAME/KEY: SITE
<222> LOCATION: 143
<223> OTHER INFORMATION: X is for L or S or A
<220> FEATURE:
<221> NAME/KEY: SITE
<222> LOCATION: 144
<223> OTHER INFORMATION: X is for S or T
<220> FEATURE:
<221> NAME/KEY: SITE
<222> LOCATION: 146
<223> OTHER INFORMATION: X is for P or S
<220> FEATURE:
<221> NAME/KEY: SITE
<222> LOCATION: 148
<223> OTHER INFORMATION: X is for T or S
<220> FEATURE:
<221> NAME/KEY: SITE
<222> LOCATION: 149
<223> OTHER INFORMATION: X is for L or P
<220> FEATURE:
<221> NAME/KEY: SITE
```

```
<222> LOCATION: 151
<223> OTHER INFORMATION: X is for E or D
<220> FEATURE:
<221> NAME/KEY: SITE
<222> LOCATION: 152
<223> OTHER INFORMATION: X is for P or R
<220> FEATURE:
<221> NAME/KEY: SITE
<222> LOCATION: 153
<223> OTHER INFORMATION: X is for A or V
<220> FEATURE:
<221> NAME/KEY: SITE
<222> LOCATION: 154
<223> OTHER INFORMATION: X is for S or T
<220> FEATURE:
<221> NAME/KEY: SITE
<222> LOCATION: 176
<223> OTHER INFORMATION: X is for L or Q
<220> FEATURE:
<221> NAME/KEY: SITE
<222> LOCATION: 182
<223> OTHER INFORMATION: X is for S or A
<220> FEATURE:
<221> NAME/KEY: SITE
<222> LOCATION: 197
<223> OTHER INFORMATION: X is for V or I
<220> FEATURE:
<221> NAME/KEY: SITE
<222> LOCATION: 213
<223> OTHER INFORMATION: X is for K or T
<220> FEATURE:
<221> NAME/KEY: SITE
<222> LOCATION: 217
<223> OTHER INFORMATION: X is for V or L
<220> FEATURE:
<221> NAME/KEY: SITE
<222> LOCATION: 219
<223> OTHER INFORMATION: X is for A or P
<220> FEATURE:
<221> NAME/KEY: SITE
<222> LOCATION: 222
<223> OTHER INFORMATION: X is for L or F
<220> FEATURE:
<221> NAME/KEY: SITE
<222> LOCATION: 223
<223> OTHER INFORMATION: X is for G or A

<400> SEQUENCE: 77

Ser Gln Val Gln Leu Val Gln Ser Gly Pro Glu Val Lys Lys Pro Gly
1               5                   10                  15

Ala Ser Val Lys Val Ser Cys Lys Ala Ser Gly Tyr Thr Phe Thr Ser
            20                  25                  30

Tyr His Ile Gln Trp Val Arg Gln Ala Pro Gly Gln Gly Leu Glu Trp
        35                  40                  45

Ile Gly Trp Ile Tyr Pro Gly Asp Gly Ser Thr Gln Tyr Asn Glu Lys
50                  55                  60

Phe Lys Gly Arg Val Thr Ile Thr Ala Asp Lys Ser Thr Ser Thr Ala
65                  70                  75                  80

Tyr Met Glu Leu Ser Ser Leu Thr Ser Glu Asp Thr Ala Val Tyr Tyr
                85                  90                  95

Cys Ala Arg Glu Gly Thr Tyr Tyr Ala Met Asp Tyr Trp Gly Gln Gly
            100                 105                 110

Thr Ser Val Thr Val Ser Ser Gly Gly Gly Ser Gly Gly Gly Gly
        115                 120                 125

Ser Gly Gly Gly Gly Ser Asp Xaa Val Met Thr Gln Xaa Pro Xaa Xaa
    130                 135                 140

Leu Xaa Val Xaa Xaa Gly Xaa Xaa Xaa Xaa Ile Ser Cys Arg Ser Ser
145                 150                 155                 160
```

```
Gln Ser Ile Val His Ser Asn Gly Asn Thr Tyr Leu Glu Trp Tyr Xaa
                165                 170                 175

Gln Lys Pro Gly Gln Xaa Pro Arg Leu Leu Ile Tyr Lys Val Ser Asn
            180                 185                 190

Arg Phe Ser Gly Xaa Pro Asp Arg Phe Ser Gly Ser Gly Ser Gly Thr
                195                 200                 205

Asp Phe Thr Leu Xaa Ile Ser Arg Xaa Glu Xaa Glu Asp Xaa Xaa Val
            210                 215                 220

Tyr Tyr Cys Phe Gln Gly Ser His Val Pro Arg Thr Phe Gly Gly Gly
225                 230                 235                 240

Thr Lys Leu Glu Ile Lys Arg Thr Thr Thr Pro Ala Pro Arg Pro
                245                 250                 255

Pro Thr Pro Ala Pro Thr Ile Ala Ser Gln Pro Leu Ser Leu Arg Pro
                260                 265                 270

Glu Ala Cys Arg Pro Ala Ala Gly Gly Ala Val His Thr Arg Gly Leu
            275                 280                 285

Asp Phe Ala Cys Asp Ile Tyr Ile Trp Ala Pro Leu Ala Gly Thr Cys
            290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
                340                 345                 350

Glu Glu Gly Gly Cys Glu Leu Arg Val Lys Phe Ser Arg Ser Ala Asp
            355                 360                 365

Ala Pro Ala Tyr Gln Gln Gly Gln Asn Gln Leu Tyr Asn Glu Leu Asn
            370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
                420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
            450                 455                 460

Met Gln Ala Leu Pro Pro Arg
465                 470

<210> SEQ ID NO 78
<211> LENGTH: 471
<212> TYPE: PRT
<213> ORGANISM: Artificial Sequence
<220> FEATURE:
<223> OTHER INFORMATION: CAR

<400> SEQUENCE: 78

Ser Gln Val Gln Leu Val Gln Ser Gly Pro Glu Val Lys Lys Pro Gly
1               5                   10                  15

Ala Ser Val Lys Val Ser Cys Lys Ala Ser Gly Tyr Thr Phe Thr Ser
            20                  25                  30

Tyr His Ile Gln Trp Val Arg Gln Ala Pro Gly Gln Gly Leu Glu Trp
            35                  40                  45
```

```
Ile Gly Trp Ile Tyr Pro Gly Asp Gly Ser Thr Gln Tyr Asn Glu Lys
 50                  55                  60
Phe Lys Gly Arg Val Thr Ile Thr Ala Asp Lys Ser Thr Ser Thr Ala
 65                  70                  75                  80
Tyr Met Glu Leu Ser Ser Leu Thr Ser Glu Asp Thr Ala Val Tyr Tyr
                 85                  90                  95
Cys Ala Arg Glu Gly Thr Tyr Tyr Ala Met Asp Tyr Trp Gly Gln Gly
                100                 105                 110
Thr Ser Val Thr Val Ser Ser Gly Gly Gly Ser Gly Gly Gly Gly
                115                 120                 125
Ser Gly Gly Gly Gly Ser Asp Val Val Met Thr Gln Thr Pro Leu Ser
130                 135                 140
Leu Pro Val Thr Leu Gly Glu Pro Ala Ser Ile Ser Cys Arg Ser Ser
145                 150                 155                 160
Gln Ser Ile Val His Ser Asn Gly Asn Thr Tyr Leu Glu Trp Tyr Leu
                165                 170                 175
Gln Lys Pro Gly Gln Ser Pro Arg Leu Leu Ile Tyr Lys Val Ser Asn
                180                 185                 190
Arg Phe Ser Gly Val Pro Asp Arg Phe Ser Gly Ser Gly Ser Gly Thr
                195                 200                 205
Asp Phe Thr Leu Lys Ile Ser Arg Val Glu Ala Glu Asp Leu Gly Val
210                 215                 220
Tyr Tyr Cys Phe Gln Gly Ser His Val Pro Arg Thr Phe Gly Gly Gly
225                 230                 235                 240
Thr Lys Leu Glu Ile Lys Arg Arg Thr Thr Pro Ala Pro Arg Pro
                245                 250                 255
Pro Thr Pro Ala Pro Thr Ile Ala Ser Gln Pro Leu Ser Leu Arg Pro
                260                 265                 270
Glu Ala Cys Arg Pro Ala Ala Gly Gly Ala Val His Thr Arg Gly Leu
                275                 280                 285
Asp Phe Ala Cys Asp Ile Tyr Ile Trp Ala Pro Leu Ala Gly Thr Cys
                290                 295                 300
Gly Val Leu Leu Leu Ser Leu Val Ile Thr Leu Tyr Cys Lys Arg Gly
305                 310                 315                 320
Arg Lys Lys Leu Leu Tyr Ile Phe Lys Gln Pro Phe Met Arg Pro Val
                325                 330                 335
Gln Thr Thr Gln Glu Glu Asp Gly Cys Ser Cys Arg Phe Pro Glu Glu
                340                 345                 350
Glu Glu Gly Gly Cys Glu Leu Arg Val Lys Phe Ser Arg Ser Ala Asp
                355                 360                 365
Ala Pro Ala Tyr Gln Gln Gly Gln Asn Gln Leu Tyr Asn Glu Leu Asn
370                 375                 380
Leu Gly Arg Arg Glu Glu Tyr Asp Val Leu Asp Lys Arg Arg Gly Arg
385                 390                 395                 400
Asp Pro Glu Met Gly Gly Lys Pro Arg Arg Lys Asn Pro Gln Glu Gly
                405                 410                 415
Leu Tyr Asn Glu Leu Gln Lys Asp Lys Met Ala Glu Ala Tyr Ser Glu
                420                 425                 430
Ile Gly Met Lys Gly Glu Arg Arg Arg Gly Lys Gly His Asp Gly Leu
                435                 440                 445
Tyr Gln Gly Leu Ser Thr Ala Thr Lys Asp Thr Tyr Asp Ala Leu His
450                 455                 460
Met Gln Ala Leu Pro Pro Arg
```

-continued

```
465                 470

<210> SEQ ID NO 79
<211> LENGTH: 471
<212> TYPE: PRT
<213> ORGANISM: Artificial Sequence
<220> FEATURE:
<223> OTHER INFORMATION: CAR

<400> SEQUENCE: 79

Ser Gln Val Gln Leu Val Gln Ser Gly Pro Glu Val Lys Lys Pro Gly
1               5                   10                  15

Ala Ser Val Lys Val Ser Cys Lys Ala Ser Gly Tyr Thr Phe Thr Ser
            20                  25                  30

Tyr His Ile Gln Trp Val Arg Gln Ala Pro Gly Gln Gly Leu Glu Trp
        35                  40                  45

Ile Gly Trp Ile Tyr Pro Gly Asp Gly Ser Thr Gln Tyr Asn Glu Lys
    50                  55                  60

Phe Lys Gly Arg Val Thr Ile Thr Ala Asp Lys Ser Ser Thr Thr Ala
65                  70                  75                  80

Tyr Met Glu Leu Ser Ser Leu Thr Ser Glu Asp Thr Ala Val Tyr Tyr
                85                  90                  95

Cys Ala Arg Glu Gly Thr Tyr Tyr Ala Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Val Val Met Thr Gln Ser Pro Ser Ser
130                 135                 140

Leu Ser Val Thr Leu Gly Asp Arg Val Ser Ile Ser Cys Arg Ser Ser
145                 150                 155                 160

Gln Ser Ile Val His Ser Asn Gly Asn Thr Tyr Leu Glu Trp Tyr Gln
                165                 170                 175

Gln Lys Pro Gly Gln Ser Pro Arg Leu Leu Ile Tyr Lys Val Ser Asn
            180                 185                 190

Arg Phe Ser Gly Val Pro Asp Arg Phe Ser Gly Ser Gly Ser Gly Thr
        195                 200                 205

Asp Phe Thr Leu Thr Ile Ser Arg Val Glu Pro Glu Asp Leu Gly Val
    210                 215                 220

Tyr Tyr Cys Phe Gln Gly Ser His Val Pro Arg Thr Phe Gly Gly Gly
225                 230                 235                 240

Thr Lys Leu Glu Ile Lys Arg Thr Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
```

```
                   355                 360                 365
Ala Pro Ala Tyr Gln Gln Gly Gln Asn Gln Leu Tyr Asn Glu Leu Asn
            370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Gly Lys Gly His Asp Gly Leu
            435                 440                 445

Tyr Gln Gly Leu Ser Thr Ala Thr Lys Asp Thr Tyr Asp Ala Leu His
            450                 455                 460

Met Gln Ala Leu Pro Pro Arg
465                 470

<210> SEQ ID NO 80
<211> LENGTH: 471
<212> TYPE: PRT
<213> ORGANISM: Artificial Sequence
<220> FEATURE:
<223> OTHER INFORMATION: CAR

<400> SEQUENCE: 80

Ser Gln Val Gln Leu Val Gln Ser Gly Pro Glu Val Lys Lys Pro Gly
1               5                   10                  15

Ala Ser Val Lys Val Ser Cys Lys Ala Ser Gly Tyr Thr Phe Thr Ser
            20                  25                  30

Tyr His Ile Gln Trp Val Arg Gln Ala Pro Gly Gln Gly Leu Glu Trp
        35                  40                  45

Ile Gly Trp Ile Tyr Pro Gly Asp Gly Ser Thr Gln Tyr Asn Glu Lys
    50                  55                  60

Phe Lys Gly Arg Val Thr Ile Thr Ala Asp Lys Ser Thr Ser Thr Ala
65                  70                  75                  80

Tyr Met Glu Leu Ser Ser Leu Thr Ser Glu Asp Thr Ala Val Tyr Tyr
                85                  90                  95

Cys Ala Arg Glu Gly Thr Tyr Tyr Ala Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Gly Gly Gly Gly Ser Asp Ile Val Met Thr Gln Ser Pro Ala Thr
    130                 135                 140

Leu Ser Val Ser Pro Gly Glu Arg Ala Thr Ile Ser Cys Arg Ser Ser
145                 150                 155                 160

Gln Ser Ile Val His Ser Asn Gly Asn Thr Tyr Leu Glu Trp Tyr Gln
                165                 170                 175

Gln Lys Pro Gly Gln Ala Pro Arg Leu Leu Ile Tyr Lys Val Ser Asn
            180                 185                 190

Arg Phe Ser Gly Ile Pro Asp Arg Phe Ser Gly Ser Gly Ser Gly Thr
        195                 200                 205

Asp Phe Thr Leu Thr Ile Ser Arg Leu Glu Pro Glu Asp Phe Ala Val
    210                 215                 220

Tyr Tyr Cys Phe Gln Gly Ser His Val Pro Arg Thr Phe Gly Gly Gly
225                 230                 235                 240

Thr Lys Leu Glu Ile Lys Arg Arg Thr Thr Thr Pro Ala Pro Arg Pro
```

-continued

```
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Gly Ala Val His Thr Arg Gly Leu
        275                 280                 285

Asp Phe Ala Cys Asp Ile Tyr Ile Trp Ala Pro Leu Ala Gly Thr Cys
    290                 295                 300

Gly Val Leu Leu Leu Ser Leu Val Ile Thr Leu Tyr Cys Lys Arg Gly
305                 310                 315                 320

Arg Lys Lys Leu Leu Tyr Ile Phe Lys Gln Pro Phe Met Arg Pro Val
                325                 330                 335

Gln Thr Thr Gln Glu Glu Asp Gly Cys Ser Cys Arg Phe Pro Glu Glu
            340                 345                 350

Glu Glu Gly Gly Cys Glu Leu Arg Val Lys Phe Ser Arg Ser Ala Asp
        355                 360                 365

Ala Pro Ala Tyr Gln Gln Gly Gln Asn Gln Leu Tyr Asn Glu Leu Asn
    370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465                 470

<210> SEQ ID NO 81
<211> LENGTH: 492
<212> TYPE: PRT
<213> ORGANISM: Artificial Sequence
<220> FEATURE:
<223> OTHER INFORMATION: CAR
<220> FEATURE:
<221> NAME/KEY: SITE
<222> LOCATION: 157
<223> OTHER INFORMATION: X is for V or I
<220> FEATURE:
<221> NAME/KEY: SITE
<222> LOCATION: 162
<223> OTHER INFORMATION: X is for T or S
<220> FEATURE:
<221> NAME/KEY: SITE
<222> LOCATION: 164
<223> OTHER INFORMATION: X is for L or S or A
<220> FEATURE:
<221> NAME/KEY: SITE
<222> LOCATION: 165
<223> OTHER INFORMATION: X is for S or T
<220> FEATURE:
<221> NAME/KEY: SITE
<222> LOCATION: 167
<223> OTHER INFORMATION: X is for P or S
<220> FEATURE:
<221> NAME/KEY: SITE
<222> LOCATION: 169
<223> OTHER INFORMATION: X is for T or S
<220> FEATURE:
<221> NAME/KEY: SITE
<222> LOCATION: 170
<223> OTHER INFORMATION: X is for L or P
```

```
<220> FEATURE:
<221> NAME/KEY: SITE
<222> LOCATION: 172
<223> OTHER INFORMATION: X is for E or D
<220> FEATURE:
<221> NAME/KEY: SITE
<222> LOCATION: 173
<223> OTHER INFORMATION: X is for P or R
<220> FEATURE:
<221> NAME/KEY: SITE
<222> LOCATION: 174
<223> OTHER INFORMATION: X is for A or V
<220> FEATURE:
<221> NAME/KEY: SITE
<222> LOCATION: 175
<223> OTHER INFORMATION: X is for S or T
<220> FEATURE:
<221> NAME/KEY: SITE
<222> LOCATION: 197
<223> OTHER INFORMATION: X is for L or Q
<220> FEATURE:
<221> NAME/KEY: SITE
<222> LOCATION: 203
<223> OTHER INFORMATION: X is for S or A
<220> FEATURE:
<221> NAME/KEY: SITE
<222> LOCATION: 218
<223> OTHER INFORMATION: X is for V or I
<220> FEATURE:
<221> NAME/KEY: SITE
<222> LOCATION: 234
<223> OTHER INFORMATION: X is for K or T
<220> FEATURE:
<221> NAME/KEY: SITE
<222> LOCATION: 238
<223> OTHER INFORMATION: X is for V or L
<220> FEATURE:
<221> NAME/KEY: SITE
<222> LOCATION: 240
<223> OTHER INFORMATION: X is for A or P
<220> FEATURE:
<221> NAME/KEY: SITE
<222> LOCATION: 243
<223> OTHER INFORMATION: X is for L or F
<220> FEATURE:
<221> NAME/KEY: SITE
<222> LOCATION: 244
<223> OTHER INFORMATION: X is for G or A

<400> SEQUENCE: 81

Met Ala Leu Pro Val Thr Ala Leu Leu Leu Pro Leu Ala Leu Leu Leu
1               5                   10                  15

His Ala Ala Arg Pro Ser Gln Val Gln Leu Val Gln Ser Gly Pro Glu
            20                  25                  30

Val Lys Lys Pro Gly Ala Ser Val Lys Val Ser Cys Lys Ala Ser Gly
        35                  40                  45

Tyr Thr Phe Thr Ser Tyr His Ile Gln Trp Val Arg Gln Ala Pro Gly
    50                  55                  60

Gln Gly Leu Glu Trp Ile Gly Trp Ile Tyr Pro Gly Asp Gly Ser Thr
65                  70                  75                  80

Gln Tyr Asn Glu Lys Phe Lys Gly Arg Val Thr Ile Thr Ala Asp Lys
                85                  90                  95

Ser Thr Ser Thr Ala Tyr Met Glu Leu Ser Ser Leu Thr Ser Glu Asp
            100                 105                 110

Thr Ala Val Tyr Tyr Cys Ala Arg Glu Gly Thr Tyr Tyr Ala Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Gly Ser Asp Xaa Val Met Thr
```

```
            145                 150                 155                 160
Gln Xaa Pro Xaa Xaa Leu Xaa Val Xaa Xaa Gly Xaa Xaa Xaa Xaa Ile
                165                 170                 175

Ser Cys Arg Ser Ser Gln Ser Ile Val His Ser Asn Gly Asn Thr Tyr
                180                 185                 190

Leu Glu Trp Tyr Xaa Gln Lys Pro Gly Gln Xaa Pro Arg Leu Leu Ile
            195                 200                 205

Tyr Lys Val Ser Asn Arg Phe Ser Gly Xaa Pro Asp Arg Phe Ser Gly
    210                 215                 220

Ser Gly Ser Gly Thr Asp Phe Thr Leu Xaa Ile Ser Arg Xaa Glu Xaa
225                 230                 235                 240

Glu Asp Xaa Xaa Val Tyr Tyr Cys Phe Gln Gly Ser His Val Pro Arg
                245                 250                 255

Thr Phe Gly Gly Gly Thr Lys Leu Glu Ile Lys Arg Thr Thr Thr
                260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
            355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 82
<211> LENGTH: 492
<212> TYPE: PRT
<213> ORGANISM: Artificial Sequence
<220> FEATURE:
<223> OTHER INFORMATION: CAR

<400> SEQUENCE: 82

Met Ala Leu Pro Val Thr Ala Leu Leu Leu Pro Leu Ala Leu Leu Leu
1               5                   10                  15

His Ala Ala Arg Pro Ser Gln Val Gln Leu Val Gln Ser Gly Pro Glu
```

```
            20                  25                  30
Val Lys Lys Pro Gly Ala Ser Val Lys Val Ser Cys Lys Ala Ser Gly
            35                  40                  45
Tyr Thr Phe Thr Ser Tyr His Ile Gln Trp Val Arg Gln Ala Pro Gly
            50                  55                  60
Gln Gly Leu Glu Trp Ile Gly Trp Ile Tyr Pro Gly Asp Gly Ser Thr
65                  70                  75                  80
Gln Tyr Asn Glu Lys Phe Lys Gly Arg Val Thr Ile Thr Ala Asp Lys
            85                  90                  95
Ser Thr Ser Thr Ala Tyr Met Glu Leu Ser Ser Leu Thr Ser Glu Asp
            100                 105                 110
Thr Ala Val Tyr Tyr Cys Ala Arg Glu Gly Thr Tyr Tyr Ala Met Asp
            115                 120                 125
Tyr Trp Gly Gln Gly Thr Ser Val Thr Val Ser Ser Gly Gly Gly Gly
            130                 135                 140
Ser Gly Gly Gly Gly Ser Gly Gly Gly Gly Ser Asp Val Val Met Thr
145                 150                 155                 160
Gln Thr Pro Leu Ser Leu Pro Val Thr Leu Gly Glu Pro Ala Ser Ile
            165                 170                 175
Ser Cys Arg Ser Ser Gln Ser Ile Val His Ser Asn Gly Asn Thr Tyr
            180                 185                 190
Leu Glu Trp Tyr Leu Gln Lys Pro Gly Gln Ser Pro Arg Leu Leu Ile
            195                 200                 205
Tyr Lys Val Ser Asn Arg Phe Ser Gly Val Pro Asp Arg Phe Ser Gly
            210                 215                 220
Ser Gly Ser Gly Thr Asp Phe Thr Leu Lys Ile Ser Arg Val Glu Ala
225                 230                 235                 240
Glu Asp Leu Gly Val Tyr Tyr Cys Phe Gln Gly Ser His Val Pro Arg
            245                 250                 255
Thr Phe Gly Gly Gly Thr Lys Leu Glu Ile Lys Arg Arg Thr Thr Thr
            260                 265                 270
Pro Ala Pro Arg Pro Pro Thr Pro Ala Pro Thr Ile Ala Ser Gln Pro
            275                 280                 285
Leu Ser Leu Arg Pro Glu Ala Cys Arg Pro Ala Ala Gly Gly Ala Val
            290                 295                 300
His Thr Arg Gly Leu Asp Phe Ala Cys Asp Ile Tyr Ile Trp Ala Pro
305                 310                 315                 320
Leu Ala Gly Thr Cys Gly Val Leu Leu Leu Ser Leu Val Ile Thr Leu
            325                 330                 335
Tyr Cys Lys Arg Gly Arg Lys Lys Leu Leu Tyr Ile Phe Lys Gln Pro
            340                 345                 350
Phe Met Arg Pro Val Gln Thr Thr Gln Glu Glu Asp Gly Cys Ser Cys
            355                 360                 365
Arg Phe Pro Glu Glu Glu Glu Gly Gly Cys Glu Leu Arg Val Lys Phe
            370                 375                 380
Ser Arg Ser Ala Asp Ala Pro Ala Tyr Gln Gln Gly Gln Asn Gln Leu
385                 390                 395                 400
Tyr Asn Glu Leu Asn Leu Gly Arg Glu Glu Tyr Asp Val Leu Asp
            405                 410                 415
Lys Arg Arg Gly Arg Asp Pro Glu Met Gly Gly Lys Pro Arg Arg Lys
            420                 425                 430
Asn Pro Gln Glu Gly Leu Tyr Asn Glu Leu Gln Lys Asp Lys Met Ala
            435                 440                 445
```

```
Glu Ala Tyr Ser Glu Ile Gly Met Lys Gly Glu Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 83
<211> LENGTH: 492
<212> TYPE: PRT
<213> ORGANISM: Artificial Sequence
<220> FEATURE:
<223> OTHER INFORMATION: CAR

<400> SEQUENCE: 83

Met Ala Leu Pro Val Thr Ala Leu Leu Leu Pro Leu Ala Leu Leu Leu
1               5                   10                  15

His Ala Ala Arg Pro Ser Gln Val Gln Leu Val Gln Ser Gly Pro Glu
            20                  25                  30

Val Lys Lys Pro Gly Ala Ser Val Lys Val Ser Cys Lys Ala Ser Gly
        35                  40                  45

Tyr Thr Phe Thr Ser Tyr His Ile Gln Trp Val Arg Gln Ala Pro Gly
    50                  55                  60

Gln Gly Leu Glu Trp Ile Gly Trp Ile Tyr Pro Gly Asp Gly Ser Thr
65                  70                  75                  80

Gln Tyr Asn Glu Lys Phe Lys Gly Arg Val Thr Ile Thr Ala Asp Lys
                85                  90                  95

Ser Thr Ser Thr Ala Tyr Met Glu Leu Ser Ser Leu Thr Ser Glu Asp
            100                 105                 110

Thr Ala Val Tyr Tyr Cys Ala Arg Glu Gly Thr Tyr Tyr Ala Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Gly Ser Asp Val Val Met Thr
145                 150                 155                 160

Gln Ser Pro Ser Ser Leu Ser Val Thr Leu Gly Asp Arg Val Ser Ile
                165                 170                 175

Ser Cys Arg Ser Ser Gln Ser Ile Val His Ser Asn Gly Asn Thr Tyr
            180                 185                 190

Leu Glu Trp Tyr Gln Gln Lys Pro Gly Gln Ser Pro Arg Leu Leu Ile
        195                 200                 205

Tyr Lys Val Ser Asn Arg Phe Ser Gly Val Pro Asp Arg Phe Ser Gly
    210                 215                 220

Ser Gly Ser Gly Thr Asp Phe Thr Leu Thr Ile Ser Arg Val Glu Pro
225                 230                 235                 240

Glu Asp Leu Gly Val Tyr Tyr Cys Phe Gln Gly Ser His Val Pro Arg
                245                 250                 255

Thr Phe Gly Gly Gly Thr Lys Leu Glu Ile Lys Arg Arg Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320
```

```
Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 84
<211> LENGTH: 492
<212> TYPE: PRT
<213> ORGANISM: Artificial Sequence
<220> FEATURE:
<223> OTHER INFORMATION: CAR

<400> SEQUENCE: 84

Met Ala Leu Pro Val Thr Ala Leu Leu Leu Pro Leu Ala Leu Leu Leu
1               5                   10                  15

His Ala Ala Arg Pro Ser Gln Val Gln Leu Val Gln Ser Gly Pro Glu
                20                  25                  30

Val Lys Lys Pro Gly Ala Ser Val Lys Val Ser Cys Lys Ala Ser Gly
            35                  40                  45

Tyr Thr Phe Thr Ser Tyr His Ile Gln Trp Val Arg Gln Ala Pro Gly
        50                  55                  60

Gln Gly Leu Glu Trp Ile Gly Trp Ile Tyr Pro Gly Asp Gly Ser Thr
65                  70                  75                  80

Gln Tyr Asn Glu Lys Phe Lys Gly Arg Val Thr Ile Thr Ala Asp Lys
                85                  90                  95

Ser Thr Ser Thr Ala Tyr Met Glu Leu Ser Ser Leu Thr Ser Glu Asp
            100                 105                 110

Thr Ala Val Tyr Tyr Cys Ala Arg Glu Gly Thr Tyr Tyr Ala Met Asp
        115                 120                 125

Tyr Trp Gly Gln Gly Thr Ser Val Thr Val Ser Ser Gly Gly Gly Gly
    130                 135                 140

Ser Gly Gly Gly Gly Ser Gly Gly Gly Gly Ser Asp Ile Val Met Thr
145                 150                 155                 160

Gln Ser Pro Ala Thr Leu Ser Val Ser Pro Gly Glu Arg Ala Thr Ile
                165                 170                 175

Ser Cys Arg Ser Ser Gln Ser Ile Val His Ser Asn Gly Asn Thr Tyr
            180                 185                 190
```

-continued

Leu Glu Trp Tyr Gln Gln Lys Pro Gly Gln Ala Pro Arg Leu Leu Ile
            195                 200                 205

Tyr Lys Val Ser Asn Arg Phe Ser Gly Ile Pro Asp Arg Phe Ser Gly
        210                 215                 220

Ser Gly Ser Gly Thr Asp Phe Thr Leu Thr Ile Ser Arg Leu Glu Pro
225                 230                 235                 240

Glu Asp Phe Ala Val Tyr Tyr Cys Phe Gln Gly Ser His Val Pro Arg
            245                 250                 255

Thr Phe Gly Gly Gly Thr Lys Leu Glu Ile Lys Arg Arg Thr Thr Thr
            260                 265                 270

Pro Ala Pro Arg Pro Pro Thr Pro Ala Pro Thr Ile Ala Ser Gln Pro
            275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
            325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
            355                 360                 365

Arg Phe Pro Glu Glu Glu Glu Gly Gly Cys Glu Leu Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
            405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
            435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
            485                 490

<210> SEQ ID NO 85
<211> LENGTH: 9
<212> TYPE: PRT
<213> ORGANISM: Artificial Sequence
<220> FEATURE:
<223> OTHER INFORMATION: LAGLIDADG motif

<400> SEQUENCE: 85

Leu Ala Gly Leu Ile Asp Ala Asp Gly
1               5

<210> SEQ ID NO 86
<211> LENGTH: 354
<212> TYPE: DNA
<213> ORGANISM: Artificial Sequence
<220> FEATURE:
<223> OTHER INFORMATION: VH

<400> SEQUENCE: 86

```
caggtccagc tagtacaaag cggccctgaa gtaaagaaac ctggtgcctc tgtgaaggtg      60
agctgcaagg ccagcggcta caccttcacc agctaccaca tccagtgggt tcgacaggcc     120
cctggacagg gactagagtg gatcggctgg atctatcctg cgacggcag cacccagtac      180
aacgagaagt tcaagggcag agttaccatc accgccgaca gagcaccag cacagcctat      240
atggagctga gcagcctgac cagcgaggac acagctgttt actattgtgc cagagagggc     300
acctactacg caatggatta ttggggccag gggaccagcg tgaccgtttc ttct            354
```

<210> SEQ ID NO 87
<211> LENGTH: 339
<212> TYPE: DNA
<213> ORGANISM: Artificial Sequence
<220> FEATURE:
<223> OTHER INFORMATION: VL

<400> SEQUENCE: 87

```
gatgttgtaa tgacccagac acctctgagc ctgcctgtga ccctgggaga accagcatcc      60
atcagctgtc ggagcagcca gagcatcgtt cacagcaacg gcaacaccta cctggaatgg     120
tatctacaga agcccggaca gagccccagg ctgctgatct acaaggtgtc caaccgcttc     180
agtggtgtgc ccgatagatt ttctggcagc ggctctggca ccgacttcac cctgaagatc     240
tccagagtgg aagccgagga cctgggcgtg tactactgct tccaaggcag ccatgtgcca     300
agaacctttg gtggaggcac aaagctggaa atcaagcgg                             339
```

<210> SEQ ID NO 88
<211> LENGTH: 339
<212> TYPE: DNA
<213> ORGANISM: Artificial Sequence
<220> FEATURE:
<223> OTHER INFORMATION: VL

<400> SEQUENCE: 88

```
gatgttgtaa tgacccagag ccctagtagc ctgtctgtga ccctgggaga tcgagtatcc      60
atcagctgtc ggagcagcca gagcatcgtt cacagcaacg gcaacaccta cctggaatgg     120
tatcaacaga agcccggaca gagccccagg ctgctgatct acaaggtgtc caaccgcttc     180
agtggtgtgc ccgatagatt ttctggcagc ggctctggca ccgacttcac cctgacgatc     240
tccagagtgg aaccgagga cctgggcgtg tactactgct tccaaggcag ccatgtgcca      300
agaacctttg gtggaggcac aaagctggaa atcaagcgg                             339
```

<210> SEQ ID NO 89
<211> LENGTH: 339
<212> TYPE: DNA
<213> ORGANISM: Artificial Sequence
<220> FEATURE:
<223> OTHER INFORMATION: VL

<400> SEQUENCE: 89

```
gatattgtaa tgacccagag ccctgcaaca ctgtctgtgt ccctggaga acgagcaaca       60
atcagctgtc ggagcagcca gagcatcgtt cacagcaacg gcaacaccta cctggaatgg     120
tatcaacaga agcccggaca ggcccccagg ctgctgatct acaaggtgtc caaccgcttc     180
agtggaatac ccgatagatt ttctggcagc ggctctggca ccgacttcac cctgacgatc     240
```

```
tccagattag aaccagagga ctttgcagtg tactactgct tccaaggcag ccatgtgcca      300
agaacctttg gtggaggcac aaagctggaa atcaagcgg                             339
```